United States Patent
Beck et al.

(10) Patent No.: US 8,003,648 B2
(45) Date of Patent: *Aug. 23, 2011

(54) HETEROCYCLIC GPR40 MODULATORS

(75) Inventors: Hilary Beck, San Carlos, CA (US); Paul Dransfield, San Francisco, CA (US); Zice Fu, Foster City, CA (US); Jonathan B. Houze, San Mateo, CA (US); XianYun Jiao, Belmont, CA (US); Todd J. Kohn, San Mateo, CA (US); SuJen Lai, Burlingame, CA (US); Jinqian Liu, Palo Alto, CA (US); Jiwen Liu, Foster City, CA (US); Zhihua Ma, San Mateo, CA (US); Julio C. Medina, San Carlos, CA (US); Michael J. Schmitt, Oakland, CA (US); Rajiv Sharma, Fremont, CA (US); Wang Shen, San Mateo, CA (US); Marc Vimolratana, San Mateo, CA (US); Yingcai Wang, Millbrae, CA (US); Zhongyu Wang, Ewing, NJ (US)

(73) Assignee: Amgen Inc., Thousand Oaks, CA (US)

( * ) Notice: Subject to any disclaimer, the term of this patent is extended or adjusted under 35 U.S.C. 154(b) by 5 days.

This patent is subject to a terminal disclaimer.

(21) Appl. No.: 12/613,418

(22) Filed: Nov. 5, 2009

(65) Prior Publication Data

US 2010/0075974 A1  Mar. 25, 2010

Related U.S. Application Data

(62) Division of application No. 11/900,006, filed on Sep. 6, 2007, now Pat. No. 7,714,008.

(60) Provisional application No. 60/843,262, filed on Sep. 7, 2006, provisional application No. 60/857,665, filed on Nov. 7, 2006, provisional application No. 60/923,437, filed on Apr. 13, 2007.

(51) Int. Cl.
| | |
|---|---|
| A61K 31/498 | (2006.01) |
| A61K 31/42 | (2006.01) |
| A61K 31/426 | (2006.01) |
| A61K 31/4245 | (2006.01) |
| A61K 31/443 | (2006.01) |
| C07D 261/06 | (2006.01) |
| C07D 277/22 | (2006.01) |
| C07D 271/06 | (2006.01) |
| C07D 413/02 | (2006.01) |
| C07D 241/36 | (2006.01) |
| A61P 3/10 | (2006.01) |
| A61P 9/00 | (2006.01) |

(52) U.S. Cl. ........ 514/250; 514/378; 514/365; 514/364; 514/340; 548/247; 548/203; 548/131; 546/272.1; 544/344

(58) Field of Classification Search .......... 514/250, 514/378, 365, 364, 340; 548/247, 203, 131; 546/272.1; 544/344
See application file for complete search history.

(56) References Cited

U.S. PATENT DOCUMENTS

| | | | |
|---|---|---|---|
| 3,507,881 A | 4/1970 | Sandberg et al. | |
| 4,760,089 A | 7/1988 | Chambers et al. | |
| 6,037,367 A | 3/2000 | Christensen, IV et al. | |
| 6,506,757 B1 | 1/2003 | Tajima et al. | |
| 6,620,832 B2 | 9/2003 | Eastwood | |
| 6,645,939 B1 | 11/2003 | Durette et al. | |
| 6,710,063 B1 | 3/2004 | Chao et al. | |
| 6,723,740 B2 | 4/2004 | Chao et al. | |
| 6,875,780 B2 | 4/2005 | Auerbach et al. | |
| 6,939,875 B2 | 9/2005 | Auerbach et al. | |
| 6,964,983 B2 | 11/2005 | Auerbach et al. | |
| 7,338,960 B2 | 3/2008 | Bell et al. | |
| 7,345,068 B2 | 3/2008 | Endou et al. | |
| 7,687,526 B2 * | 3/2010 | Brown et al. | 514/359 |
| 2004/0058965 A1 | 3/2004 | Momose et al. | |
| 2005/0089866 A1 | 4/2005 | Hinuma et al. | |
| 2005/0119256 A1 | 6/2005 | Endo et al. | |
| 2006/0003344 A1 | 1/2006 | Houseknecht et al. | |
| 2006/0004012 A1 | 1/2006 | Akerman et al. | |
| 2006/0270724 A1 | 11/2006 | Houze et al. | |
| 2007/0066647 A1 | 3/2007 | Akerman et al. | |
| 2007/0142384 A1 | 6/2007 | Akerman et al. | |

(Continued)

FOREIGN PATENT DOCUMENTS

AU    A 27141/77    1/1979

(Continued)

OTHER PUBLICATIONS

Bachmann, W. E. et al., "The Synthesis of an Analog of the Sex Hormones," *J. Am. Chem. Soc.*, 64, 94-97 (1942).

(Continued)

*Primary Examiner* — Yong Chu
(74) *Attorney, Agent, or Firm* — Bernard P. Friedrichsen

(57) ABSTRACT

The present invention provides compounds useful, for example, for treating metabolic disorders in a subject. Such compounds have the general formula I:

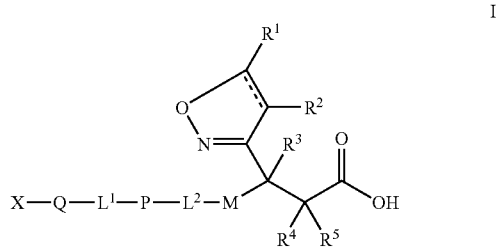

where the definitions of the variables are provided herein. The present invention also provides compositions that include, and methods for using, the compounds in preparing medicaments and for treating metabolic disorders such as, for example, type II diabetes.

10 Claims, No Drawings

U.S. PATENT DOCUMENTS

| | | | |
|---|---|---|---|
| 2007/0244155 A1 | 10/2007 | Sharma et al. | |
| 2007/0265332 A1 | 11/2007 | Ge et al. | |
| 2008/0090840 A1 | 4/2008 | Beck et al. | |
| 2008/0119511 A1 | 5/2008 | Brown et al. | |
| 2010/0075974 A1* | 3/2010 | Beck et al. | 514/250 |

FOREIGN PATENT DOCUMENTS

| | | |
|---|---|---|
| AU | A 52306/93 | 6/1994 |
| CA | 2111035 | 6/1994 |
| DE | 199 41 567 A1 | 4/2000 |
| EP | 0 250 264 A1 | 12/1987 |
| EP | 0 414 289 B1 | 2/1994 |
| EP | 1 357 115 A1 | 10/2003 |
| EP | 1 380 562 A1 | 1/2004 |
| EP | 1 535 915 A1 | 6/2005 |
| EP | 1 559 422 A1 | 8/2005 |
| EP | 1 630 152 A1 | 3/2006 |
| JP | 10316641 A | 2/1998 |
| JP | 2001242165 | 9/2001 |
| JP | 2002003368 | 1/2002 |
| WO | WO 93/23040 | 11/1993 |
| WO | WO 93/23041 | 11/1993 |
| WO | WO 95/01326 | 1/1995 |
| WO | WO 95/01348 | 1/1995 |
| WO | WO 97/12867 | 4/1997 |
| WO | WO 99/11255 | 3/1999 |
| WO | WO 00/63196 | 10/2000 |
| WO | WO 01/00603 A1 | 1/2001 |
| WO | WO 01/36351 A2 | 5/2001 |
| WO | WO 01/36365 A2 | 5/2001 |
| WO | WO 02/057783 A2 | 7/2002 |
| WO | WO 02/062774 A1 | 8/2002 |
| WO | WO 02/100403 A1 | 12/2002 |
| WO | WO 03/074050 A1 | 9/2003 |
| WO | WO 03/099793 A1 | 12/2003 |
| WO | WO 04/000315 A1 | 12/2003 |
| WO | WO 2004/092117 A1 | 10/2004 |
| WO | WO 2004/106276 A1 | 12/2004 |
| WO | WO 2005/051890 A1 | 6/2005 |
| WO | WO 2005/058848 A1 | 6/2005 |
| WO | WO 2005/063725 A1 | 7/2005 |
| WO | WO 2005/063729 A1 | 7/2005 |
| WO | WO 2005/086661 A2 | 9/2005 |
| WO | WO 2005/087710 A1 | 9/2005 |
| WO | WO 2006/001092 A1 | 1/2006 |
| WO | WO 2006/011615 A1 | 2/2006 |
| WO | WO 2006/083612 A1 | 8/2006 |
| WO | WO 2006/083781 A1 | 8/2006 |
| WO | WO 2007/123225 A1 | 11/2007 |
| WO | WO 2007/131619 A1 | 11/2007 |
| WO | WO 2007/131620 A1 | 11/2007 |
| WO | WO 2007/131622 A1 | 11/2007 |

OTHER PUBLICATIONS

Berthelot et al., "Synthesis and Pharmacological Evaluation of γ-Aminobutyric Acid Analogues. New Ligand for GABAa Sites," *J. Med. Chem.*, 30, 743-746 (1987).

Booth, C. J. et al., "The Synthesis and Transition Temperatures of Novel Low Molar Mass Chosesteric materials Derives from (R)-2-(4-Hydroxyphenoxy)propanoic Acid," Mol. Cryst. Liq. Cryst., vol. 210, pp. 31-57 (1992).

Booth, C. J. et al., "The Influence of the Liquid Crystalline Core Geometry on the Mesogenicity of Novel Chiral 2-(4-Substituted-phenoxy)propanonitriles," Liquid Crystals, vol. 16(6), pp. 925-940, (1994).

Boyle, Thomas F. et al., "Applications of the Spiroannulation of Tetralins with Alkynes; Towards New Anti-Estrogenic Compounds," *J. Chem. Soc. Perkin Trans. I: Organic and Bioorganic Chem.*, 18, 2707-2711 (1997).

Briscoe et al., "The Orphan G Protein-Coupled Receptor GPR40 is Activated by Medium and Long Chain Fatty Acids," *J. of Biol. Chem.*, 278(13), 11303-11311 (2003).

Briscoe, C. P. et al., "Pharmacological Regulation of Insulin Secretion in MIN6 Cells Through the Fatty Acid Receptor GPR40: Identification of Agonist and Antagonist Small Molecules," *Brit. J. of Pharmacology*, 148, 619-628 (2006).

Burnop, V.C.E. et al., "Fused Carbon Rings. Part XIX. Experiments on the Synthesis of Tetracyclic Compounds of the Sexual Hormonal Type," *J. Chem. Soc.*, 727-735 (1940).

Chatterjee, A., et al., "Studies on Nucleophilic Ring Opening of Some Epoxides in Polar Protic Solvents," *Tetrahedron*, 33, 85-94 (1977).

Collins, David J. et al., "The Structure and Function of Oestrogens. IX. Synthesis of the trans Isomer of 5,5,10b-Trimtehyl-4b,5,6,10b,11,12-hexahydrocvhrysene-2,8-diol," *Aust. J. Chem.*, 41, 735-744 (1988).

Deb, Soumitra et al., "A Stereocontrolled Synthesis of (1'RS,2'SR)-3-oxo-3',4'-dihydrospiro[cyclopentane-1,1'(2'H)-naphthalen]-2-yl Acetic Acid and its Methoxy Derivatives," *J. Chem. Res. Synops.*, 12, 406 (1985).

DeWolf et al., "Inactivation of Dopamine β-Hydroxylase by β-Ethynyltyramine: Kinetic Characterization and Covalent Modification of an Active Site Peptide," *Biochemistry*, 28, 3833-3842 (1989).

Egan, R. W. et al., "Naphthalenes as Inhibitors of Myeloperoxidase: Direct and Indirect Mechanisms of Inhibition," *Agents and Actions*, 29 3/4 266-276 (1990).

Frey et al., "Total Synthesis of Pentacyclic Diterpenoid Tropone Hainanolidol," *Aust. J. Chem.*, 53, 819-830 (2000).

Galemmo et al., "The Development of a Novel Series of (Quinolin-2-ylmethoxy) phenyl-Containing Compounds as High-Affinity Leukotriene Receptor Antagonists. 3. Structural Variation of the Acidic Side Chain to Give Antagonists of Enhanced Potency," *J. Med. Chem.*, 33, 2828-2841 (1990).

Garrido, D. M., et al., "Synthesis and Activity of Small Molecule GPR40 Agonists," *Bioorg. and Med. Chem. Lett.*, 16, 1840-1845 (2006).

Ghosal, Probir Kumar, et al., "Stereospecific Synthesis of 9bβ-Carbomethoxy-7-methoxy-2,3,3aα,4,5,9bβ-Hexahydro-1H-Benz[e]-Inden-2-one; An Intermediate Towards Physiologically Active Compounds," *Tet. Lett.*, 17, 1463-1464 (1977).

Guthrie, R. W. et al., "Synthesis in the Series of Diterpene Alkaloids VI. A Simple Synthesis of Atisine," *Tet. Lett.*, 38, 4645-4654 (1966).

Haigh et al., "Non-thiazolidinedione Antihyperglycaemic Agents. Part 3: The Effects of Stereochemistry on the Potency of α-Methoxy-β-phenylpropanoic Acids," *Bioorg. and Med. Chem.*, 7, 821-830 (1999).

Hares, Owen et al., "Sythetic Studies of Tricyclospirodienones: Model Chemistry for Novel Mimics of Steroid Substrates," *J. Chem. Soc. Perkin Trans. I: Organic and Bioorganic Chem.*, 13, 1481-1492 (1993).

Houze, J. et al., "Beta-substituted Carboxylic Acids as Potent, Bioavailable Agonists of GPR40", 234th ACS National Meeting Boston, MA Aug. 19-23, 2007.

Iizuka et al., "β-Substituted Phenethylamines as High Affinity Mechanism-Based Inhibitors of Dopamine β-Hydroxylase," *J. Med. Chem.*, 31, 704-706 (1988).

Ishikawa et al., "Actions of the Novel Oral Antidiabetic Agent HQL-975 in Insulin-Resistant Non-Insulin—Dependent Diabetes Mellitus Model Animals," *Diabetes Res. and Clin. Pract.*, 41, 101-111 (1998).

Ishikawa et al., "Effects of the Novel Oral Antidiabetic Agent HQL-975 on Glucose and Lipid Metabolism in Diabetic db/db Mice," *Arzneim. Forsch. Drug Res.*, 48(3), 245-250 (1998).

Itoh et al., "Free Fatty Acids Regulate Insulin Secretion from Pancreatic β Cells Through GPR40," *Nature*, 422, 173-176 (2003).

Johns, William F. et al., "Total Synthesis of Estrajervatetraene," *J. Org. Chem.*, 44(6), 958-961 (1979).

Kao et al., "One-Pot Synthesis of the Hydroximoyl Chlorides and [3.3.0] Bicyclic Compounds from the Reactions of β-Nitrostyrenese with Stabilized Nucleophiles," Tetrahedron, 54(46), 13997-14014 (1998).

Kolasa et al., "Symmetrical Bis (heteroarylmethoxyphenyl) alkylcarboxylic Acids as Inhibitors of Leukotriene Biosynthesis," *J. Med. Chem.*, 43, 3322-3334 (2000).

Kotarsky et al., "A Human Cell Surface Receptor Activated by Free Fatty Acids and Thiazolidinedione Drugs", *Biochem. and Biophys. Res. Comm.*, 301, 406-410 (2003).

Kuchar et al., "Benzyloxyarylaliphatic Acids: Synthesis and Quantitative Relations Between Structure and Antiinflammatory Activity," *Collection Czechoslovak Chem, Comm.*, 47, 2514-2524 (1982).

Kuchar et al., "The Effects of Lopophilicity on the Inhibition of Denaturation of Serum Albumin and on the Activation of Fibrionolysis Observed with a Serixes of Benzyloxyarylaliphatic Acids," *Collection Czechoslovak Chem, Comm.*, 48, 1077-1088 (1983).

Lin, Llnus S. et al., "The Discovery of Acylated β-Amino Acids as Potent and Orally Bioavailable VLA-4 Antagonists," *Bioorg. and Med. Chem. Lett.*, 12, 611-614 (2002).

Liu et al., "Synthesis and Biological Activity of L-Tyrosine-based PPAR$_\gamma$ Agonists with Reduced Molecular Weight," *Bioorg. and Med. Chem. Lett.*, 11, 3111-3113 (2001).

McKeown, S.C. et al., "Solid Phase Synthesis and SAR of Small Molecule Agonists for the GPR40 Receptor," Bioorg. and Med. Chem. Lett., 17, pp. 1584-1589 (2007).

Nilsson, N. E. et al., "Identification of a Free Fatty Acid Receptor, FFA$_2$R, Expressed on Leukocytes and Activated by Short-Chain Fatty Acids," *Biochem. and Biophys. Res. Comm.*, 303 1047-1052 (2003).

Oliver et al., "A Selective Peroxisome Proliferator-Activated Receptor δ Agonist Promotes Reverse Cholesterol Transport," *PNAS*, 98(9), 5306-5311 (2001).

Poitout, Vincent, "The Ins and Outs of Fatty Acids on the Pancreatic β Cells," *Trends in Endocrinology and Metabolism*, 14(5), 201-203 (2003).

Ray, Chhanda et al., "Synthesis of some angularly cyclopentanone fused hydrophenanthrene and hydrofluorene derivatives by acid-catalyzed intramolecular C-alkylation of γ, δ-unsaturated α'-diazomethyl ketones," *Synthetic Commun.*, 21(10-11), 1223-1242 (1991).

Sandberg, Rune et al., "N-Aminoalkylsuccinimides as Local Anaesthetics," *Acta Pharmaceutica Suecica*, 17(4) 169-176 (1980).

Sanyal, Utpal et al., "A Novel Synthesis of a Tricyclo $(7.5.0^{1,5}.0^{1,9})$ Tetradecane Ring System Related to Gascardic Acid," *Tet. Lett.*, 25, 2187-2190 (1978).

Sarma, Aluru Sudarsana et al., "Synthetic Studies on Terpenoids. Parts XVIII. Stereocontrolled Synthesis of (+/−)-1,2,3,4,4a,9,10,10aα-Octahydro-1α-methylenephenanthrene-1β,4aβ-dicarboxylic acid and the 7-Methoxy Analog: A Potential Intermediate for Diterpinoid Synthesis," *J. Chem. Soc. Perkin Trans. I: Organic and Bioorganic Chem.*, 7, 722-727 (1976).

Sawzdargo et al., "A Cluster of Four Novel Human G Protein-Coupled Receptor Genes Occurring in Close Proximity to CD22 Gene on Chromosome 19q13.1", *Biochem. and Biophys. Res. Comm.*, 239, 543-547 (1997).

Shaw et al., "Enantioselective Synthesis of (+)-(2S, 3S)-3-Ethyltyrosine," *Tet. Lett.*, 31(35), 5081-84 (1990).

Shiotani, Shunsaku et al., "Synthesis of 1,3-Bridged 1,2,3,4,5,6-Hexahydro-2,6-methano-3-benzazocine Derivatives," *Chem. Pharm. Bull.*, 28(6), 1928-1931 (1980).

Song, F. et al., "Synthesis and Biological Evaluation of 3-Aryl-3-(4-phenoxy)-propionic Acid as a Novel Series of G Protein-Coupled REceptor 40 Agonists," J. Med. Chem. 50 pp. 2807-2817 (2007).

Vippagunta, S. R. et al., "Crystalline Solids," Adv. Drug Del. Rev., 48 pp. 3-26 (2001).

Waid et al., "Constrained Amino Acids. An Approach to the Synthesis of 3-Substituted Prolines," *Tet. Lett.*, 37(24), 4091-4094 (1996).

Wu, K__M. et al., "Regulatory Perspectives of Type II Prodrug Development and Time-Dependent Toxicity Management: Nonclinical Pharm/Tox Analysis and the Role of Comparative Toxicology," Toxicology, 236 pp. 1-6, (2007).

PCT/US2007/019454 International Search Report and Written Opinion WO 2008/030520) mailed on Jan. 28, 2008.

U.S. Appl. No. 11/067,377 Office Action dated Oct. 2, 2008.

U.S. Appl. No. 11/067,377 Response, to Office Action, Filed Oct. 16, 2008.

U.S. Appl. No. 11/900,014 Office Action dated Jul. 17, 2009.

U.S. Appl. No. 11/900,014 Response to Office Action Filed Aug. 6, 2009.

U.S. Appl. No. 11/900,006 Selected Excerpts from Prosecution History of Parent Patent Application.

Examiner STN Search from U.S. Appl. No. 11/900,006, performed on Apr. 29, 2009.

English Language Abstract of DE 199 41567 A1, Apr. 20, 2000.
English Language Abstract of JP 10,316,641 A, Feb. 12, 1998.
English Language Abstract of JP 2001242165, Sep. 7, 2001.
English Language Abstract of JP 2002003368, Jan. 9, 2002.

* cited by examiner

HETEROCYCLIC GPR40 MODULATORS

1. CROSS REFERENCES TO RELATED APPLICATIONS

This application is a divisional of, and claims priority to, U.S. patent application Ser. No. 11/900,006, filed on Sep. 6, 2007, now U.S. Pat. No. 7,714,008, which claims the benefit of U.S. Provisional Application No. 60/843,262, filed on Sep. 7, 2006, U.S. Provisional Application No. 60/857,665, filed on Nov. 7, 2006, and U.S. Provisional Application No. 60/923,437, filed on Apr. 13, 2007, which are each hereby incorporated by reference in their entireties and for all purposes as if fully set forth herein.

2. FIELD OF THE INVENTION

The present invention relates to compounds capable of modulating the G-protein-coupled receptor GPR40, compositions comprising the compounds, and methods for their use for controlling insulin levels in vivo and for the treatment of conditions such as type II diabetes, hypertension, ketoacidosis, obesity, glucose intolerance, and hypercholesterolemia and related disorders associated with abnormally high or low plasma lipoprotein, triglyceride or glucose levels.

3. BACKGROUND OF THE INVENTION

The production of insulin is central to the regulation of carbohydrate and lipid metabolism. Insulin imbalances lead to conditions such as type II diabetes mellitus, a serious metabolic disease that afflicts around 5% of the population in Western Societies and over 150 million people worldwide. Insulin is secreted from pancreatic β cells in response to elevated plasma glucose which is augmented by the presence of fatty acids. The recent recognition of the function of the G-protein coupled receptor GPR40 in modulating insulin secretion has provided insight into regulation of carbohydrate and lipid metabolism in vertebrates, and further provided targets for the development of therapeutic agents for disorders such as obesity, diabetes, cardiovascular disease and dyslipidemia.

GPR40 is a member of the gene superfamily of G-protein coupled receptors ("GPCRs"). GPCRs are membrane proteins characterized as having seven putative transmembrane domains that respond to a variety of molecules by activating intra-cellular signaling pathways critical to a diversity of physiological functions. GPR40 was first identified as an orphan receptor (i.e., a receptor without a known ligand) from a human genomic DNA fragment. Sawzdargo et al. (1997) Biochem. Biophys. Res. Comm un. 239: 543-547. GPR40 is highly expressed in pancreatic β cells and insulin-secreting cell lines. GPR40 activation is linked to modulation of the $G_q$ family of intra-cellular signaling proteins and concomitant induction of elevated calcium levels. It has been recognized that fatty acids serve as ligands for GPR40, and that fatty acids regulate insulin secretion through GPR40. Itoh et al. (2003) Nature 422:173-176; Briscoe et al. (2003) J. Biol. Chem. 278: 11303-11311; Kotarsky et al. (2003) Biochem. Biophys. Res. Commun. 301: 406-410.

Various documents have disclosed compounds reportedly having activity with respect to GPR40. For example, WO 2004/041266 and EP 1559422 disclose compounds that purportedly act as GPR40 receptor function regulators. WO 2004/106276 and EP 1630152 are directed to condensed ring compounds that purportedly possess GPR40 receptor function modulating action. More recently, WO 2005/086661, U.S. Patent Publication No. 2006/0004012, US Patent Publication No. 2006/0270724, and US Patent Publication No. 2007/0066647 disclose compounds useful for modulating insulin levels in subjects and useful for treating type II diabetes.

Although a number of compounds have been disclosed that reportedly modulate GPR40 activity, the prevalence of type II diabetes, obesity, hypertension, cardiovascular disease and dyslipidemia underscores the need for new therapies to effectively treat or prevent these conditions.

4. SUMMARY OF THE INVENTION

Provided herein are compounds, pharmaceutical compositions, and methods useful for treating or preventing a condition or disorder such as type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer or edema.

In one aspect, the present invention provides a compound having the formula I or a pharmaceutically acceptable salt, solvate, stereoisomer, or prodrug thereof; or a tautomer or a pharmaceutically acceptable salt, solvate, stereoisomer, or prodrug thereof; or a mixture thereof:

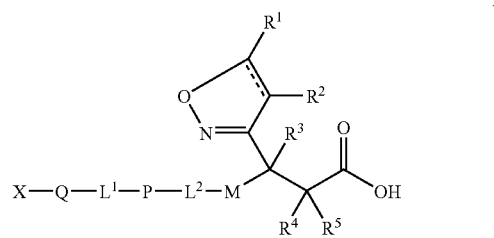

I where X, Q, $L^1$, P, $L^2$, M, $R^1$, $R^2$, $R^3$, $R^4$ and $R^5$ are defined below, and the dashed line indicates that there is a single or double bond between the carbon atom bearing the $R^1$ substituent and the carbon atom bearing the $R^2$ substituent.

X is absent or is selected from H, ($C_1$-$C_6$)alkyl, Cl, Br, F, I, CN, $NO_2$, perfluoro($C_1$-$C_4$)alkyl, ($C_1$-$C_6$)alkoxy, perfluoro ($C_1$-$C_4$)alkoxy, or an optionally substituted aryl($C_1$-$C_4$) alkoxy.

Q is an optionally substituted aromatic ring, an optionally substituted heteroaromatic ring, ($C_1$-$C_6$)alkyl, ($C_2$-$C_6$)heteroalkyl, H, Cl, Br, F, I, CN, $NO_2$, perfluoro($C_1$-$C_4$)alkyl, ($C_1$-$C_6$)alkoxy, or perfluoro($C_1$-$C_4$)alkoxy.

$L^1$ is a bond, ($C_1$-$C_4$)alkylene, ($C_2$-$C_4$)heteroalkylene, O, S(O)$_k$, N($R^a$), C(O)—($C_5$-$C_7$)heterocycloalkylene, ($C_1$-$C_4$) alkylene-$SO_2$N($R^b$), ($C_1$-$C_4$)alkylene-N($R^b$)$SO_2$, or C(O)N ($R^b$).

P is an optionally substituted aromatic ring or an optionally substituted heteroaromatic ring.

$L^2$ is a bond, ($C_1$-$C_6$)alkylene, ($C_2$-$C_6$)heteroalkylene, oxymethylene, O, S(O)$_k$, N($R^a$), C(O)N($R^b$), $SO_2$N($R^b$), ($C_1$-$C_4$)alkylene-C(O)N($R^b$), ($C_1$-$C_4$)alkylene-N($R^b$)C(O), ($C_2$-$C_4$)alkenylene-C(O)N($R^b$), ($C_2$-$C_4$)alkenylene-N($R^b$)C(O), ($C_1$-$C_4$)alkylene-$SO_2$N($R^b$), ($C_1$-$C_4$)alkylene-N($R^b$)$SO_2$, ($C_2$-$C_4$)alkenylene-$SO_2$N($R^b$), or ($C_2$-$C_4$)alkenylene-N($R^b$) $SO_2$.

M is an optionally substituted aromatic ring or an optionally substituted heteroaromatic ring.

$R^a$ is H, $(C_1-C_6)$alkyl, aryl$(C_1-C_3)$alkyl, or $(C_2-C_6)$heteroalkyl.

$R^b$ is H, $(C_1-C_6)$alkyl, or $(C_2-C_6)$heteroalkyl.

$R^1$, $R^2$, $R^3$, $R^4$, and $R^5$ are independently selected from H, or $(C_1-C_6)$alkyl.

The subscript k is, in each instance, independently selected from 0, 1, or 2.

In another aspect, the present invention provides a compound having the formula I or a pharmaceutically acceptable salt, solvate, stereoisomer, or prodrug thereof; or a tautomer or a pharmaceutically acceptable salt, solvate, stereoisomer, or prodrug thereof; or a mixture thereof where X, Q, $L^1$, P, $L^2$, M, $R^1$, $R^2$, $R^3$, $R^4$ and $R^5$ are defined below, and the dashed line indicates that there is a single or double bond between the carbon atom bearing the $R^1$ substituent and the carbon atom bearing the $R^2$ substituent.

X is absent or is selected from H, $(C_1-C_6)$alkyl, Cl, Br, F, I, CN, $NO_2$, perfluoro$(C_1-C_4)$alkyl, $(C_1-C_6)$alkoxy, perfluoro$(C_1-C_4)$alkoxy, or an optionally substituted aryl$(C_1-C_4)$alkoxy.

Q is an optionally substituted aromatic ring, an optionally substituted heteroaromatic ring, an optionally substituted $(C_4-C_8)$cycloalkyl, an optionally substituted $(C_5-C_8)$cycloalkenyl, an optionally substituted heterocycloalkenyl ring comprising from 5 to 8 ring members, $(C_2-C_6)$alkenyl, $(C_1-C_6)$alkyl, $(C_2-C_6)$heteroalkyl, H, Cl, Br, F, I, CN, $NO_2$, perfluoro$(C_1-C_4)$alkyl, $(C_1-C_6)$alkoxy, or perfluoro$(C_1-C_4)$alkoxy. In some embodiments, Q is an optionally substituted $(C_4-C_8)$cycloalkyl, an optionally substituted $(C_5-C_8)$cycloalkenyl, an optionally substituted heterocycloalkenyl ring comprising from 5 to 8 ring members, or a $(C_2-C_6)$alkenyl.

$L^1$ is a bond, $(C_1-C_4)$alkylene, $(C_2-C_4)$heteroalkylene, O, $S(O)_k$, $N(R^a)$, $C(O)$—$(C_5-C_7)$heterocycloalkylene, $(C_1-C_4)$alkylene-$SO_2N(R^b)$, $(C_1-C_4)$alkylene-$N(R^b)SO_2$, $S(O)_2N(R^b)$, or $C(O)N(R^b)$.

P is an optionally substituted aromatic ring or an optionally substituted heteroaromatic ring.

$L^2$ is a bond, $(C_1-C_6)$alkylene, $(C_2-C_6)$heteroalkylene, oxymethylene, O, $S(O)_k$, $N(R^a)$, $C(O)N(R^b)$, $SO_2N(R^b)$, $(C_1-C_4)$alkylene-$C(O)N(R^b)$, $(C_1-C_4)$alkylene-$N(R^b)C(O)$, $(C_2-C_4)$alkenylene-$C(O)N(R^b)$, $(C_2-C_4)$alkenylene-$N(R^b)C(O)$, $(C_1-C_4)$alkylene-$SO_2N(R^b)$, $(C_1-C_4)$alkylene-$N(R^b)SO_2$, $(C_2-C_4)$alkenylene-$SO_2N(R^b)$, or $(C_2-C_4)$alkenylene-$N(R^b)SO_2$.

M is an optionally substituted aromatic ring or an optionally substituted heteroaromatic ring.

$R^a$ is H, $(C_1-C_6)$alkyl, aryl$(C_1-C_3)$alkyl, or $(C_2-C_6)$heteroalkyl.

$R^b$ is H, $(C_1-C_6)$alkyl, or $(C_2-C_6)$heteroalkyl.

$R^1$, $R^2$, $R^3$, $R^4$, and $R^5$ are independently selected from H, or $(C_1-C_6)$alkyl.

The subscript k is, in each instance, independently selected from 0, 1, or 2.

In some embodiments of the compound of formula I, X is absent or is selected from H, $(C_1-C_6)$alkyl, Cl, $CF_3$, $(C_1-C_6)$alkoxy, or an optionally substituted phenylmethoxy group; Q is an optionally substituted aromatic ring; $L^1$ is a bond; and $L^2$ is an oxymethylene.

In some embodiments of the compound of formula I, P is selected from an optionally substituted phenyl, an optionally substituted thiazole, an optionally substituted oxadiazole, an optionally substituted oxazole, an optionally substituted thiophene, an optionally substituted furan, an optionally substituted imidazole, an optionally substituted pyrrole, or an optionally substituted pyrazole.

In some embodiments, the compound of formula I is a compound of formula II or a pharmaceutically acceptable salt, solvate, stereoisomer, or prodrug thereof; or a tautomer or a pharmaceutically acceptable salt, solvate, stereoisomer, or prodrug thereof; or a mixture thereof. The compound of formula II has the following structure:

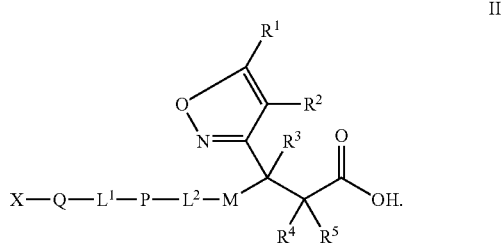

II

In some embodiments, the compound of formula I is a compound of formula III or a pharmaceutically acceptable salt, solvate, stereoisomer, or prodrug thereof; or a tautomer or a pharmaceutically acceptable salt, solvate, stereoisomer, or prodrug thereof; or a mixture thereof. The compound of formula III has the following structure:

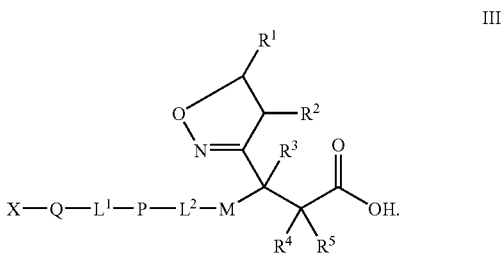

III

In some embodiments, the compound of formula I is a compound of formula IV or a pharmaceutically acceptable salt, solvate, stereoisomer, or prodrug thereof; or a tautomer or a pharmaceutically acceptable salt, solvate, stereoisomer, or prodrug thereof; or a mixture thereof. The compound of formula IV has the following structure:

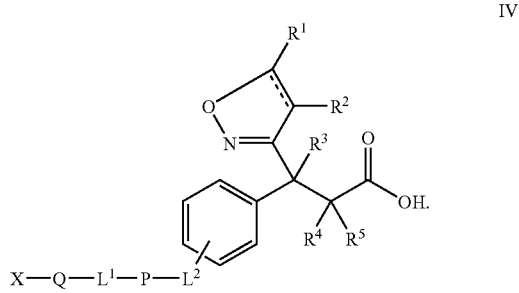

IV

In some such embodiments, the compound has the formula VA or VB or is a pharmaceutically acceptable salt, solvate, stereoisomer, or prodrug thereof; or a tautomer or a pharmaceutically acceptable salt, solvate, stereoisomer, or prodrug thereof; or a mixture thereof VA
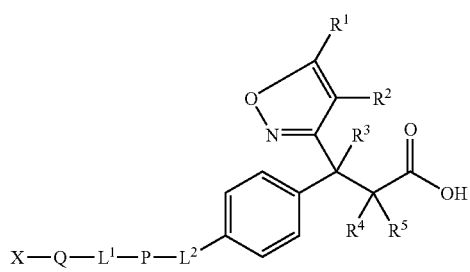

VB
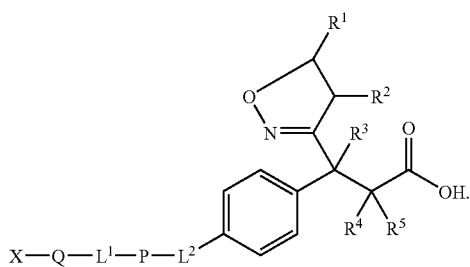

In other such embodiments, the compound has the formula VI or is a pharmaceutically acceptable salt, solvate, stereoisomer, or prodrug thereof; or a tautomer or a pharmaceutically acceptable salt, solvate, stereoisomer, or prodrug thereof; or a mixture thereof VI
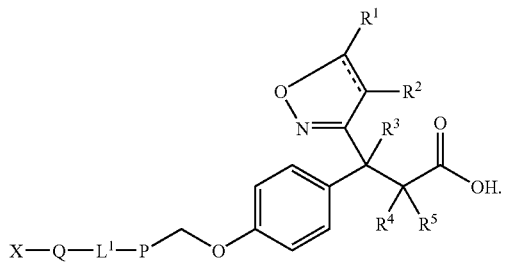

In some embodiments of any of those described above, $X-Q-L^1-P-L^2-M-$ has a formula selected from VIIA
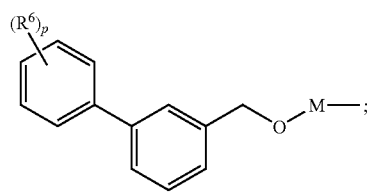

VIIB
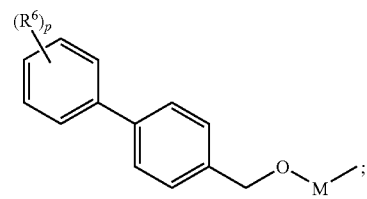

VIIC
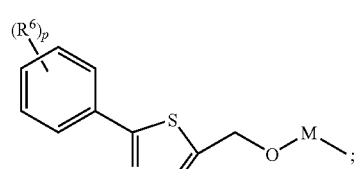

VIID
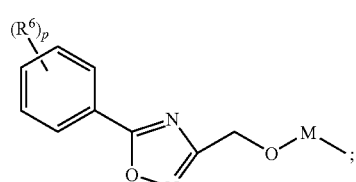

VIIE
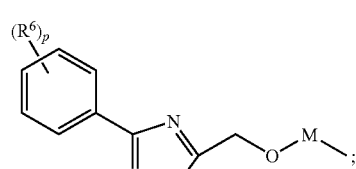

VIIF
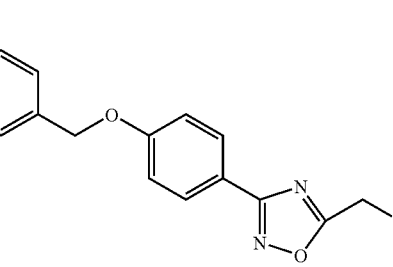

VIIG
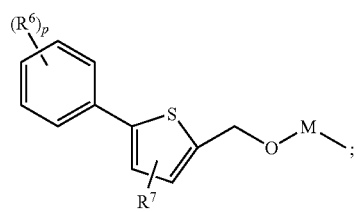

VIIH
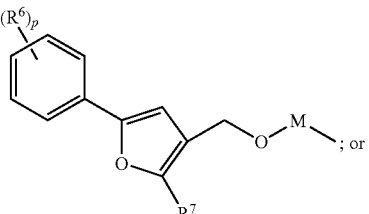

; or

VIIJ
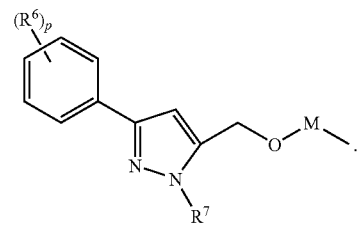

In such embodiments, p is selected from 0, 1, 2, 3, 4, or 5; each $R^6$ is independently selected from $(C_1-C_6)$alkyl, Cl, Br, F, I, CN, $NO_2$, perfluoro$(C_1-C_4)$alkyl, $(C_1-C_6)$alkoxy, or a perfluoro($C_1$-$C_4$)alkoxy and $R^7$ is selected from H or ($C_1$-$C_6$) alkyl. Such compounds include pharmaceutically acceptable salts, solvates, stereoisomers, and prodrugs thereof; and tautomers and pharmaceutically acceptable salts, solvates, stereoisomers, and prodrugs thereof; and mixture thereof. In some such embodiments, $R^7$ is H or methyl. In other such embodiments, p is 0, 1, or 2.

In some embodiments, X-Q-$L^1$-P-$L^2$-M- has a formula selected from

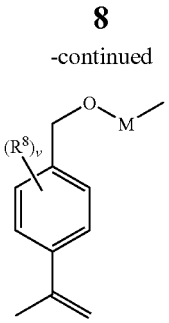

VIIK

VIIL

VIIM

VIIN

VIIO

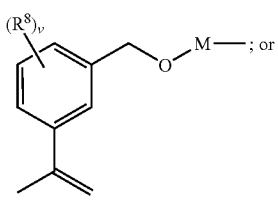

VIIP wherein, v is selected from 0, 1, 2, 3, or 4;

w is selected from 1 or 2;

$R^c$ and $R^d$ are independently selected from H or $C_1$-$C_4$ alkyl; and each $R^8$ is independently selected from ($C_1$-$C_6$)alkyl, Cl, Br, F, I, CN, $NO_2$, perfluoro($C_1$-$C_4$)alkyl, ($C_1$-$C_6$) alkoxy, or perfluoro($C_1$-$C_4$)alkoxy, or a pharmaceutically acceptable salt, solvate, stereoisomer, or prodrug thereof; or a tautomer or a pharmaceutically acceptable salt, solvate, stereoisomer, or prodrug thereof; or a mixture thereof. In some such embodiments, v is 0, 1, or 2. In some such embodiments, w is 1.

In some embodiments of any of those described above, $R^3$, $R^4$, and $R^5$ are all H.

In some embodiments of any of those described above, $R^2$ is H.

In some embodiments of any of those described above, $R^1$ is H or methyl and in some embodiments is H.

In still other embodiments, the compound has the formula IA or IB or is a mixture of these

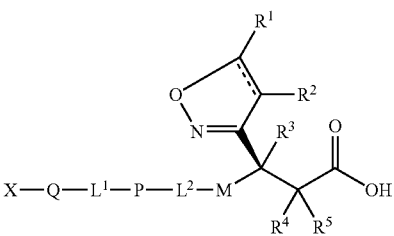

IA

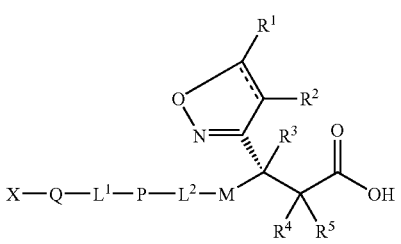

IB or is a pharmaceutically acceptable salt, solvate, or prodrug thereof; or a tautomer or a pharmaceutically acceptable salt, solvate, or prodrug thereof; or a mixture thereof.

In still other embodiments, the compound has the formula IIA or IIB or is a mixture of these

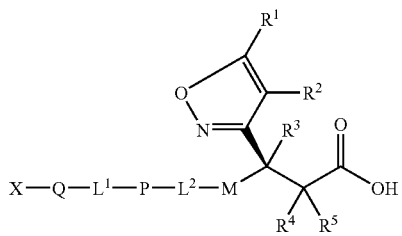

IIA

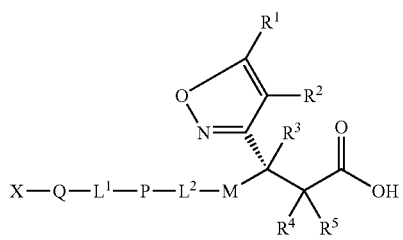

IIB or is a pharmaceutically acceptable salt, solvate, or prodrug thereof; or a tautomer or a pharmaceutically acceptable salt, solvate, or prodrug thereof; or a mixture thereof.

In still other embodiments, the compound has the formula IIIA or IIIB or is a mixture of these

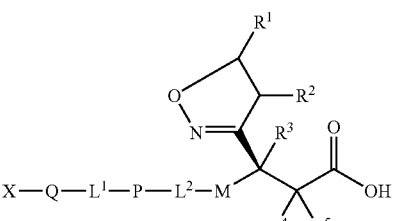

IIIA

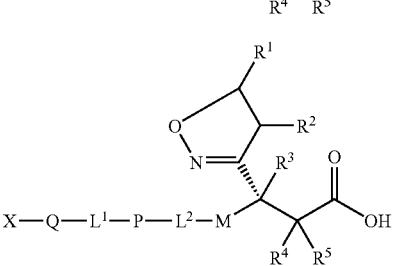

IIIB or is a pharmaceutically acceptable salt, solvate, or prodrug thereof; or a tautomer or a pharmaceutically acceptable salt, solvate, or prodrug thereof; or a mixture thereof.

In some embodiments, the compound is selected from

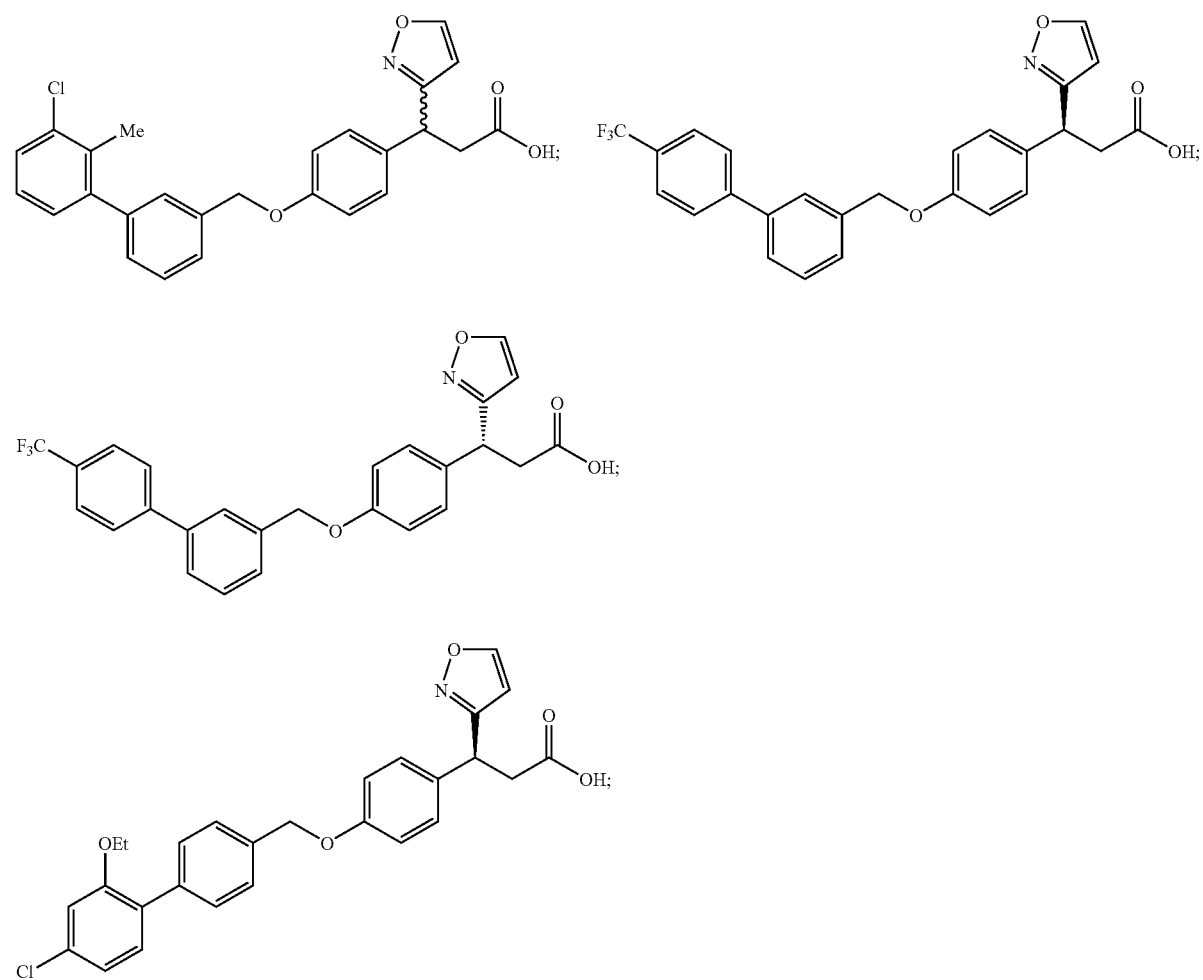

-continued
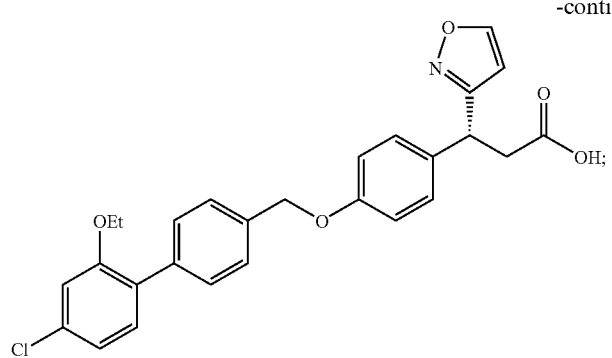
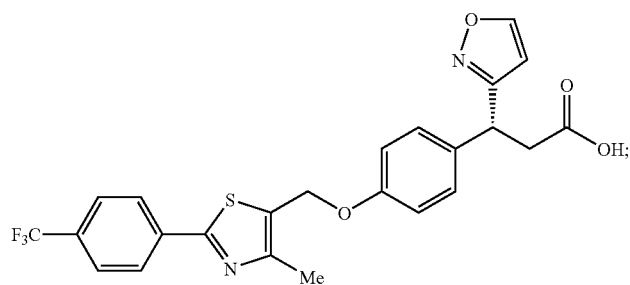
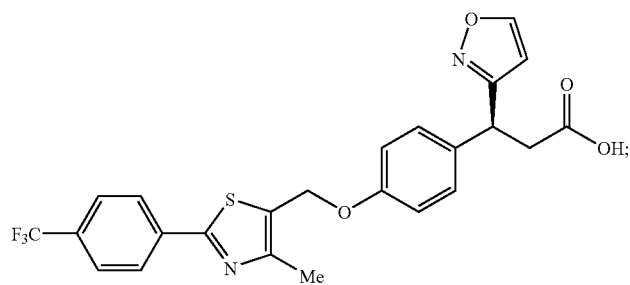
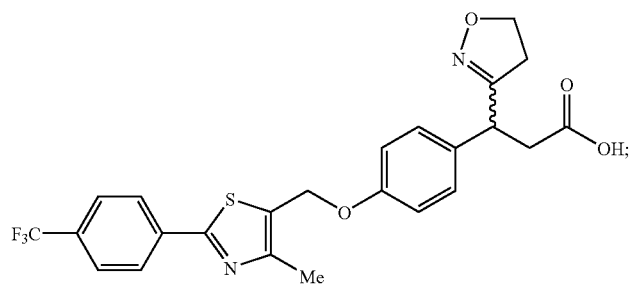
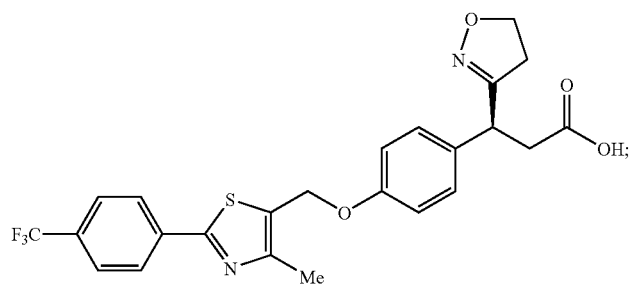

-continued
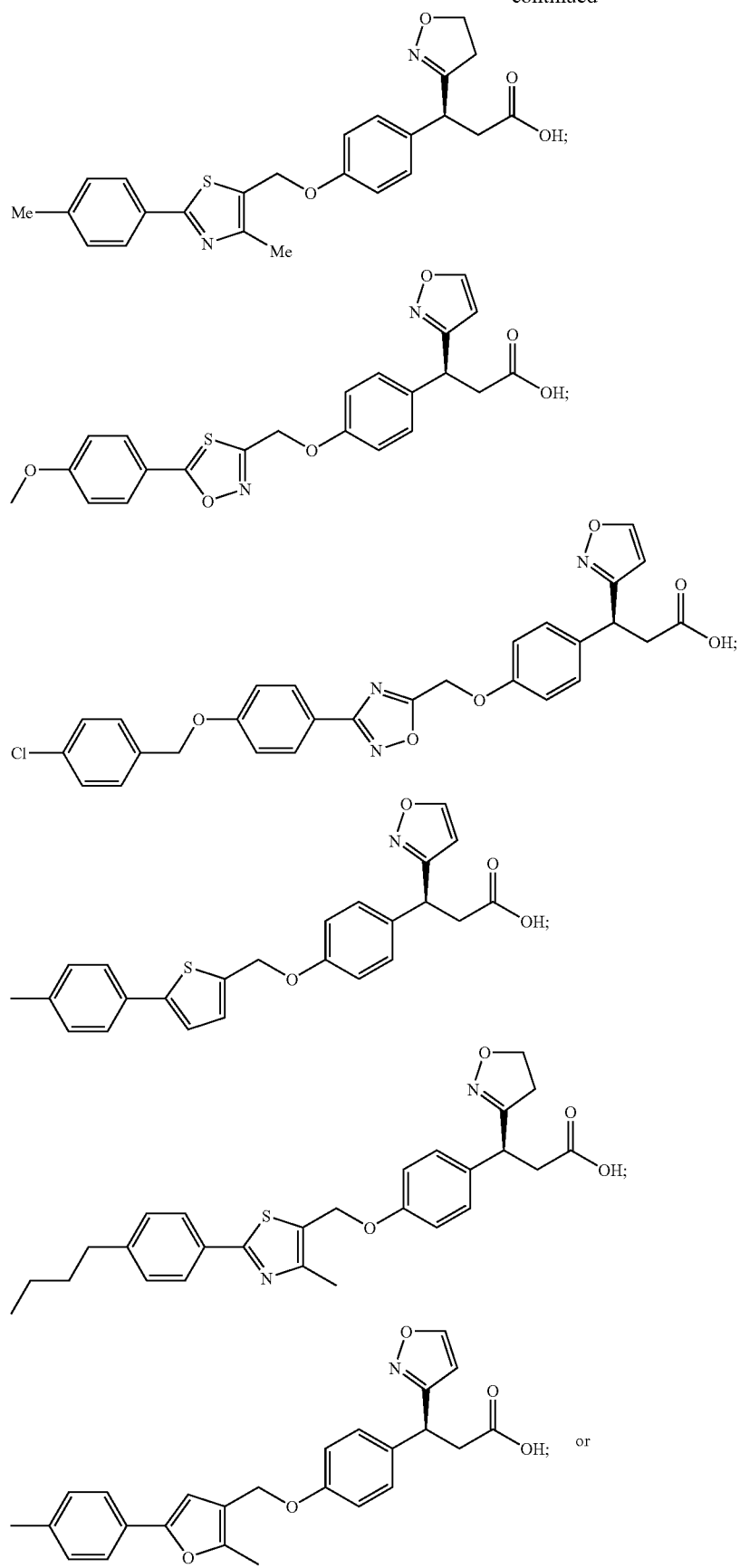

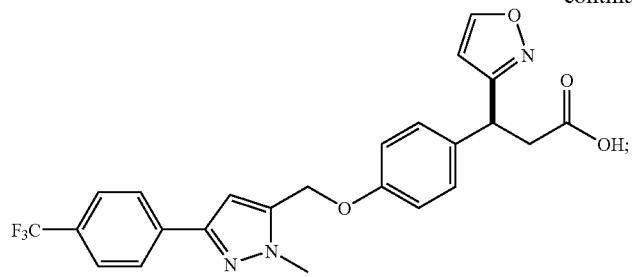
or a pharmaceutically acceptable salt, solvate, or prodrug thereof; or a tautomer or a pharmaceutically acceptable salt, solvate, or prodrug thereof; or a mixture thereof.
In some embodiments, the compound is selected from
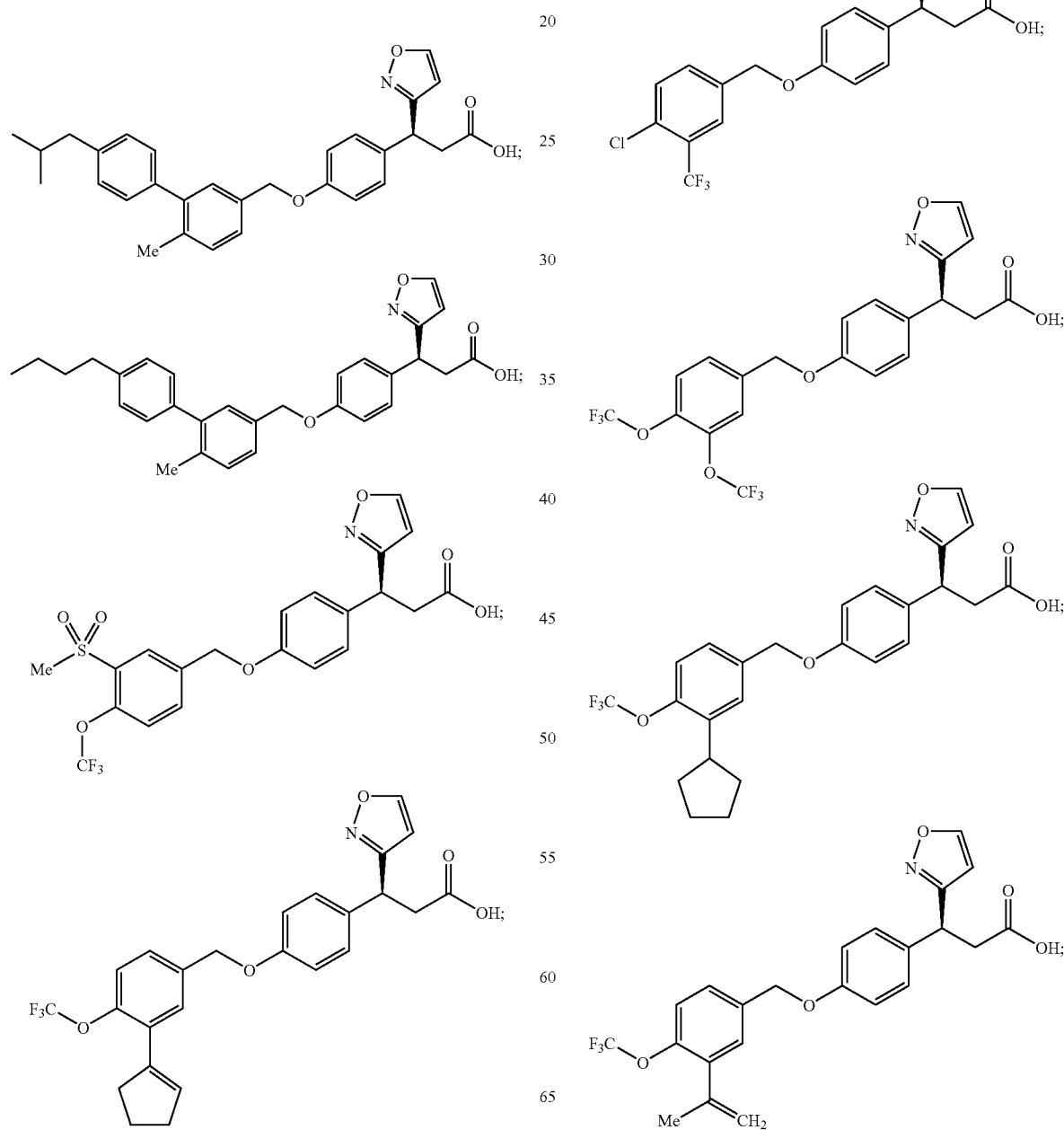

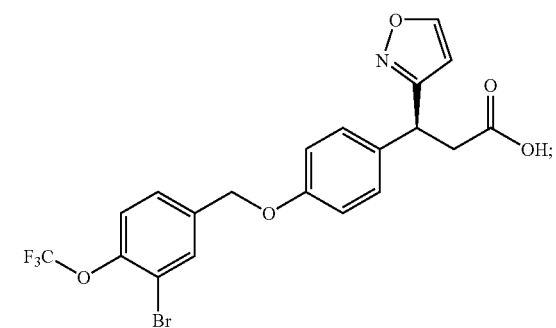
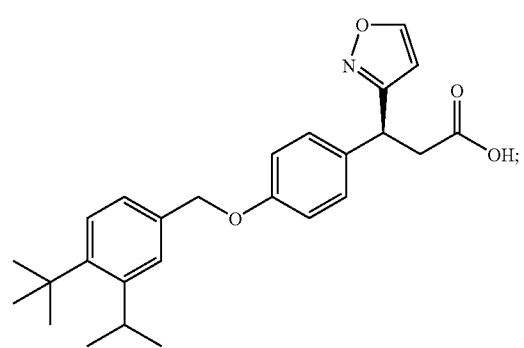
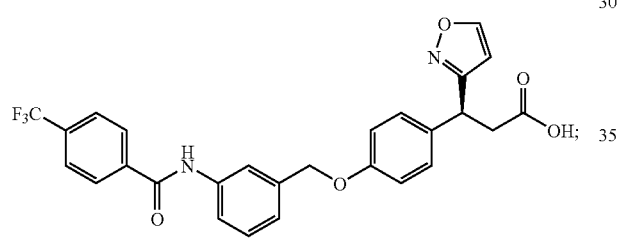
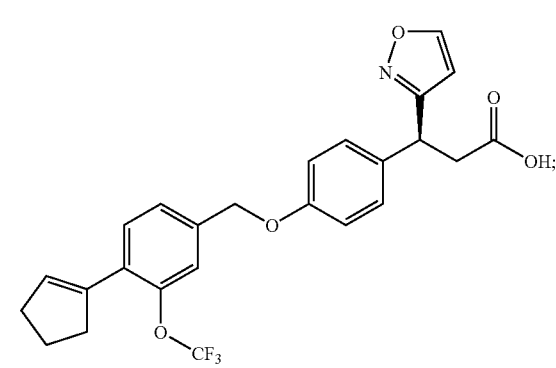
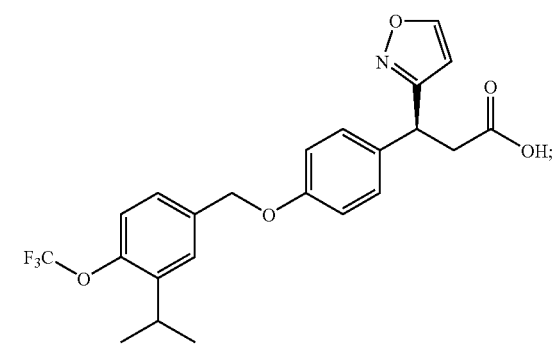
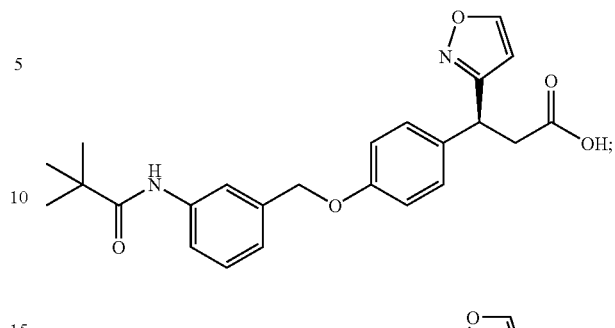
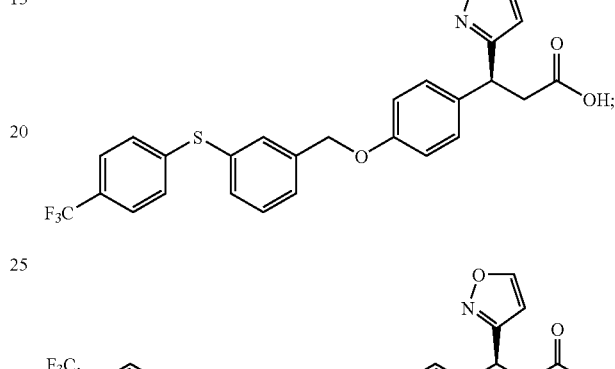
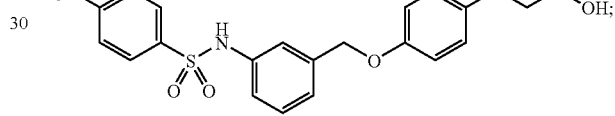
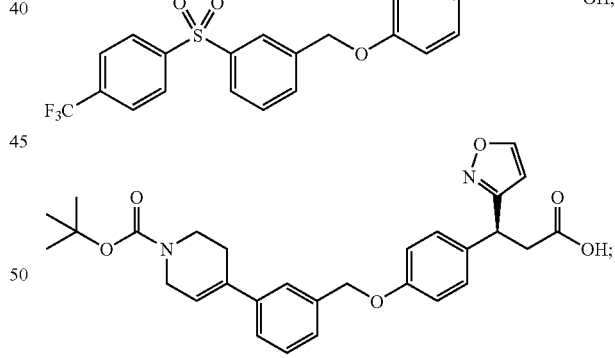
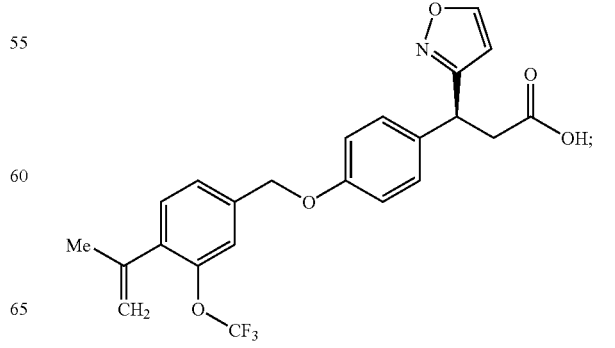

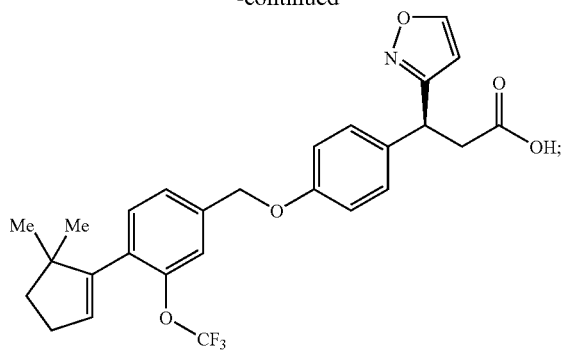

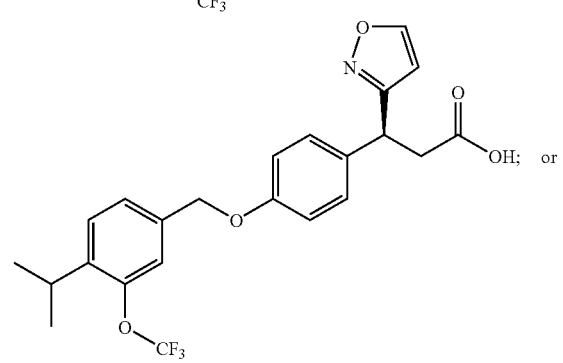

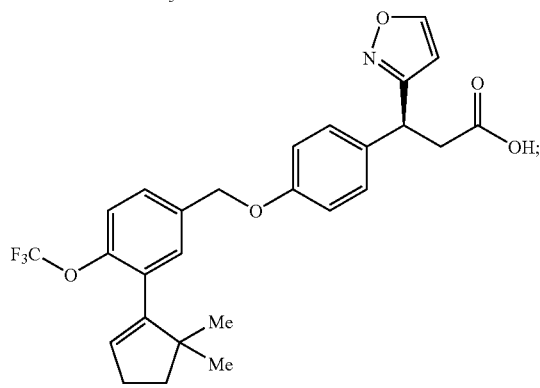

or a pharmaceutically acceptable salt, solvate, or prodrug thereof; or a tautomer or a pharmaceutically acceptable salt, solvate, or prodrug thereof; or a mixture thereof.

In another aspect, the present invention provides a compound having the formula I' or a pharmaceutically acceptable salt, solvate, stereoisomer, or prodrug thereof; or a tautomer or a pharmaceutically acceptable salt, solvate, stereoisomer, or prodrug thereof; or a mixture thereof:

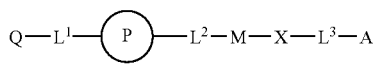

where Q, $L^1$, P, $L^2$, M, X, $L^3$, and A are defined below.

In compounds of formula I', Q is hydrogen, aryl, heteroaryl, $(C_1-C_6)$alkyl, or $(C_2-C_6)$heteroalkyl. In certain embodiments, Q is hydrogen, aryl, or heteroaryl. In certain embodiments, Q is a substituted or unsubstituted phenyl.

In compounds of formula I', $L^1$ is a bond, $(C_1-C_4)$alkylene, $(C_2-C_4)$heteroalkylene, O, $S(O)_k$, $N(R^a)$, C(O)—$(C_5-C_7)$heterocycloalkylene, $(C_1-C_4)$alkylene-$SO_2N(R^b)$, $(C_1-C_4)$alkylene-$N(R^b)SO_2$, or $C(O)N(R^b)$. In certain embodiments, $L^1$ is a bond. In some such embodiments, Q is H.

In compounds of formula I',

represents an optionally substituted benzo-fused $(C_5-C_8)$cycloalkane ring comprising a benzene ring fused to a $(C_5-C_8)$ cycloalkane ring, an optionally substituted heterobenzo-fused $(C_5-C_8)$cycloalkane ring comprising a six-membered heteroaryl ring comprising 1 or 2 N atoms fused to a $(C_5-C_8)$ cycloalkane ring, or a heteroaryl-fused $(C_5-C_8)$cycloalkane ring comprises a five-membered heteroaryl ring comprising 1 or 2 heteroatoms fused to a $(C_5-C_8)$cycloalkane ring, wherein the benzene ring of the benzo-fused $(C_5-C_8)$cycloalkane ring, the heteroaryl ring of the heterobenzo-fused $(C_5-C_8)$cycloalkane ring, or the heteroaryl ring of the heteroaryl-fused $(C_5-C_8)$cycloalkane ring is bonded to $L^2$ or M, if $L^2$ is a bond. In some embodiments,

is a benzo-fused $(C_5-C_8)$cycloalkane ring. In some embodiments,

is a substituted benzo-fused $(C_5-C_8)$cycloalkane ring. In some embodiments,

is an unsubstituted benzo-fused $(C_5-C_8)$cycloalkane ring. In some embodiments,

is a heterobenzo-fused $(C_5-C_8)$cycloalkane ring. In some such embodiments, the heteroaryl ring of the heterobenzo-fused $(C_5-C_8)$cycloalkane ring comprises 1 N atom. In other such embodiments, the heteroaryl ring of the heterobenzo-fused $(C_5-C_8)$cycloalkane ring comprises 2 N atoms. In some embodiments,

is a substituted heterobenzo-fused $(C_5-C_8)$cycloalkane ring.

In some embodiments, (P)

is an unsubstituted heterobenzo-fused $(C_5-C_8)$cycloalkane ring. In some embodiments, (P)

is a heteroaryl-fused $(C_5-C_8)$cycloalkane ring. In some such embodiments, the heteroaryl ring of the heteroaryl-fused $(C_5-C_8)$cycloalkane ring comprises 1 N atom. In some embodiment the heteroaryl ring of the heteroaryl-fused $(C_5-C_8)$cycloalkane ring comprises 1 N atom and either 1 O atom or 1 S atom. In other such embodiments, the heteroaryl ring of the heteroaryl-fused $(C_5-C_8)$cycloalkane ring comprises 2 N atoms. In some embodiments, (P)

is a substituted heteroaryl-fused $(C_5-C_8)$cycloalkane ring. In some embodiments, (P)

is an unsubstituted heteroaryl-fused $(C_5-C_8)$cycloalkane ring. In some embodiments, the $(C_5-C_8)$cycloalkane ring of the benzo-fused $(C_5-C_8)$cycloalkane ring, the heterobenzo-fused $(C_5-C_8)$cycloalkane ring, or the heteroaryl-fused $(C_5-C_8)$cycloalkane ring of (P)

comprises 0-3 heteroatoms selected from O, N, or S. In some such embodiments, the cycloalkane ring comprises 1 or 2 heteroatom ring members selected from O or N, and in some embodiments 1 heteroatom ring member, selected from O or N. In some such embodiments, the cycloalkane comprises 0 heteroatom ring atoms such that each of the cycloalkane ring members of the benzo-fused $(C_5-C_8)$cycloalkane, the heterobenzo-fused $(C_5-C_8)$cycloalkane, or the heteroaryl-fused $(C_5-C_8)$cycloalkane ring is a carbon atom. In some such embodiments, (P)

is selected from the group consisting of dihydroindene (i.e., indane or a benzo-cyclopentyl ring), tetrahydronaphthalene (i.e., benzo-cyclohexyl ring), tetrahydrobenzo[7]annulene (i.e., a benzo-cycloheptyl ring), and hexahydrobenzo[8]annulene (i.e., a benzo-cyclooctyl ring). In some embodiments, (P)

is a heteroaryl-fused $(C_5-C_8)$cycloalkane ring and the heteroaryl of the heteroaryl-fused $(C_5-C_8)$cycloalkane ring is selected from pyrrole, furan, thiophene, imidazole, thiazole, or oxazole.

In compounds of formula I', $L^2$ is a bond, $(C_1-C_6)$alkylene, $(C_2-C_6)$heteroalkylene, oxymethylene, O, $S(O)_k$, $N(R^a)$, $C(O)N(R^b)$, $SO_2N(R^b)$, $(C_1-C_4)$alkylene-$C(O)N(R^b)$, $(C_1-C_4)$alkylene-$N(R^b)C(O)$, $(C_2-C_4)$alkenylene-$C(O)N(R^b)$, $(C_2-C_4)$alkenylene-$N(R^b)C(O)$, $(C_1-C_4)$alkylene-$SO_2N(R^b)$, $(C_1-C_4)$alkylene-$N(R^b)SO_2$, $(C_2-C_4)$alkenylene-$SO_2N(R^b)$, or $(C_2-C_4)$alkenylene-$N(R^b)SO_2$. In some embodiments, $L^2$ is selected from $(C_1-C_6)$alkylene, $(C_2-C_6)$heteroalkylene, oxymethylene, O, or $S(O)_k$. In some embodiments, $L^2$ is selected from —$CH_2$—O—, substituted oxymethylene, or O. In some embodiments, $L^2$ is selected from —$CH_2$—O— or —$CH(CH_3)$—O—. In some embodiments, $L^2$ is selected from —$CH_2$—O— or an alkyl-substituted oxymethylene. In certain embodiments, $L^2$ is O or $S(O)_k$.

In compounds of formula I', M is an aromatic ring, a heteroaromatic ring, $(C_5-C_8)$cycloalkylene, aryl$(C_1-C_4)$alkylene or heteroaryl$(C_1-C_4)$alkylene. In certain embodiments where M is an aromatic ring, the term aromatic includes aryl. In other embodiments where M is a heteroaromatic ring, the term heteroaromatic includes heteroaryl. In some embodiments, M is an aromatic ring or is a heteroaromatic ring. In certain embodiments, M is a monocyclic aromatic or is a monocyclic heteroaromatic ring. In some embodiments, M is an unsubstituted monocyclic aromatic ring or is an unsubstituted monocyclic heteroaromatic ring. In certain embodiments, M is a substituted benzene ring. In other embodiments, M is an unsubstituted benzene ring. In some embodiments, M is a heteroaromatic ring comprising six ring members. In some such embodiments, the heteroaromatic ring comprises 1 or 2 N atoms. In some such embodiments, the heteroaromatic ring comprises 1 N atom, and in other such embodiments, the heteroaromatic ring comprises 2 N atoms.

In compounds of formula I', X is $CR^1R^{1'}$.

In certain embodiments of the compounds of formula I', M is a substituted or unsubstituted benzene ring and X is para to $L^2$.

In compounds of formula I', $L^3$ is a $(C_1-C_5)$alkylene, or $(C_2-C_5)$heteroalkylene. In some embodiments, $L^3$ is a $(C_1-C_5)$alkylene or is a $(C_2-C_5)$heteroalkylene. In certain embodiments, $L^3$ is $(C_1-C_3)$alkylene. In some embodiments, $L^3$ is methylene. In certain embodiments, $L^3$ is a methylene substituted with a monocyclic aryl or monocyclic heteroaryl.

In compounds of formula I', A is —$CO_2H$, tetrazol-5-yl, —$SO_3H$, —$PO_3H_2$, —$SO_2NH_2$, —$C(O)NHSO_2CH_3$, —CHO, thiazolidinedion-yl, hydroxyphenyl, or pyridyl. In some embodiments, A is —$CO_2H$, tetrazol-5-yl, —$SO_3H$, —$PO_3H_2$, —$SO_2NH_2$, —$C(O)NHSO_2CH_3$, thiazolidinedionyl, hydroxyphenyl, or pyridyl In certain embodiments, A is —$CO_2H$ or a salt thereof. In some embodiments, A is —$CO_2H$ or an alkyl ester thereof. In some such embodiments, A is a $C_1-C_6$ alkyl ester such as a methyl, ethyl, propyl, butyl, pentyl, or hexyl ester.

In compounds of formula I', $R^a$ is hydrogen, $(C_1-C_6)$alkyl, aryl$(C_1-C_3)$ alkyl, or $(C_2-C_6)$heteroalkyl. In certain embodiments, $R^a$ is $(C_1-C_6)$alkyl or $(C_2-C_6)$heteroalkyl.

In compounds of formula I', $R^b$ is hydrogen, $(C_1-C_6)$alkyl, or $(C_2-C_6)$heteroalkyl.

In compounds of formula I', R¹ is a group of formula:

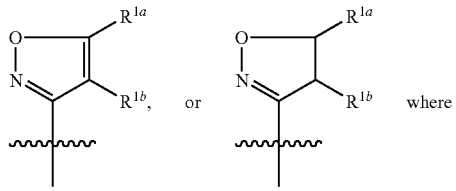

where $R^{1a}$ is selected from H, or $(C_1-C_6)$alkyl, and $R^{1b}$ is selected from H, or $(C_1-C_6)$alkyl. In some embodiments, one or $R^{1a}$ and $R^{1b}$ is H. In other embodiments, both of $R^{1a}$ and $R^{1b}$ are H.

In compounds of formula I', $R^{1'}$ is hydrogen, cyano, aryl, heteroaryl, $(C_1-C_8)$alkyl, $(C_2-C_8)$alkenyl, or $(C_2-C_8)$alkynyl. In some embodiments, $R^{1'}$ is hydrogen or methyl. In some such embodiments, $R^{1'}$ is hydrogen.

In compounds of formula I', the subscript k is, in each instance, independently selected from 0, 1, or 2. In some embodiments, k is 0.

In certain embodiments, the compound of the present invention is a pharmaceutically acceptable salt, solvate, stereoisomer, or prodrug of the compound of formula I'; or a tautomer, or a pharmaceutically acceptable salt, solvate, stereoisomer, or prodrug of the tautomer; or a mixture thereof.

In certain embodiments, the present invention provides a compound having the formula II' or a pharmaceutically acceptable salt, solvate, stereoisomer, or prodrug thereof; or a tautomer, or a pharmaceutically acceptable salt, solvate, stereoisomer, or prodrug thereof; or a mixture thereof:

II' where Q is selected from hydrogen, aryl, or heteroaryl; $L^2$ is selected from $(C_1-C_6)$alkylene, $(C_2-C_6)$heteroalkylene, oxymethylene, O, or $S(O)_k$; $R^1$ is a group having the formula described above with respect to the compound of formula I'; $R^4$ is independently selected from substituted $(C_1-C_6)$alkyl, —R', —OR', =O, =NR', =N—OR', —NR'R", —SR', halogen, —OC(O)R', —C(O)R', —CO₂R', —CONR'R'", —OC(O)NR'R", —NR"C(O)R', —NR'—C(O)NR"R'", —NR'—SO₂NR"R'", —NR"CO₂R', —NH—C(NH₂)=NH, —NR'C(NH₂)=NH, —NH—C(NH₂)=NR', —SiR'R"R'", —S(O)R', —SO₂R', —SO₂NR'R", —NR"SO₂R, —CN, —(C₂-C₅)alkynyl, —(C₂-C₅) alkenyl, or —NO₂, where R', R" and R'" each independently refer to hydrogen, unsubstituted $(C_1-C_8)$ alkyl or heteroalkyl, unsubstituted aryl, aryl substituted with one to three halogens, unsubstituted alkyl, alkoxy or thioalkoxy groups, halo$(C_1-C_4)$alkyl, or aryl-$(C_1-C_4)$alkyl groups; $R^5$ is independently selected from $(C_1-C_6)$alkyl, halogen, $(C_1-C_6)$alkoxy, cyano, or nitro; the subscript k is 0, 1 or 2; the subscript n is 0, 1, 2, 3, 4, 5, 6, 7, 8, 9, 10, 11, 12, 13, or 14; and the subscript p is 0, 1, 2, 3, or 4. In some such embodiments, $R^4$ is independently selected from $(C_1-C_6)$ alkyl, halogen, $(C_1-C_6)$alkoxy, cyano, or nitro. In certain embodiments,

is a benzo-fused $(C_5-C_8)$cycloalkane ring selected from substituted or unsubstituted dihydroindene, tetrahydronaphthalene, tetrahydrobenzo[7]annulene, or hexahydrobenzo[8]annulene. In some embodiments, the subscript p is 0.

It will be apparent that, in certain embodiments of formula II', the carbon with a bond to $R^1$ is a chiral carbon. Thus, in certain embodiments, the present invention provides a compound having formula IIIA' or IIIB' or a pharmaceutically acceptable salt, solvate, or prodrug thereof; or a tautomer, or a pharmaceutically acceptable salt, solvate, or prodrug thereof; or a mixture thereof:

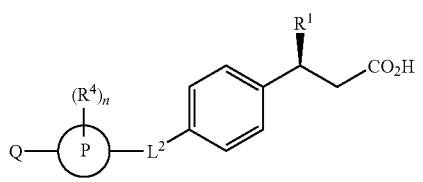

IIIA'

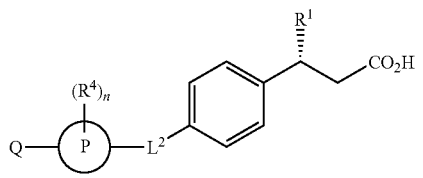

IIIB' where the variables can have any of the values in any of the embodiments described above.

In some embodiments, the compound of formula II' comprises a stereomerically pure S-enantiomer. In other embodiments, the compound of formula II' comprises a stereomerically pure R-enantiomer. In yet other embodiments, the compound of formula II' comprises a mixture of S- and R-enantiomers.

In certain embodiments, the compound of the present invention is a pharmaceutically acceptable salt, solvate, stereoisomer, or prodrug of the compound of formula II'; or a tautomer, or a pharmaceutically acceptable salt, solvate, stereoisomer, or prodrug thereof; or a mixture thereof.

In some embodiments of formula II', IIIA', and IIIB', the hydrogen on the carboxylic group in formula II' is replaced with an alkyl group to form an ester. For example, the compound of the present invention can be a methyl or ethyl ester of the compound of formula II'.

In certain embodiments of the compound of formula I', the compound has the formula IV' or is a pharmaceutically acceptable salt, solvate, stereoisomer, or prodrug thereof; or a tautomer, or a pharmaceutically acceptable salt, solvate, stereoisomer, or prodrug thereof; or a mixture thereof:

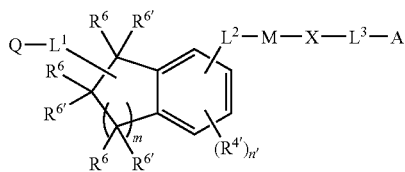

where $R^{4'}$ is independently selected from substituted ($C_1$-$C_6$) alkyl, —R', —OR', =O, =NR', =N—OR', —NR'R", —SR', halogen, —OC(O)R', —C(O)R', —CO$_2$R', —CONR'R", —OC(O)NR'R", —NR"C(O)R', —NR'—C(O)NR'R"', —NR'—SO$_2$NR'R"', —NR"CO$_2$R', —NH—C(NH$_2$)=NH, —NR'C(NH$_2$)=NH, —NH—C(NH$_2$)=NR', —SiR'R"R"', —S(O)R', —SO$_2$R', —SO$_2$NR'R", —NR"SO$_2$R, —CN, —($C_2$-$C_5$) alkynyl, —($C_2$-$C_5$) alkenyl, or —NO$_2$, where R', R" and R"' each independently refer to hydrogen, unsubstituted ($C_1$-$C_8$)alkyl or heteroalkyl, unsubstituted aryl, aryl substituted with one to three halogens, unsubstituted alkyl, alkoxy or thioalkoxy groups, halo($C_1$-$C_4$)alkyl, or aryl-($C_1$-$C_4$)alkyl groups; one of $R^6$ and $R^{6'}$ is $L^1$ or Q, if $L^1$ is a bond, and the others of $R^6$ and $R^{6'}$ are independently selected from H, ($C_1$-$C_6$)alkyl, halogen, ($C_1$-$C_6$) alkoxy, cyano, or nitro, or one of $R^6$ and one of $R^{6'}$ on adjacent or non-adjacent carbon atoms, or on the same carbon atom, may join together to form a $C_5$-$C_8$ cycloalkane ring, or two of $R^6$ or two of $R^{6'}$, on adjacent or non-adjacent carbon atoms, may join together to form a $C_5$-$C_8$ cycloalkane ring; the subscript n' is 0, 1, 2, or 3; and the subscript m is 1, 2, 3, or 4.

In some embodiments, the compound of formula IV' comprises a stereomerically pure S-enantiomer. In other embodiments, the compound of formula IV' comprises a stereomerically pure R-enantiomer. In yet other embodiments, the compound of formula IV' comprises a mixture of S- and R-enantiomers.

In some embodiments, the compound of formula IV' has the formula V':

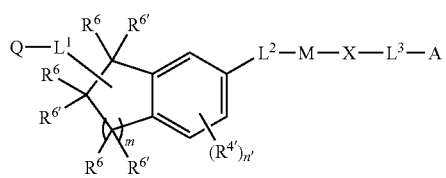

or is a pharmaceutically acceptable salt, solvate, stereoisomer or prodrug thereof; or a tautomer, or a pharmaceutically acceptable salt, solvate, stereoisomer, or prodrug thereof; or a mixture thereof.

In some embodiments, the compound of formula IV' or V', the compound has the formula VI':

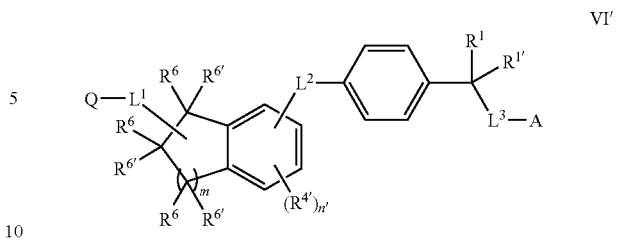

or is a pharmaceutically acceptable salt, solvate, stereoisomer or prodrug thereof; or a tautomer, or a pharmaceutically acceptable salt, solvate, stereoisomer, or prodrug thereof; or a mixture thereof.

It will be apparent that, in certain embodiments of formula VI', the carbon with a bond to $R^1$ is a chiral carbon. Thus, in certain embodiments, the present invention provides a compound having formula VIA' or VIB' or a pharmaceutically acceptable salt, solvate, or prodrug thereof or a tautomer, or a pharmaceutically acceptable salt, solvate, or prodrug thereof; or a mixture thereof:

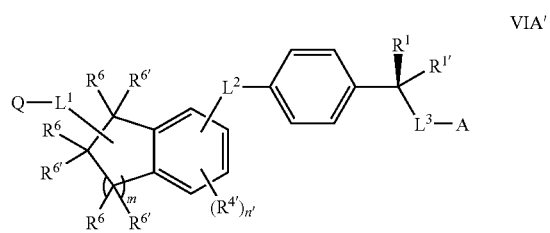

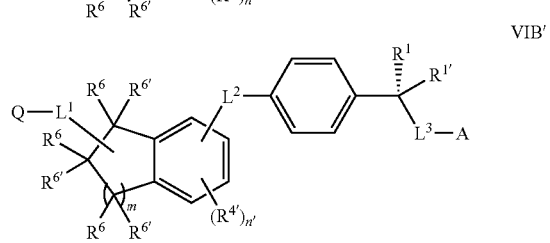

where the variables can have any of the values in any of the embodiments described above.

In some embodiments, the compound of formula VI' comprises a stereomerically pure S-enantiomer. In other embodiments, the compound of formula VI' comprises a stereomerically pure R-enantiomer. In yet other embodiments, the compound of formula VI' comprises a mixture of S- and R-enantiomers.

In certain embodiments, the compound of the present invention is a pharmaceutically acceptable salt, solvate, stereoisomer, or prodrug of the compound of formula II'; or a tautomer, or a pharmaceutically acceptable salt, solvate, stereoisomer, or prodrug thereof; or a mixture thereof.

In some embodiments of formula IV', V', VI', VIA', and VIB', A is —CO$_2$H or is a salt thereof. In some embodiments, the hydrogen on the carboxylic group of A is replaced with an alkyl group to form an ester. For example, the compound of the present invention can be a methyl or ethyl ester of the compound of formula IV', V', VI', VIA', or VIB'.

In some embodiments of the compounds of formula IV', V', VI', VIA', and VIB', the subscript m is 1 or 2.

In some embodiments of the compounds of formula IV', V', VI', VIA', and VIB', the subscript m is 1 or 2; the subscript n' is 0; $L^1$ is a bond; $L^2$ is selected from —CH$_2$—O—, substituted oxymethylene, or O; $R^{1'}$ is H; and A is —CO$_2$H.

In some embodiments of the compounds of formula IV', V', VI', VIA', and VIB', Q is H; $L^3$ is $CH_2$; and $L^2$ is —$CH_2$—O— or —$CH(CH_3)$—O—.

In some embodiments of the compounds of formula IV', V', VI', VIA', and VIB', $R^6$ and $R^{6'}$ are independently selected from H and $(C_1\text{-}C_6)$alkyl and at least two of $R^6$ and $R^{6'}$ are $(C_1\text{-}C_6)$alkyl. In some such embodiments, $R^6$ and $R^{6'}$ are independently selected from H and methyl and at least two of $R^6$ and $R^{6'}$ are methyl groups. In some such embodiments, two of $R^6$ and $R^{6'}$ are methyl groups. In some embodiments, $R^6$ and $R^{6'}$ are independently selected from H and methyl and at least four of $R^6$ and $R^{6'}$ are methyl groups. In some such embodiments, $R^6$ and $R^{6'}$ are independently selected from H and methyl and four of $R^6$ and $R^{6'}$ are methyl groups.

In certain embodiments, the compound has the formula VIIA', VIIB', VIIC', or VIID':

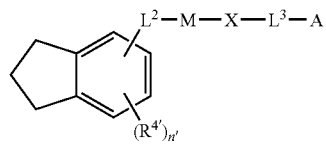

VIIA'

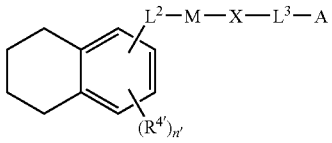

VIIB'

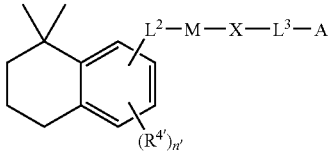

VIIC'

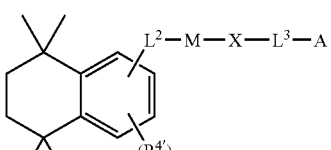

VIID' or a pharmaceutically acceptable salt, solvate, or prodrug thereof; or a tautomer or a pharmaceutically acceptable salt, solvate, or prodrug thereof; or a mixture thereof.

In certain embodiments, the compound of formula VIIA', VIIB', VIIC', or VIID', has the formula VIIIA', VIIIB', VIIIC', or VIIID':

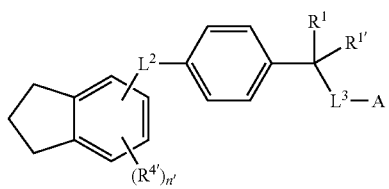

VIIIA'

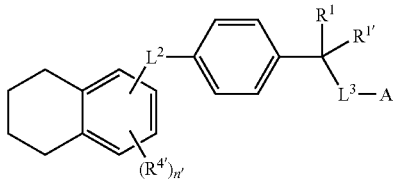

VIIIB'

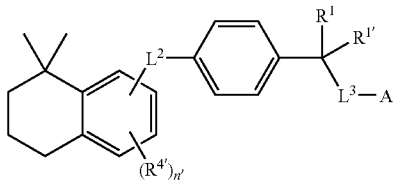

VIIIC'

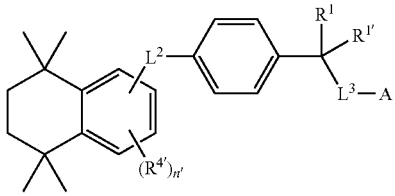

VIIID' or a pharmaceutically acceptable salt, solvate, or prodrug thereof; or a tautomer or a pharmaceutically acceptable salt, solvate, or prodrug thereof; or a mixture thereof.

In certain embodiments, the compound of formula VIIIA', VIIIB', VIIIC', or VIIID', has the formula IXA', IXB', IXC', or IXD':

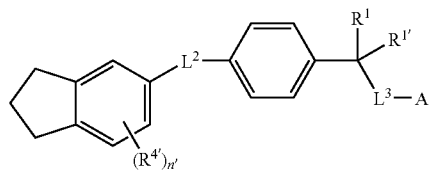

IXA'

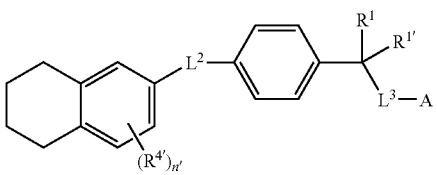

IXB'

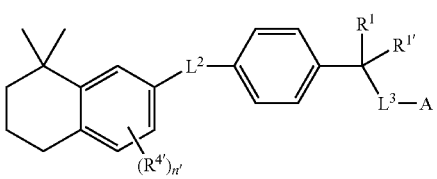

IXC'

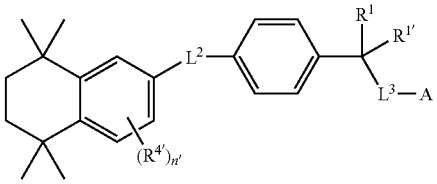

IXD' or a pharmaceutically acceptable salt, solvate, or prodrug thereof; or a tautomer or a pharmaceutically acceptable salt, solvate, or prodrug thereof; or a mixture thereof.

In certain embodiments of the compound of formula VIIA', VIIB', VIIC', VIID', VIIIA', VIIIB', VIIIC', VIIID', IXA', IXB', IXC', or IXD', L² is —CH₂—O— or an alkyl-substituted oxymethylene; the subscript n' is 0; R¹ is (C₂-C₃)alkynyl, heteroaryl, or heterocycloalkyl; R¹' is H; and A is —CO₂H. In some embodiments, the compound is a compound of formula VIIA.' In some embodiments, the compound is a compound of formula VIIB'. In some embodiments, the compound is a compound of formula VIIC'. In some embodiments, the compound is a compound of formula VIID'. In some embodiments, the compound is a compound of formula VIIIA'. In some embodiments, the compound is a compound of formula VIIIB'. In some embodiments, the compound is a compound of formula VIIIC'. In some embodiments, the compound is a compound of formula VIIID'. In some embodiments, the compound is a compound of formula IXA'. In some embodiments, the compound is a compound of formula IXB'. In some embodiments, the compound is a compound of formula IXC'. In some embodiments, the compound is a compound of formula IXD'.

In certain embodiments, the compound of formula IXA', IXB', IXC', or IXD', has the formula XA', XB', XC', or XD':

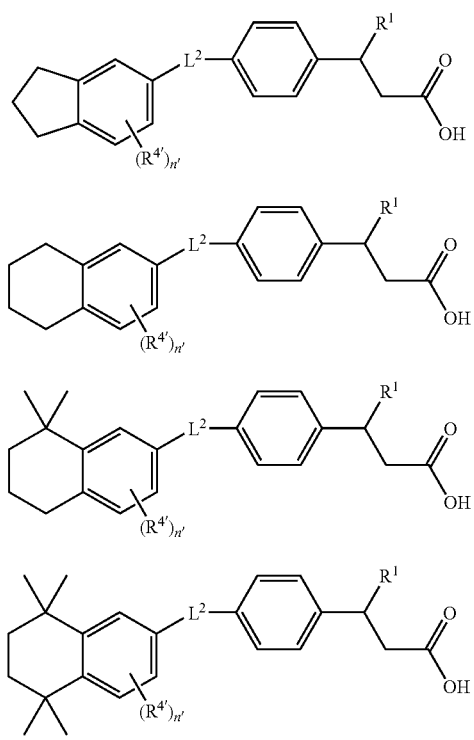

or a pharmaceutically acceptable salt, solvate, or prodrug thereof; or a tautomer or a pharmaceutically acceptable salt, solvate, or prodrug thereof; or a mixture thereof.

In certain embodiments of the compound of formula XA', XB', XC', or XD', L² is —CH₂—O— or an alkyl-substituted oxymethylene; the subscript n' is 0; and R¹' is H. In some embodiments, the compound is a compound of formula XA'. In some embodiments, the compound is a compound of formula XB'. In some embodiments, the compound is a compound of formula XC'. In some embodiments, the compound is a compound of formula XD'.

The compounds of the invention include pharmaceutically acceptable salts, solvates, stereoisomers, and prodrugs thereof, and tautomers and pharmaceutically acceptable salts, solvates, stereoisomers, and prodrugs thereof, and mixtures thereof. In some embodiments, the compounds are pharmaceutically acceptable salts. In other embodiments, the compounds are prodrugs such as esters of a carboxylic acid.

In certain embodiments of the compound of formula I', the compound has the formula of any one of XIa'-XIm' or is a pharmaceutically acceptable salt, solvate, stereoisomer, or prodrug thereof; or a tautomer, or a pharmaceutically acceptable salt, solvate, stereoisomer, or prodrug thereof; or a mixture thereof:

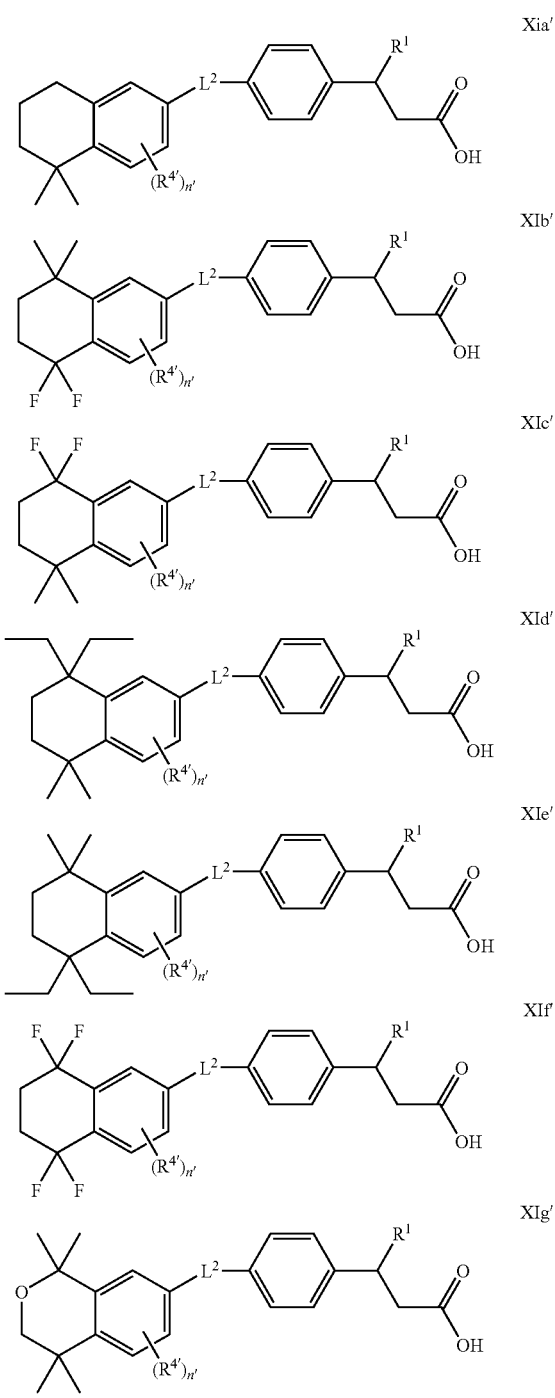

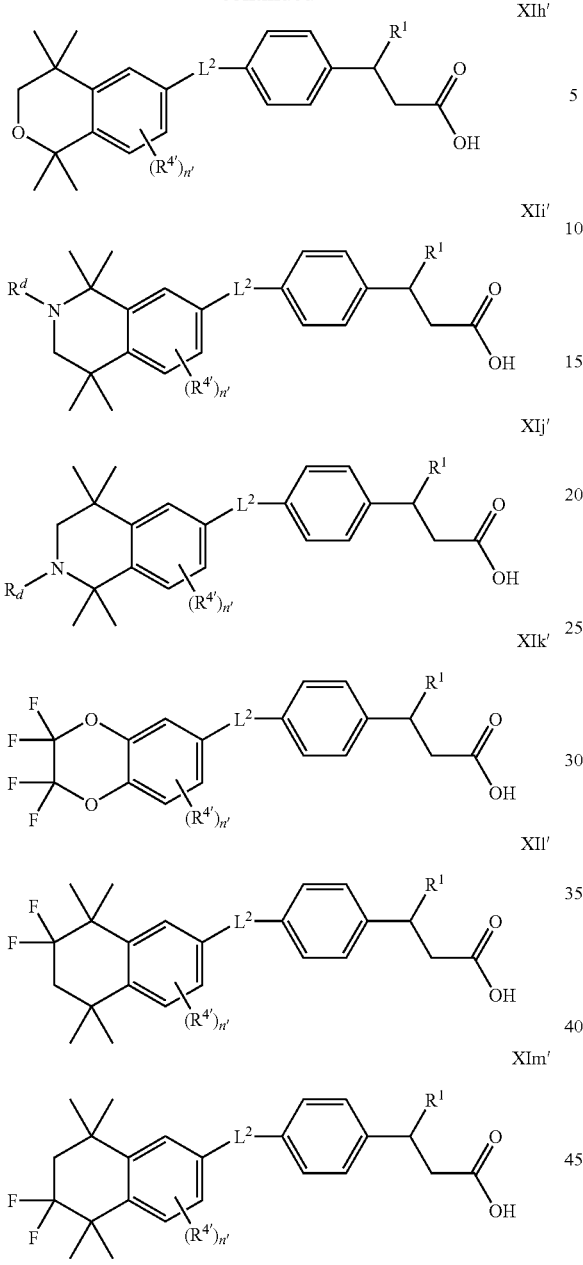

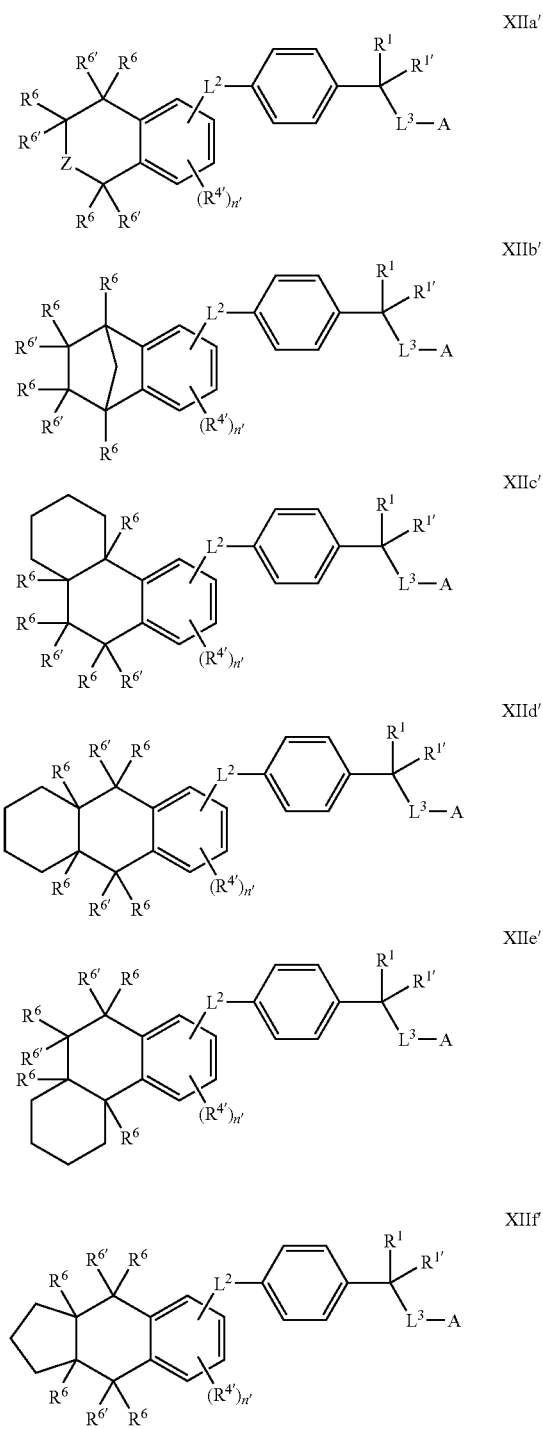

where $R^{4'}$ is independently selected from substituted $(C_1-C_6)$ alkyl, —R', —OR', =O, =NR', =N—OR', —NR'R", —SR', halogen, —OC(O)R', —C(O)R', —CO$_2$R', —CONR'R", —OC(O)NR'R", —NR"C(O)R', —NR'—C(O)NR"R''', —NR'—SO$_2$NR"R''', —NR"CO$_2$R', —NH—C(NH$_2$)=NH, —NR'C(NH$_2$)=NH, —NH—C(NH$_2$)=NR', —SiR'R"R''', —S(O)R', —SO$_2$R', —SO$_2$NR'R", —NR"SO$_2$R, —CN, —(C$_2$-C$_5$) alkynyl, —(C$_2$-C$_5$) alkenyl, or —NO$_2$, where R', R" and R''' each independently refer to hydrogen, unsubstituted $(C_1-C_8)$alkyl or heteroalkyl, unsubstituted aryl, aryl substituted with one to three halogens, unsubstituted alkyl, alkoxy or thioalkoxy groups, halo($C_1$-$C_4$)alkyl, or aryl-($C_1$-$C_4$)alkyl groups; the subscript n' is 0, 1, 2, or 3; and $R^d$ is selected from optionally substituted $C_1$-$C_6$ alkyl or optionally substituted aryl.

In some embodiments, the compound of any one of formula Xia'-XIm' comprises a stereomerically pure S-enantiomer. In other embodiments, the compound comprises a stereomerically pure R-enantiomer. In yet other embodiments, the compound comprises a mixture of S- and R-enantiomers.

In certain embodiments of the compound of formula I, the compound has the formula of any one of XIIa'-XIIm' or is a pharmaceutically acceptable salt, solvate, stereoisomer, or prodrug thereof; or a tautomer, or a pharmaceutically acceptable salt, solvate, stereoisomer, or prodrug thereof; or a mixture thereof:

-continued

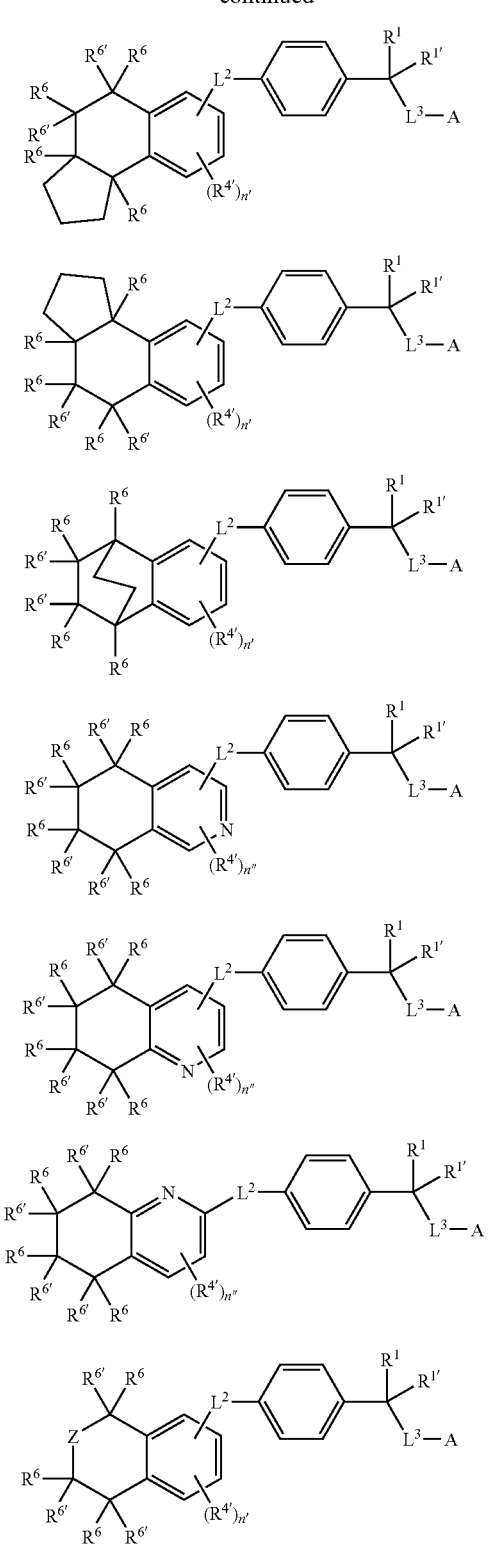

where $R^{4'}$ is independently selected from substituted $(C_1\text{-}C_6)$ alkyl, —R', —OR', =O, =NR', =N—OR', —NR'R", —SR', halogen, —OC(O)R', —C(O)R', —CO$_2$R', —CONR'R", —OC(O)NR'R", —NR"C(O)R', —NR'—C(O)NR"R'", —NR'—SO$_2$NR"R'", —NR"CO$_2$R', —NH—C(NH$_2$)=NH, —NR'C(NH$_2$)=NH, —NH—C(NH$_2$)=NR', —SiR'R"R'", —S(O)R', —SO$_2$R', —SO$_2$NR'R", —NR"SO$_2$R, —CN, —(C$_2$-C$_5$) alkynyl, —(C$_2$-C$_5$) alkenyl, or —NO$_2$, where R', R" and R'" each independently refer to hydrogen, unsubstituted (C$_1$-C$_8$)alkyl or heteroalkyl, unsubstituted aryl, aryl substituted with one to three halogens, unsubstituted alkyl, alkoxy or thioalkoxy groups, halo(C$_1$-C$_4$)alkyl, or aryl-(C$_1$-C$_4$)alkyl groups; $R^6$ and $R^{6'}$ are independently selected from H, (C$_1$-C$_6$)alkyl, halogen, (C$_1$-C$_6$) alkoxy, cyano, or nitro; Z is selected from O, NR$^d$, or S; R$^d$ is selected from optionally substituted C$_1$-C$_6$ alkyl or optionally substituted aryl; the subscript n' is 0, 1, 2, or 3; and the subscript n" is 0, 1, or 2.

In some embodiments, the compound of any one of formula XIIa'-XIIm' comprises a stereomerically pure S-enantiomer. In other embodiments, the compound comprises a stereomerically pure R-enantiomer. In yet other embodiments, the compound comprises a mixture of S- and R-enantiomers.

In some embodiments, the compound of any of the embodiments is a salt. In other embodiments, the compound of any of the embodiments is a prodrug. In some such embodiments, the prodrug is a C$_1$-C$_6$ alkyl ester such as a methyl, ethyl, propyl, butyl, isopropyl, pentyl, or hexyl ester. In some such embodiments, the ester is a methyl or ethyl ester.

In some embodiments, the compound comprises a stereomerically pure S-enantiomer. In other embodiments, the compound comprises a stereomerically pure R-enantiomer. In yet other embodiments, the compound comprises a mixture of S- and R-enantiomers.

In another aspect, the invention provides pharmaceutical compositions comprising a pharmaceutically acceptable carrier, diluent, or excipient, and a compound of any of the embodiments of the invention.

In another aspect, the invention provides methods for treating or preventing a disease or condition selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer, and edema. Such methods include administering to a subject in need thereof, a therapeutically effective amount of a compound of any of the embodiments. In some such embodiments, the disease or condition is type II diabetes. In some embodiments, a compound of any of the embodiments is administered in combination with a second therapeutic agent. In some such embodiments, the second therapeutic agent is metformin or is a thiazolidinedione. The second therapeutic agent may be administered before, during, or after administration of the compound of any of the embodiments.

In another aspect, the invention provides methods for treating or preventing a disease or condition responsive to the modulation of GPR40. Such methods include administering to a subject in need thereof, a therapeutically effective amount of a compound of any of the embodiments.

In another aspect, the invention provides methods for treating or preventing a disease or condition mediated, regulated, or influenced by pancreatic β cells. Such methods include administering to a subject in need thereof, a therapeutically effective amount of a compound of any of the embodiments.

In another aspect, the invention provides methods for modulating GPR40 function in a cell. Such methods include contacting a cell with a compound of any of the embodiments.

In another aspect, the invention provides methods for modulating GPR40 function. Such methods include contacting GPR40 with a compound of any of the embodiments.

In another aspect, the invention provides methods for modulating circulating insulin concentration in a subject. Such methods include administering a compound of any of the embodiments to the subject. In some such embodiments, the circulating insulin concentration is increased in the subject after administration whereas in other such embodiments, the circulating insulin concentration is decreased in the subject after administration.

In another aspect, the invention provides the use of a compound of any of the embodiments for treating a disease or condition or for preparing a medicament for treating a disease or condition where the disease or condition is selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer, and edema. In some such embodiments, the disease or condition is type II diabetes. The compounds of the invention may also be used to prepare medicaments that include a second therapeutic agent such as metformin or a thiazolidinedione.

In another aspect, the invention provides the use of a compound of any of the embodiments for modulating GPR40 or for use in the preparation of a medicament for modulating GPR40.

In another aspect, the invention provides a therapeutic composition that includes a compound of any of the embodiments and a second therapeutic agent such as those described herein, for example, metformin or a thiazolidinedione, as a combined preparation for simultaneous, separate, or sequential use in the treatment of a disease or condition mediated by GPR40. In some such embodiments, the disease or condition is type II diabetes. In some embodiments, the compound of any of the embodiments and the second therapeutic agent are provided as a single composition, whereas in other embodiments they are provided separately as parts of a kit.

Other objects, features and advantages of the invention will become apparent to those skilled in the art from the following description and claims.

5. DETAILED DESCRIPTION OF THE INVENTION

5.1 Abbreviations and Definitions

The terms "treat", "treating" and "treatment", as used herein, are meant to include alleviating or abrogating a condition or disease and/or its attendant symptoms. The terms "prevent", "preventing" and "prevention", as used herein, refer to a method of delaying or precluding the onset of a condition or disease and/or its attendant symptoms, barring a subject from acquiring a condition or disease, or reducing a subject's risk of acquiring a condition or disease.

The term "therapeutically effective amount" refers to that amount of the compound that will elicit the biological or medical response of a tissue, system, or subject that is being sought. The term "therapeutically effective amount" includes that amount of a compound that, when administered, is sufficient to prevent development of, or alleviate to some extent, one or more of the symptoms of the condition or disorder being treated in a subject. The therapeutically effective amount in a subject will vary depending on the compound, the disease and its severity, and the age, weight, etc., of the subject to be treated.

The term "subject" is defined herein to include animals such as mammals, including, but not limited to, primates (e.g., humans), cows, sheep, goats, horses, dogs, cats, rabbits, rats, mice and the like. In preferred embodiments, the subject is a human.

The terms "modulate", "modulation" and the like refer to the ability of a compound to increase or decrease the function or activity of GPR40 either directly or indirectly. Inhibitors are compounds that, for example, bind to, partially or totally block stimulation, decrease, prevent, delay activation, inactivate, desensitize, or down regulate signal transduction, such as, for instance, antagonists. Activators are compounds that, for example, bind to, stimulate, increase, activate, facilitate, enhance activation, sensitize or up regulate signal transduction, such as agonists for instance. Modulation may occur in vitro or in vivo.

As used herein, the phrases "GPR40-mediated condition or disorder", "disease or condition mediated by GPR40", and the like refer to a condition or disorder characterized by inappropriate, for example, less than or greater than normal, GPR40 activity. A GPR40-mediated condition or disorder may be completely or partially mediated by inappropriate GPR40 activity. However, a GPR40-mediated condition or disorder is one in which modulation of GPR40 results in some effect on the underlying condition or disease (e.g., a GPR40 modulator results in some improvement in patient well-being in at least some patients). Exemplary GPR40-mediated conditions and disorders include cancer and metabolic disorders, e.g., diabetes, type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, ketoacidosis, hypoglycemia, thrombotic disorders, metabolic syndrome, syndrome X and related disorders, e.g., cardiovascular disease, atherosclerosis, kidney disease, nephropathy, diabetic neuropathy, diabetic retinopathy, sexual dysfunction, dermatopathy, dyspepsia, and edema.

The term "alkyl", by itself or as part of another substituent, means, unless otherwise stated, a straight or branched chain, or cyclic hydrocarbon radical, or combination thereof, which is fully saturated, having the number of carbon atoms designated (e.g., $C_1$-$C_{10}$ means one to ten carbons). Examples of alkyl groups include methyl, ethyl, n-propyl, isopropyl, n-butyl, t-butyl, isobutyl, sec-butyl, cyclohexyl, (cyclohexyl)methyl, cyclopropyl, cyclopropylmethyl, and homologs and isomers of, for example, n-pentyl, n-hexyl, n-heptyl, n-octyl, and the like.

The term "alkenyl", by itself or as part of another substituent, means a straight or branched chain, or cyclic hydrocarbon radical, or combination thereof, which may be mono- or polyunsaturated, having the number of carbon atoms designated (i.e., $C_2$-$C_8$ means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl), and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e., $C_2$-$C_8$ means two to eight carbons) and one or more triple bonds. Examples of alkynyl groups include ethynyl, 1- and 3-propynyl, 3-butynyl, and higher homologs and isomers thereof.

The term "alkylene" by itself or as part of another substituent means a divalent radical derived from alkyl, as exemplified by —CH$_2$CH$_2$CH$_2$CH$_2$—. Typically, an alkyl (or alkylene) group will have from 1 to 24 carbon atoms, with those groups having 12 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Similarly, the term dialkylamino refers to an amino group having two attached alkyl groups. The alkyl groups of a dialkylamino may be the same or different.

The term "heteroalkyl," by itself or in combination with another term, means, unless otherwise stated, a stable straight or branched chain, or cyclic hydrocarbon radical, or combinations thereof, consisting of carbon atoms and from one to three heteroatoms selected from the group consisting of O, N, and S, and wherein the nitrogen and sulfur atoms may optionally be oxidized, and the nitrogen heteroatom may optionally be quaternized. The heteroatom(s) O, N, and S may be placed at any position of the heteroalkyl group. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, and —CH$_2$—CH=N—OCH$_3$. Up to two heteroatoms may be consecutive, such as, for example, —CH$_2$—NH—OCH$_3$. When a prefix such as (C$_2$-C$_8$) is used to refer to a heteroalkyl group, the number of carbons (2 to 8, in this example) is meant to include the heteroatoms as well. For example, a C$_2$-heteroalkyl group is meant to include, for example, —CH$_2$OH (one carbon atom and one heteroatom replacing a carbon atom) and —CH$_2$SH.

To further illustrate the definition of a heteroalkyl group, where the heteroatom is oxygen, a heteroalkyl group is an oxyalkyl group. For instance, (C$_2$-C$_5$)oxyalkyl is meant to include, for example —CH$_2$—O—CH$_3$ (a C$_3$-oxyalkyl group with two carbon atoms and one oxygen replacing a carbon atom), —CH$_2$CH$_2$CH$_2$CH$_2$OH, and the like.

The term "heteroalkylene" by itself or as part of another substituent means a divalent radical derived from heteroalkyl, as exemplified by —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied. Heteroalkylene groups such as oxymethyl groups (—CH$_2$—O—) may be substituted or unsubstituted. In some embodiments, heteroalkylene groups may be substituted with an alkyl group. For example, the carbon atom of an oxymethylene group may be substituted with a methyl group in a group of formula —CH(CH$_3$)—O—.

The terms "cycloalkyl" and "heterocycloalkyl," by themselves or in combination with other terms, represent, unless otherwise stated, cyclic versions of "alkyl" and "heteroalkyl," respectively. Thus, the terms "cycloalkyl" and "heterocycloalkyl" are meant to be included in the terms "alkyl" and "heteroalkyl," respectively. Additionally, for heterocycloalkyl, a heteroatom can occupy the position at which the heterocycle is attached to the remainder of the molecule.

Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, 4,5-dihydroisoxazol-3-yl, and the like. The term "heterocycloalkyl" includes fully saturated compounds such as piperidine and compounds with partial saturation that are not aromatic. Examples of such groups include, but are not limited to, an imidazole, oxazole, or isoxazole which has been partially hydrogenated so that it only contains one double bond.

The term "cycloalkenyl" means, unless otherwise stated, a "cycloalkyl" group that includes one or more double bonds. Cycloalkenyl groups may be further substituted. Examples of cycloalkenyl groups include, but are not limited to cyclobutenyl, cyclopentenyl, cyclopentadienyl, cyclohexenyl, cyclohexadienyl, cycloheptenyl, cycloheptadienyl, cyclooctenyl, cyclooctadienyl, and the like.

The term "heterocycloalkenyl" means, unless otherwise stated, a "cycloalkenyl" group in which one or more of the carbon atoms has been replaced with a heteroatom such as a N, O, or S atom. Heterocycloalkenyl groups may be further substituted. Examples of heterocycloalkenyl groups include, but are not limited to, 2,5-dihydro-1H-pyrrolyl, 1,2,3,6-tetrahydropyridinyl, 4-azacycloheptenyl, 4-azacyclooctenyl, 4-oxacyclooctenyl, and the like.

The term "cycloalkylene" and "heterocycloalkylene," by themselves or in combination with other terms, represent, unless otherwise stated, cyclic versions of "alkylene" and "heteroalkylene," respectively. Thus, the terms "cycloalkylene" and "heterocycloalkylene" are meant to be included in the terms "alkylene" and "heteroalkylene," respectively. Additionally, for heterocycloalkylene, one or more heteroatoms can occupy positions at which the heterocycle is attached to the remainder of the molecule. Typically, a cycloalkylene or heterocycloalkylene will have from 3 to 9 atoms forming the ring, more typically, 4 to 7 atoms forming the ring, and even more typically, 5 or 6 atoms will form the cycloalkylene or heterocycloalkylene ring.

The terms "halo" or "halogen," by themselves or as part of another substituent, mean, unless otherwise stated, a fluorine, chlorine, bromine, or iodine atom. Additionally, terms such as "haloalkyl", are meant to include alkyl substituted with halogen atoms which can be the same or different, in a number ranging from one to (2m'+1), where m' is the total number of carbon atoms in the alkyl group. For example, the term "halo (C$_1$-C$_4$)alkyl" is meant to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms). The term "perhaloalkyl" means, unless otherwise stated, alkyl substituted with (2m'+1) halogen atoms, where m' is the total number of carbon atoms in the alkyl group. For example, the term "perhalo(C$_1$-C$_4$)alkyl", is meant to include trifluoromethyl, pentachloroethyl, 1,1,1-trifluoro-2-bromo-2-chloroethyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from one to four heteroatoms selected from the group consisting of N, O and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 1-pyrazolyl, 3-pyrazolyl, 5-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, dibenzofuryl, 2-thienyl, 3-thienyl, 2-pyridyl, 3-pyridyl, 4-pyridyl, 2-pyrimidyl, 4-pyrimidyl, 2-pyrimidinyl, 4-pyrimidinyl, 5-pyrimidinyl, 3-pyridazinyl, 4-pyridazinyl, 5-benzothiazolyl, 2-benzoxazolyl, 5-benzoxazolyl, benzo[c][1,2,5]oxadiazolyl, purinyl, 2-benzimidazolyl, 5-indolyl, 1H-indazolyl, carbazolyl, α-carbolinyl, β-carbolinyl, γ-carbolinyl, 1-isoquinolyl, 5-isoquinolyl, 2-quinoxalinyl, 5-quinoxalinyl, 2-quinolyl, 3-quinolyl, 4-quinolyl, 5-quinolyl, 6-quinolyl, 7-quinolyl, and 8-quinolyl.

Preferably, the term "aryl" refers to a phenyl or naphthyl group which is unsubstituted or substituted. Preferably, the term "heteroaryl" refers to a pyrrolyl, pyrazolyl, imidazolyl, pyrazinyl, oxazolyl, oxadiazolyl, isoxazolyl, thiazolyl, furyl, thienyl (thiophenyl), pyridyl, pyrimidyl, benzothiazolyl, purinyl, benzimidazolyl, indolyl, isoquinolyl, triazolyl, tetrazolyl, quinoxalinyl. or quinolyl group which is unsubstituted or substituted.

For brevity, the term "aryl" when used in combination with other terms (e.g., aryloxy, arylalkoxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). As another example, the term "aryl($C_1$-$C_4$)alkoxy" is mean to include radicals in which an aryl group is attached to an alkyl group having 1 to 4 carbon atoms that is bonded to an O which is attached to the rest of the molecule. Examples include substituted and unsubstituted phenylmethoxy, phenylethoxy, phenylpropoxy, pyridylmethoxy, and the like.

Each of the above terms (e.g., "alkyl," "heteroalkyl," "aryl" and "heteroaryl") is meant to include both substituted and unsubstituted forms of the indicated radical, unless otherwise indicated. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR', halogen, —OC(O)R', —C(O)R', —$CO_2$R', —CONR'R", —OC(O)NR'R", —NR"C(O)R', —NR'—C(O)NR"R"', —NR'—$SO_2$NR"R"', —NR"$CO_2$R', —NH—C(NH$_2$)=NH, —NR'C(NH$_2$)=NH, —NH—C(NH$_2$)=NR', —SiR'R"R"', —S(O)R', —$SO_2$R', —$SO_2$NR'R", —NR"$SO_2$R, —CN, —($C_2$-$C_5$) alkynyl, —($C_2$-$C_5$) alkenyl, and —$NO_2$, in a number ranging from zero to three, with those groups having zero, one or two substituents being particularly preferred. Other suitable substituents include aryl and heteroaryl groups. R', R" and R"' each independently refer to hydrogen, unsubstituted ($C_1$-$C_8$)alkyl and heteroalkyl, unsubstituted aryl, aryl substituted with one to three halogens, unsubstituted alkyl, alkoxy or thioalkoxy groups, halo($C_1$-$C_4$)alkyl, or aryl-($C_1$-$C_4$)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl.

Typically, an alkyl or heteroalkyl group will have from zero to three substituents, with those groups having two or fewer substituents being preferred in the present invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —$CF_3$ and —$CH_2CF_3$).

Preferred substituents for the alkyl and heteroalkyl radicals are selected from: —OR', =O, —NR'R", —SR', halogen, —OC(O)R', —C(O)R', —$CO_2$R', —CONR'R", —OC(O)NR'R", —NR"C(O)R', —NR"$CO_2$R', —NR'—$SO_2$NR"R"', —S(O)R', —$SO_2$R', —$SO_2$NR'R", —NR"$SO_2$R, —CN, —($C_2$-$C_5$) alkynyl, —($C_2$-$C_5$) alkenyl and —$NO_2$, where R' and R" are as defined above. Further preferred substituents are selected from: —OR', =O, —NR'R", halogen, —OC(O)R', —$CO_2$R', —CONR'R", —OC(O)NR'R", —NR"C(O)R', —NR"$CO_2$R', —NR'—$SO_2$NR"R"', —$SO_2$R', —$SO_2$NR'R", —NR"$SO_2$R, —CN, —($C_2$-$C_5$) alkynyl, —($C_2$-$C_5$) alkenyl, and —$NO_2$.

Similarly, substituents for the aryl and heteroaryl groups are varied and are selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R"', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R"' are independently selected from hydrogen, ($C_1$-$C_8$)alkyl and heteroalkyl, unsubstituted aryl and heteroaryl, (unsubstituted aryl)-($C_1$-$C_4$)alkyl, (unsubstituted aryl)oxy-($C_1$-$C_4$)alkyl, —($C_2$-$C_5$) alkynyl, and —($C_2$-$C_5$) alkenyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$—, or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'—, or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$-$C_6$)alkyl. Otherwise, R' is as defined above.

As used herein, the term "benzo-fused cycloalkane ring" is meant to include bicyclic structures in which benzene is fused with a cycloalkane (or cycloheteroalkane). To illustrate, in some embodiments, "benzo-fused cycloalkane ring" includes the following structures:

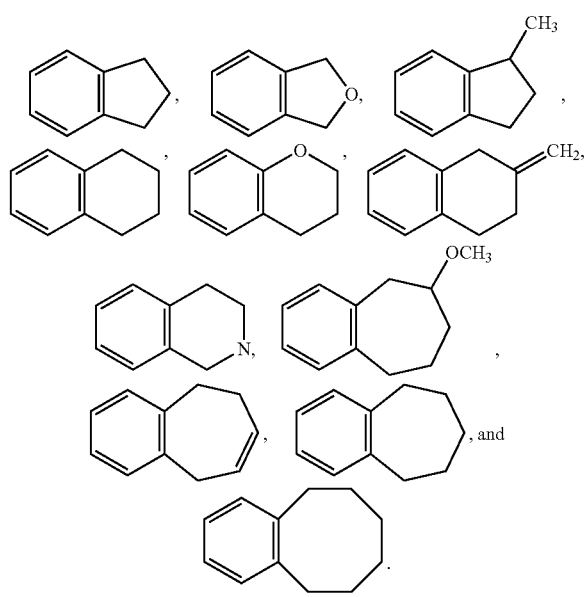

As used herein, the term "heterobenzo-fused ($C_5$-$C_8$)cycloalkane ring" has the same meaning as "benzo-fused ($C_5$-$C_8$) cycloalkane ring" except the benzene of the benzo-fused ($C_5$-$C_8$)cycloalkane ring is replaced with a six-membered heteroaryl ring comprising 1 or 2 nitrogen (N) atoms. As indicated in the structures shown above, the ($C_5$-$C_8$)cycloalkane of benzo-fused ($C_5$-$C_8$)cycloalkane rings and heterobenzo-fused ($C_5$-$C_8$)cycloalkane ring may include only carbon atoms, but may also include one or more heteroatoms. Such heteroatoms typically are selected from O, N, or S.

As used herein, the term "heteroatom" is meant to include oxygen (O), nitrogen (N), and sulfur (S).

The term "pharmaceutically acceptable salt" is meant to include a salt of the active compound which is prepared with relatively nontoxic acids or bases, depending on the particular substituents found on the compound described herein. When a compound of the invention contains relatively acidic functionalities, a base addition salt can be obtained by contacting the neutral form of such compound with a sufficient amount of the desired base, either neat or in a suitable inert solvent. Examples of pharmaceutically acceptable base addition salts include sodium, potassium, calcium, ammonium, organic amino, or magnesium salt, or a similar salt. When a compound of the invention contains relatively basic functionalities, an acid addition salt can be obtained by contacting the neutral form of such compound with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginine and the like, and salts of organic acids like glucuronic or galacturonic acids and the like (see, for example, Berge et al. (1977) *J. Pharm. Sci.* 66:1-19). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound.

As used herein, "solvate" refers to a compound of the present invention or a salt thereof, that further includes a stoichiometric or non-stoichiometric amount of solvent bound by non-covalent intermolecular forces. Where the solvent is water, the solvate is a hydrate.

Certain compounds of the invention may exist in multiple crystalline or amorphous forms. In general, all physical forms are equivalent for the uses contemplated by the invention and are intended to be within the scope of the invention.

As known by those skilled in the art, certain compounds of the invention may exist in one or more tautomeric forms. Because one chemical structure may only be used to represent one tautomeric form, it will be understood that convenience, referral to a compound of a given structural formula includes tautomers of the structure represented by the structural formula.

Certain compounds of the invention possess asymmetric carbon atoms (optical centers) or double bonds; the racemates, enantiomers, diastereomers, geometric isomers and individual isomers are all intended to be encompassed within the scope of the invention.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed.

Various compounds of the invention contain one or more chiral centers, and can exist as racemic mixtures of enantiomers, mixtures of diastereomers or enantiomerically or optically pure compounds. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al. (1997) *Tetrahedron* 33:2725; Eliel, E. L., *Stereochemistry of Carbon Compounds* (McGraw-Hill, NY, 1962); and Wilen, S. H., *Tables of Resolving Agents and Optical Resolutions* p. 268 (E.L. Eliel, Ed., Univ. of Notre Dame Press, Notre Dame, IN, 1972).

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic or prophylactic agents, research reagents, e.g., GPR40 assay reagents, and diagnostic agents, e.g., in vivo imaging agents. All isotopic variations of the compounds of the invention, whether radioactive or not, are intended to be encompassed within the scope of the invention.

5.2 Embodiments of the Invention

In one aspect, a class of compounds that modulates GPR40 is described herein. Depending on the biological environment (e.g., cell type, pathological condition of the subject, etc.), these compounds can modulate, e.g., activate or inhibit, the actions of GPR40. By modulating GPR40, the compounds find use as therapeutic agents capable of regulating insulin levels in a subject. The compounds find use as therapeutic agents for modulating diseases and conditions responsive to modulation of GPR40 and/or mediated by GPR40 and/or mediated by pancreatic β cells. As noted above, examples of such diseases and conditions include diabetes, obesity, hyperglycemia, glucose intolerance, insulin resistance, cancer, hyperinsulinemia, hypercholesterolemia, hypertension, hyperlipoproteinemia, hyperlipidemia, hypertriglylceridemia, dyslipidemia, ketoacidosis, hypoglycemia, metabolic syndrome, syndrome X, cardiovascular disease, atherosclerosis, kidney disease, nephropathy, thrombotic disorders, diabetic neuropathy, diabetic retinopathy, dermatopathy, dyspepsia and edema. Additionally, the compounds are useful for the treatment and/or prevention of complications of these diseases and disorders (e.g., type II diabetes, sexual dysfunction, dyspepsia and so forth).

While the compounds of the invention are believed to exert their effects by interacting with GPR40, the mechanism of action by which the compounds act is not a limiting embodiment of the invention.

Compounds contemplated by the invention include, but are not limited to, the exemplary compounds provided herein.

5.2.1 Compounds

In one aspect, the present invention provides a compound having the formula I or a pharmaceutically acceptable salt, solvate, stereoisomer, or prodrug thereof; or a tautomer or a pharmaceutically acceptable salt, solvate, stereoisomer, or prodrug thereof; or a mixture thereof:

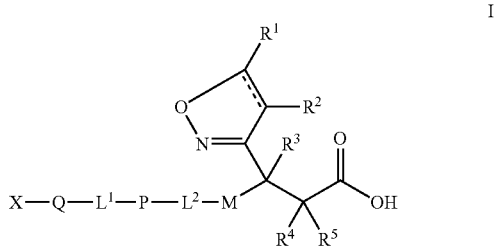

where X, Q, $L^1$, P, $L^2$, M, $R^1$, $R^2$, $R^3$, $R^4$ and $R^5$ are defined below, and the dashed line indicates that there is a single or double bond between the carbon atom bearing the $R^1$ and the carbon atom bearing the $R^2$.

X may be absent or is selected from H, $(C_1-C_6)$alkyl, Cl, Br, F, I, CN, $NO_2$, perfluoro$(C_1-C_4)$alkyl, $(C_1-C_6)$alkoxy, perfluoro$(C_1-C_4)$alkoxy, or an optionally substituted aryl$(C_1-C_4)$alkoxy. In some embodiments, X is absent. In other embodiments, X is H. In still further embodiments, X is selected from a $(C_1-C_6)$alkyl, Cl, Br, F, perfluoro$(C_1-C_4)$alkyl, $(C_1-C_6)$alkoxy, perfluoro$(C_1-C_4)$alkoxy, or an optionally substituted aryl$(C_1-C_4)$alkoxy such as an optionally substituted phenylmethoxy group.

Q is an optionally substituted aromatic ring, an optionally substituted heteroaromatic ring, $(C_1-C_6)$alkyl, $(C_2-C_6)$heteroalkyl, H, Cl, Br, F, I, CN, $NO_2$, perfluoro$(C_1-C_4)$alkyl, $(C_1-C_6)$alkoxy, or perfluoro$(C_1-C_4)$alkoxy. In some embodiments, Q is a optionally substituted phenyl group.

$L^1$ is a bond, $(C_1-C_4)$alkylene, $(C_2-C_4)$heteroalkylene, O, S(O)$_k$, N(R$^a$), C(O)—$(C_5-C_7)$heterocycloalkylene, $(C_1-C_4)$alkylene-SO$_2$N(R$^b$), $(C_1-C_4)$alkylene-N(R$^b$)SO$_2$, or C(O)N(R$^b$). In some embodiments, $L^1$ is a bond.

P is an optionally substituted aromatic ring or an optionally substituted heteroaromatic ring. In some embodiments, P is an optionally substituted phenyl group and the carbons attached to $L^1$ and $L^2$ are para to one another. In other embodiments, P is an optionally substituted phenyl group and the carbons attached to $L^1$ and $L^2$ are meta to one another. In still other embodiments, P is an optionally substituted heteroaryl group such as an optionally substituted thiazole, an optionally substituted oxadiazole, an optionally substituted oxazole, an optionally substituted thiophene, an optionally substituted furan, an optionally substituted imidazole, an optionally substituted pyrrole, or an optionally substituted pyrazole.

$L^2$ is a bond, $(C_1-C_6)$alkylene, $(C_2-C_6)$heteroalkylene, oxymethylene, O, S(O)$_k$, N(R$^a$), C(O)N(R$^b$), SO$_2$N(R$^b$), $(C_1-C_4)$alkylene-C(O)N(R$^b$), $(C_1-C_4)$alkylene-N(R$^b$)C(O), $(C_2-C_4)$alkenylene-C(O)N(R$^b$), $(C_2-C_4)$alkenylene-N(R$^b$)C(O), $(C_1-C_4)$alkylene-SO$_2$N(R$^b$), $(C_1-C_4)$alkylene-N(R$^b$)SO$_2$, $(C_2-C_4)$alkenylene-SO$_2$N(R$^b$), or $(C_2-C_4)$alkenylene-N(R$^b$)SO$_2$. In some embodiments, $L^2$ is an oxymethylene.

M is an optionally substituted aromatic ring or an optionally substituted heteroaromatic ring. In some embodiments, M is a substituted or unsubstituted benzene ring and the carbon bearing the $R^3$ and the carbon attached to $L^2$ are para to one another. In other embodiments, the carbon bearing the $R^3$ and the carbon attached to $L^2$ are meta to one another $R^a$ is H, $(C_1-C_6)$alkyl, aryl$(C_1-C_3)$alkyl, or $(C_2-C_6)$heteroalkyl.

$R^b$ is H, $(C_1-C_6)$alkyl, or $(C_2-C_6)$heteroalkyl.

$R^1$, $R^2$, $R^3$, $R^4$, and $R^5$ are independently selected from H, or $(C_1-C_6)$alkyl. In some embodiments, $R^3$, $R^4$, and $R^5$ are all H. In other embodiments, $R^1$ is H or methyl. In some such embodiments, $R^1$ is H. In other embodiments, $R^2$ is H. In some embodiments, $R^1$, $R^2$, $R^3$, $R^4$, and $R^5$ are all H.

The subscript k is, in each instance, independently selected from 0, 1, or 2.

In another aspect, the present invention provides a compound having the formula I or a pharmaceutically acceptable salt, solvate, stereoisomer, or prodrug thereof; or a tautomer or a pharmaceutically acceptable salt, solvate, stereoisomer, or prodrug thereof; or a mixture thereof where X, Q, $L^1$, P, $L^2$, M, $R^1$, $R^2$, $R^3$, $R^4$ and $R^5$ are defined below, and the dashed line indicates that there is a single or double bond between the carbon atom bearing the $R^1$ substituent and the carbon atom bearing the $R^2$ substituent. In this aspect, X is absent or is selected from H, $(C_1-C_6)$alkyl, Cl, Br, F, I, CN, $NO_2$, perfluoro$(C_1-C_4)$alkyl, $(C_1-C_6)$alkoxy, perfluoro$(C_1-C_4)$alkoxy, or an optionally substituted aryl$(C_1-C_4)$alkoxy; and Q is an optionally substituted aromatic ring, an optionally substituted heteroaromatic ring, an optionally substituted $(C_4-C_8)$cycloalkyl, an optionally substituted $(C_5-C_8)$cycloalkenyl, an optionally substituted heterocycloalkenyl ring comprising from 5 to 8 ring members, $(C_2-C_6)$alkenyl, $(C_1-C_6)$alkyl, $(C_2-C_6)$heteroalkyl, H, Cl, Br, F, I, CN, $NO_2$, perfluoro$(C_1-C_4)$alkyl, $(C_1-C_6)$alkoxy, or perfluoro$(C_1-C_4)$alkoxy. In some embodiments of this aspect, Q is an optionally substituted $(C_4-C_8)$cycloalkyl, an optionally substituted $(C_5-C_8)$cycloalkenyl, an optionally substituted heterocycloalkenyl ring comprising from 5 to 8 ring members, or a $(C_2-C_6)$alkenyl. In this aspect, $L^1$ is a bond, $(C_1-C_4)$alkylene, $(C_2-C_4)$heteroalkylene, O, $S(O)_k$, $N(R^a)$, $C(O)$—$(C_5-C_7)$heterocycloalkylene, $(C_1-C_4)$alkylene-$SO_2N(R^b)$, $(C_1-C_4)$alkylene-$N(R^b)SO_2$, $S(O)_2N(R^b)$, or $C(O)N(R^b)$; P is an optionally substituted aromatic ring or an optionally substituted heteroaromatic ring; $L^2$ is a bond, $(C_1-C_6)$alkylene, $(C_2-C_6)$heteroalkylene, oxymethylene, O, $S(O)_k$, $N(R^a)$, $C(O)N(R^b)$, $SO_2N(R^b)$, $(C_1-C_4)$alkylene-$C(O)N(R^b)$, $(C_1-C_4)$alkylene-$N(R^b)C(O)$, $(C_2-C_4)$alkenylene-$C(O)N(R^b)$, $(C_2-C_4)$alkenylene-$N(R^b)C(O)$, $(C_1-C_4)$alkylene-$SO_2N(R^b)$, $(C_1-C_4)$alkylene-$N(R^b)SO_2$, $(C_2-C_4)$alkenylene-$SO_2N(R^b)$, or $(C_2-C_4)$alkenylene-$N(R^b)SO_2$; M is an optionally substituted aromatic ring or an optionally substituted heteroaromatic ring; $R^a$ is H, $(C_1-C_6)$alkyl, aryl$(C_1-C_3)$alkyl, or $(C_2-C_6)$heteroalkyl; $R^b$ is H, $(C_1-C_6)$alkyl, or $(C_2-C_6)$heteroalkyl; $R^1$, $R^2$, $R^3$, $R^4$, and $R^5$ are independently selected from H, or $(C_1-C_6)$alkyl; and the subscript k is, in each instance, independently selected from 0, 1, or 2.

In some embodiments of the compound of formula I, X is absent or is selected from H, $(C_1-C_6)$alkyl, Cl, $CF_3$, $(C_1-C_6)$alkoxy, or an optionally substituted phenylmethoxy group; Q is an optionally substituted aromatic ring; $L^1$ is a bond; and $L^2$ is an oxymethylene.

In some embodiments of the compound of formula I, P is selected from an optionally substituted phenyl, an optionally substituted thiazole, an optionally substituted oxadiazole, an optionally substituted oxazole, an optionally substituted thiophene, an optionally substituted furan, an optionally substituted imidazole, an optionally substituted pyrrole, or an optionally substituted pyrazole.

In some embodiments, the compound of formula I is a compound of formula II or a pharmaceutically acceptable salt, solvate, stereoisomer, or prodrug thereof; or a tautomer or a pharmaceutically acceptable salt, solvate, stereoisomer, or prodrug thereof; or a mixture thereof. The compound of formula II has the following structure:

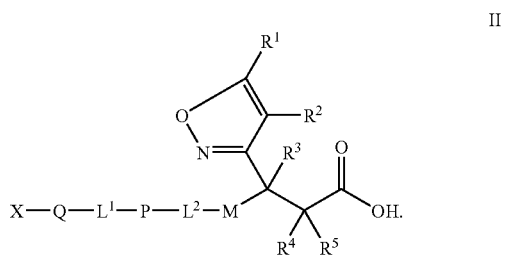

II

In some embodiments, the compound of formula I is a compound of formula III or a pharmaceutically acceptable salt, solvate, stereoisomer, or prodrug thereof; or a tautomer or a pharmaceutically acceptable salt, solvate, stereoisomer, or prodrug thereof; or a mixture thereof. The compound of formula III has the following structure:

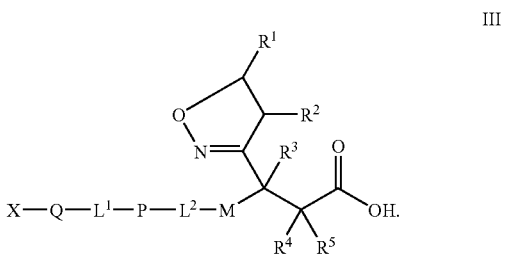

III

In some embodiments, the compound of formula I is a compound of formula IV or a pharmaceutically acceptable salt, solvate, stereoisomer, or prodrug thereof; or a tautomer or a pharmaceutically acceptable salt, solvate, stereoisomer, or prodrug thereof; or a mixture thereof. The compound of formula IV has the following structure:

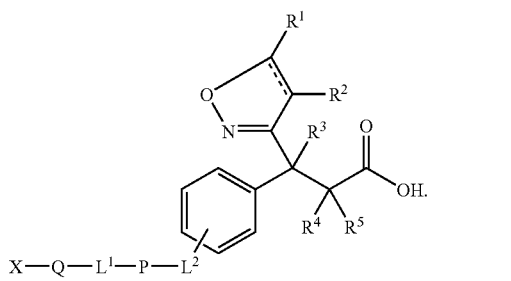

IV

In some such embodiments, the compound has the formula VA or VB or is a pharmaceutically acceptable salt, solvate, stereoisomer, or prodrug thereof; or a tautomer or a pharmaceutically acceptable salt, solvate, stereoisomer, or prodrug thereof; or a mixture thereof

VA

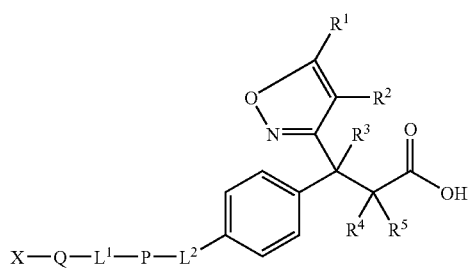

VB

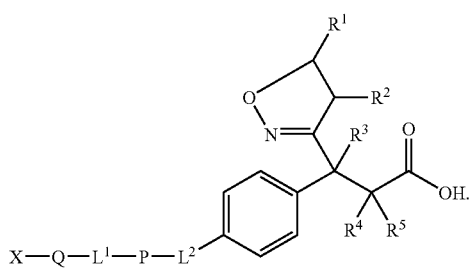

In other such embodiments, the compound has the formula VI or is a pharmaceutically acceptable salt, solvate, stereoisomer, or prodrug thereof; or a tautomer or a pharmaceutically acceptable salt, solvate, stereoisomer, or prodrug thereof; or a mixture thereof

VI

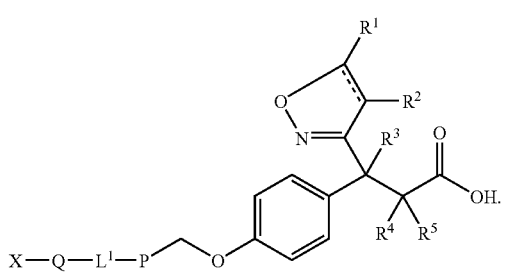

In some embodiments of any of those described above, X-Q-L$^1$-P-L$^2$-M- has a formula selected from

VIIA

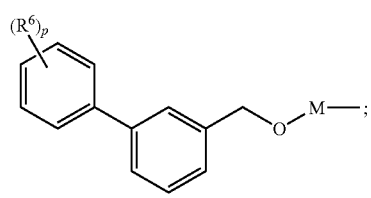

VIIB

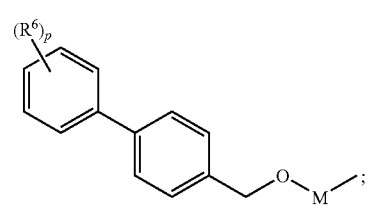

VIIC

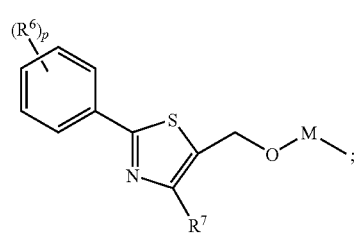

VIID

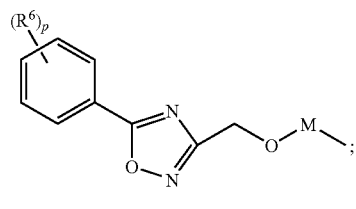

VIIE

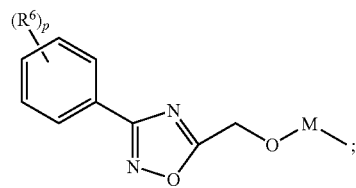

VIIF

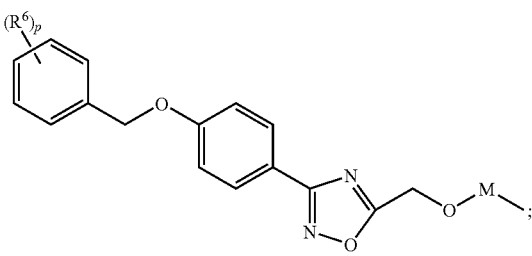

VIIG

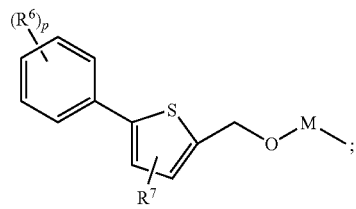

VIIH

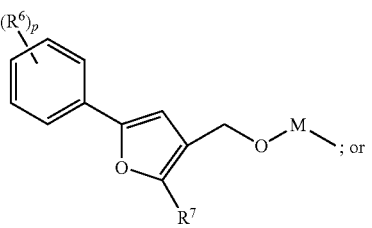

; or

VIIJ

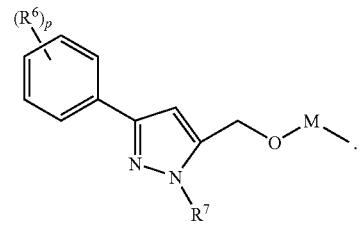

In such embodiments, p is selected from 0, 1, 2, 3, 4, or 5; each R$^6$ is independently selected from (C$_1$-C$_6$)alkyl, Cl, Br, F, I, CN, NO$_2$, perfluoro(C$_1$-C$_4$)alkyl, (C$_1$-C$_6$)alkoxy, or perfluoro($C_1$-$C_4$)alkoxy; and $R^7$ is selected from H or ($C_1$-$C_6$) alkyl. Such compounds include pharmaceutically acceptable salts, solvates, stereoisomers, and prodrugs thereof; and tautomers and pharmaceutically acceptable salts, solvates, stereoisomers, and prodrugs thereof; and mixture thereof. In some such embodiments, $R^7$ is H or methyl. In other such embodiments, p is 0, 1, or 2.

In some embodiments, X-Q-$L^1$-P-$L^2$-M- has a formula selected from

VIIK
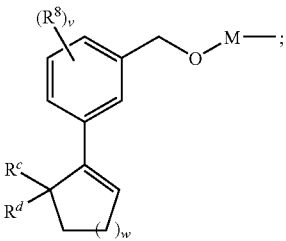

VIIL
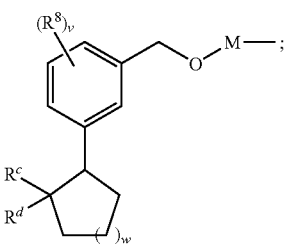

VIIM
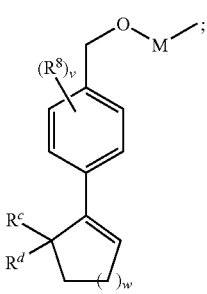

VIIN
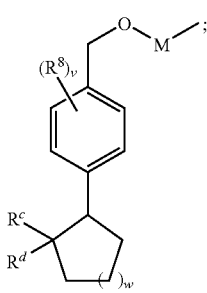

VIIO
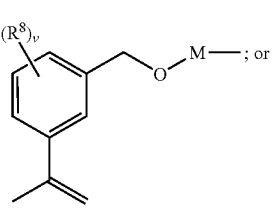

VIIP
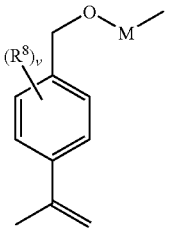

wherein, v is selected from 0, 1, 2, 3, or 4;

w is selected from 1 or 2;

$R^c$ and $R^d$ are independently selected from H or $C_1$-$C_4$ alkyl; and each $R^8$ is independently selected from ($C_1$-$C_6$)alkyl, Cl, Br, F, I, CN, $NO_2$, perfluoro($C_1$-$C_4$)alkyl, ($C_1$-$C_6$)alkoxy, or perfluoro($C_1$-$C_4$)alkoxy, or a pharmaceutically acceptable salt, solvate, stereoisomer, or prodrug thereof; or a tautomer or a pharmaceutically acceptable salt, solvate, stereoisomer, or prodrug thereof; or a mixture thereof. In some such embodiments, v is 0, 1, or 2. In some such embodiments, w is 1.

In some embodiments of any of those described above, $R^3$, $R^4$, and $R^5$ are all H.

In some embodiments of any of those described above, $R^2$ is H.

In some embodiments of any of those described above, $R^1$ is H or methyl and in some embodiments is H.

In still other embodiments, the compound has the formula IA or IB or is a mixture of these IA
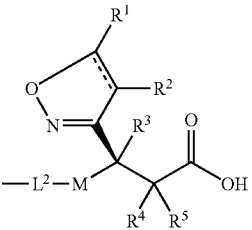

IB
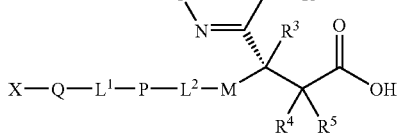

or is a pharmaceutically acceptable salt, solvate, or prodrug thereof; or a tautomer or a pharmaceutically acceptable salt, solvate, or prodrug thereof; or a mixture thereof.

In still other embodiments, the compound has the formula IIA or IIB or is a mixture of these

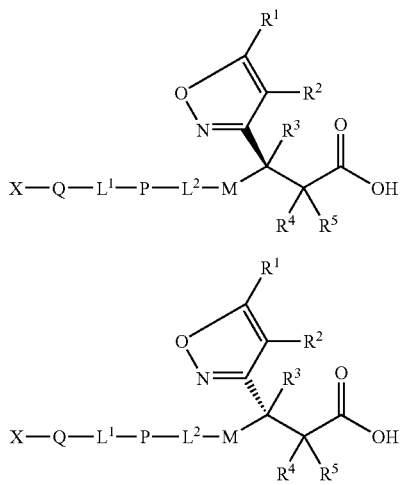

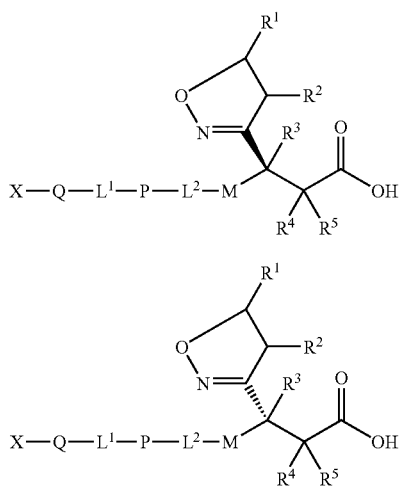

or is a pharmaceutically acceptable salt, solvate, or prodrug thereof; or a tautomer or a pharmaceutically acceptable salt, solvate, or prodrug thereof; or a mixture thereof.

In still other embodiments, the compound has the formula IIIA or IIIB or is a mixture of these or is a pharmaceutically acceptable salt, solvate, or prodrug thereof; or a tautomer or a pharmaceutically acceptable salt, solvate, or prodrug thereof; or a mixture thereof.

In some embodiments, the compound is selected from

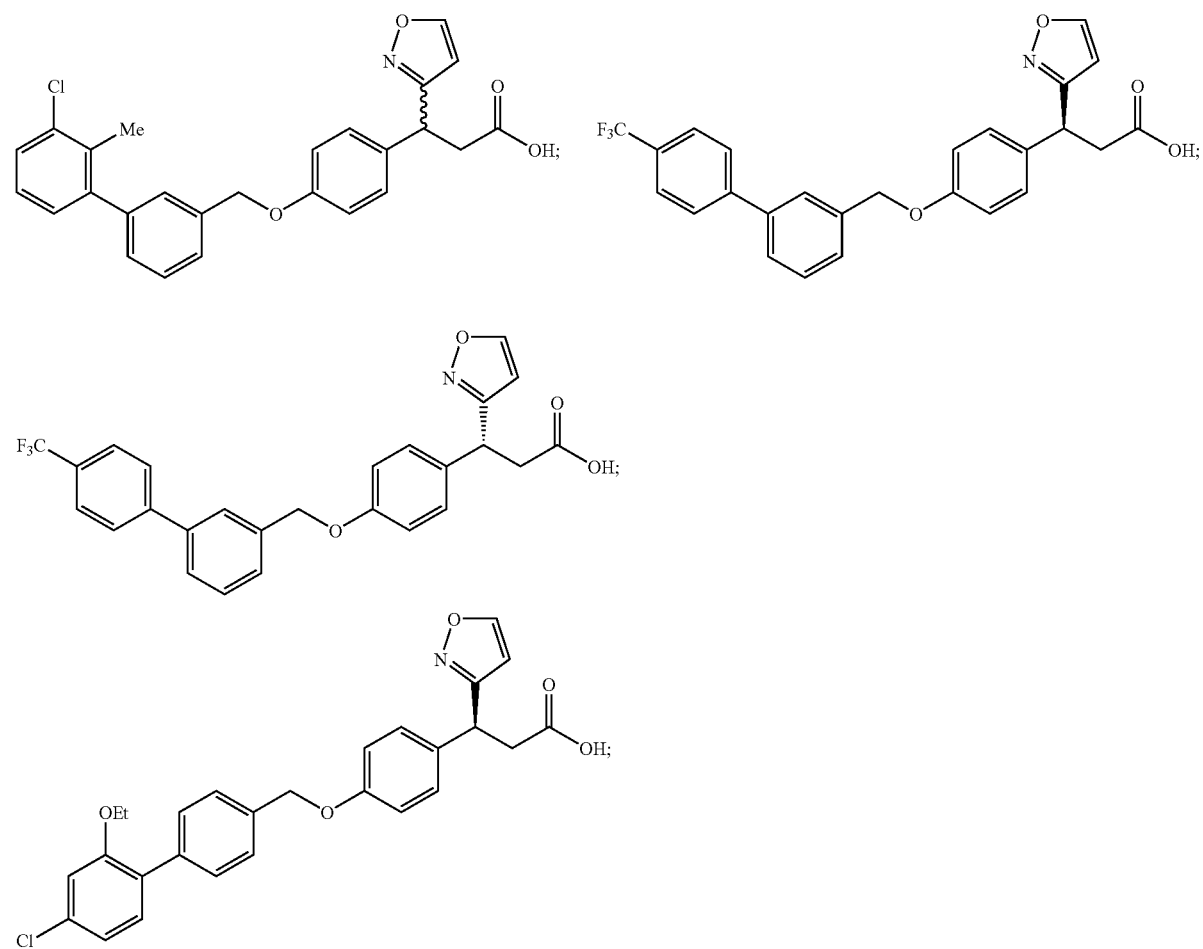

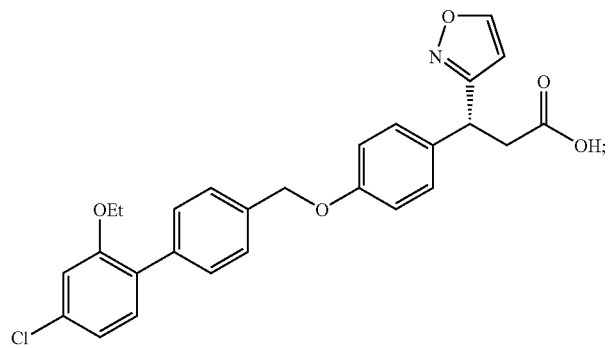
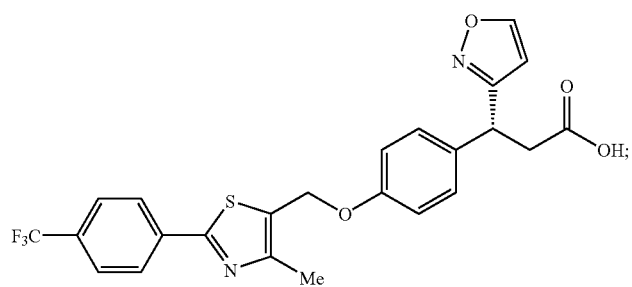
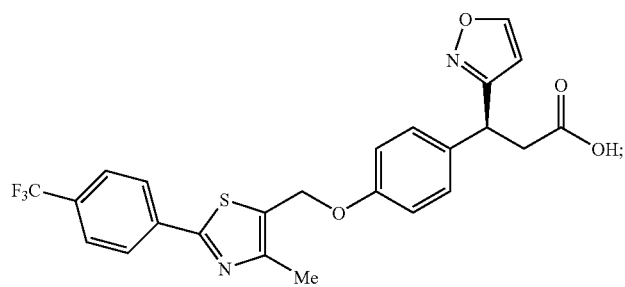
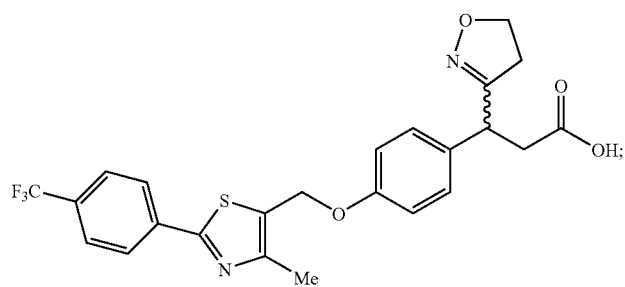
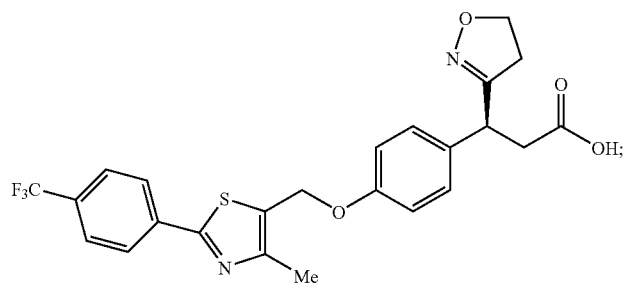

-continued
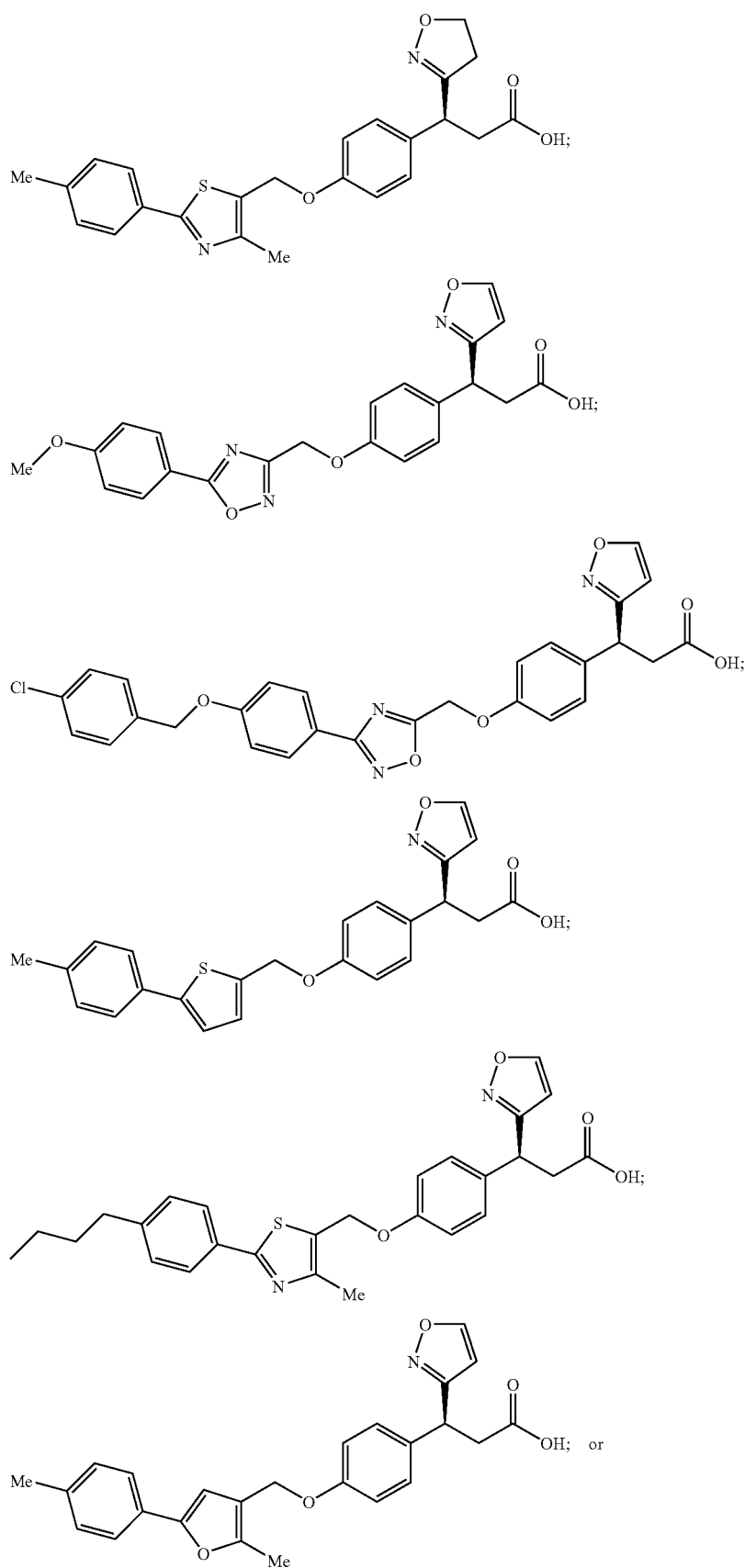

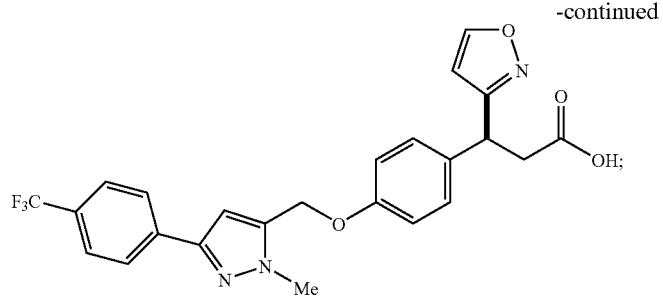
or a pharmaceutically acceptable salt, solvate, or prodrug thereof; or a tautomer or a pharmaceutically acceptable salt, solvate, or prodrug thereof; or a mixture thereof.
In some embodiments, the compound is selected from
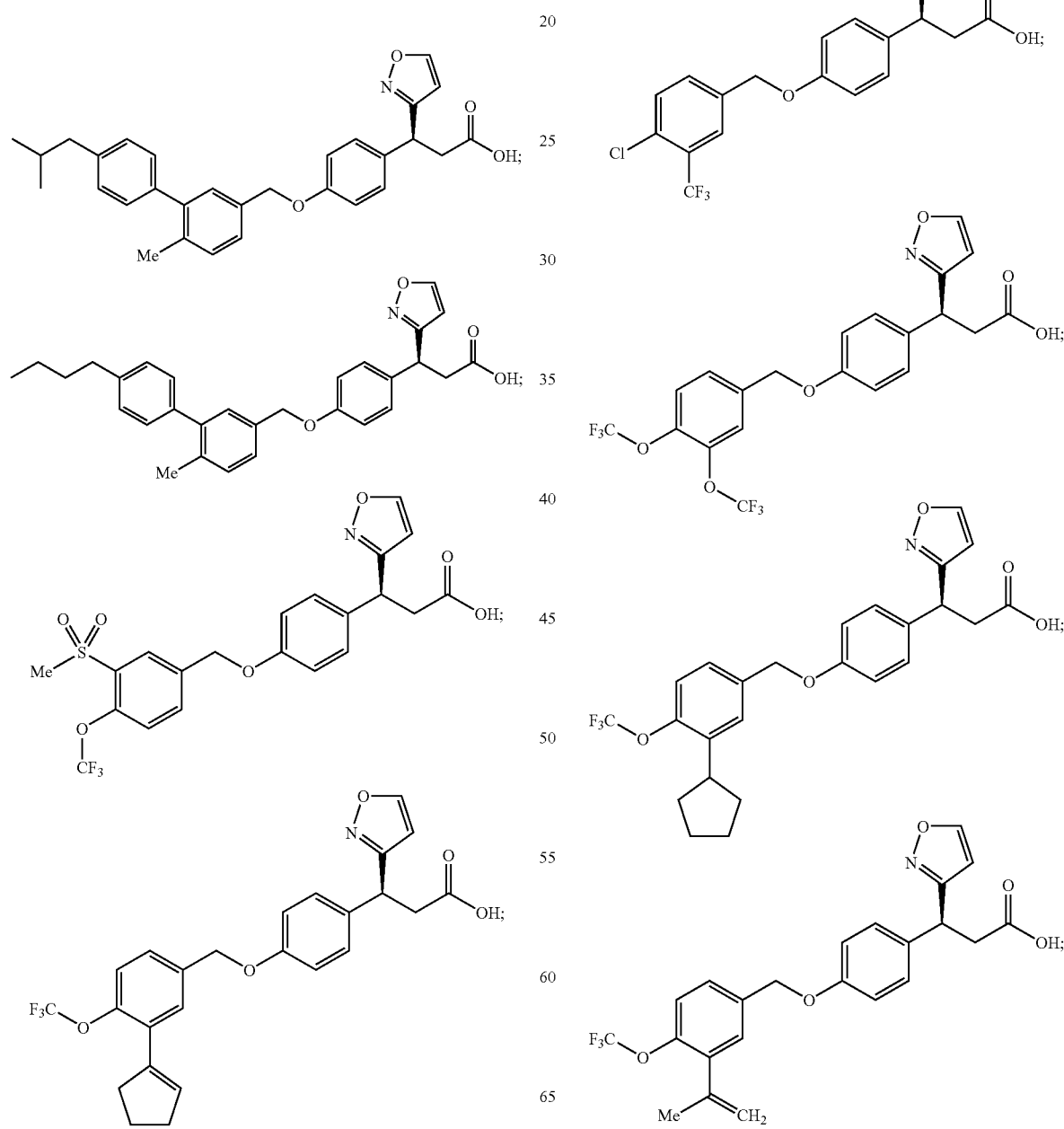

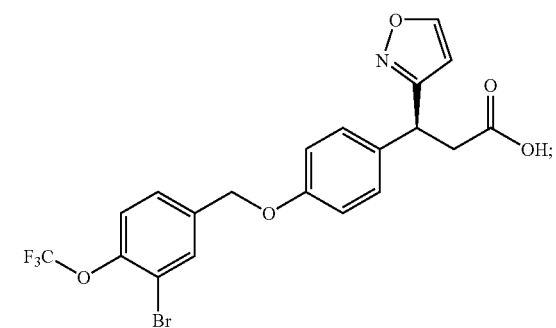

-continued

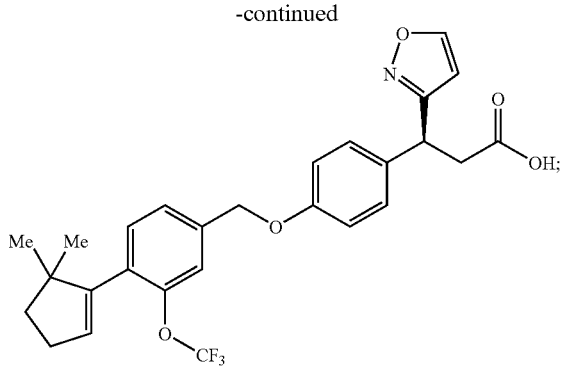

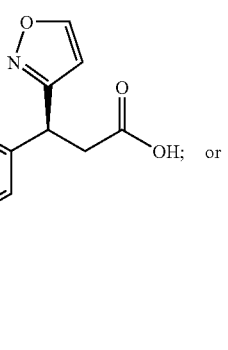

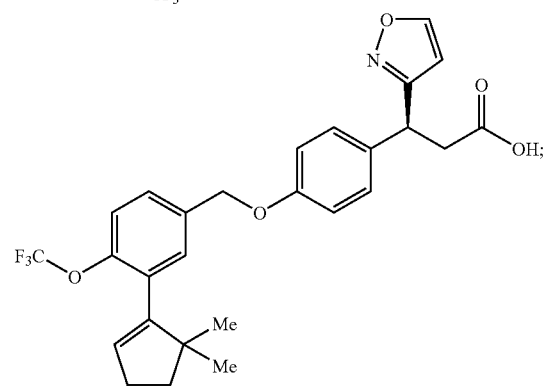

or a pharmaceutically acceptable salt, solvate, or prodrug thereof; or a tautomer or a pharmaceutically acceptable salt, solvate, or prodrug thereof; or a mixture thereof.

In another aspect, the present invention provides a compound having the formula I' or a pharmaceutically acceptable salt, solvate, stereoisomer, or prodrug thereof; or a tautomer or a pharmaceutically acceptable salt, solvate, stereoisomer, or prodrug thereof; or a mixture thereof:

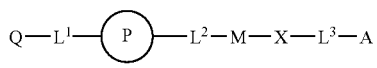

I' where Q, $L^1$, P, $L^2$, M, X, $L^3$, and A are defined below.

In compounds of formula I', Q is hydrogen, aryl, heteroaryl, $(C_1-C_6)$alkyl, or $(C_2-C_6)$heteroalkyl. In certain embodiments, Q is hydrogen, aryl, or heteroaryl. In certain embodiments, Q is a substituted or unsubstituted phenyl.

In compounds of formula I', $L^1$ is a bond, $(C_1-C_4)$alkylene, $(C_2-C_4)$heteroalkylene, O, $S(O)_k$, $N(R^a)$, $C(O)-(C_5-C_7)$heterocycloalkylene, $(C_1-C_4)$alkylene-$SO_2N(R^b)$, $(C_1-C_4)$alkylene-$N(R^b)SO_2$, or $C(O)N(R^b)$. In certain embodiments, $L^1$ is a bond. In some such embodiments, Q is H.

In compounds of formula I',

represents an optionally substituted benzo-fused $(C_5-C_8)$cycloalkane ring comprising a benzene ring fused to a $(C_5-C_8)$ cycloalkane ring, an optionally substituted heterobenzo-fused $(C_5-C_8)$cycloalkane ring comprising a six-membered heteroaryl ring comprising 1 or 2 N atoms fused to a $(C_5-C_8)$ cycloalkane ring, or a heteroaryl-fused $(C_5-C_8)$cycloalkane ring comprises a five-membered heteroaryl ring comprising 1 or 2 N heteroatoms, generally selected from O, N, and S, fused to a $(C_5-C_8)$cycloalkane ring, wherein the benzene ring of the benzo-fused $(C_5-C_8)$cycloalkane ring, the heteroaryl ring of the heterobenzo-fused $(C_5-C_8)$cycloalkane ring, or the heteroaryl ring of the heteroaryl-fused $(C_5-C_8)$cycloalkane ring is bonded to $L^2$ or M, if $L^2$ is a bond. In some embodiments,

is a benzo-fused $(C_5-C_8)$cycloalkane ring. In some embodiments,

is a substituted benzo-fused $(C_5-C_8)$cycloalkane ring. In some embodiments,

is an unsubstituted benzo-fused $(C_5-C_8)$cycloalkane ring. In some embodiments,

is a heterobenzo-fused $(C_5-C_8)$cycloalkane ring. In some such embodiments, the heteroaryl ring of the heterobenzo-fused $(C_5-C_8)$cycloalkane ring comprises 1 N atom. For example, the heteroaryl ring of the heterobenzo-fused $(C_5-C_8)$cycloalkane ring may be a pyridine ring. In other such embodiments, the heteroaryl ring of the heterobenzo-fused $(C_5-C_8)$cycloalkane ring comprises 2 N atoms. For example, the heteroaryl ring of the heterobenzo-fused $(C_5-C_8)$cycloalkane ring may be a pyrimidine, pyrazine, or pyridazine ring. In some embodiments,

is a substituted heterobenzo-fused ($C_5$-$C_8$)cycloalkane ring. In some embodiments,

is an unsubstituted heterobenzo-fused ($C_5$-$C_8$)cycloalkane ring. In some embodiments,

is a heteroaryl-fused ($C_5$-$C_8$)cycloalkane ring. In some such embodiments, the heteroaryl ring of the heteroaryl-fused ($C_5$-$C_8$)cycloalkane ring comprises 1 N atom. In some embodiment the heteroaryl ring of the heteroaryl-fused ($C_5$-$C_8$)cycloalkane ring comprises 1 N atom and either 1 O atom or 1 S atom. In other such embodiments, the heteroaryl ring of the heteroaryl-fused ($C_5$-$C_8$)cycloalkane ring comprises 2 N atoms. In some embodiments,

is a substituted heteroaryl-fused ($C_5$-$C_8$)cycloalkane ring. In some embodiments,

is an unsubstituted heteroaryl-fused ($C_5$-$C_8$)cycloalkane ring. In some embodiments, the ($C_5$-$C_8$)cycloalkane ring of the benzo-fused ($C_5$-$C_8$)cycloalkane ring, the heterobenzo-fused ($C_5$-$C_8$)cycloalkane ring, or the heteroaryl-fused ($C_5$-$C_8$)cycloalkane ring of

comprises 0-3 heteroatoms selected from O, N, or S. In some such embodiments, the cycloalkane ring comprises 1 or 2 heteroatom ring members selected from O or N, and in some embodiments 1 heteroatom ring member, selected from O or N. In some such embodiments, the cycloalkane comprises 0 heteroatom ring atoms such that each of the cycloalkane ring members of the benzo-fused ($C_5$-$C_8$)cycloalkane, the heterobenzo-fused ($C_5$-$C_8$)cycloalkane, or the heteroaryl-fused ($C_5$-$C_8$)cycloalkane ring is a carbon atom. In some such embodiments,

is selected from the group consisting of dihydroindene (i.e., indane or a benzo-cyclopentyl ring), tetrahydronaphthalene (i.e., a benzo-cyclohexyl ring), tetrahydrobenzo[7]annulene (i.e., a benzo-cycloheptyl ring), and hexahydrobenzo[8]annulene (i.e., a benzo-cyclooctyl ring). In some embodiments,

is a heteroaryl-fused ($C_5$-$C_8$)cycloalkane ring and the heteroaryl of the heteroaryl-fused ($C_5$-$C_8$)cycloalkane ring is selected from pyrrole, furan, thiophene, imidazole, thiazole, or oxazole.

In compounds of formula I', $L^2$ is a bond, ($C_1$-$C_6$)alkylene, ($C_2$-$C_6$)heteroalkylene, oxymethylene, O, $S(O)_k$, $N(R^a)$, $C(O)N(R^b)$, $SO_2N(R^b)$, ($C_1$-$C_4$)alkylene-$C(O)N(R^b)$, ($C_1$-$C_4$)alkylene-$N(R^b)C(O)$, ($C_2$-$C_4$)alkenylene-$C(O)N(R^b)$, ($C_2$-$C_4$)alkenylene-$N(R^b)C(O)$, ($C_1$-$C_4$)alkylene-$SO_2N(R^b)$, ($C_1$-$C_4$)alkylene-$N(R^b)SO_2$, ($C_2$-$C_4$)alkenylene-$SO_2N(R^b)$, or ($C_2$-$C_4$)alkenylene-$N(R^b)SO_2$. In some embodiments, $L^2$ is selected from ($C_1$-$C_6$)alkylene, ($C_2$-$C_6$)heteroalkylene, oxymethylene, O, or $S(O)_k$. In some embodiments, $L^2$ is selected from —$CH_2$—O—, substituted oxymethylene, or O. In some embodiments, $L^2$ is selected from —$CH_2$—O— or —$CH(CH_3)$—O—. In some embodiments, $L^2$ is selected from —$CH_2$—O— or an alkyl-substituted oxymethylene. In certain embodiments, $L^2$ is O or $S(O)_k$.

In compounds of formula I', M is an aromatic ring, a heteroaromatic ring, ($C_5$-$C_8$)cycloalkylene, aryl($C_1$-$C_4$)alkylene or heteroaryl($C_1$-$C_4$)alkylene. In certain embodiments where M is an aromatic ring, the term aromatic includes aryl. In other embodiments where M is a heteroaromatic ring, the term heteroaromatic includes heteroaryl. In some embodiments, M is an aromatic ring or is a heteroaromatic ring. In certain embodiments, M is a monocyclic aromatic or is a monocyclic heteroaromatic ring. In some embodiments, M is an unsubstituted monocyclic aromatic ring or is an unsubstituted monocyclic heteroaromatic ring. In certain embodiments, M is a substituted benzene ring. In other embodiments, M is an unsubstituted benzene ring. In some embodiments, M is a heteroaromatic ring comprising six ring members. In some such embodiments, the heteroaromatic ring comprises 1 or 2 N atoms. In some such embodiments, the heteroaromatic ring comprises 1 N atom, and in other such embodiments, the heteroaromatic ring comprises 2 N atoms.

In compounds of formula I', X is $CR^1R^1$.

In certain embodiments of the compounds of formula I', M is a substituted or unsubstituted benzene ring and X is para to $L^2$.

In compounds of formula I', $L^3$ is a ($C_1$-$C_5$)alkylene, or ($C_2$-$C_5$)heteroalkylene. In some embodiments, $L^3$ is a ($C_1$-$C_5$)alkylene or is a ($C_2$-$C_5$)heteroalkylene. In certain embodiments, $L^3$ is ($C_1$-$C_3$)alkylene. In some embodiments, $L^3$ is methylene. In certain embodiments, $L^3$ is a methylene substituted with a monocyclic aryl or monocyclic heteroaryl.

In compounds of formula I', A is —$CO_2H$, tetrazol-5-yl, —$SO_3H$, —$PO_3H_2$, —$SO_2NH_2$, —$C(O)NHSO_2CH_3$, —CHO, thiazolidinedion-yl, hydroxyphenyl, or pyridyl. In some embodiments, A is —$CO_2H$, tetrazol-5-yl, —$SO_3H$, —$PO_3H_2$, —$SO_2NH_2$, —$C(O)NHSO_2CH_3$, thiazolidinedio-nyl, hydroxyphenyl, or pyridyl In certain embodiments, A is —$CO_2H$ or a salt thereof. In some embodiments, A is —$CO_2H$ or an alkyl ester thereof. In some such embodiments, A is a $C_1$-$C_6$ alkyl ester such as a methyl, ethyl, propyl, butyl, pentyl, or hexyl ester.

In compounds of formula I', $R^a$ is hydrogen, ($C_1$-$C_6$)alkyl, aryl($C_1$-$C_3$) alkyl, or ($C_2$-$C_6$)heteroalkyl. In certain embodiments, $R^a$ is ($C_1$-$C_6$)alkyl or ($C_2$-$C_6$)heteroalkyl.

In compounds of formula I', $R^b$ is hydrogen, $(C_1-C_6)$alkyl, or $(C_2-C_6)$heteroalkyl.

In compounds of formula I', $R^1$ is a group of formula:

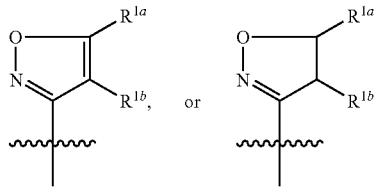

where $R^{1a}$ is selected from H, or $(C_1-C_6)$alkyl, and $R^{1b}$ is selected from H, or $(C_1-C_6)$alkyl. In some embodiments, one or $R^{1a}$ and $R^{1b}$ is H. In other embodiments, both of $R^{1a}$ and $R^{1b}$ are H.

In compounds of formula I', $R^{1'}$ is hydrogen, cyano, aryl, heteroaryl, $(C_1-C_8)$alkyl, $(C_2-C_8)$alkenyl, or $(C_2-C_8)$alkynyl. In some embodiments, $R^{1'}$ is hydrogen or methyl. In some such embodiments, $R^{1'}$ is hydrogen.

The subscript k is, in each instance, independently selected from 0, 1, or 2. In some embodiments, k is 0.

In certain embodiments, the compound of the present invention is a pharmaceutically acceptable salt, solvate, stereoisomer, or prodrug of the compound of formula I'; or a tautomer, or a pharmaceutically acceptable salt, solvate, stereoisomer, or prodrug of the tautomer; or a mixture thereof.

In certain embodiments, the present invention provides a compound having the formula II' or a pharmaceutically acceptable salt, solvate, stereoisomer, or prodrug thereof; or a tautomer, or a pharmaceutically acceptable salt, solvate, stereoisomer, or prodrug thereof; or a mixture thereof:

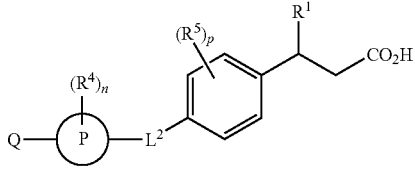

II' where Q is selected from hydrogen, aryl, or heteroaryl; $L^2$ is selected from $(C_1-C_6)$alkylene, $(C_2-C_6)$heteroalkylene, oxymethylene, O, or $S(O)_k$; $R^1$ is a group having the formula described above with respect to the compound of formula I', $R^4$ is independently selected from substituted $(C_1-C_6)$alkyl, —R', —OR', =O, =NR', =N—OR', —NR'R", —SR', halogen, —OC(O)R', —C(O)R', —CO$_2$R', —CONR'R", —OC(O)NR'R", —NR"C(O)R', —NR'—C(O)NR"R''', —NR'—SO$_2$NR"R''', —NR"CO$_2$R', —NH—C(NH$_2$)=NH, —NR'C(NH$_2$)=NH, —NH—C(NH$_2$)=NR', —SiR'R"R''', —S(O)R', —SO$_2$R', —SO$_2$NR'R", —NR"SO$_2$R, —CN, —(C$_2$-C$_5$) alkynyl, —(C$_2$-C$_5$) alkenyl, or —NO$_2$, where R', R" and R''' each independently refer to hydrogen, unsubstituted $(C_1-C_8)$ alkyl or heteroalkyl, unsubstituted aryl, aryl substituted with one to three halogens, unsubstituted alkyl, alkoxy or thioalkoxy groups, halo$(C_1-C_4)$alkyl, or aryl-$(C_1-C_4)$alkyl groups; $R^5$ is independently selected from $(C_1-C_6)$alkyl, halogen, $(C_1-C_6)$alkoxy, cyano, or nitro; the subscript k is 0, 1, or 2; the subscript n is 0, 1, 2, 3, 4, 5, 6, 7, 8, 9, 10, 11, 12, 13, or 14; and the subscript p is 0, 1, 2, 3, or 4. In some such embodiments, $R^4$ is independently selected from $(C_1-C_6)$ alkyl, halogen, $(C_1-C_6)$alkoxy, cyano, or nitro. In certain embodiments,

is a benzo-fused $(C_5-C_8)$cycloalkane ring selected from substituted or unsubstituted dihydroindene, tetrahydronaphthalene, tetrahydrobenzo[7]annulene, or hexahydrobenzo[8]annulene. In certain embodiments, the subscript p is 0.

It will be apparent that, in certain embodiments of formula II', the carbon with a bond to $R^1$ is a chiral carbon. Thus, in certain embodiments, the present invention provides a compound having formula IIIA' or IIIB' or a pharmaceutically acceptable salt, solvate, or prodrug thereof or a tautomer, or a pharmaceutically acceptable salt, solvate, or prodrug thereof; or a mixture thereof:

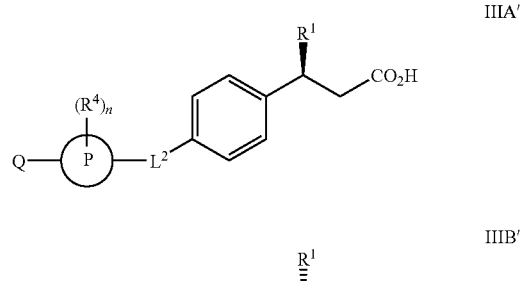

where the variables can have any of the values in any of the embodiments described above.

In some embodiments, the compound of formula II' comprises a stereomerically pure S-enantiomer. In other embodiments, the compound of formula II' comprises a stereomerically pure R-enantiomer. In yet other embodiments, the compound of formula II' comprises a mixture of S- and R-enantiomers.

In certain embodiments, the compound of the present invention is a pharmaceutically acceptable salt, solvate, stereoisomer, or prodrug of the compound of formula II'; or a tautomer, or a pharmaceutically acceptable salt, solvate, stereoisomer, or prodrug thereof; or a mixture thereof.

In some embodiments of formula II', IIIA', and IIIB', the hydrogen on the carboxylic group in formula II' is replaced with an alkyl group to form an ester. For example, the compound of the present invention can be a methyl or ethyl ester of the compound of formula II'.

In certain embodiments of the compound of formula I', the compound has the formula IV' or is a pharmaceutically acceptable salt, solvate, stereoisomer, or prodrug thereof; or a tautomer, or a pharmaceutically acceptable salt, solvate, stereoisomer, or prodrug thereof; or a mixture thereof:

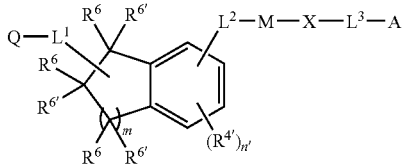

where $R^{4'}$ is independently selected from substituted ($C_1$-$C_6$) alkyl, —R', —OR', =O, =NR', =N—OR', —NR'R", —SR', halogen, —OC(O)R', —C(O)R', —CO$_2$R', —CONR'R", —OC(O)NR'R", —NR"C(O)R', —NR'—C(O)NR"R"', —NR'—SO$_2$NR"R"', —NR"CO$_2$R', —NH—C(NH$_2$)=NH, —NR'C(NH$_2$)=NH, —NH—C(NH$_2$)=NR', —SiR'R"R"', —S(O)R', —SO$_2$R', —SO$_2$NR'R", —NR"SO$_2$R, —CN, —($C_2$-$C_5$) alkynyl, —($C_2$-$C_5$) alkenyl, or —NO$_2$, where R', R" and R"' each independently refer to hydrogen, unsubstituted ($C_1$-$C_8$)alkyl or heteroalkyl, unsubstituted aryl, aryl substituted with one to three halogens, unsubstituted alkyl, alkoxy or thioalkoxy groups, halo($C_1$-$C_4$)alkyl, or aryl-($C_1$-$C_4$)alkyl groups; one of $R^6$ and $R^{6'}$ is $L^1$ or Q, if $L^1$ is a bond, and the others of $R^6$ and $R^{6'}$ are independently selected from H, ($C_1$-$C_6$)alkyl, halogen, ($C_1$-$C_6$) alkoxy, cyano, or nitro, or one of $R^6$ and one of $R^{6'}$ on adjacent or non-adjacent carbon atoms, or on the same carbon atom, may join together to form a $C_5$-$C_8$ cycloalkane ring, or two of $R^6$ or two of $R^{6'}$, on adjacent or non-adjacent carbon atoms, may join together to form a $C_5$-$C_8$ cycloalkane ring; the subscript n' is 0, 1, 2, or 3; and the subscript m is 1, 2, 3, or 4.

In some embodiments, the compound of formula IV' comprises a stereomerically pure S-enantiomer. In other embodiments, the compound of formula IV' comprises a stereomerically pure R-enantiomer. In yet other embodiments, the compound of formula IV' comprises a mixture of S- and R-enantiomers.

In some embodiments, the compound of formula IV' has the formula V':

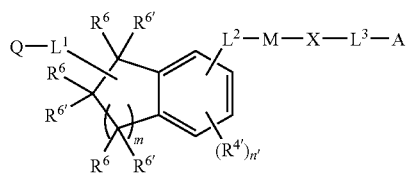

or is a pharmaceutically acceptable salt, solvate, stereoisomer or prodrug thereof; or a tautomer, or a pharmaceutically acceptable salt, solvate, stereoisomer, or prodrug thereof; or a mixture thereof.

In some embodiments, the compound of formula IV' or V', the compound has the formula VI':

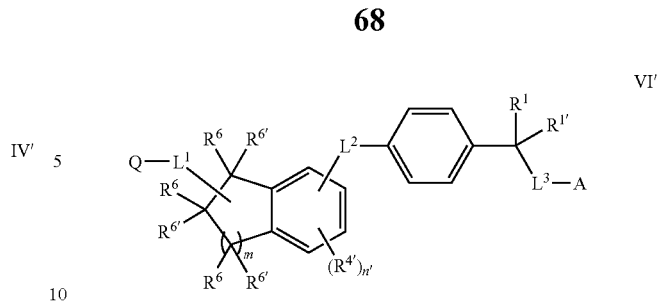

or is a pharmaceutically acceptable salt, solvate, stereoisomer or prodrug thereof; or a tautomer, or a pharmaceutically acceptable salt, solvate, stereoisomer, or prodrug thereof; or a mixture thereof.

It will be apparent that, in certain embodiments of formula VI', the carbon with a bond to $R^1$ is a chiral carbon. Thus, in certain embodiments, the present invention provides a compound having formula VIA' or VIB' or a pharmaceutically acceptable salt, solvate, or prodrug thereof or a tautomer, or a pharmaceutically acceptable salt, solvate, or prodrug thereof; or a mixture thereof:

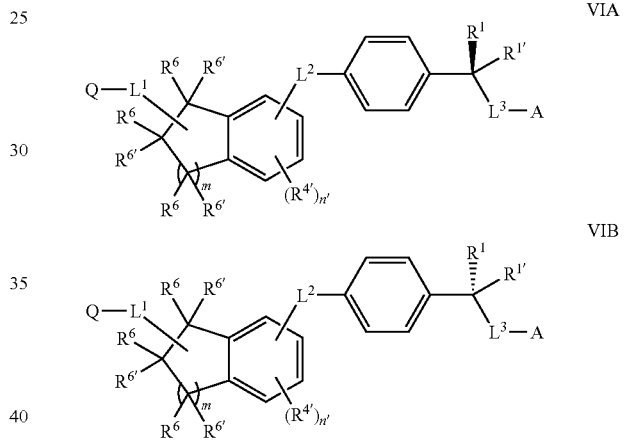

where the variables can have any of the values in any of the embodiments described above.

In some embodiments, the compound of formula VI' comprises a stereomerically pure S-enantiomer. In other embodiments, the compound of formula VI' comprises a stereomerically pure R-enantiomer. In yet other embodiments, the compound of formula VI' comprises a mixture of S- and R-enantiomers.

In certain embodiments, the compound of the present invention is a pharmaceutically acceptable salt, solvate, stereoisomer, or prodrug of the compound of formula II'; or a tautomer, or a pharmaceutically acceptable salt, solvate, stereoisomer, or prodrug thereof; or a mixture thereof.

In some embodiments of formula IV', V', VI', VIA', and VIB', A is —CO$_2$H or is a salt thereof. In some embodiments, the hydrogen on the carboxylic group of A is replaced with an alkyl group to form an ester. For example, the compound of the present invention can be a methyl or ethyl ester of the compound of formula IV', V', VI', VIA', or VIB'.

In some embodiments of the compounds of formula IV', V', VI', VIA', and VIB', the subscript m is 1 or 2.

In some embodiments of the compounds of formula IV', V', VI', VIA', and VIB', the subscript m is 1 or 2; the subscript n' is 0; $L^1$ is a bond; $L^2$ is selected from —CH$_2$—O—, substituted oxymethylene, or O; $R^{1'}$ is H; and A is —CO$_2$H.

In some embodiments of the compounds of formula IV', V', VI', VIA', and VIB', Q is H; $L^3$ is $CH_2$; and $L^2$ is —$CH_2$—O— or —$CH(CH_3)$—O—.

In some embodiments of the compounds of formula IV', V', VI', VIA', and VIB', $R^6$ and $R^{6'}$ are independently selected from H and $(C_1-C_6)$alkyl and at least two of $R^6$ and $R^{6'}$ are $(C_1-C_6)$alkyl. In some such embodiments, $R^6$ and $R^{6'}$ are independently selected from H and methyl and at least two of $R^6$ and $R^{6'}$ are methyl groups. In some such embodiments, two of $R^6$ and $R^{6'}$ are methyl groups. In some embodiments, $R^6$ and $R^{6'}$ are independently selected from H and methyl and at least four of $R^6$ and $R^{6'}$ are methyl groups. In some such embodiments, $R^6$ and $R^{6'}$ are independently selected from H and methyl and four of $R^6$ and $R^{6'}$ are methyl groups.

In certain embodiments, the compound has the formula VIIA', VIIB', VIIC', or VIID':

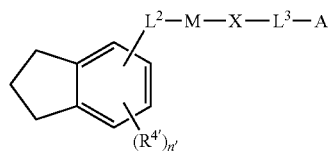
VIIA'

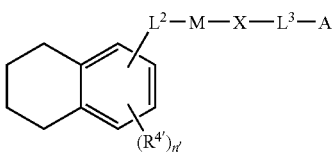
VIIB'

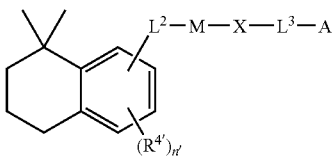
VIIC'

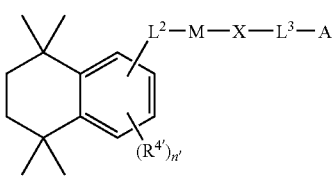
VIID' or a pharmaceutically acceptable salt, solvate, or prodrug thereof; or a tautomer or a pharmaceutically acceptable salt, solvate, or prodrug thereof; or a mixture thereof.

In certain embodiments, the compound of formula VIIA', VIIB', VIIC', or VIID', has the formula VIIIA', VIIIB', VIIIC', or VIIID':

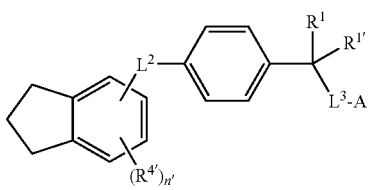
VIIIA'

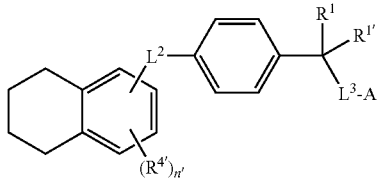
VIIIB'

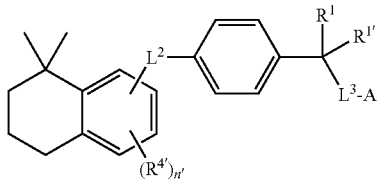
VIIIC'

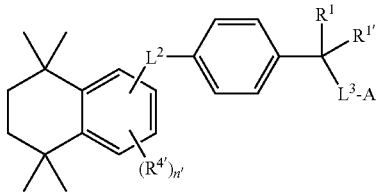
VIIID' or a pharmaceutically acceptable salt, solvate, or prodrug thereof; or a tautomer or a pharmaceutically acceptable salt, solvate, or prodrug thereof; or a mixture thereof.

In certain embodiments, the compound of formula VIIIA', VIIIB', VIIIC', or VIIID', has the formula IXA', IXB', IXC', or IXD':

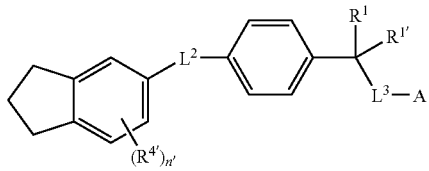
IXA'

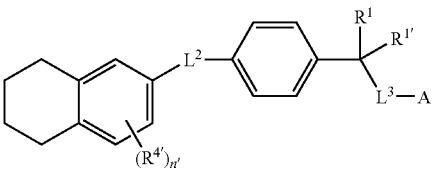
IXB'

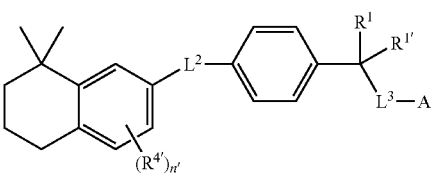
IXC'

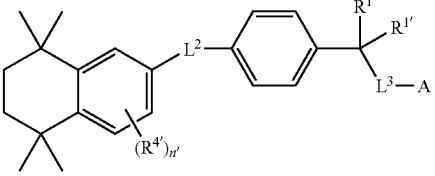
IXD' or a pharmaceutically acceptable salt, solvate, or prodrug thereof; or a tautomer or a pharmaceutically acceptable salt, solvate, or prodrug thereof; or a mixture thereof.

In certain embodiments of the compound of formula VIIA', VIIB', VIIC', VIID', VIIIA', VIIIB', VIIIC', VIIID', IXA', IXB', IXC', or IXD', $L^2$ is —$CH_2$—O— or an alkyl-substituted oxymethylene; the subscript n' is 0; $R^{1'}$ is H; and A is —$CO_2H$. In some embodiments, the compound is a compound of formula VIIA'. In some embodiments, the compound is a compound of formula VIIB'. In some embodiments, the compound is a compound of formula VIIC'. In some embodiments, the compound is a compound of formula VIID'. In some embodiments, the compound is a compound of formula VIIIA'. In some embodiments, the compound is a compound of formula VIIIB'. In some embodiments, the compound is a compound of formula VIIIC'. In some embodiments, the compound is a compound of formula VIIID'. In some embodiments, the compound is a compound of formula IXA'. In some embodiments, the compound is a compound of formula IXB'. In some embodiments, the compound is a compound of formula IXC'. In some embodiments, the compound is a compound of formula IXD'.

In certain embodiments, the compound of formula IXA', IXB', IXC', or IXD', has the formula XA', XB', XC', or XD':

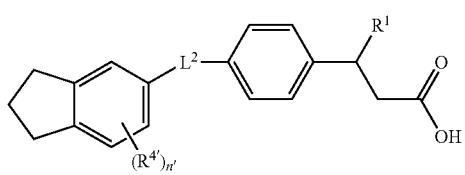

XA'

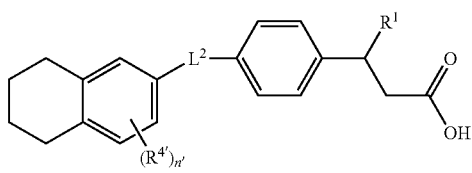

XB'

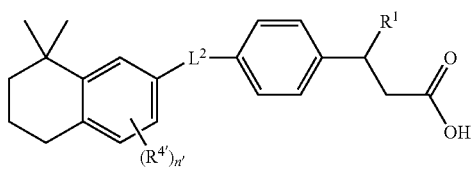

XC'

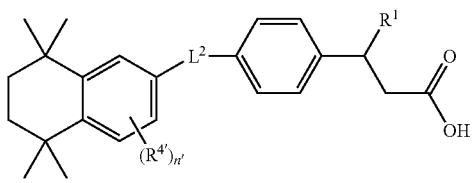

XD' or a pharmaceutically acceptable salt, solvate, or prodrug thereof; or a tautomer or a pharmaceutically acceptable salt, solvate, or prodrug thereof; or a mixture thereof.

In certain embodiments of the compound of formula XA', XB', XC', or XD', $L^2$ is —$CH_2$—O— or an alkyl-substituted oxymethylene; the subscript n' is 0; and $R^{1'}$ is H. In some embodiments, the compound is a compound of formula XA'. In some embodiments, the compound is a compound of formula XB'. In some embodiments, the compound is a compound of formula XC'. In some embodiments, the compound is a compound of formula XD'.

In certain embodiments of the compound of formula I', the compound has the formula of any one of XIa'-XIm' or is a pharmaceutically acceptable salt, solvate, stereoisomer, or prodrug thereof; or a tautomer, or a pharmaceutically acceptable salt, solvate, stereoisomer, or prodrug thereof; or a mixture thereof:

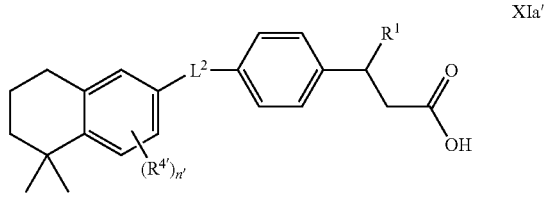

XIa'

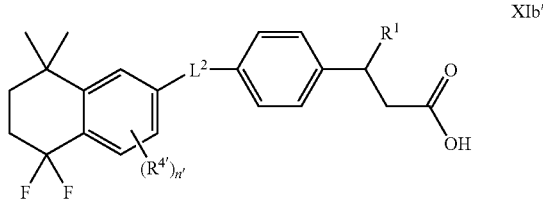

XIb'

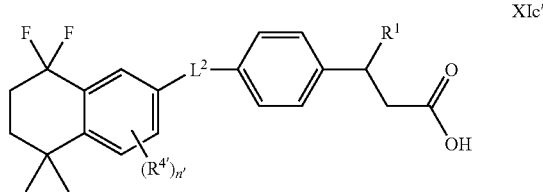

XIc'

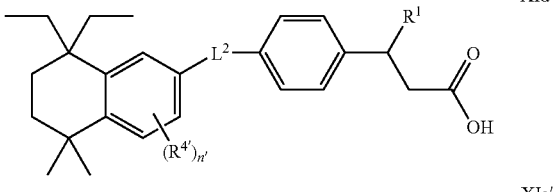

XId'

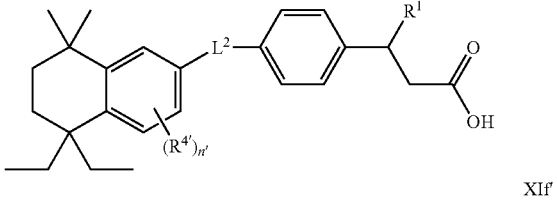

XIe'

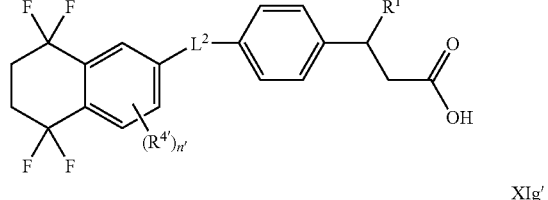

XIf'

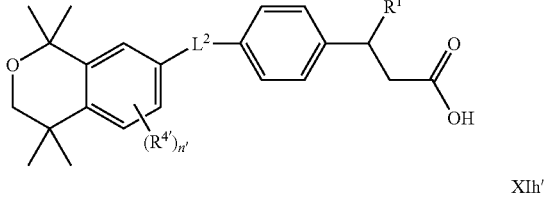

XIg'

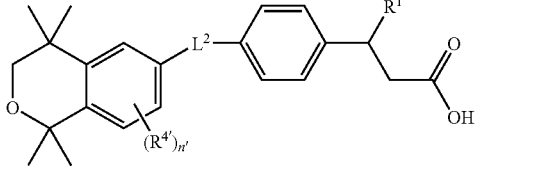

XIh'

-continued

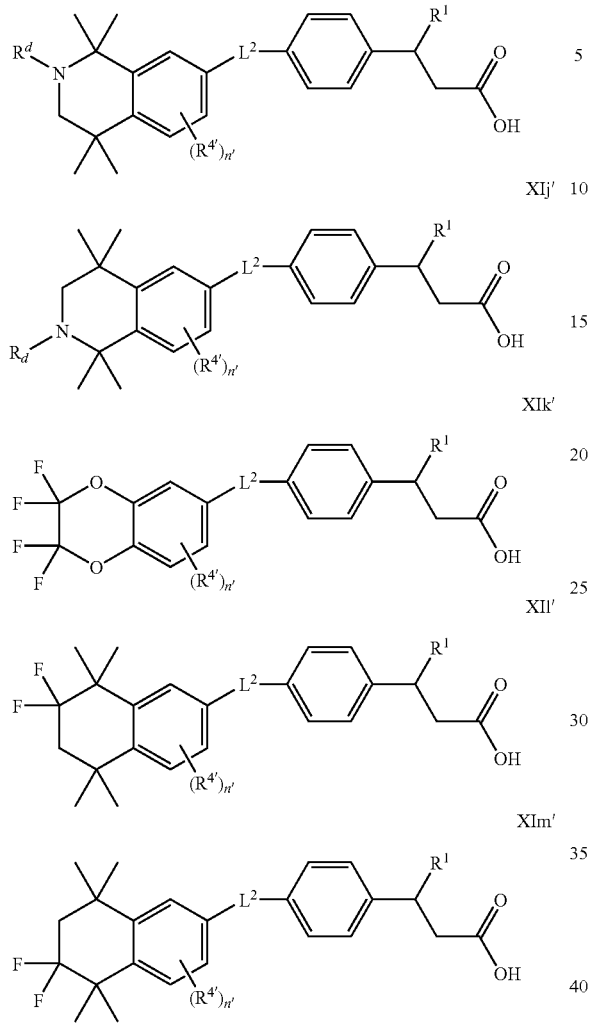

where R⁴' is independently selected from substituted $(C_1-C_6)$ alkyl, —R', —OR', =O, =NR', =N—OR', —NR'R", —SR', halogen, —OC(O)R', —C(O)R', —CO₂R', —CONR'R", —OC(O)NR'R", —NR"C(O)R', —NR'—C(O) NR"R'", —NR'—SO₂NR"R'", —NR"CO₂R', —NH—C (NH₂)=NH, —NR'C(NH₂)=NH, —NH—C(NH₂)=NR', —SiR"R"R'", —S(O)R', —SO₂R', —SO₂NR'R", —NR"SO₂R, —CN, —$(C_2-C_5)$ alkynyl, —$(C_2-C_5)$ alkenyl, or —NO₂, where R', R" and R'" each independently refer to hydrogen, unsubstituted $(C_1-C_8)$alkyl or heteroalkyl, unsubstituted aryl, aryl substituted with one to three halogens, unsubstituted alkyl, alkoxy or thioalkoxy groups, halo($C_1$-$C_4$)alkyl, or aryl-($C_1$-$C_4$)alkyl groups; the subscript n' is 0, 1, 2, or 3; and $R^d$ is selected from optionally substituted $C_1$-$C_6$ alkyl or optionally substituted aryl.

In some embodiments, the compound of any one of formula XIa'-XIm' comprises a stereomerically pure S-enantiomer. In other embodiments, the compound comprises a stereomerically pure R-enantiomer. In yet other embodiments, the compound comprises a mixture of S- and R-enantiomers.

In certain embodiments of the compound of formula I, the compound has the formula of any one of XIIa'-XIIm' or is a pharmaceutically acceptable salt, solvate, stereoisomer, or prodrug thereof; or a tautomer, or a pharmaceutically acceptable salt, solvate, stereoisomer, or prodrug thereof; or a mixture thereof:

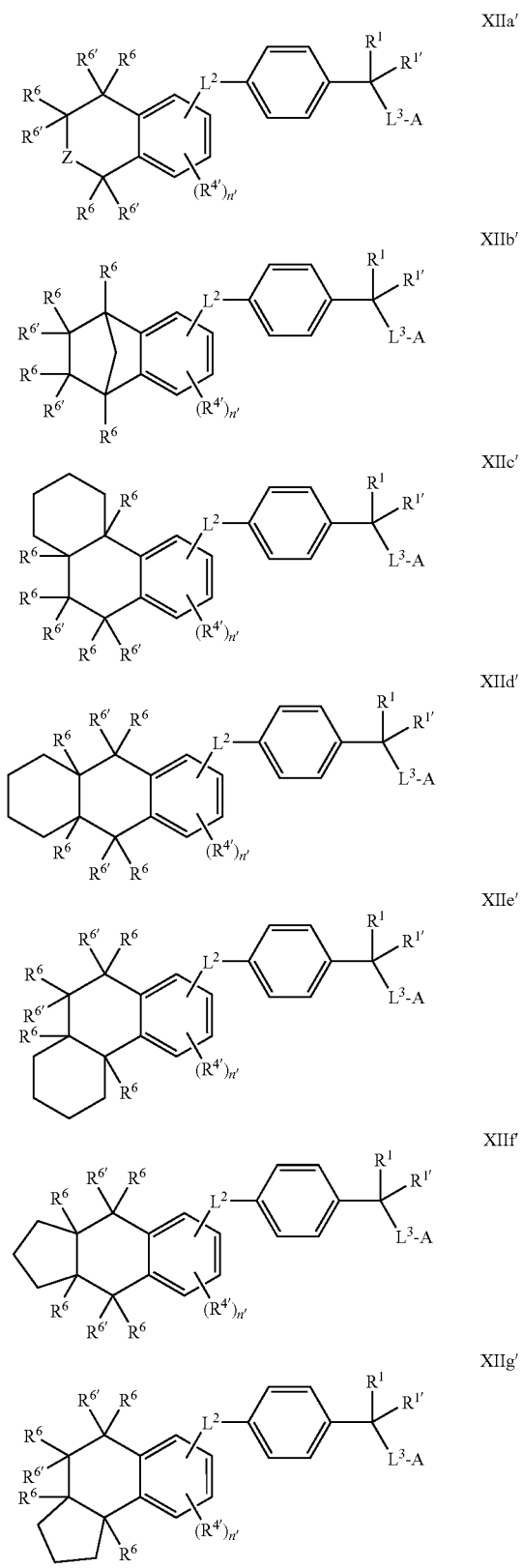

-continued

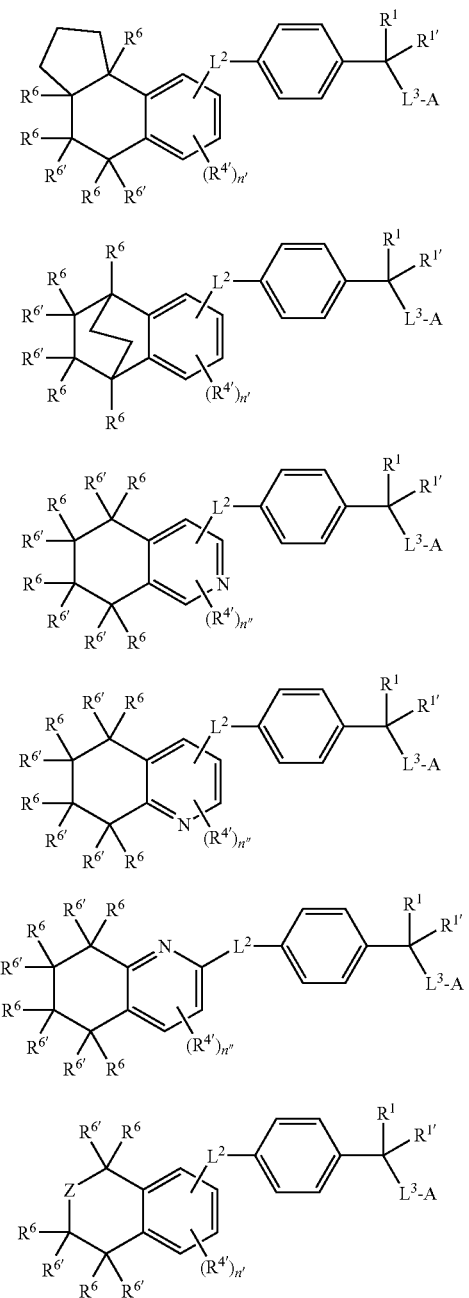

where $R^{4'}$ is independently selected from substituted $(C_1-C_6)$ alkyl, —R', —OR', =O, =NR', =N—OR', —NR'R''', —SR', halogen, —OC(O)R', —C(O)R', —CO$_2$R', —CONR'R'', —OC(O)NR'R'', —NR''C(O)R', —NR'—C(O)NR''R''', —NR'—SO$_2$NR''R''', —NR''CO$_2$R', —NH—C(NH$_2$)=NH, —NR'C(NH$_2$)=NH, —NH—C(NH$_2$)=NR', —SiR'R''R''', —S(O)R', —SO$_2$R', —SO$_2$NR'R'', —NR''SO$_2$R, —CN, —(C$_2$-C$_5$) alkynyl, —(C$_2$-C$_5$) alkenyl, or —NO$_2$, where R', R'' and R''' each independently refer to hydrogen, unsubstituted $(C_1-C_8)$alkyl or heteroalkyl, unsubstituted aryl, aryl substituted with one to three halogens, unsubstituted alkyl, alkoxy or thioalkoxy groups, halo(C$_1$-C$_4$)alkyl, or aryl-(C$_1$-C$_4$)alkyl groups; $R^6$ and $R^{6'}$ are independently selected from H, $(C_1-C_6)$alkyl, halogen, $(C_1-C_6)$ alkoxy, cyano, or nitro; Z is selected from O, $NR^d$, or S; $R^d$ is selected from optionally substituted $C_1-C_6$ alkyl or optionally substituted aryl; the subscript n' is 0, 1, 2, or 3; and the subscript n'' is 0, 1, or 2.

In some embodiments, the compound of any one of formula XIIa'-XIIm' comprises a stereomerically pure S-enantiomer. In other embodiments, the compound comprises a stereomerically pure R-enantiomer. In yet other embodiments, the compound comprises a mixture of S- and R-enantiomers.

In some embodiments, the compound of any of the embodiments is a salt. In other embodiments, the compound of any of the embodiments is a prodrug. In some such embodiments, the prodrug is a $C_1-C_6$ alkyl ester such as a methyl, ethyl, propyl, butyl, isopropyl, pentyl, or hexyl ester. In some such embodiments, the ester is a methyl or ethyl ester.

In some embodiments, the compound comprises a stereomerically pure S-enantiomer. In other embodiments, the compound comprises a stereomerically pure R-enantiomer. In yet other embodiments, the compound comprises a mixture of S- and R-enantiomers.

In another aspect, the invention provides pharmaceutical compositions comprising a pharmaceutically acceptable carrier, diluent, or excipient, and a compound of any of the embodiments of the invention.

5.2.2 Preparation of the Compounds

The compounds of the invention can be prepared by a variety of synthetic or semisynthetic techniques. Scheme 1 provides a general synthetic scheme for exemplary compounds of the invention utilizing ester A where the variables X, Q, $L^1$, P, $R^1$, $R^2$, $R^3$, $R^4$, and $R^5$ in Scheme 1 have any of the values described above with respect to any of the embodiments, W is a OH or a halogen such as, but not limited to a Cl, Br, or I, and Alk is a straight or branched chain alkyl group having from 1-8 carbon atoms. It will be understood that the phenolic OH group of A can be replaced with an SH and reacted with a compound where W is a halogen to produce the analogous S-containing derivative to the compounds shown. The synthesis of various groups of formula X-Q-$L^1$-P—CH$_2$—W are described in WO 2005/086661 and US 2006/0004012 which are both hereby incorporated by reference in their entireties and for all purposes as if fully set forth herein. Further relevant synthetic routes for related compounds are also described in these references. Appropriate starting materials can be prepared by techniques known or apparent to those of skill in the art or the starting materials may be commercially available. One of skill in the art will understand that the synthetic routes can be modified to use different starting materials or alternative reagents and that suitable adjustments in conditions (e.g., temperatures, solvents, etc.) can be made to accomplish the desired transformations. For example, one of skill in the art, will recognize that X-Q-$L^1$-P—CH$_2$—CH$_2$—W and other similar compounds are suitably used in place of X-Q-$L^1$-P—CH$_2$—W to produce compounds with a wide variety of $L^2$ groups. Additionally, one of skill in the art will recognize that protecting groups may be necessary for the preparation of certain compounds and will be aware of those conditions compatible with a selected protecting group. Examples of such protecting groups include, for example, those set forth in Protective Groups in Organic Synthesis, Greene, T. W.; Wuts, P. G. M., John Wiley & Sons, New York, N.Y., (3rd Edition, 1999). Accordingly, the exemplary methods and the examples described herein are illustrative of the present invention and are not to be construed as limiting the scope thereof.

Scheme 1

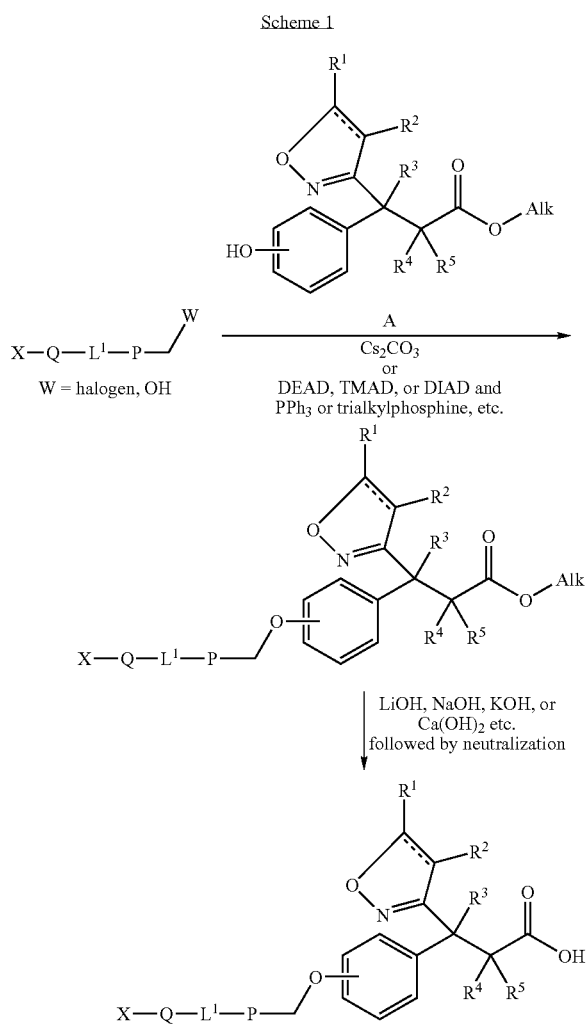

Scheme 2 shows a general synthetic route that can be used to prepare compounds of formula XV and XVI, and salts thereof. In the compound of formula XIII and XV, Alk is a straight or branched chain alkyl group having from 1 to 8 carbon atoms. Examples of such groups include methyl, ethyl, propyl, butyl, pentyl, hexyl, heptyl, octyl, i-propyl, s-butyl, t-butyl groups, and the like. In some embodiments, Alk is a methyl or ethyl group. In the compounds of formula XIII, XV and XVI, $R^1$ is any of the $R^1$ groups described herein. In the compounds of formula XIII, XV and XVI $R^5$ is independently selected from $(C_1\text{-}C_6)$alkyl, halogen, $(C_1\text{-}C_6)$ alkoxy, cyano, or nitro, and p is selected from 0, 1, 2, 3, or 4. In the compounds of formula XIII, XIV, XV, and XVI, $R^{4'}$ is independently selected from substituted $(C_1\text{-}C_6)$alkyl, —R', —OR', =O, =NR', =N—OR', —NR'R", —SR', halogen, —OC(O)R', —C(O)R', —CO$_2$R', —CONR'R", —OC(O)NR'R", —NR"C(O)R', —NR'—C(O)NR"R"', —NR'—SO$_2$NR"R"', —NR"CO$_2$R', —NH—C(NH$_2$)=NH, —NR'C(NH$_2$)=NH, —NH—C(NH$_2$)=NR', —SiR'R"R"', —S(O)R', —SO$_2$R', —SO$_2$NR'R", —NR"SO$_2$R, —CN, —(C$_2$-C$_5$) alkynyl, —(C$_2$-C$_5$) alkenyl, or —NO$_2$, where R', R" and R"' are each independently selected from hydrogen, unsubstituted $(C_1\text{-}C_8)$alkyl or heteroalkyl, unsubstituted aryl, aryl substituted with one to three halogens, unsubstituted alkyl, alkoxy or thioalkoxy groups, halo$(C_1\text{-}C_4)$alkyl, or aryl-$(C_1\text{-}C_4)$alkyl groups; m is selected from 1, 2, 3, or 4; n' is selected from 0, 1, 2, or 3; one of $R^6$ and $R^{6'}$ is $L^1$ or Q, if $L^1$ is a bond, and the others of $R^6$ and $R^{6'}$ are independently selected from H, $(C_1\text{-}C_6)$alkyl, halogen, $(C_1\text{-}C_6)$alkoxy, cyano, or nitro, wherein one of $R^6$ and one of $R^{6'}$ on adjacent or non-adjacent carbon atoms, or on the same carbon atom may join together to form a $C_5\text{-}C_8$ cycloalkane ring, or two of $R^6$ or two of $R^{6'}$, on adjacent or non-adjacent carbon atoms, may join together to form a $C_5\text{-}C_8$ cycloalkane ring, z is selected from 1, 2, or 3, $L^1$ is selected from a bond, $(C_1\text{-}C_4)$alkylene, $(C_2\text{-}C_4)$heteroalkylene, O, S(O)$_k$, N(R$^a$), C(O)—(C$_5$-C$_7$)heterocycloalkylene, $(C_1\text{-}C_4)$alkylene-SO$_2$N(R$^b$), $(C_1\text{-}C_4)$alkylene-N(R$^b$)SO$_2$, or C(O)N(R$^b$), R$^a$ is selected from hydrogen, $(C_1\text{-}C_6)$alkyl, aryl$(C_1\text{-}C_3)$ alkyl, or $(C_2\text{-}C_6)$heteroalkyl, R$^b$ is selected from hydrogen, $(C_1\text{-}C_6)$alkyl, or $(C_2\text{-}C_6)$heteroalkyl, and Q is selected from hydrogen, aryl, heteroaryl, $(C_1\text{-}C_6)$ alkyl, or $(C_2\text{-}C_6)$heteroalkyl. In the compound of formula XIV, W represents a leaving group such as a halogen like Br or Cl or OH. Coupling of a compound of formula XIV with a compound of formula XIII may be accomplished using different procedures. For example, when W is a halogen such as Br, Cl, or I (conveniently synthesized from the other two using the Finkelstein reaction as known to those skilled in the art), then a compound of formula XIII may be coupled with a compound of formula XIV by reacting the two in the presence of any appropriate base such as, but not limited to, Cs$_2$CO$_3$ in an appropriate solvent such as, but not limited to DMF. When W is an OH, then a compound of formula XIII may be coupled with a compound of formula XIV using an azodicarboxylate such as DEAD, TMAD, or DIAD in combination with a suitable phosphine such as a trialkylphosphine, a triarylphosphine, an alkyldiarylphosphine, or a dialkylarylphosphine. This highly flexible approach allows a large number of compounds of formula XV to be synthesized and then converted to compounds of formula XVI by removal of the ester functionality. Conversion of a compound of formula XV to a compound of formula XVI may be accomplished by reacting the compound of formula XV with a base such as a metal hydroxide base such as, but not limited to, LiOH, NaOH, KOH, Ca(OH)$_2$, or the like. Those skilled in the art will recognize that the carbon atom bonded to $R^1$ in compounds of formula XIII, XV, and XVI is a chiral center. In accordance with the method described above, XIII, XV, and XVI may be a mixture of the R and S enantiomers, may be the R enantiomer, or may be the S enantiomer. Therefore, in some embodiments each of the compounds of formula XIII, XV, and XVI are a mixture of the R and S enantiomers. In other embodiments, each of the compounds of formula XIII, XV, and XVI are the R enantiomer. In other embodiments, each of the compounds of formula XIII, XV, and XVI are the R enantiomer.

Scheme 2

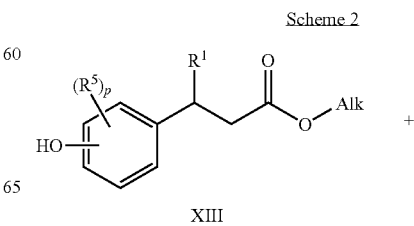

XIII

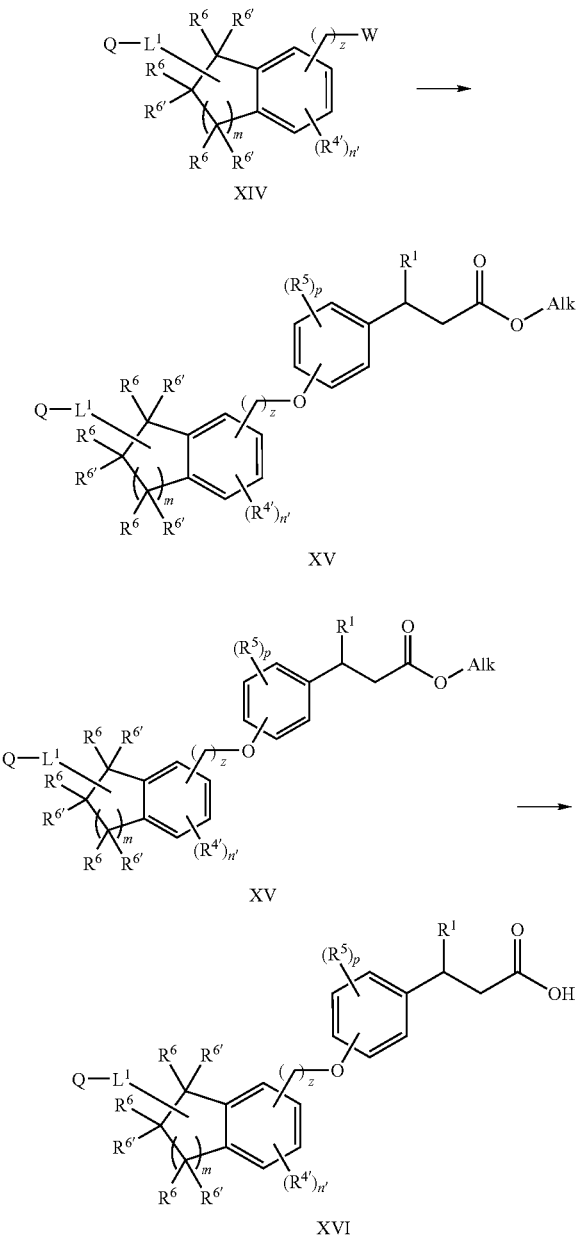

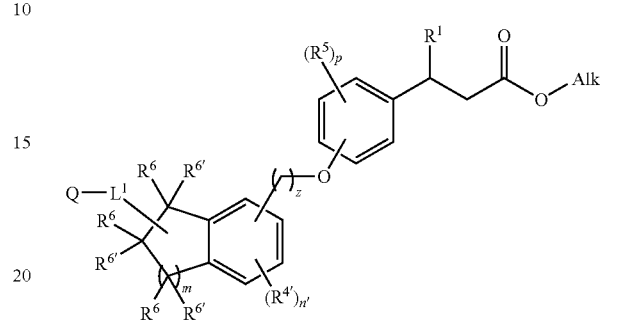

In one aspect, the invention provides a method of synthesizing a compound of formula XV as shown in Scheme 2. The method includes: reacting a compound of formula XIII with a compound of formula XIV to produce the compound of formula XV, wherein the compounds of formula XIII, XIV, and XV have the following structures:

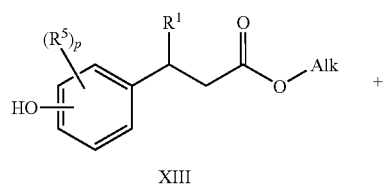

wherein, Alk is a straight or branched chain alkyl group having from 1 to 8 carbon atoms; $R^1$ is a group as defined above with respect to compounds of formula I'; and; $R^5$ is independently selected from $(C_1-C_6)$alkyl, halogen, $(C_1-C_6)$ alkoxy, cyano, or nitro; p is selected from 0, 1, 2, 3, or 4; z is selected from 1, 2, or 3; $R^{4'}$ is independently selected from substituted $(C_1-C_6)$alkyl, —R', —OR', =O, =NR', =N—OR', —NR'R", —SR', halogen, —OC(O)R', —C(O)R', —CO$_2$R', —CONR'R", —OC(O)NR"R'", —NR"C(O)R', —NR'—C(O)NR"R'", —NR'—SO$_2$NR"R'", —NR"CO$_2$R', —NH—C(NH$_2$)=NH, —NR'C(NH$_2$)=NH, —NH—C(NH$_2$)=NR', —SiR'R"R'", —S(O)R', —SO$_2$R', —SO$_2$NR'R", —NR"SO$_2$R, —CN, —$(C_2-C_5)$ alkynyl, —$(C_2-C_5)$ alkenyl, or —NO$_2$, wherein R', R" and R'" are each independently selected from hydrogen, unsubstituted $(C_1-C_8)$alkyl or heteroalkyl, unsubstituted aryl, aryl substituted with one to three halogens, unsubstituted alkyl, alkoxy or thioalkoxy groups, halo$(C_1-C_4)$alkyl, or aryl-$(C_1-C_4)$alkyl groups; n' is 0, 1, 2, or 3; m is 1, 2, 3, or 4; one of $R^6$ and $R^{6'}$ is $L^1$ or Q, if $L^1$ is a bond, and the others of $R^6$ and $R^{6'}$ are independently selected from H, $(C_1-C_6)$alkyl, halogen, $(C_1-C_6)$alkoxy, cyano, or nitro, wherein one of $R^6$ and one of $R^{6'}$ on adjacent or non-adjacent carbon atoms, or on the same carbon atom may join together to form a $C_5-C_8$ cycloalkane ring, or two of $R^6$ or two of $R^{6'}$, on adjacent or non-adjacent carbon atoms, may join together to form a $C_5-C_8$ cycloalkane ring; $L^1$ is selected from a bond, $(C_1-C_4)$alkylene, $(C_2-C_4)$ heteroalkylene, O, S(O)$_k$, N(R$^a$), C(O)—$(C_5-C_7)$heterocycloalkylene, $(C_1-C_4)$alkylene-SO$_2$N(R$^b$), $(C_1-C_4)$alkylene-N(R$^b$)SO$_2$, or C(O)N(R$^b$); R$^a$ is selected from hydrogen, $(C_1-C_6)$alkyl, aryl$(C_1-C_3)$ alkyl, or $(C_2-C_6)$heteroalkyl; R$^b$ is selected from hydrogen, $(C_1-C_6)$alkyl, or $(C_2-C_6)$heteroalkyl; Q is selected from hydrogen, aryl, heteroaryl, $(C_1-C_6)$alkyl, or $(C_2-C_6)$heteroalkyl; W is a leaving group; and further wherein, the compounds of formula XIII and XV can be a mixture of compounds having the R and S stereochemistry at the carbon bonded to $R^1$, can have the R stereochemistry at the carbon bonded to $R^1$, or can have the S stereochemistry at the carbon bonded to $R^1$.

In some embodiments, W is selected from OH, a halogen, an OTs, an OMs, or an OTf where OTs represents the tosylate (Ts is p-toluenesulfonyl) OMs represents mesylate (Ms is methanesulfonyl), and OTf represents triflate (Tf is trifluoromethanesulfonyl). In some such embodiments, W is OH and a phosphine selected from a trialkylphosphine, a dialkylarylphosphine, a alkyldiarylphosphine, or a triarylphosphine and an azodicarboxylate are used to react the compound of formula XIII with the compound of formula XIV. In other such embodiments, W is a halogen selected from Br or Cl, and a base is used to react the compound of formula XXII with the compound of formula XXIII.

In some embodiments, Alk is selected from methyl or ethyl.

In some embodiments, m is 1 or 2.

In some embodiments, n' is 0 In some embodiments, z is 1.

In some embodiments, the method further includes removing the Alk group of the compound of formula XV to form a compound of formula XVI or a salt thereof, and the compound of formula XVI has the following structure:

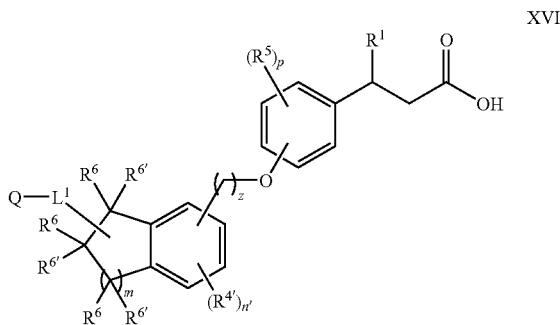

XVI wherein the variables have the definitions provided with respect to the compounds of any of the embodiments of formula XIII, XIV, and XV. In some such embodiments, the compound of formula XV is reacted in the presence of a hydroxide base to produce the compound of formula XVI. In some such embodiments, the hydroxide base is selected from LiOH, NaOH, KOH, or Ca(OH)$_2$ 5.2.3 Compositions In another aspect, the invention provides pharmaceutical compositions suitable for pharmaceutical use comprising one or more compounds of the invention and a pharmaceutically acceptable carrier, excipient, or diluent.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the carrier, excipient, or diluent is compatible with the other ingredients of the formulation and is not deleterious to the recipient thereof.

Composition formulation may improve one or more pharmacokinetic properties (e.g., oral bioavailability, membrane permeability) of a compound of the invention (herein referred to as the active ingredient).

The pharmaceutical compositions for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The pharmaceutical compositions and methods of the invention may further comprise other therapeutically active compounds, as noted herein, useful in the treatment of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema.

5.2.4 Methods of Use

In another aspect, the invention provides methods of treating or preventing a disease or condition selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema, comprising administering to a subject in need thereof a therapeutically effective amount of a compound or composition of the invention.

In one embodiment, the disease or condition is type II diabetes.

In another aspect, the present invention provides a method for treating a disease or condition responsive to the modulation of GPR40 comprising administering to a subject in need thereof a therapeutically effective amount of a compound or composition of the invention.

In some embodiments, the disease or condition is selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema.

In certain embodiments, the disease or condition is type II diabetes.

In some embodiments, the disease or condition is obesity.

In some embodiments, the disease or condition is hypertension.

In some embodiments of administering the compounds or compositions of the invention, the compound or composition is administered orally.

In other embodiments, the compound or composition is administered parenterally.

In other embodiments, the compound or composition is administered in combination with a second therapeutic agent.

In other embodiments, the second therapeutic agent is an insulin sensitizing agent, such as metformin or a thiazolidinedione, for example.

In another aspect, the invention provides methods of treating or preventing a disease or disorder responsive to modulation of GPR40 comprising administering to a subject having such a disease or disorder, a therapeutically effective amount of one or more of the subject compounds or compositions.

In yet another aspect, the invention provides methods of treating or preventing a GPR40-mediated condition, disease or disorder comprising administering to a subject having such a condition, disease or disorder, a therapeutically effective amount of one or more of the subject compounds or compositions.

In yet another aspect, the invention provides methods of modulating GPR40 comprising contacting a cell with one or more of the subject compounds or compositions.

For example, in some embodiments, a cell that constitutively expresses GPR40 is contacted with one or more of the subject compounds or compositions.

In certain embodiments, a cell to be contacted can be made to express or overexpress GPR40, for example, by expressing GPR40 from heterologous nucleic acid introduced into the cell or, as another example, by upregulating the expression of GPR40 from nucleic acid endogenous to the cell.

Depending on the disease to be treated and the subject's condition, the compounds of the invention may be administered by oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration and may be formulated, alone or together, in suitable dosage unit formulations containing conventional non-toxic pharmaceutically acceptable carriers, adjuvants and vehicles appropriate for each route of administration. The invention also contemplates administration of the compounds of the invention in a depot formulation, in which the active ingredient is released over a defined time period.

In the treatment or prevention type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema or other conditions or disorders associated with GPR40, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range, the dosage may be 0.005 to 0.05, 0.05 to 0.5 or 0.5 to 5.0 mg/kg per day. For oral administration, the compositions are preferably provided in the form of tablets containing from 1.0 to 1000 milligrams of the active ingredient, particularly 1.0, 3.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the invention can be combined or used in combination with other agents useful in the treatment, prevention, suppression or amelioration of the diseases or conditions for which compounds of the invention are useful, including type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema. Such other agents, or drugs, may be administered, by a route and in an amount commonly used therefore, simultaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the invention include those that also contain one or more other active ingredients or therapeutic agents, in addition to a compound of the invention.

The compounds of the invention may be used in combination with a second therapeutic agent such as those described herein. Thus, in some embodiments, therapeutic compositions are provided that include a compound of the invention and a second therapeutic agent as a combined preparation for simultaneous, separate or sequential use in the treatment of a subject with a disease or condition mediated by GPR40. In some embodiments, therapeutic compositions are provided that include a compound of the invention and a second therapeutic agent as a combined preparation for simultaneous, separate or sequential use in the prophylactic treatment of a subject at risk for a disease or condition mediated by GPR40. In some such embodiments, the components are provided as a single composition. In other embodiments, the compound and the second therapeutic agent are provided separately as parts of a kit.

Examples of other therapeutic agents that may be combined with a compound of the invention, either administered separately or in the same pharmaceutical compositions, include, but are not limited to: (a) cholesterol lowering agents such as HMG-CoA reductase inhibitors (e.g., lovastatin, simvastatin, pravastatin, fluvastatin, atorvastatin and other statins), bile acid sequestrants (e.g., cholestyramine and colestipol), vitamin $B_3$ (also known as nicotinic acid, or niacin), vitamin $B_6$ (pyridoxine), vitamin $B_{12}$ (cyanocobalamin), fibric acid derivatives (e.g., gemfibrozil, clofibrate, fenofibrate and benzafibrate), probucol, nitroglycerin, and inhibitors of cholesterol absorption (e.g., beta-sitosterol and acyl-CoA-cholesterol acyltransferase (ACAT) inhibitors such as melinamide), HMG-CoA synthase inhibitors, squalene epoxidase inhibitors and squalene synthetase inhibitors; (b) antithrombotic agents, such as thrombolytic agents (e.g., streptokinase, alteplase, anistreplase and reteplase), heparin, hirudin and warfarin derivatives, β-blockers (e.g., atenolol), β-adrenergic agonists (e.g., isoproterenol), ACE inhibitors and vasodilators (e.g., sodium nitroprusside, nicardipine hydrochloride, nitroglycerin and enaloprilat); and (c) antidiabetic agents such as insulin and insulin mimetics, sulfonylureas (e.g., glyburide, meglinatide), biguanides, e.g., metformin (GLUCOPHAGE®), α-glucosidase inhibitors (acarbose), insulin sensitizers, e.g., thiazolidinone compounds, rosiglitazone (AVANDIA®), troglitazone (REZULIN®), ciglitazone, pioglitazone (ACTOS®) and englitazone, DPP-IV inhibitors, e.g., vildagliptin (Galvus™), sitagliptin (Januvia™), and GLP-I analogs, e.g., exenatide (Byetta™). In some embodiments, a compound of the invention may be administered along with a DPP-IV inhibitor or a GLP-I analog.

The weight ratio of the compound of the invention to the second active ingredient may be varied and will depend upon the effective dose of each ingredient. Generally, an effective dose of each will be used. Combinations of a compound of the invention and other active ingredients will generally also be within the aforementioned range, but in each case, an effective dose of each active ingredient should be used.

In another aspect, the present invention provides a method for modulating circulating insulin concentration in a subject, comprising administering a compound or composition of the invention.

In some embodiments, the insulin concentration is increased.

In other embodiments, the insulin concentration is decreased.

The following examples are offered by way of illustration and are not intended to limit the scope of the invention. Those of skill in the art will readily recognize a variety of noncritical parameters that could be modified to yield essentially similar results.

6. EXAMPLES

Unless otherwise stated, all compounds were obtained from commercial sources or were prepared using the methods and experimental procedures described herein. Various procedures are also set forth in published U.S. Patent Application No. 2006/0004012 which is hereby incorporated by reference in its entirety and for all purposes as if set forth herein. The following abbreviations are used to refer to various reagents, solvents, experimental procedures, or analytical techniques that are described in the examples:

| | |
|---|---|
| ACN | Acetonitrile |
| AIBN | 2,2' Azobisisobutyronitrile |
| AcOH | Acetic Acid |
| DCE | 1,2-dichloroethane |
| DCM | Dichloromethane |
| DEAD | Diethyl azodicarboxylate |
| DIAD | Diisopropyl azodicarboxylate |
| DMF | N,N'-Dimethyl Formamide |
| DMAP | Dimethylaminopyridine |
| DMSO | Dimethyl Sulfoxide |
| ESI | Electrospray Ionization |
| EtOAc | Ethyl acetate |
| EtOH | Ethanol |
| HPLC | High Performance Liquid Chromatography |
| HSA | Human Serum Albumin |
| LAH | Lithium Aluminum Hydride |
| MeOH | Methanol |
| MS | Mass Spectrometry |
| NBS | N-Bromosuccinimide |
| NCS | N-Chlorosuccinimide |
| NMR | Nuclear Magnetic Resonance |
| TEA | Triethlamine |
| TFA | Trifluoroacetic Acid |
| THF | Tetrahydrofuran |
| SPA | Scintilliation Proximity Assay |

6.1 Method A

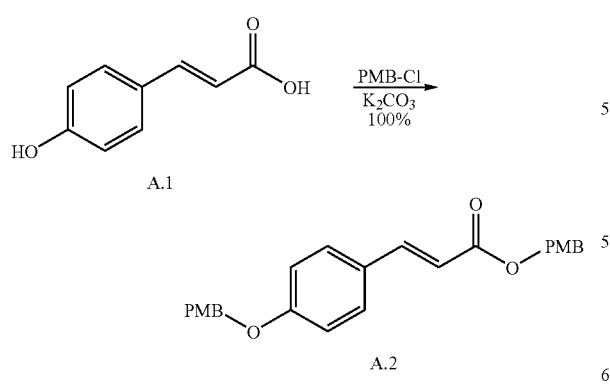

(E)-4-Methoxybenzyl 3-(4-(4-methoxybenzyloxy)phenyl)acrylate (A.2). Potassium carbonate (21 g, 152 mmol) was added to a mixture of 4-hydroxycinnamic acid A.1 (6.25 g, 38.1 mmol) and p-methoxy benzyl chloride (10.35 mL, 76 mmol) in DMF (100 mL). The mixture was stirred at 80° C. for five hours. After cooling, the mixture was poured into water (700 mL). The solid was collected by filtration, washed with water, and dried to give A.2 (15 g). MS ESI (pos.) m/e: 405 (M+H). $^1$H NMR (CDCl$_3$) δ 7.68 (d, 1H), 7.47 (d, 2H), 7.38 (m, 4H), 6.95 (m, 6H), 6.35 (d, 1H), 5.20 (s, 2H), 5.03 (s, 2H), 3.84 (s, 3H), 3.83 (s, 3H).

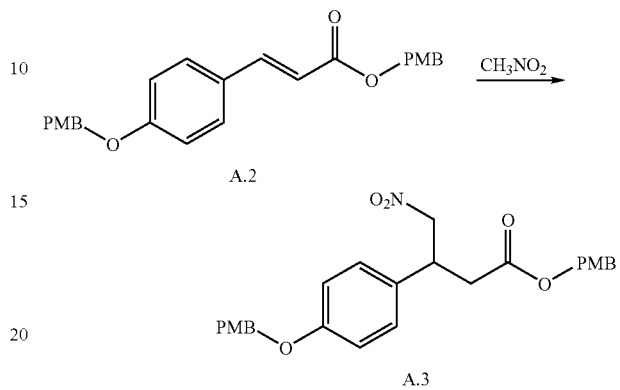

4-Methoxybenzyl 3-(4-(4-methoxybenzyloxy)phenyl)-4-nitrobutanoate (A.3). 1,1,3,3-Tetramethylguanidine (0.31 mL, 2.48 mmol) was added to A.2 (5 g, 12.4 mmol) in nitromethane (20 mL). The mixture was stirred at room temperature for 3 hours, at 50° C. for 3 hours, and at 100° C. for 8 hours. Nitromethane was removed under vacuum, and the crude product was purified by flash chromatography to give A.3 (4.5 g). MS ESI (pos.) m/e: 466 (M+H). $^1$H NMR (CDCl$_3$) δ 7.37 (d, 2H), 7.19 (d, 2H), 7.12 (d, 2H), 6.92 (m, 6H), 5.01 (s, 2H), 4.97 (s, 2H), 4.68 (m, 1H), 4.59 (m, 1H), 3.96 (m, 1H), 3.84 (s, 3H), 3.82 (s, 3H), 2.77 (m, 2H).

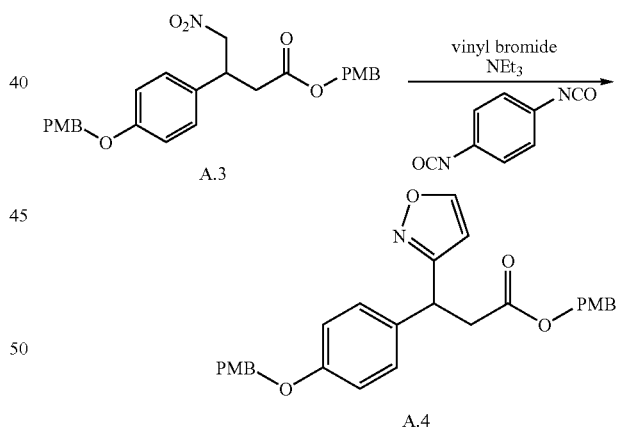

4-Methoxybenzyl 3-(4-(4-methoxybenzyloxy)phenyl)-3-(isoxazol-3-yl)propanoate (A.4). TEA (1 mL) was added to a mixture of A.3 (1.89 g, 4.1 mmol), vinyl bromide (32.5 mL, 1.0 M solution in THF) and 1,4-phenylene diisocyanate (2.3 g, 14.35 mmol). The mixture was stirred at 80° C. for 8 hours. After cooling, the solid was removed from the mixture by filtration, and the filtrate was concentrated and purified by flash chromatography to give A.4 (3 g). MS ESI (pos.) m/e: 474 (M+H). $^1$H NMR (CDCl$_3$) δ 8.28 (d, 1H), 7.37 (d, 2H), 7.18 (m, 4H), 6.92 (m, 6H), 6.07 (d, 1H), 5.02 (s, 2H), 4.97 (s, 2H), 4.59 (t, 1H), 3.84 (s, 3H), 3.82 (s, 3H), 3.33 (dd, 1H), 3.00 (dd, 1H).

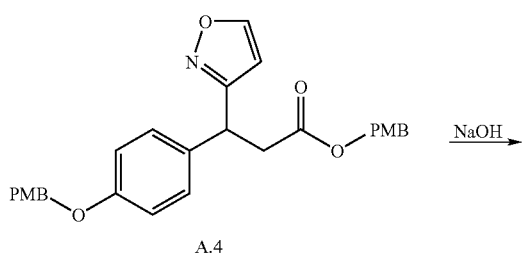

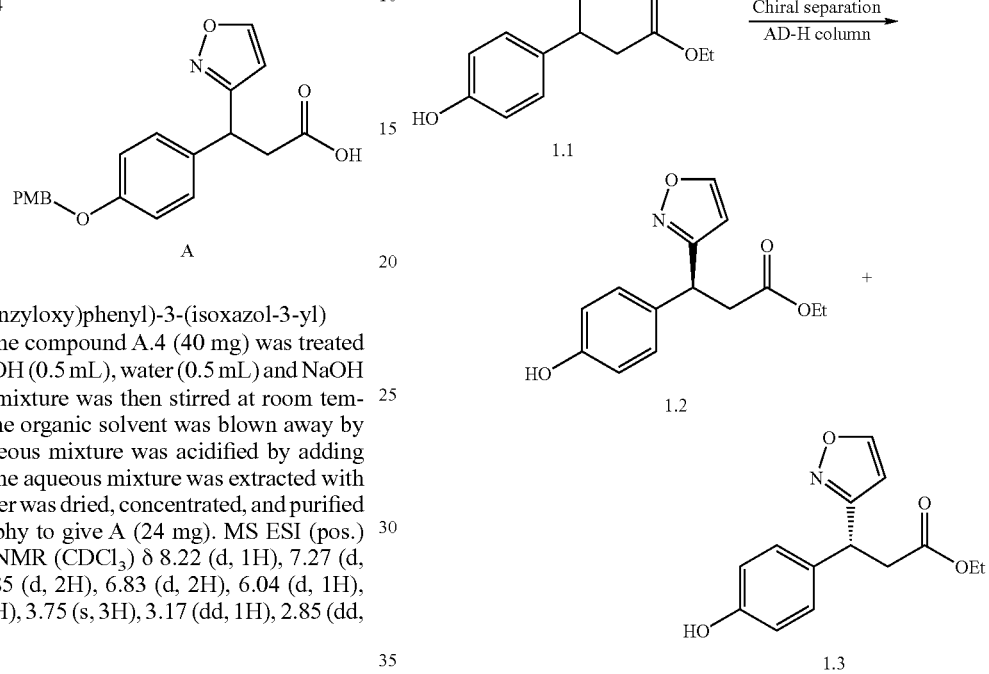

3-(4-(4-Methoxybenzyloxy)phenyl)-3-(isoxazol-3-yl)propanoic acid (A). The compound A.4 (40 mg) was treated with THF (1 mL), MeOH (0.5 mL), water (0.5 mL) and NaOH (0.1 mL, 10 N). The mixture was then stirred at room temperature overnight. The organic solvent was blown away by nitrogen, and the aqueous mixture was acidified by adding HCl (0.35 mL, 3N). The aqueous mixture was extracted with DCM. The organic layer was dried, concentrated, and purified by flash chromatography to give A (24 mg). MS ESI (pos.) m/e: 354 (M+H). $^1$H NMR (CDCl$_3$) δ 8.22 (d, 1H), 7.27 (d, 2H), 7.13 (d, 2H), 6.85 (d, 2H), 6.83 (d, 2H), 6.04 (d, 1H), 4.88 (s, 2H), 4.51 (t, 1H), 3.75 (s, 3H), 3.17 (dd, 1H), 2.85 (dd, 1H).

6.2 Example 1

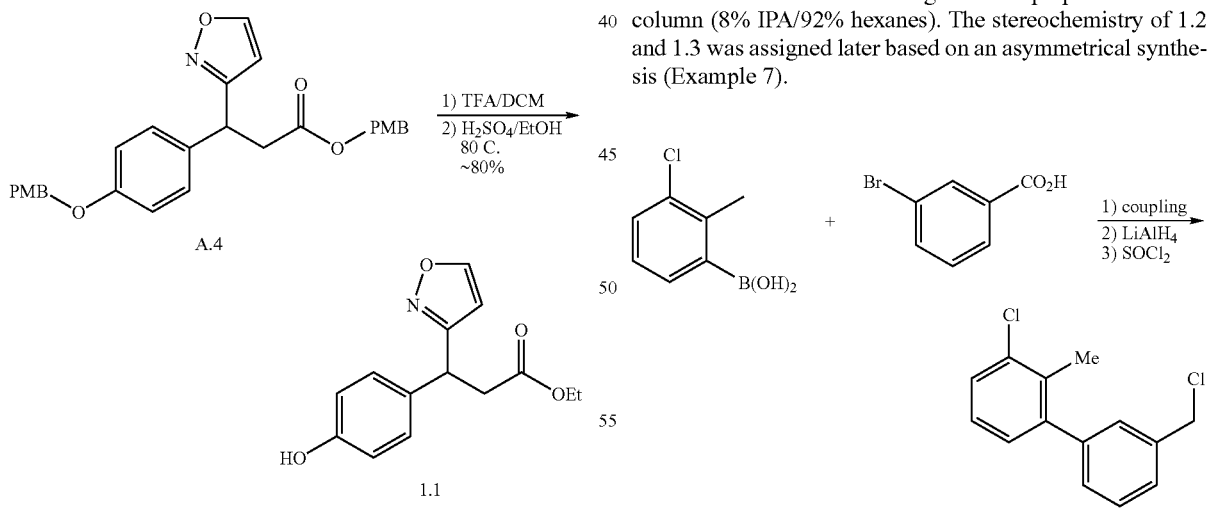

Ethyl 3-(4-hydroxyphenyl)-3-(isoxazol-3-yl)propanoate (1.1). TFA (10 mL) was added to A.4 (940 mg) in DCM (10 mL). The mixture was stirred at room temperature for 1.5 hours. TFA and DCM were removed under vacuum, and the residue was treated with EtOH (50 mL). The insoluble solid was removed by filtration. To the filtrate was added concentrated sulfuric acid (2 drops), and the mixture was stirred at 80° C. overnight. After concentration, the crude product was purified by flash chromatography to give 1.1 (410 mg). MS ESI (pos.) m/e: 262 (M+H). $^1$H NMR (CDCl$_3$) δ 8.29 (d, 1H), 7.12 (d, 2H), 6.76 (d, 2H), 6.10 (d, 1H), 4.56 (t, 1H), 4.10 (q, 2H), 3.27 (dd, 1H), 2.97 (dd, 1H), 1.19 (t, 3H).

The racemic compound 1.1 was separated into the two enantiomers 1.2 and 1.3 using a chiral preparative AD-H column (8% IPA/92% hexanes). The stereochemistry of 1.2 and 1.3 was assigned later based on an asymmetrical synthesis (Example 7).

3-(3-Chloro-2-methylphenyl)benzyl chloride (1.4). The benzyl chloride 1.4 was synthesized using the compounds shown and the procedures described for preparing compound 2.3, except thionyl chloride was used instead of thionyl bromide.

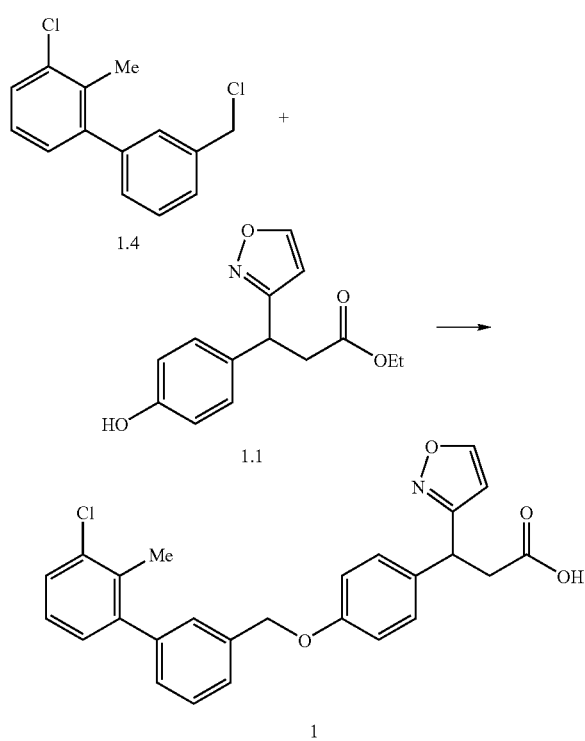

3-(4-(3-(3-Chloro-2-methylphenyl)benzyloxy)phenyl)-3-(isoxazol-3-yl)propanoic acid (1). Cesium carbonate (80 mg, 0.24 mmol) was added to a mixture of 1.1 (50 mg, 0.2 mmol), the benzyl chloride 1.4 (60 mg, 0.24 mmol) and CsI (catalytic amount) in DMSO (1 mL). The mixture was stirred at room temperature for 2 hours and at 35° C. for 4 hours. After cooling, the mixture was treated with EtOAc (5 mL) and brine (5 mL). The organic layer was separated, washed twice with brine, dried, and concentrated. The crude product was treated with THF (2 mL), MeOH (2 mL), water (1 mL) and NaOH (0.11 mL, 10 N). The mixture was stirred at room temperature for 4 hours. The organic solvent was blown away by nitrogen, and the aqueous mixture was acidified by adding HCl (0.35 mL, 3 N). The aqueous was extracted with DCM. The organic layer was dried, concentrated, and purified by flash chromatography to give 1 (40 mg). MS ESI (pos.) m/e: 448 (M+H). $^1$H NMR (CDCl$_3$) δ 8.29 (d, 1H), 7.40 (m, 4H), 7.25 (m, 2H), 7.18 (m, 4H), 6.95 (d, 2H), 6.08 (d, 1H), 5.10 (s, 2H), 4.57 (t, 1H), 3.28 (dd, 1H), 2.99 (dd, 1H), 2.26 (s, 3H).

6.3 Example 2

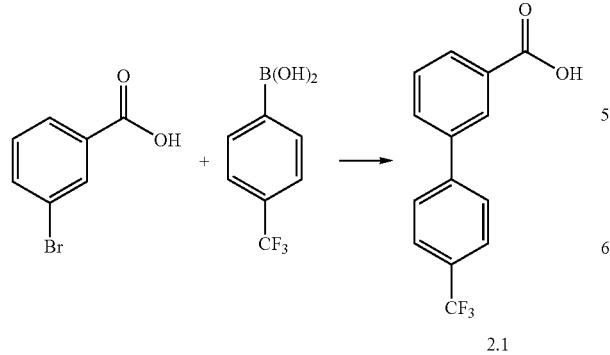

3-(4-Trifluoromethylphenyl)-benzoic acid (3.1). The Suzuki coupling was carried out according to the method of Dyer et al. (2001) Tetrahedron Letters 42: 1765-1767. Commercially available 4-(trifluoromethyl)phenylboronic acid (15 g, 78.7 mmol) and 3-bromobenzoic acid (15.1 g, 75 mmol) were suspended in 2-propanol:water (1:4, 72 mL). 10% Pd/C (1.5 g) was added and then aqueous Na$_2$CO$_3$ (39 mL, 20% by weight) was added. The resulting mixture was heated at 70° C. for 4 hours. The precipitate was filtered and rinsed with a 20% aqueous Na$_2$CO$_3$ solution. The filtrate was diluted with water and acidified to a pH of 2. The white solid was filtered and dried in vacuo. The crude material (2.1) (19.69 g) was used in the next step without further purification

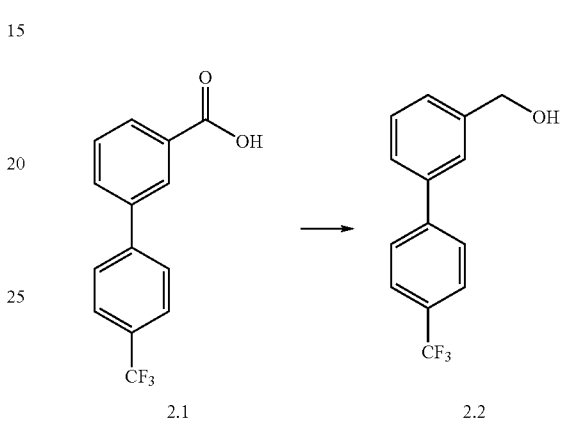

3-(4-Trifluoromethylphenyl)-benzyl alcohol (3.2). The carboxylic acid 2.1 (13.3 g, 50 mmol) in anhydrous THF (100 mL) was added dropwise to LAH (2.9 g, 75 mmol) in anhydrous THF (150 mL) at 0° C. over 30 minutes. The resulting mixture was slowly warmed to room temperature and stirred for 4 hours. The reaction was slowly quenched with water (2.9 mL) at 0° C., a 15% NaOH aqueous solution (2.9 mL), and another portion of water (8.7 mL). The mixture was dried over Na$_2$SO$_4$ and concentrated to give a white solid (11.9 g). The crude product (2.2) was used in the next step without further purification.

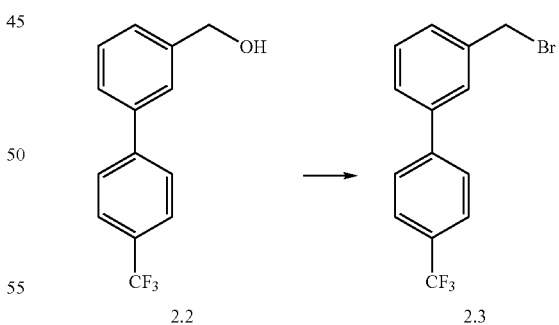

3-(4-Trifluoromethylphenyl)benzyl bromide (2.3). The alcohol 2.2 (15 g, 59.5 mmol) was dissolved in anhydrous DCM (100 mL). Thionyl bromide (15 mL) was slowly added dropwise to the solution. The resulting mixture was stirred at room temperature for 24 hours. The organic solvent was removed under vacuo. The residue was then purified by flash chromatography (SiO$_2$ gel 60, eluted with 20% DCM in hexanes). Fractions containing the desired product 2.3 were combined and concentrated to provide a white solid (15.2 g).

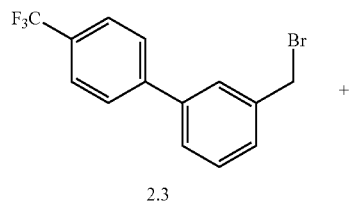

2.3

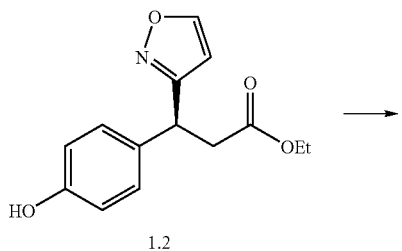

1.2

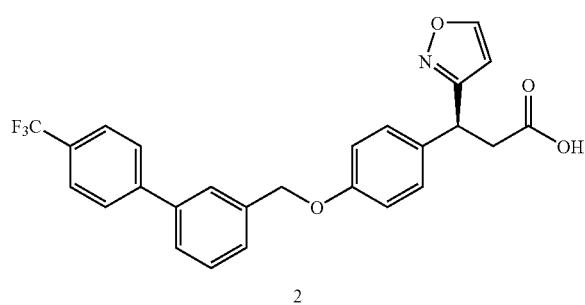

2

(S)-3-(4-(3-(4-(Trifluoromethyl)phenyl)benzyloxy)phenyl)-3-(isoxazol-3-yl)propanoic acid (2). Compound 2 was synthesized from 2.3 and 1.2 using the procedure described above for preparing compound 1. MS ESI (pos.) m/e: 468 (M+H). $^1$H NMR (500 MHz) (DMSO-d$_6$) δ 8.75 (1H, s); 7.91 (2H, m); 7.81-7.84 (3H, m); 7.70 (1H, m); 7.51-7.55 (2H, m); 7.24 (2H, d, J=8.3Hz); 7.99 (2H, d, J=8.3Hz); 6.50 (1H, s); 5.17 (2H, s); 4.49 (1H, m); 3.07 (1H, m), 2.90 (1H, m).

6.4 Example 3

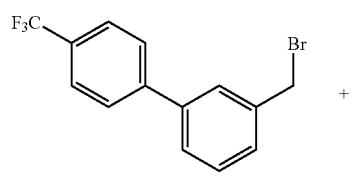

2.3

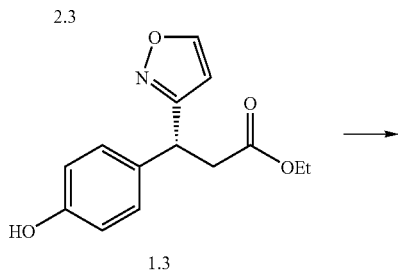

1.3

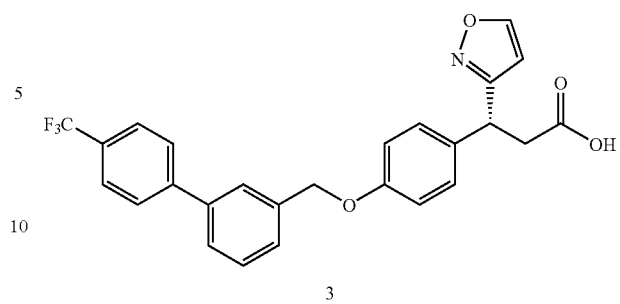

3

(R)-3-(4-(3-(4-(Trifluoromethyl)phenyl)benzyloxy)phenyl)-3-(isoxazol-3-yl)propanoic acid (3). Compound 3 was synthesized from 2.3 and 1.3 using the procedure described above for preparing compound 1. MS ESI (pos.) m/e: 468 (M+H). $^1$H NMR (500 MHz) (DMSO-d$_6$) δ 8.75 (1H, s); 7.91 (2H, m); 7.81-7.84 (3H, m); 7.70 (1H, m); 7.51-7.55 (2H, m); 7.24 (2H, d, J=8.3Hz); 7.99 (2H, d, J=8.3Hz); 6.50 (1H, s); 5.17 (2H, s); 4.49 (1H, m); 3.07 (1H, m), 2.90 (1H, m).

6.5 Example 4

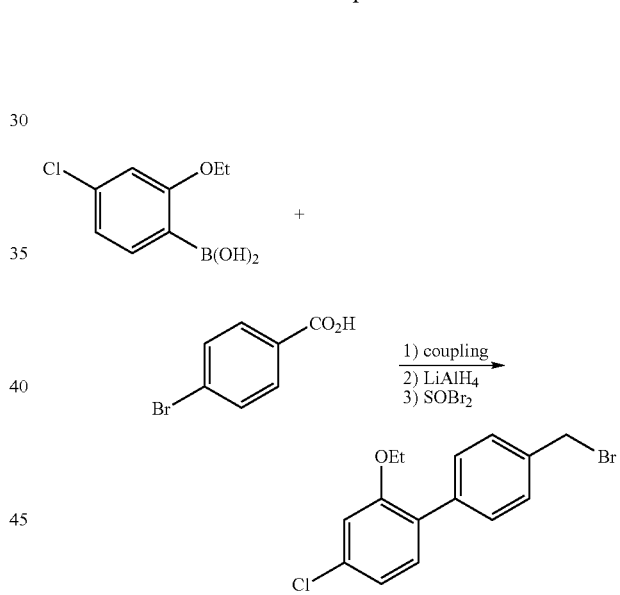

4.1

4-(4-Chloro-2-ethoxyphenyl)benzyl bromide (4.1). The benzyl chloride 4.1 was synthesized according to the procedure described above for preparing compound 2.3 using the starting materials shown.

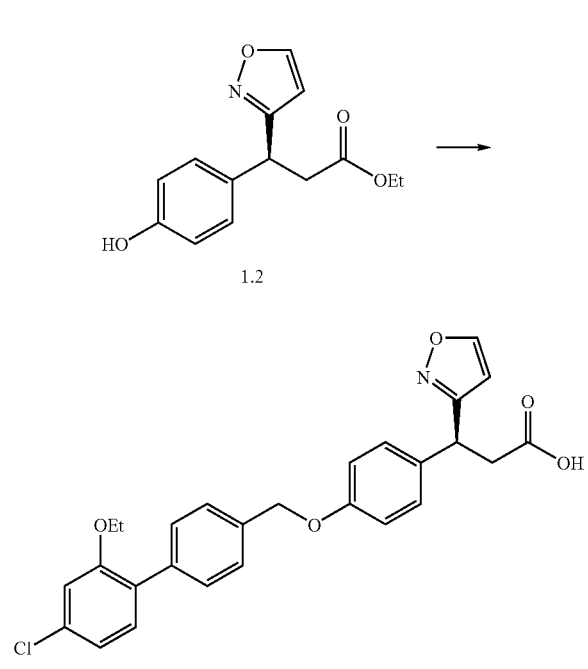

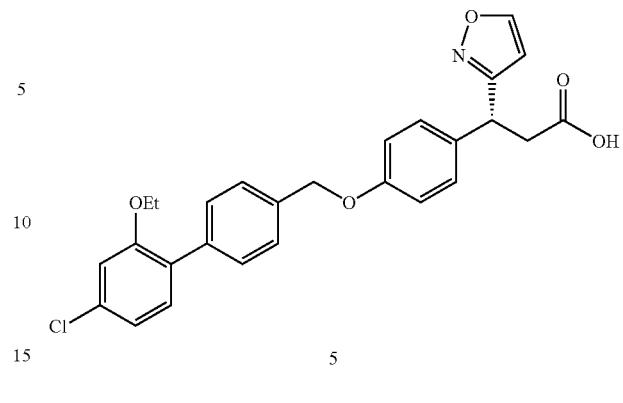

(R)-3-(4-(4-(4-Chloro-2-ethoxyphenyl)benzyloxy)phenyl)-3-(isoxazol-3-yl)propanoic acid (5). Compound 5 was synthesized from 4.1 and 1.3 using the procedure described above for preparing compound 1. MS ESI (pos.) m/e: 478 (M+H). ¹H NMR (CDCl₃) δ 8.29 (d, 1H), 7.55 (d, 2H), 7.46 (d, 2H), 7.28 (d, 1H), 7.20 (d, 2H), 7.00 (m, 4H), 6.09 (d, 1H), 5.08 (s, 2H), 4.57 (t, 1H), 4.06 (q, 2H), 3.38 (dd, 1H), 2.99 (dd, 1H), 1.37 (t, 3H).

(S)-3-(4-(4-(4-Chloro-2-ethoxyphenyl)benzyloxy)phenyl)-3-(isoxazol-3-yl)propanoic acid (4). Compound 4 was synthesized from 4.1 and 1.2 using the procedure described above for preparing compound 1. MS ESI (pos.) m/e: 478 (M+H). ¹H NMR (CDCl₃) δ 8.29 (d, 1H), 7.55 (d, 2H), 7.46 (d, 2H), 7.28 (d, 1H), 7.20 (d, 2H), 7.00 (m, 4H), 6.09 (d, 1H), 5.08 (s, 2H), 4.57 (t, 1H), 4.06 (q, 2H), 3.38 (dd, 1H), 2.99 (dd, 1H), 1.37 (t, 3H).

6.7 Example 6

6.6 Example 5

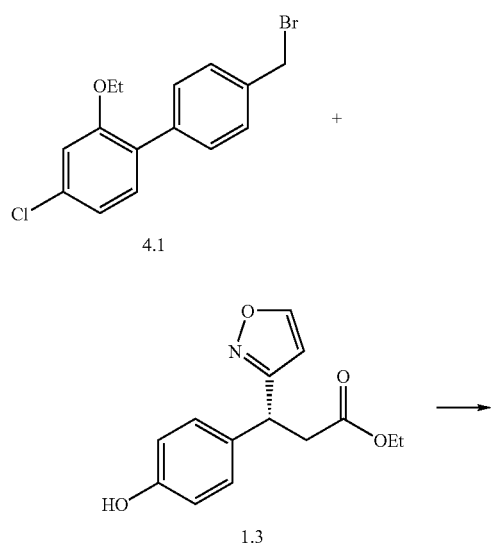

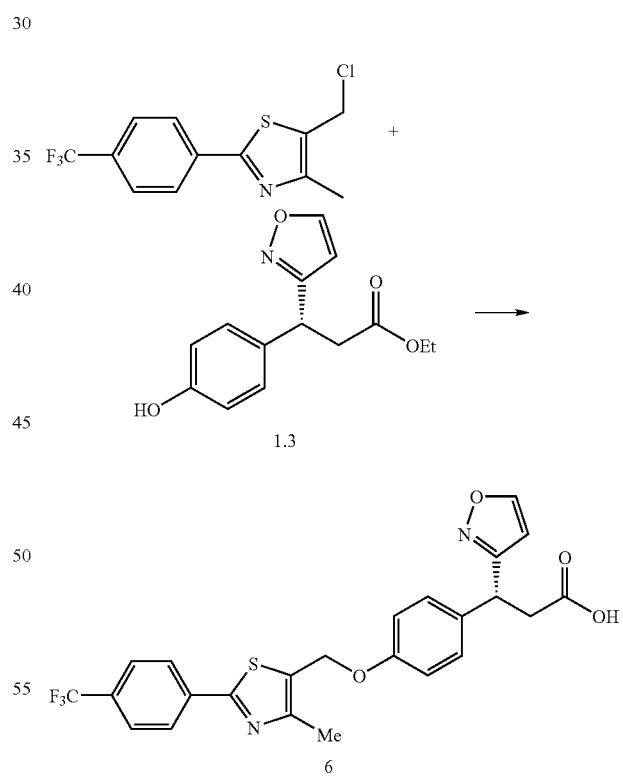

(R)-3-(Isoxazol-3-yl)-3-(4-((4-methyl-2-(4-(trifluoromethyl)phenyl)thiazol-5-yl)methoxy)phenyl)propanoic acid (6). Compound 6 was synthesized using the procedure described above for preparing compound 1 from compound 1.3 and the chloro compound which is commercially available from Maybridge. MS API-ES m/e: 487.0 (M−H). ¹H NMR (500 MHz) (DMSO-d₆) δ 8.76 (1H, s); 8.13 (2H, d, J=7Hz); 7.86 (2H, m); 7.26 (2H, d, J=6Hz); 7.01 (2H, m); 6.50 (1H, s); 5.23 (2H, s); 4.51 (1H, m); 3.20 (1H, m), 2.80 (1H, m), 2.47 (3H, s).

6.8 Example 7

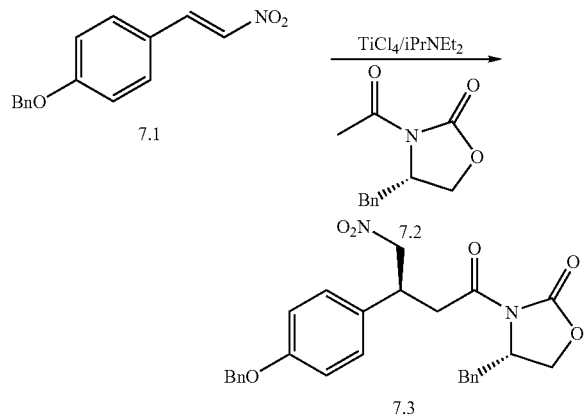

(S)-4-Benzyl-3-((S)-3-(4-(benzyloxy)phenyl)-4-nitrobutanoyl)oxazolidin-2-one (7.3). TiCl$_4$ (43 mL, 1.0 M solution in DCM) was added slowly to a mixture of 7.2 (8.55 g, 39 mmol, commercially available from Aldrich) in DCM (200 mL) at −78° C., followed by slow addition of iPrNEt$_2$ (8.14 mL, 46.8 mmol). The mixture was stirred at −78° C. for 45 minutes and then a mixture of 7.1 (9.95 g, 39 mmol, commercially available from Aldrich) in DCM (40 mL) was added over 15 minutes. TiCl$_4$ (39 mL, 1.0 M solution in DCM) was then added to the reaction. During all the additions, the internal temperature was kept below −72° C. The mixture was stirred at −78° C. for another 4 hours before it was slowly warmed to −10° C. and then quenched by adding NH$_4$Cl (saturated 100 mL). The organic layer was separated, washed with brine, dried, and concentrated. The crude product was taken into hot MeOH (700 mL). The mixture was stirred vigorously at 75° C. for 3 hours. The mixture was then cooled to room temperature and allowed to stand for 3 hours. The solid product was collected by filtration and washed with MeOH. The product 7.3 (8.5 g) had a d.e.>99%. MS ESI (pos.) m/e: 475 (M+H). $^1$H NMR (CDCl$_3$) δ 7.40 (m, 8H), 7.28 (m, 4H), 6.97 (d, 2H), 5.05 (s, 2H), 4.63 (m, 3H), 4.17 (m, 3H), 3.53 (dd, 1H), 3.34 (dd, 1H), 3.28 (dd, 1H), 2.75 (dd, 1H).

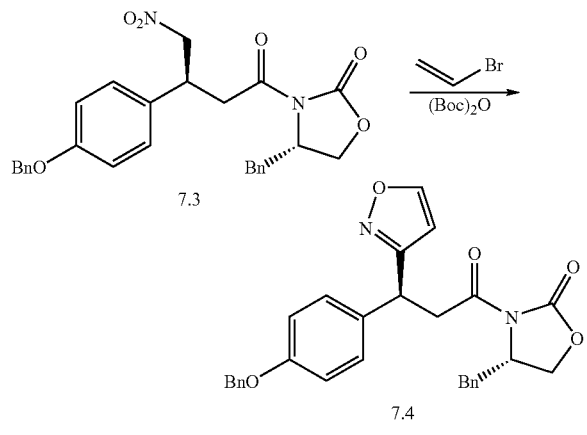

(S)-4-Benzyl-3-((S)-3-(4-(benzyloxy)phenyl)-3-(isoxazol-3-yl)propanoyl)oxazolidin-2-one (7.4). (Boc)$_2$O (6.9 g, 31.65 mmol) was added at room temperature to a solution of 7.3 (10 g, 21.1 mmol), vinyl bromide (230 mL, 1.0 M solution in THF), DMAP (256 mg, 2.1 mmol), and TEA (3.5 mL, 25.3 mmol). The mixture was stirred at room temperature for 2.5 days. During the reaction, more (Boc)$_2$O (2 g twice) was added. After HPLC indicated that all 7.3 was consumed, the reaction mixture was taken into EtOAc (500 mL), and saturated sodium bicarbonate (400 mL) was added. The organic layer was separated, washed with brine, dried, and concentrated under vacuum. The crude product was taken into hot MeOH (70 mL). The mixture was stirred vigorously at 75° C. for 5 hours. The mixture was then cooled to room temperature and allowed to stand for 3 hours. The solid product was collected by filtration and washed with MeOH to give 7.4 (9.5 g). MS ESI (pos.) m/e: 483 (M+H). $^1$H NMR (CDCl$_3$) δ 8.30 (d, 1H), 7.30 (m, 12H), 6.95 (d, 2H), 6.15 (d, 1H), 5.05 (s, 2H), 4.76 (dd, 1H), 4.64 (m, 1H), 4.15 (d, 2H), 4.05 (dd, 1H), 3.56 (dd, 1H), 3.23 (dd, 1H), 2.78 (dd, 1H).

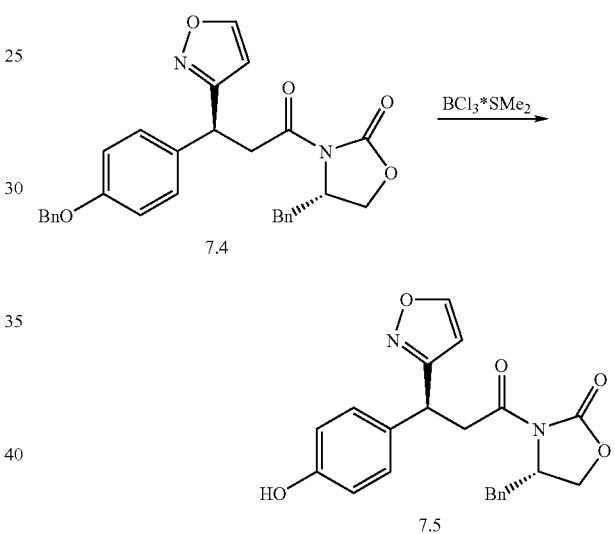

(S)-4-Benzyl-3-((S)-3-(4-hydroxyphenyl)-3-(isoxazol-3-yl)propanoyl)oxazolidin-2-one (7.5). Boron trichloride methyl sulfide complex (51 mL, 2.0 M solution in DCM) was added to 7.4 (8.2 g, 17 mmol) in DCM (100 mL) at 0° C. After addition, the ice bath was removed, and the mixture was stirred at room temperature for 7 hours. The mixture was cooled in an ice bath and quenched by adding saturated sodium bicarbonate until the mixture was neutralized. More DCM (400 mL) was added, and the organic layer was separated, washed with brine, dried, and concentrated under vacuum. The crude product (6.5 g) was dissolved in 50 mL of hot MeOH. After cooling, the crystallized product was collected by filtration and washed once with MeOH to give 7.5 (4.2 g). The filtrate was concentrated, and the solid that formed was collected and washed to give an additional 1.2 g of compound 7.5. MS ESI (pos.) m/e: 393 (M+H). $^1$H NMR (CDCl$_3$) δ 8.29 (d, 1H), 7.30 (m, 3H), 7.20 (d, 2H), 7.15 (d, 2H), 6.95 (d, 2H), 6.14 (d, 1H), 4.71 (dd, 1H), 4.63 (m, 1H), 4.16 (d, 2H), 4.00 (dd, 1H), 3.54 (dd, 1H), 3.21 (dd, 1H), 2.76 (dd, 1H).

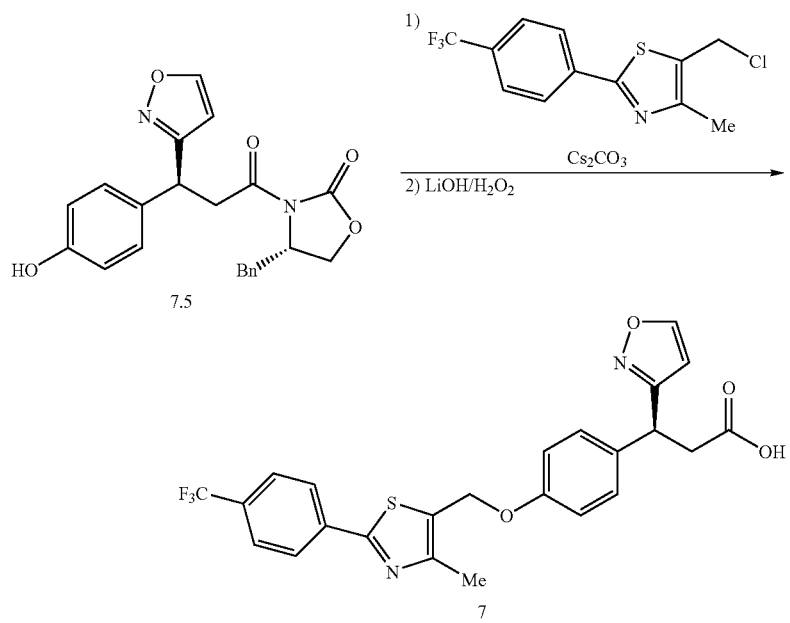

(S)-3-(Isoxazol-3-yl)-3-(4-((4-methyl-2-(4-(trifluoromethyl)phenyl)thiazol-5-yl)methoxy)phenyl)propanoic acid (7). Cesium carbonate (360 mg, 1.1 mmol) was added to a mixture of 7.5 (392 mg mg, 1 mmol) and 5-(chloromethyl)-4-methyl-2-(4-(trifluoromethyl)phenyl)thiazole (292 mg, 1 mmol, commercially available from Maybridge) in DMSO (8 mL). The resulting mixture was stirred at room temperature for 2 hours and at 35° C. for 4 hours. After cooling, the mixture was treated with EtOAc (5 mL) and brine (5 mL). The organic layer was separated, washed twice with brine, dried, and concentrated. The crude product (220 mg, 0.34 mmol) was treated with THF (6 mL) and hydrogen peroxide (30%, 154 mg, 1.36 mmol) and cooled to 0° C. LiOH (29 mg, 0.68 mmol) in 2 mL of water was added. The resulting mixture was stirred at 0° C. for 4 hours. The organic solvent was blown away by nitrogen, and the aqueous mixture was acidified by adding HCl (0.24 mL, 3 N). The aqueous mixture was extracted with DCM. The organic layer was dried, concentrated, and purified by flash chromatography to give 7 (150 mg). MS API-ES m/e: 487.0 (M−H). $^1$H NMR (500 MHz) (DMSO-d$_6$) δ 8.76 (1H, s); 8.13 (2H, d, J=7Hz); 7.86 (2H, m); 7.26 (2H, d, J=6Hz); 7.01 (2H, m); 6.50 (1H, s); 5.23 (2H, s); 4.51 (1H, m); 3.20 (1H, m); 2.80 (1H, m); 2.47 (3H, s).

6.9 Method B

-continued

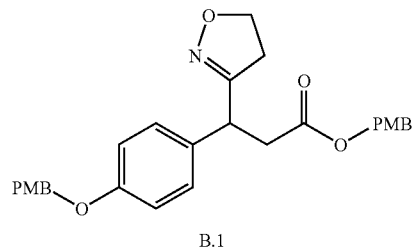

B.1

4-Methoxybenzyl 3-(4-(4-methoxybenzyloxy)phenyl)-3-(4,5-dihydroisoxazol-3-yl)propanoate (B.1). Ethylene was bubbled into a mixture of A.3 (235 mg, 0.5 mmol) in benzene (2 mL) for 20 minutes. Phenyl isocyanate (0.22 mL, 2 mmol) and TEA (3 drops) were added. The mixture was stirred at room temperature for 2 days. The solid was removed by filtration and washed with benzene. The filtrate was concentrated and purified by flash chromatography to give B.1 (200 mg). MS ESI (pos.) m/e: 476 (M+H). $^1$H NMR (CDCl$_3$) δ 7.37 (d, 2H), 7.21 (d, 2H), 7.16 (d, 2H), 6.92 (m, 6H), 5.05 (dd, 2H), 4.98 (s, 2H), 4.25 (m, 2H), 4.10 (t, 1H), 3.84 (s, 3H), 3.82 (s, 3H), 3.24 (dd, 1H), 2.79 (m, 3H).

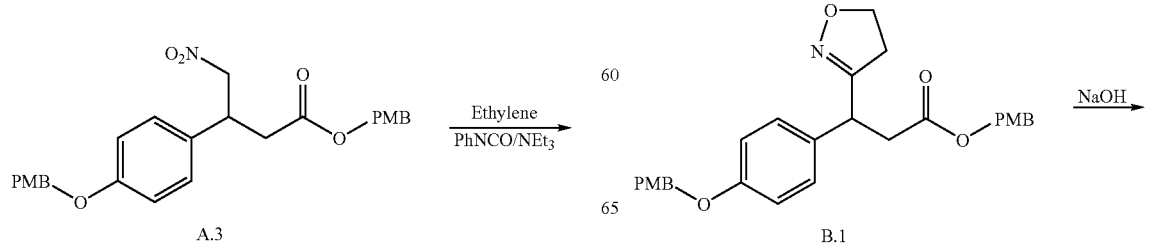

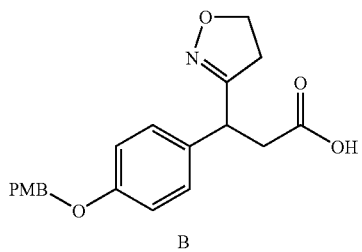

3-(4-(4-Methoxybenzyloxy)phenyl)-3-(4,5-dihydroisoxazol-3-yl)propanoic acid (B). The compound B.1 (40 mg) was treated with THF (1 mL), MeOH (0.5 mL), water (0.5 mL) and NaOH (0.11 mL, 10 N). The mixture was stirred at room temperature overnight. The organic solvent was blown away by nitrogen, and the aqueous mixture was acidified by adding HCl (0.35 mL, 3 N). The aqueous mixture was extracted with DCM. The organic layer was dried, concentrated, and purified by flash chromatography to give B (24 mg). MS ESI (pos.) m/e: 356 (M+H). $^1$H NMR (CDCl$_3$) δ 7.36 (d, 2H), 7.19 (d, 2H), 6.97 (d, 2H), 6.95 (d, 2H), 4.99 (s, 2H), 4.27 (m, 2H), 4.07 (t, 1H), 3.84 (s, 3H), 3.28 (dd, 1H), 2.80 (m, 3H).

6.10 Example 8

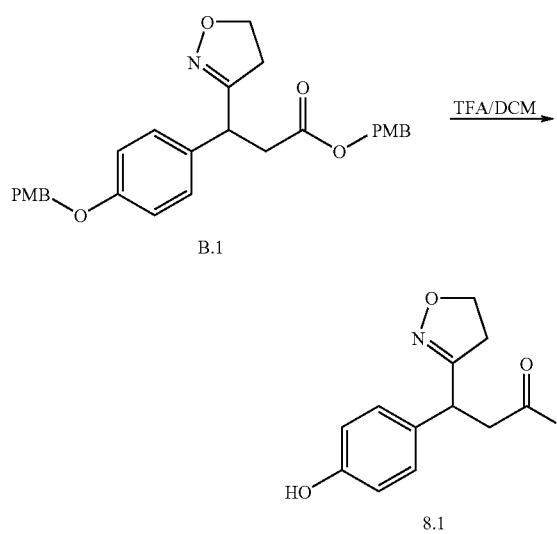

3-(4,5-Dihydroisoxazol-3-yl)-3-(4-hydroxyphenyl)propanoic acid (8.1). TFA (1 mL) was added to B.1 (100 mg) in DCM (1 mL). The mixture was stirred at room temperature for 40 hours. TFA and DCM were removed under vacuum, and the residue was treated with EtOH (50 mL). The insoluble solid was removed by filtration. The filtrate was concentrated to give 8.1 (50 mg), which was used in the next step without further purification. MS ESI (pos.) m/e: 236 (M+H).

3-(4,5-Dihydroisoxazol-3-yl)-3-(4-((5,5,8,8-tetramethyl-5,6,7,8-tetrahydronaphthalen-2-yl)methoxy)phenyl)propanoic acid (8). Cesium carbonate (108 mg, 0.33 mmol) was added into a mixture of 8.1 (25 mg, 0.11 mmol) and 5-(chloromethyl)-4-methyl-2-(4-(trifluoromethyl)phenyl)thiazole (79 mg, 0.27 mmol, commercially available from Maybridge) in DMSO (1 mL). The mixture was stirred at 45° C. for 3 hours. After cooling, the mixture was treated with EtOAc (5 mL) and brine (5 mL). The organic layer was separated, washed twice with brine, dried, and concentrated. The crude product was treated with THF (1 mL), MeOH (1 mL), water (0.5 mL) and NaOH (0.05 mL, 10 N). The resulting mixture was stirred at room temperature for 4 hours. The organic solvent was then blown away by nitrogen, and the aqueous mixture was acidified by adding HCl (0.18 mL, 3 N). The aqueous mixture was extracted with DCM and the organic layer was dried, concentrated, and purified by flash chromatography to give 8 (25 mg). MS ESI (pos.) m/e: 491 (M+H). $^1$H NMR (CDCl$_3$) δ 8.05 (d, 2H), 7.70 (d, 2H), 7.23 (d, 2H), 6.95 (d, 2H), 5.15 (s, 2H), 4.20 (m, 2H), 4.00 (t, 1H), 3.20 (dd, 1H), 2.70 (m, 3H), 2.52 (s, 3H).

6.11 Example 9

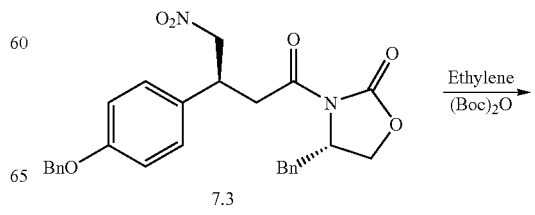

-continued

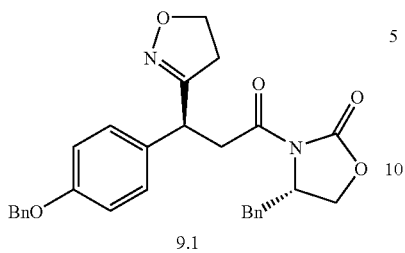
9.1

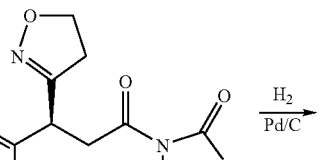

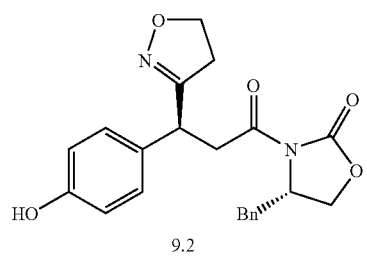
9.1

(S)-4-Benzyl-3-((S)-3-(4-(benzyloxy)phenyl)-3-(dihydroisoxazol-3-yl)propanoyl)oxazolidin-2-one (9.1). Ethylene was bubbled into 7.3 (882 mg, 1.86 mmol) in 40 mL ACN at room temperature for 20 minutes. (Boc)$_2$O (610 mg, 2.79 mmol) was added at room temperature, followed by the addition of DMAP (23 mg, 0.19 mmol). The mixture was stirred at room temperature for 6 hours. After HPLC indicated that all the 7.3 was consumed, the reaction mixture was taken into EtOAc (500 mL) and saturated sodium bicarbonate (400 mL). The organic layer was separated, washed with brine, dried, and concentrated under vacuum. The crude product was purified by flash chromatography to give 9.1 800 mg). MS ESI (pos.) m/e: 485 (M+H).

(S)-4-Benzyl-3-((S)-3-(4-hydroxyphenyl)-3-(dihydroisoxazol-3-yl)propanoyl)oxazolidin-2-one (9.2). Compound 9.1 (136 mg) and a catalytic amount of Pd/C in EtOH (2 mL) was stirred at room temperature under 1 atm of H$_2$ for 2.5 hours. The catalyst was removed by filtration, and the filtrate was concentrated to give 9.2 (100 mg). MS ESI (pos.) m/e: 395 (M+H).

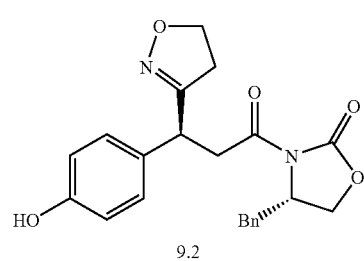
9.2

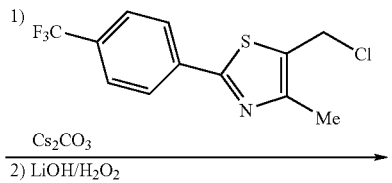

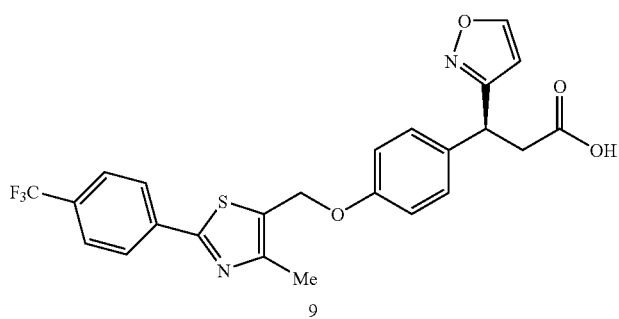
9

(S)-3-(Dihydroisoxazol-3-yl)-3-(4-((4-methyl-2-(4-(trifluoromethyl)phenyl)thiazol-5-yl)methoxy)phenyl)propanoic acid (9). Compound 9 was synthesized from 9.2 using the procedure described above for preparing compound 7 with the chloro compound shown which is commercially available from Maybridge. MS ESI (pos.) m/e: 491 (M+H). ¹H NMR (CDCl₃) δ 8.05 (d, 2H), 7.70 (d, 2H), 7.23 (d, 2H), 6.95 (d, 2H), 5.15 (s, 2H), 4.20 (m, 2H), 4.00 (t, 1H), 3.20 (dd, 1H), 2.70 (m, 3H), 2.52 (s, 3H).

1.12 Example 10

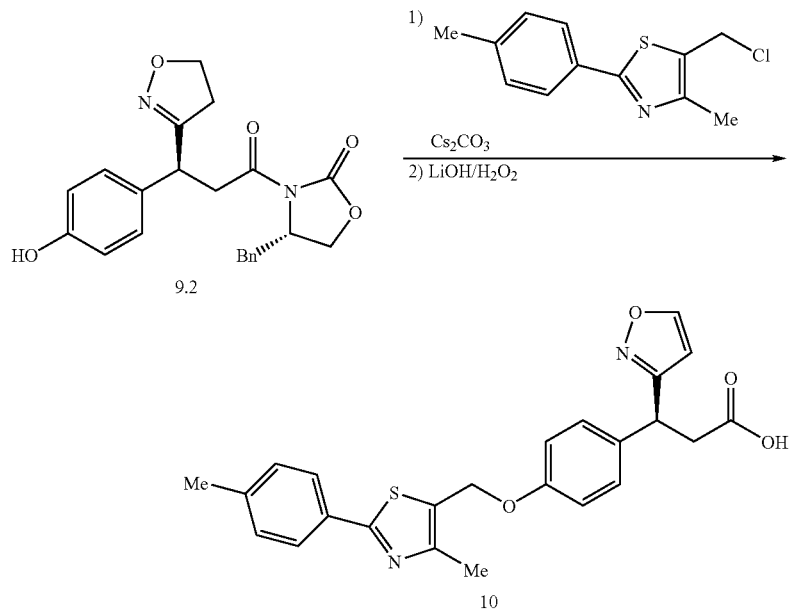

(S)-3-(Dihydroisoxazol-3-yl)-3-(4-((4-methyl-2-(4-methylphenyl)thiazol-5-yl)methoxy)phenyl)propanoic acid (10). Compound 10 was synthesized using the procedure described above for preparing compound 7 with the chloro compound shown above which was prepared as described in US 2006/0004012. MS ESI (pos.) m/e: 437 (M+H). ¹H NMR (CDCl₃) δ 7.84 (d, 2H), 7.35 (d, 2H), 7.25 (d, 2H), 6.95 (d, 2H), 5.15 (s, 2H), 4.20 (m, 2H), 4.00 (t, 1H), 3.20 (dd, 1H), 2.70 (m, 3H), 2.51 (s, 3H), 2.41 (s, 3H).

1.13 Example 11

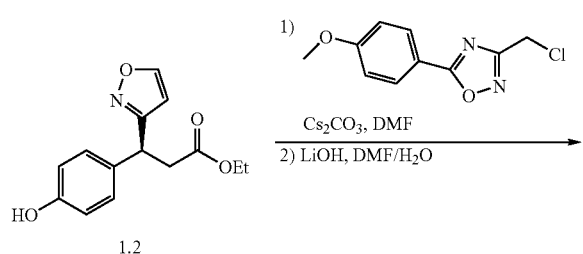

-continued

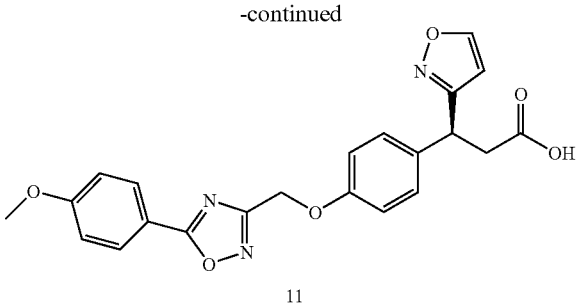

(S)-3-(Isoxazol-3-yl)-3-(4-((5-(4-methoxyphenyl)-1,2,4-oxadiazol-3-yl)methoxy)phenyl)propanoic acid (11). Cesium carbonate (64 mg, 0.2 mmol) was added to a mixture of 1.2 (26 mg, 0.1 mmol) and 3-(chloromethyl)-5-(4-methoxyphenyl)-1,2,4-oxadiazole (27 mg, 0.12 mmol, commercially available from Maybridge) in DMF (1 mL). The mixture was stirred at room temperature for 3 hours. To the reaction mixture was added LiOH in water (1 mL, 1 N solution), and the reactions was stirred at 50° C. for 3 hours. The mixture was filtered and purified by reverse phase HPLC to give 11 (40 mg, 0.095 mmol) after lyophilization. MS ESI (pos.) m/e 422.0 (M+H). ¹H NMR (500 MHz, CDCl₃) δ ppm 8.31 (1 H, s), 8.11 (2 H, d, J=8.3 Hz), 7.23 (2 H, d, J=8.6 Hz), 7.04 (2 H, d, J=8.6Hz), 7.03 (2 H, d, J=8.6 Hz), 6.09 (1H, s), 5.23 (2 H, s), 4.58 (1 H, t, J=7.7 Hz), 3.92 (3 H, s), 3.38 (1 H, dd, J=17.1, 7.8Hz), 3.01 (1 H, dd, J=16.3, 7.0 Hz)

1.14 Example 12

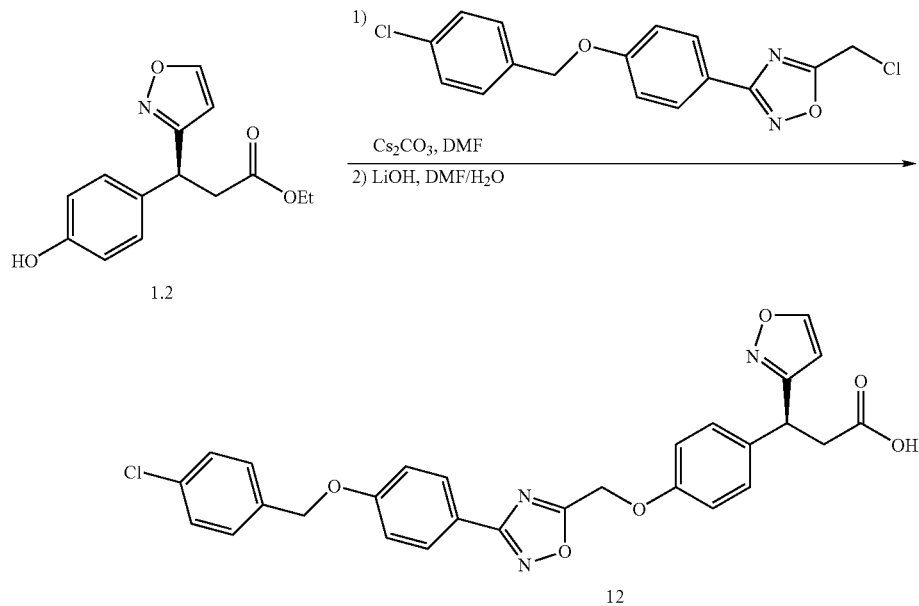

(S)-3-(4-((3-(4-(4-Chlorobenzyloxy)phenyl)-1,2,4-oxadiazol-5-yl)methoxy)phenyl)-3-(isoxazol-3-yl)propanoic acid (12). Cesium carbonate (64 mg, 0.2 mmol) was added to a mixture of 1.2 (26 mg, 0.1 mmol) and 3-(4-(4-chlorobenzyloxy)phenyl)-5-(chloromethyl)-1,2,4-oxadiazole (40 mg, 0.12 mmol, commercially available from Maybridge) in DMF (1 mL). The mixture was stirred at room temperature for 3 hours. To the reaction mixture was added LiOH in water (1 mL, 1 N solution), and the reaction was stirred at 50° C. for 3 hours. The mixture was filtered and purified by reverse phase HPLC to give 12 (26 mg, 0.049 mmol) after lyophilization. MS ESI (pos.) m/e 532.2 (M+H). $^1$H NMR (500 MHz, Acetone-d6) δ ppm 8.47 (1 H, s), 7.91 (2 H, d, J=8.8 Hz), 7.91 (2 H, d, J=8.8 Hz), 7.91 (2 H, d, J=8.8 Hz), 7.91 (2 H, d, J=8.8 Hz), 7.44 (2 H, d, J=8.6 Hz), 7.34 (2 H, d, J=8.6 Hz), 7.23 (2 H, d, J=8.8 Hz), 7.08 (2 H, d, J=8.8 Hz), 6.96 (2 H, d, J=8.8 Hz), 6.26 (1 H, s), 5.39 (2 H, s), 5.13 (2 H, s), 4.51 (1 H, t, J=7.6 Hz), 3.13 (3 H, ddd, J=16.4, 7.9, 5.0 Hz), 2.87 (3 H, ddd, J=16.4, 7.5, 5.0 Hz)

1.15 Example 13

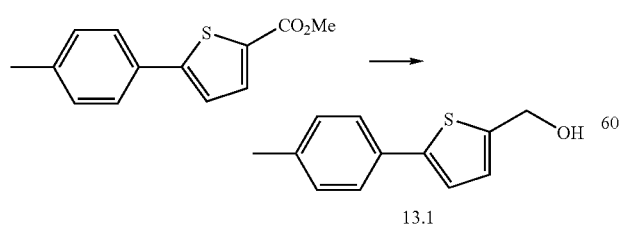

(5-p-Tolylthiophen-2-yl)methanol (13.1). To a solution of methyl (5-p-tolylthiophen-2-yl)benzoate (5.0 mmol) in THF (20 mL) at 0° C. was slowly added LAH (1.0 M in THF, 6.0 mL). The reaction was then stirred at room temperature for 3 hours, and water (0.24 mL), 15% aqueous NaOH (0.24 mL), and water (0.72 mL) were added to the reaction mixture. After 30 minutes, the reaction mixture was filtered through celite and concentrated to give the pure product 13.1 (0.95 g). MS ESI (pos.) m/e 205.0 (M+H).

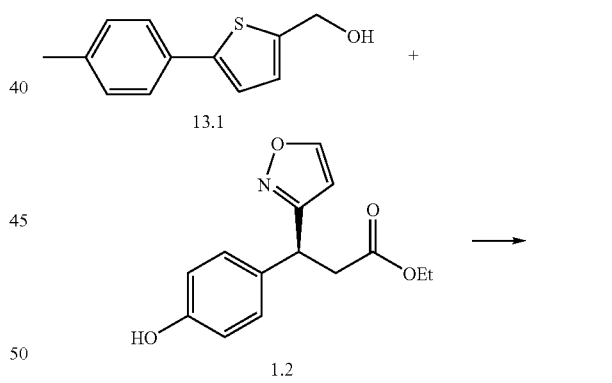

(S)-3-(Isoxazol-3-yl)-3-(4-((5-p-tolylthiophen-2-yl)methoxy)phenyl)propanoic acid (13). To a solution of (5-p-tolylthiophen-2-yl)methanol 13.1 (23 mg, 0.12 mmol), triphenylphosphine (29 mg, 0.11 mmol) and compound 1.2 (26 mg, 0.1 mmol) in THF (1 mL), was slowly added diethyl azodicarboxylate (20 μL, 0.13 mmol) at room temperature. The reaction mixture was stirred at room temperature for 30 minutes and then loaded on a silica gel cartridge and chromatographed (silica gel, 1:4 EtOAc/hexane) to afford the corresponding ester. The ester was dissolved in DMF (1 mL), and LiOH in water (1 mL, 1 N solution) was added. The mixture was then stirred at 50° C. for 3 hours. The mixture was filtered and purified by reverse phase HPLC to give 13 (3 mg, 0.007 mmol) after lyophilization. MS ESI (pos.) m/e 420.0 (M+H). 1H NMR (400 MHz, CDCl$_3$) δ ppm 8.20 (1 H, d, J=1.6 Hz), 7.39 (2 H, d, J=8.2 Hz), 7.08-7.13 (4 H, m), 7.06 (1 H, d, J=3.5 Hz), 6.96 (1 H, d, J=3.9 Hz), 6.87 (2 H, d, J=9.0 Hz), 5.99 (1 H, d, J=2.0 Hz), 5.09 (2 H, s), 4.47 (1 H, t, J=7.6 Hz), 3.28 (1 H, dd, J=16.6, 8.0 Hz), 2.91 (1 H, dd, J=16.4, 7.4 Hz), 2.28 (3 H, s)

1.16 Example 14

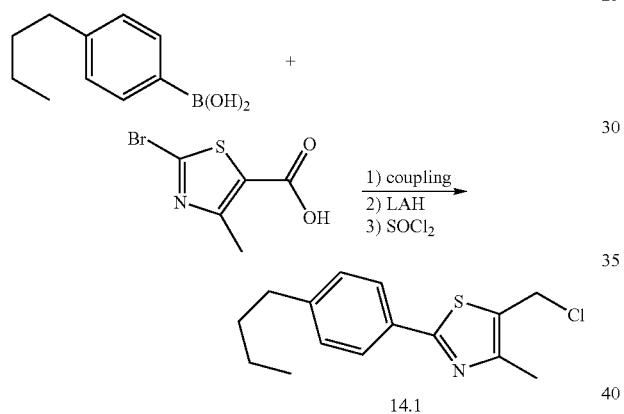

2-(4-Butylphenyl)-5-(chloromethyl)-4-methylthiazole (14.1). Compound 14.1 was synthesized using the procedures described above for preparing compound 2.3, except thionyl chloride was used instead of thionyl bromide.

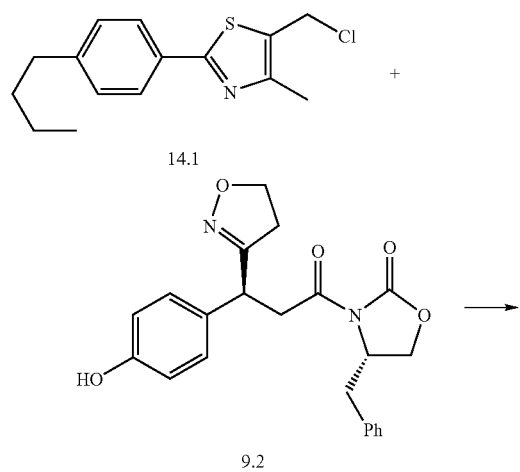

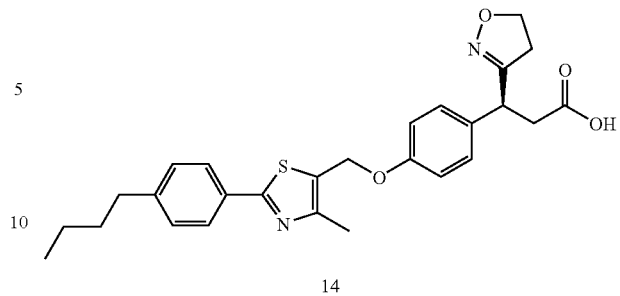

(S)-3-(4-((2-(4-Butylphenyl)-4-methylthiazol-5-yl)methoxy)phenyl)-3-(4,5-dihydroisoxazol-3-yl)propanoic acid (14). Cesium carbonate (64 mg, 0.2 mmol) was added to a mixture of 9.2 (6.1 mg, 0.015 mmol) and 2-(4-butylphenyl)-5-(chloromethyl)-4-methylthiazole hydrochloride (14.1) (6 mg, 0.018 mmol) in DMSO (0.5 mL). The mixture was stirred at room temperature for 3 hours. To the reaction mixture was added LiOH in water (0.5 mL, 1 N solution), and the mixture was stirred at 50° C. for 3 hours. The mixture was filtered and purified by reverse phase HPLC to give 14 (6 mg, 0.012 mmol) after lyophilization. MS ESI (pos.) m/e 479.2 (M+H). 1H NMR (500 MHz, CDCl$_3$) δ ppm 7.84 (2 H, d, J=8.3 Hz), 7.32 (2 H, d, J=8.1 Hz), 7.25 (2 H, d, J=8.6 Hz), 6.97 (2 H, d, J=8.8 Hz), 5.20 (2 H, s), 4.31-4.35 (1 H, m), 4.23-4.29 (1 H, m), 4.10 (1 H, t, J=8.1 Hz), 3.28 (1 H, dd, J=16.4, 7.8 Hz), 2.82-2.90 (2 H, m), 2.73-2.77 (1 H, m), 2.69 (2 H, t, J=7.8 Hz), 2.53 (3 H, s), 1.62-1.68 (2 H, m), 1.36-1.42 (2 H, m), 0.96 (3 H, t, J=7.3 Hz)

1.17 Example 15

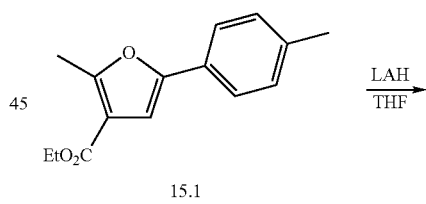

(2-Methyl-5-p-tolylfuran-3-yl)methanol (15.2). To a solution of 15.1 (5.0 mmol, commercially available from Maybridge) in THF (10 mL) at 0° C. was slowly added a solution of LAH (1.0 M in THF, 6.0 mL). After the reaction was stirred at room temperature for 2 h, water (0.24 mL), 15% aqueous NaOH (0.24 mL), and water (0.72 mL) were added sequentially to the reaction. After 30 minutes, the reaction mixture was filtered through celite, and the filtrate was concentrated to give 15.2 (0.92 g). MS ESI (pos.) m/e 203 (M+H).

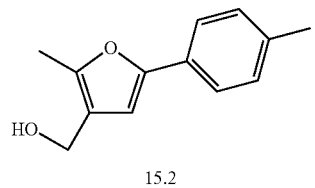

15.2

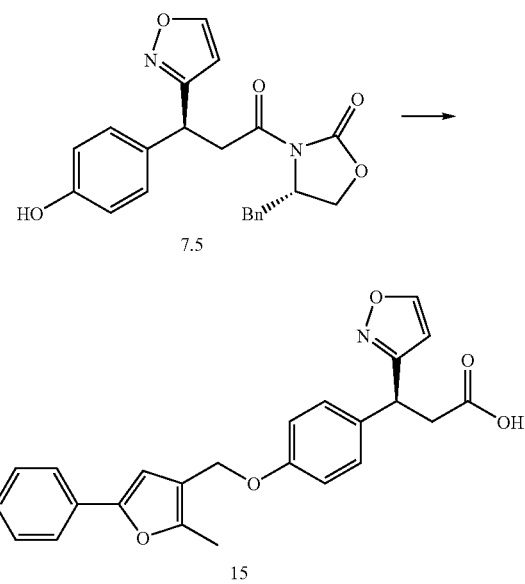

7.5

15

(S)-3-(Isoxazol-3-yl)-3-(4-((2-methyl-5-p-tolylfuran-3-yl)methoxy)phenyl)propanoic acid (15). Compound 15 was synthesized using the procedure described above for the preparation of 13. MS ESI (neg.) m/e: 416 (M−H). ¹H NMR (500 MHz) (CD$_3$CN-d$_3$) δ 8.42 (1H, d, J=1.7Hz); 7.54-7.50 (2H, m); 7.24-7.18 (4H, m); 6.93 (2H, ddd, J=9.2, 2.9, 2.6Hz); 6.69 (1H, s); 6.24 (1H, d, J=1.7Hz); 4.88 (2H, s); 4.53 (1H, t, J=7.8Hz); 3.17 (1H, dd, J=16.5, 8.2Hz); 2.93 (1H, dd, J=16.4, 7.3Hz); 2.34 (3H, s); 2.33 (3H, s).

1.18 Example 16

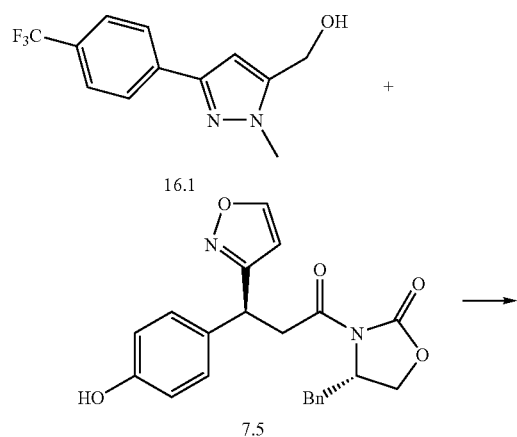

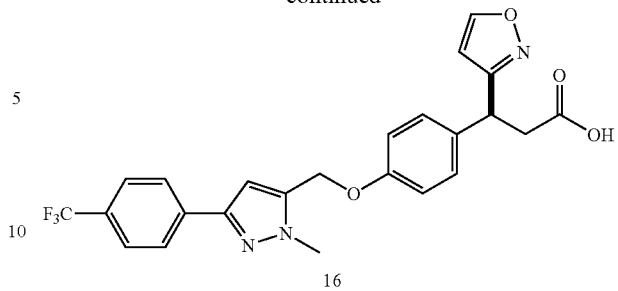

16

(S)-3-(Isoxazol-3-yl)-3-(4-((1-methyl-3-(4-(trifluoromethyl)phenyl)-1H-pyrazol-5-yl)methoxy)phenyl)propanoic acid (16). A mixture of alcohol 16.1 (0.051 mmol, prepared according to: Ackermann, J. et al. U.S. Pat. Appl. Publ., 2005/203160), Ph3P (0.056 mmol) and DIAD (0.056 mmol) in THF (100 uL) was sonicated at room temperature for 1 minute and then stirred at room temperature for 3 days. Silica gel was added, and the mixture was concentrated under reduced pressure. The resulting powder was purified using silica gel column chromatography (hexane/EtOAc=5/1 to 5/2) to give the intermediate oxazolidinone (0.013 mmol). The oxazolidinone and LiOH (3.0 M, 0.067 mmol) in THF (100 uL) were stirred at room temperature for 2 hours. The mixture was neutralized with AcOH and concentrated under reduced pressure. The resulting residue was purified using reverse phase HPLC give compound 16. MS ESI m/e: 472 (M−H).

6.12 Example 17

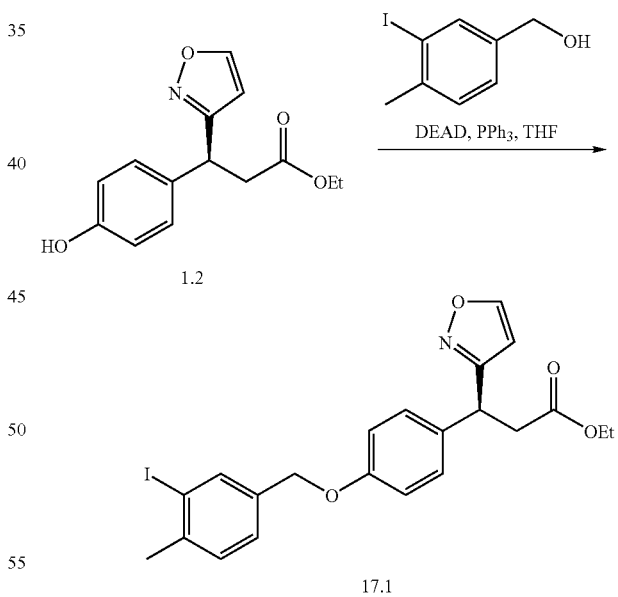

17.1

(S)-Ethyl 3-(4-(3-iodo-4-methylbenzyloxy)phenyl)-3-(isoxazol-3-yl)propanoate (17.1). To a solution of (3-iodo-4-methylphenyl)methanol (109 mg, 0.44 mmol), triphenylphosphine (115 mg, 0.44 mmol) and compound 1.2 (104 mg, 0.4 mmol) in THF (4 mL), was slowly added DEAD (81 μL, 0.52 mmol) at room temperature. The reaction mixture was stirred at room temperature for 30 minutes and then loaded on a silica gel cartridge and chromatographed (silica gel, 1:4 EtOAc/hexane) to afford the corresponding ester 17.1 (142 mg, 70%). MS ESI (pos.) m/e 492.0 (M+H).

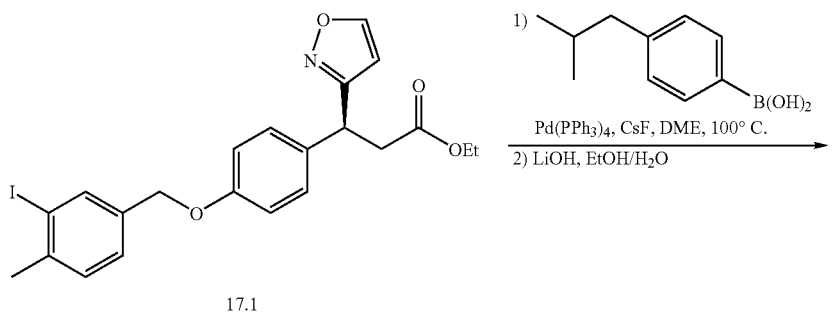

17.1

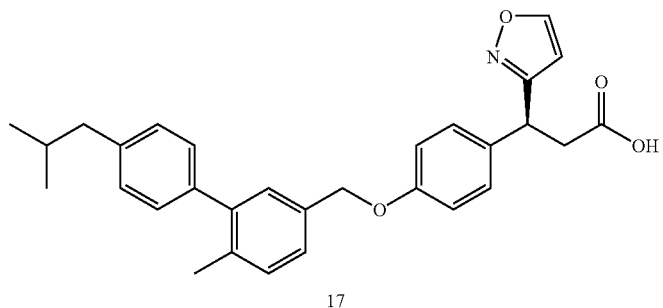

17

(S)-3-(4-(3-(4-Isobutyl)-phenyl-4-methylbenzyloxy)phenyl)-3-(isoxazol-3-yl)propanoic acid (17). A solution of (S)-ethyl 3-(4-(3-iodo-4-methylbenzyloxy)phenyl)-3-(isoxazol-3-yl)propanoate 17.1 (35 mg, 0.072 mmol), terakis(triphenylphosphine)palladium (32 mg, 0.028 mmol), CsF (85 mg, 0.56 mmol), and 4-isobutylphenylboronic acid (50 mg, 0.28 mmol) in DME (1 mL), was stirred at 100° C. for 5 hours and then loaded on a silica gel cartridge and chromatographed (silica gel, 1:4 EtOAc/hexane) to afford the corresponding ester. The ester was dissolved in EtOH (1 mL) and LiOH in water (1 mL, 1 N solution) was added. The mixture was stirred at 23° C. for 2 hours. The mixture was then filtered and purified by reverse phase HPLC to give compound 17 (1.62 mg) after lyophilization. MS ESI (pos.) m/e 470.2 (M+H). $^1$H NMR (500 MHz, CD$_3$OD) δ ppm 8.52 (1 H, s), 7.20-7.32 (8 H, m), 6.95-6.99 (2H, m), 6.30 (1 H, s), 5.07 (2 H, s), 4.59-4.56 (1 H, m), 3.21-3.17 (1 H, m), 2.97-2.92 (1 H, m), 2.55 (2 H, d, J=7.3 Hz), 2.26 (3 H, s), 1.96-1.90 (1 H, m), 0.97 (6 H, d, J=6.6 Hz).

6.13 Example 18

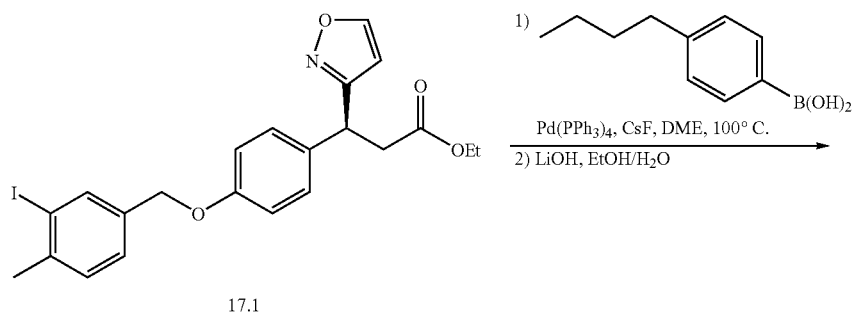

17.1

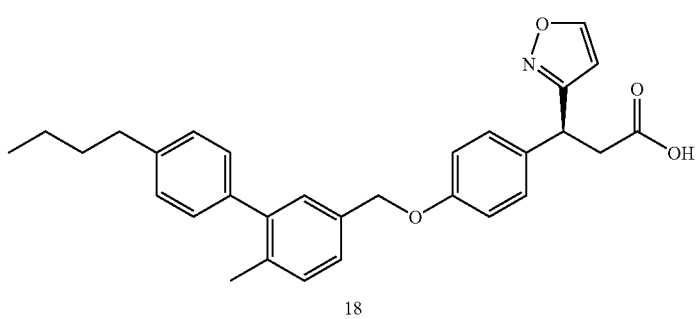

18

(S)-3-(4-(3-(4-Butyl)-phenyl-4-methylbenzyloxy)phenyl)-3-(isoxazol-3-yl)propanoic acid (18). A solution of (S)-ethyl 3-(4-(3-iodo-4-methylbenzyloxy)phenyl)-3-(isoxazol-3-yl)propanoate 17.1 (35 mg, 0.072 mmol), tetrakis (triphenylphosphine) palladium (32 mg, 0.028 mmol), CsF (85 mg, 0.56 mmol), and 4-butylphenylboronic acid (50 mg, 0.28 mmol) in DME (1 mL), was stirred at 100° C. for 5 hours and then loaded on a silica gel cartridge and chromatographed (silica gel, 1:4 EtOAc/hexane) to afford the corresponding ester. The ester was dissolved in EtOH (1 mL), and LiOH in water (1 mL, 1N solution) was added. The resulting mixture was then stirred at 23° C. for 2 hours. The mixture was filtered and purified by reverse phase HPLC to give 18 (0.56 mg) after lyophilization. MS ESI (pos.) m/e 470.2 (M+H).

6.14 Example 19

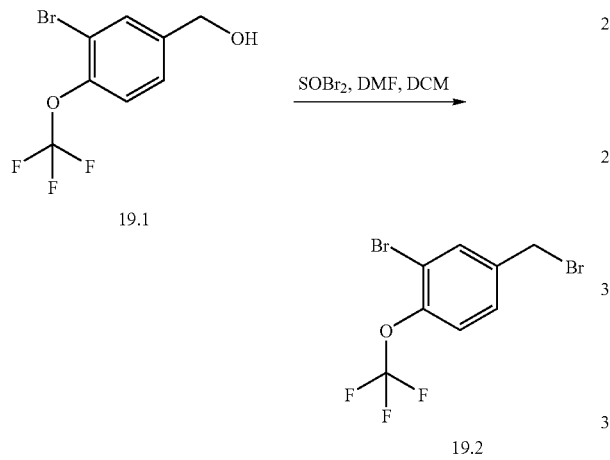

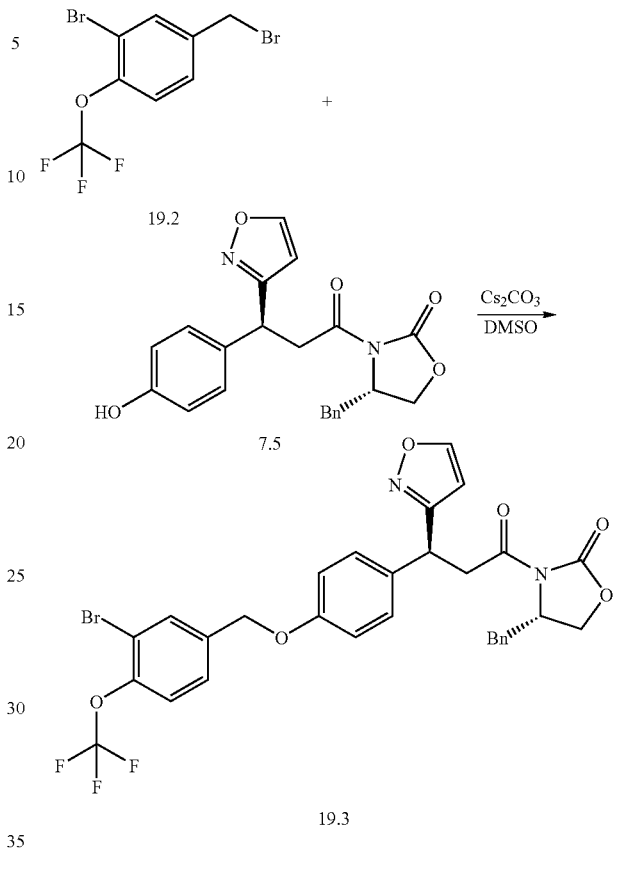

2-Bromo-4-(bromomethyl)-1-(trifluoromethoxy)benzene (19.2). To a solution of (3-bromo-4-(trifluoromethoxy)phenyl)methanol 19.1 (6.78 g, 25 mmol) in 30 mL of DCM, was added DMF (0.5 mL) and thionyl bromide (2 mL, 26 mmol). The mixture was stirred at 23° C. for 4 hours. DCM (120 mL) was added to the reaction mixture, and the resulting mixture was washed with aqueous saturated NaHCO$_3$. The organic layer was dried over Na$_2$SO$_4$ and concentrated to give 19.2 (8.3 g, 99% yield) as a yellow oil, which was used directly in the next step without further purification. $^1$H NMR (500 MHz, DMSO-d$_6$) δ ppm 7.74 (1 H, d, J=2.0 Hz), 7.38-7.53 (2 H, m), 4.53 (2 H, d, J=5.6 Hz).

(S)-3-((S)-3-(4-(3-Bromo-4-tert-butoxybenzyloxy)phenyl)-3-(isoxazol-3-yl)propanoyl)-4-benzyloxazolidin-2-one (19.3). Cesium carbonate (1.17 g, 3.6 mmol) was added to a mixture of 19.2 (1.1 g, 3.3 mmol) and (S)-4-benzyl-3-((S)-3-(4-hydroxyphenyl)-3-(isoxazol-3-yl)propanoyl)oxazolidin-2-one (7.5, 1.165 g, 2.97 mmol) in DMSO (10 mL). The mixture was stirred at room temperature for 21 hours. The reaction mixture was diluted with water and extracted with EtOAc. The organic layer was concentrated and chromatographed (silica gel, 1:4 EtOAc/hexane) to afford 19.3 (1.17 g, 1.81 mmol). MS ESI (pos.) m/e 645.0 (M+H).

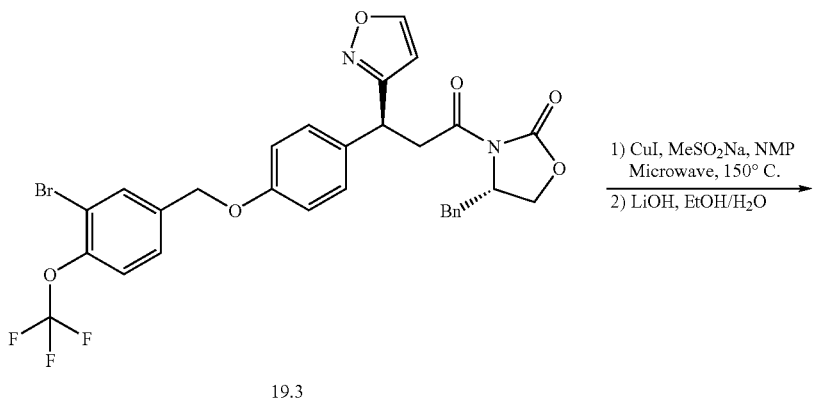

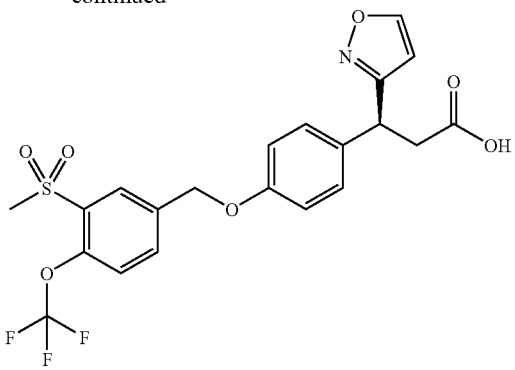

19

(S)-3-(4-(3-(Methylsulfonyl)-4-(trifluoromethoxy)benzyloxy)-phenyl)-3-(isoxazol-3-yl)propanoic acid (19). A suspension of 19.3 (65 mg, 0.1 mmol), CuI (76 mg, 04 mmol), and methanesulfinic acid sodium salt (41 mg, 0.4 mmol) in NMP (1 mL) was stirred under microwave condition at 150° C. with simultaneous cooling for maximum power for 20 minutes. The resulting mixture was filtered and purified by reverse phase HPLC to give the corresponding ester. The ester was then hydrolyzed with LiOH (0.5 mmol) in 1 mL of EtOH/H$_2$O (1:1) at room temperature for 2 hours and purified by reverse phase HPLC to give 19 (0.61 mg). MS ESI (pos.) m/e 486.1 (M+H).

6.15 Example 20

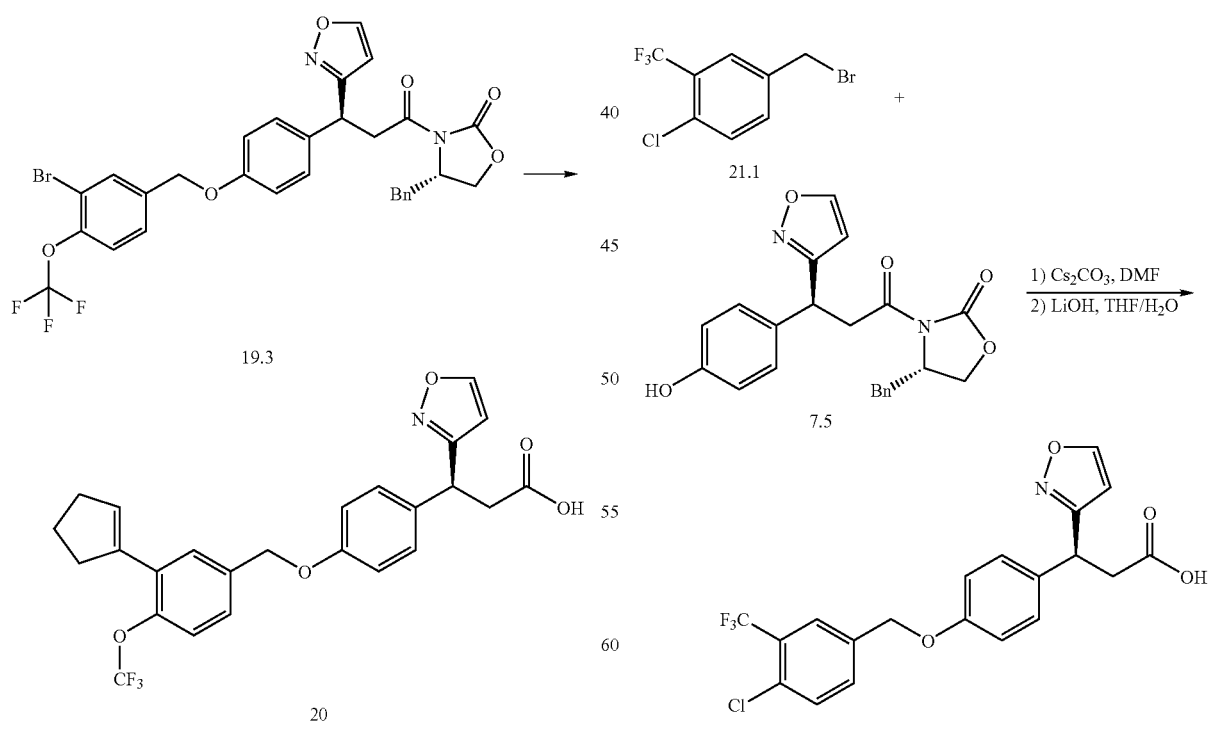

(S)-3-(4-(3-Cyclopentenyl-4-(trifluoromethoxy)benzyloxy)-phenyl)-3-(isoxazol-3-yl)propanoic acid (20). A mixture of 19.3 (0.5 mmol), 1-cyclopentenylboronic acid (1.0 mmol), Pd(OAc)$_2$ (0.1 mmol), S-phos (0.1 mmol) and K$_3$PO$_4$ (2.0 mmol) in dioxane (4.0 mL) and water (1.0 mL) was stirred at 80° C. overnight. The solvent was removed, and the residue was purified by CombiFlash to give an intermediate, which was treated with LiOH (1.0 mL, 3.33 M in water) in MeOH (6.0 mL) at room temperature overnight. The reaction mixture was purified by preparative HPLC (reverse phase) to give the title compound 20. $^1$H NMR (CD$_3$CN) δ 1.98 (m, 2 H), 2.55 (m, 2H), 2.75 (m, 2 H), 2.96 (dd, J=7.6, 16.6 Hz, 1 H), 3.21 (dd, J=7.6, 16.6 Hz, 1 H), 4.56 (t, J=7.8 Hz, 1 H), 5.09 (s, 2 H), 6.27 (m, 2 H), 6.97 (d, J=6.6 Hz, 2 H), 7.26 (d, J=6.6 Hz, 2H), 7.34 (d, J=7.1 Hz, 1 H), 7.41 (d, J=7.1 Hz, 1H), 7.54 (d, J=2.0 Hz, 1H), 8.44 (s, 1H). MS ESI (pos.) m/e=474.1 [M+H].

6.16 Example 21

(S)-3-(4-(4-Chloro-3-(trifluoromethyl)benzyloxy)phenyl)-3-(isoxazol-3-yl)propanoic acid (21). The title compound (5) was synthesized from substituted benzyl bromide 21.1 and 7.5 using the procedure described below for the preparation of compound 22. $^1$H-NMR (CD$_3$CN) δ 2.97 (dd, J=7.4, 16.4, 1 H), 3.21 (dd, J=7.4, 16.4 Hz, 1 H), 4.57 (t, J=7.8 Hz, 1 H), 5.13 (s, 2 H), 6.27 (d, J=1.5 Hz, 1 H), 6.98 (d, J=6.9 Hz, 2 H), 7.27 (d, J=6.9 Hz, 2H), 7.64 (d, J=8.3 Hz, 1 H), 7.69 (d, J=8.3 Hz, 1 H), 7.88 (d, J=1.5 Hz, 1H), 8.45, (s, 1 H). MS ESI (pos.) m/e: 426 (M+H).

6.17 Example 22

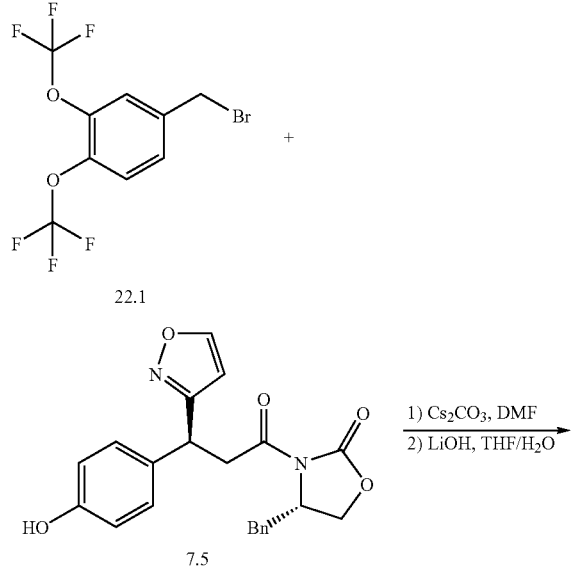

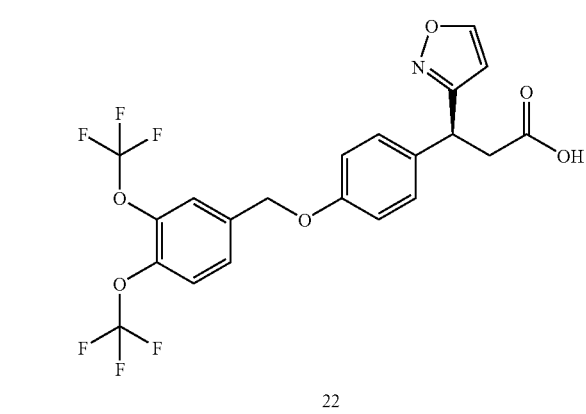

22

(S)-3-(4-(3,4-Bis(trifluoromethoxy)benzyloxy)phenyl)-3-(isoxazol-3-yl)propanoic acid (22). Cesium carbonate (137 mg, 0.4 mmol) was added to a mixture of 4-(bromomethyl)-1,2-bis(trifluoromethoxy)benzene 22.1 (71 mg, 0.21 mmol) and 7.5 (82 mg, 0.21 mmol) in DMF (2 mL). The mixture was stirred at room temperature for 16 hours. To the reaction mixture was added LiOH in water (0.5 mL, 1N solution) and THF (1 mL). The mixture was stirred at 23° C. for 3 hours. The mixture was filtered and purified by reverse phase HPLC to give 22 (19 mg) after lyophilization. MS ESI (pos.) m/e 492.1 (M+H). $^1$H NMR (400 MHz, CDCl$_3$) δ 8.31 (1 H, s), 7.45 (1 H, s), 7.39 (2 H, s), 7.21 (2 H, d, J=8.3 Hz), 6.93 (2 H, d, J=8.8 Hz), 6.08 (1 H, s), 5.05 (2 H, s), 4.57 (1 H, t, J=7.6 Hz), 3.37 (1 H, dd, J=16.6, 7.8 Hz), 3.00 (1 H, dd, J=16.6, 7.8 Hz).

6.18 Example 23

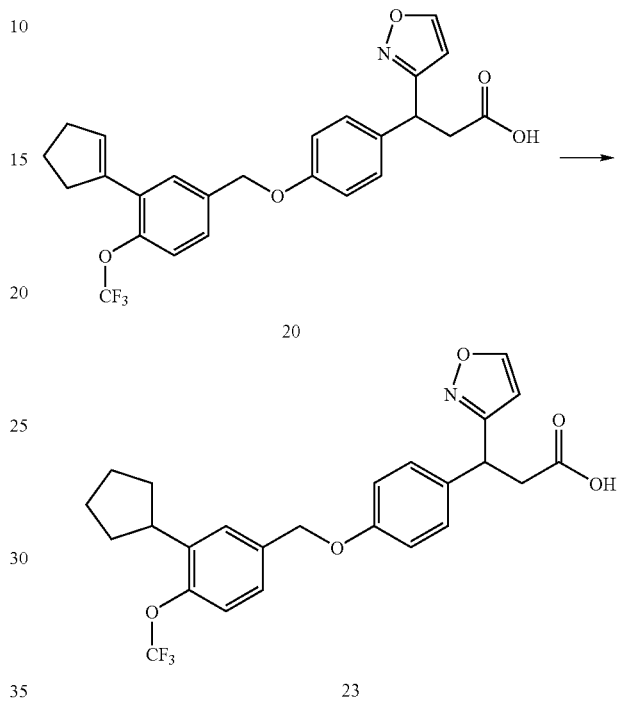

23

(S)-3-(4-(3-Cyclopentyl-4-(trifluoromethoxy)benzyloxy)-phenyl)-3-(isoxazol-3-yl)propanoic acid (23). To a suspension of Pd/C (20.0 mg, 10%) with Ph$_2$S (1.0%) in MeOH (5.0 mL), was added 20 (25.0 mg, 0.164 mmol) in MeOH (1.0 mL). The reaction mixture was purged with hydrogen three times. The mixture was then stirred under hydrogen at room temperature overnight. The catalyst was filtered off, and the solvent was evaporated to give the title compound 23. $^1$H NMR (CD$_3$CN) δ 1.55-2.02 (m, 8H), 2.93 (dd, J=7.3, 16.4 Hz, 1 H), 3.16 (dd, J=7.3, 16.4 Hz, 1 H), 3.33 (m, 1 H), 4.53 (m, 1 H), 5.05 (s, 2 H), 6.24 (d, J=1.7 Hz, 1H), 6.94 (d, J=6.6 Hz, 2H), 7.22-7.26 (m, 4H), 7.49 (d, J=5.0 Hz, 1H), 8.45 (d, J=1.7 Hz, 1H). MS ESI (pos.) m/e: 476 (M+H).

6.19 Example 24

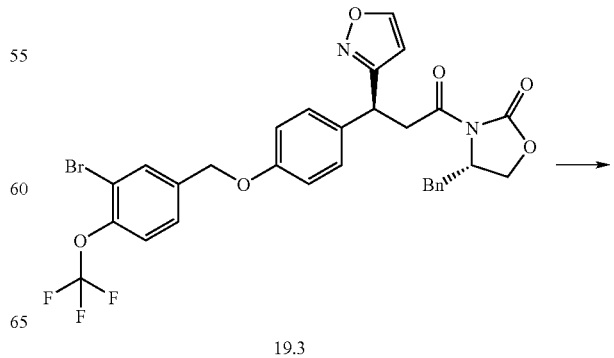

19.3

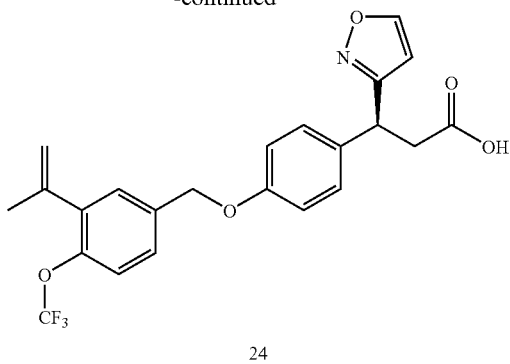

24

(S)-3-(4-(3-(Prop-1-en-2-yl)-4-(trifluoromethoxy)benzyloxy)-phenyl)-3-(isoxazol-3-yl)propanoic acid (24). Compound 24 was synthesized using the procedure described above for the preparation of compound 20. $^1$H NMR (CD$_3$CN) δ 2.09 (s, 3 H), 2.93 (dd, J=8.0, 16.3 Hz, 1 H), 3.17 (dd, J=8.0, 16.3 Hz, 1 H), 4.53 (m, 1 H), 5.07 (s, 2 H), 5.29 (m, 1 H), 6.24 (d, J=1.7 Hz, 1H), 6.95 (d, J=6.6 Hz, 2 H), 7.23 (d, J=6.6 Hz, 2H), 7.32 (d, J=7.6 Hz, 1 H), 7.42 (d, J=7.6 Hz, 1 H), 7.44 (s, 1H), 8.42 (d, J=1.7 Hz, 1H). MS ESI (pos.) m/e: 448 (M+H).

6.20 Example 25

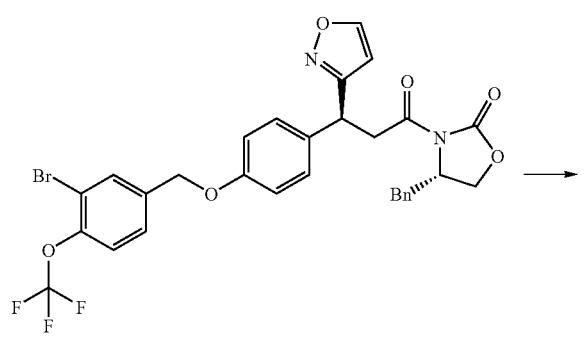

19.3

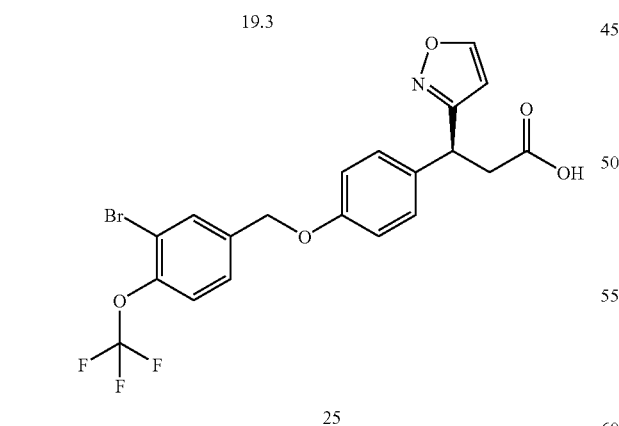

25

(S)-3-(4-(3-bromo-4-(trifluoromethoxy)benzyloxy)phenyl)-3-(isoxazol-3-yl)propanoic acid (26). To a solution of 19.3 (50 mg) in THF (2 mL) was added LiOH in water (0.5 mL, 1 N solution). The mixture was stirred at 23° C. for 3 hours. The mixture was filtered and purified by reverse phase HPLC to give 25 after lyophilization. $^1$H NMR (CD$_3$CN) δ 2.96 (dd, J=7.3, 16.4 Hz, 1H), 3.21 (dd, J=7.3, 16.4 Hz, 1 H), 4.57 (m, 1 H), 5.10 (s, 2 H), 6.28 (d, J=1.7 Hz, 1 H), 6.97 (d, J=6.6 Hz, 2 H), 7.26 (d, J=6.6 Hz, 2H), 7.45 (d, J=8.3 Hz, 1H), 7.54 (d, J=8.3 Hz, 1 H), 7.84 (d, J=2.2 Hz, 1H), 8.45, (d, J=1.7 Hz, 1 H). MS ESI (pos.) m/e: 488 (M+H).

6.21 Example 26

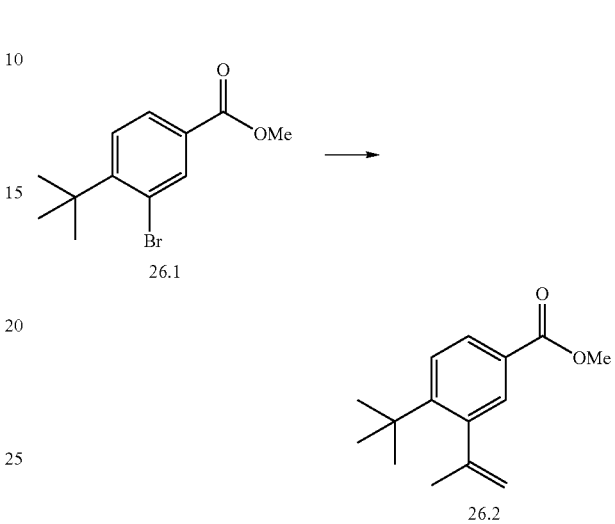

Methyl 4-tert-butyl-3-(prop-1-en-2-yl)benzoate (26.2). Methyl 3-bromo-4-tert-butylbenzoate (500 mg, 1.80 mmol, prepared according to the procedure of Hambley T. W. et al. *Aust. J. Chem.*, 1990, 43, 807-814) and commercially available isopropenylboronic acid pinacol ester (0.693 mL, 3.6 mmol) were suspended in toluene (7 mL). Potassium carbonate (765 mg, 5.5 mmol) was added followed by Pd(PPh$_3$)$_4$ (213 mg, 0.180 mmol). The resulting mixture was heated to 100° C. and stirred for 24 hours. After cooling to room temperature, the mixture was treated with EtOAc (5 mL) and brine (5 mL). The organic layer was separated, washed twice with brine, dried with MgSO$_4$, and concentrated in vacuo. The residue was purified by flash chromatography on silica gel (0-10% EtOAc/hexane) to give 26.2 (378 mg, 88%) as a clear oil.

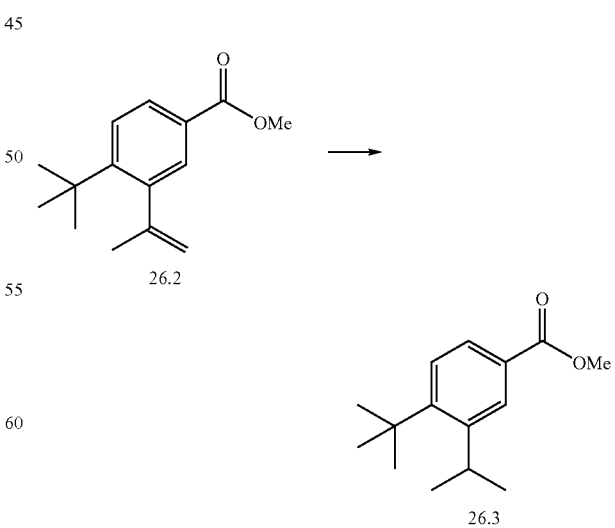

Methyl 4-tert-butyl-3-isopropylbenzoate (26.3). To the ester 26.2 (167 mg, 0.72 mmol) in EtOH/EtOAc (1/1, v/v, 3.00 mL), was added Pd(OH)₂/C (10 mg). The mixture was placed under an atmosphere of hydrogen and stirred for 8 days. The resulting mixture was filtered through Celite and concentrated in vacuo to give a clear oil (145 mg, 86%). The crude product (26.3) was used in the next step without further purification.

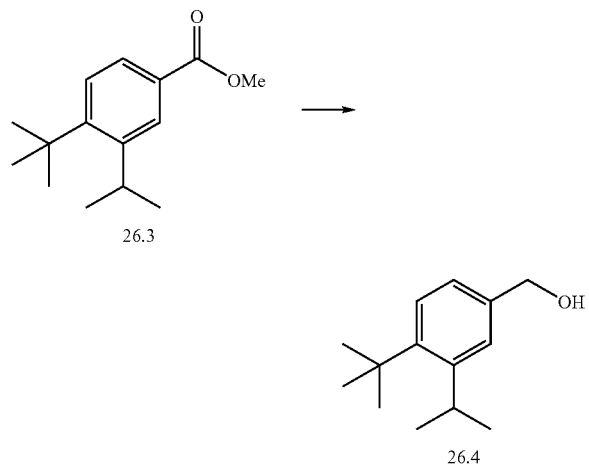

(4-tert-Butyl-3-isopropylphenyl)methanol (26.4). To the ester 26.3 (145 mg, 0.62 mmol) in anhydrous THF (5.0 mL) was added dropwise 1.0 M LiAlH₄ in THF (1.2 mL, 1.20 mmol) at 0° C. The resulting mixture was stirred for 5 minutes. The reaction was slowly quenched with 1 N NaOH aqueous solution (3.00 mL). The mixture was extracted with EtOAc (10 mL), dried over MgSO₄, and concentrated in vacuo. The crude product was purified by flash chromatography on silica gel (0-10% EtOAc/hexane) to give 26.4 (77 mg, 60%) as a clear oil.

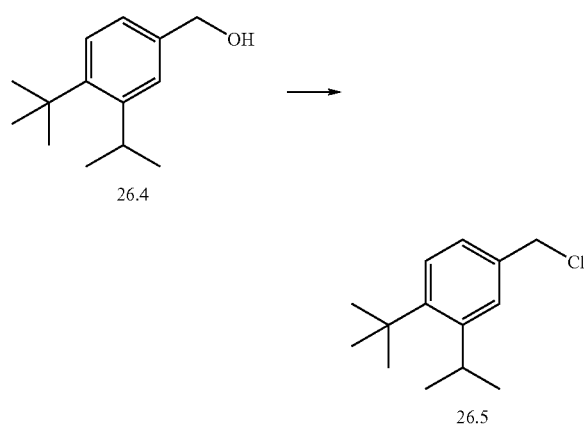

1-tert-Butyl-4-(chloromethyl)-2-isopropylbenzene (26.5). Alcohol 26.4 (77.0 mg, 0.37 mmol) was dissolved in anhydrous DCM (5.0 mL). Thionyl chloride (0.041 mL, 0.56 mmol) was added dropwise to the above solution. The resulting mixture was stirred at room temperature for 24 hours. The organic solvent was then removed under vacuo to give a white solid (80 mg). The crude product (26.5) was used in the next step without further purification.

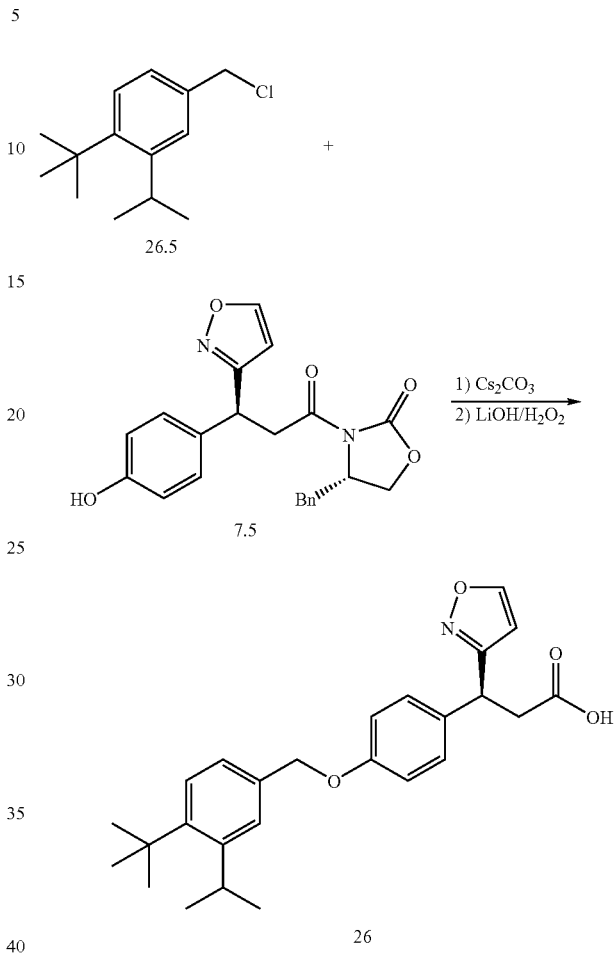

(S)-3-(4-(4-tert-Butyl-3-isopropylbenzyloxy)phenyl)-3-(isoxazol-3-yl)propanoic acid (26). Cesium carbonate (360 mg, 1.1 mmol) was added to a mixture of 7.5 (40.0 mg, 0.10 mmol) and 26.5 (27.0 mg, 0.12 mmol) in DMF (2.0 mL). The resulting mixture was stirred at room temperature for 19 hours. The mixture was then treated with water (5 mL) and extracted with EtOAc (15 mL). The organic layer was separated, washed twice with brine, dried over MgSO₄, and concentrated in vacuo. The crude product was purified by flash chromatography on silica gel (0-30% EtOAc/hexane) to give (S)-3-((S)-3-(4-(4-tert-butyl-3-isopropylbenzyloxy)phenyl)-3-(isoxazol-3-yl)propanoyl)-4-benzyloxazolidin-2-one (18.0 mg, 30%) as a clear oil. The ester (18.0 mg, 0.031 mmol) was treated with THF/H₂O (3/1, v/v, 2.0 mL) and hydrogen peroxide (30%, 0.021 mL, 0.19 mmol) and cooled to 0° C. LiOH (2.60 mg, 0.062 mmol) was added. The resulting mixture was stirred at 0° C. for 1 hour. A saturated solution of Na₂SO₃ was added to the mixture, and the reaction was stirred for 1 hour. The mixture was extracted with EtOAc (10 mL), dried over MgSO₄, and concentrated in vacuo. The residue was purified by flash chromatography on silica gel (0-30% EtOAc/hexane) to give 26 (5.80 mg, 44%) as a colorless film. MS ESI (neg.) m/e: 420 (M–H). ¹H NMR (500 MHz) (CDCl₃) δ 8.28 (1H, s); 7.37-7.34 (2H, m); 7.20-7.17 (3H, m); 6.96-6.94 (2H, d, J=8.2Hz); 6.07 (1H, s); 4.98 (2H, s); 4.56 (1H, dd, J=7.8, 7.4 Hz); 3.64 (1H, m), 2.36 (1H, dd, J=16.8, 7.8 Hz), 2.99 (1H, dd, J=16.8, 7.4Hz), 1.43 (9H, s), 1.26 (6H, d, J=7.1Hz).

6.22 Example 27

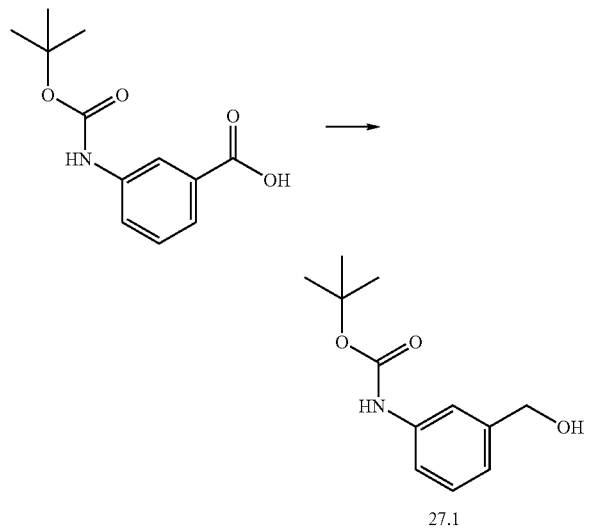

tert-Butyl 3-(hydroxymethyl)phenylcarbamate (27.1). 3-(tert-Butoxy-carbonylamino)benzoic acid (3.00 g, 12.6 mmol) was dissolved in THF (30 mL) and cooled to 0° C. A 1 M borane: THF solution (12.7 mL, 12.7 mmol) was slowly added to the reaction. The solution was then allowed to slowly warm to room temperature and stirred for six hours. The reaction was then quenched with a 50% AcOH:water mixture (2 mL). Next, the mixture was concentrated to reduced volume and poured into a saturated sodium bicarbonate solution (75 mL). The mixture was then extracted with EtOAc (2×250 mL). The organic layers were combined and washed with saturated sodium bicarbonate solution (1×75 mL), brine (1×75 mL), and then dried over magnesium sulfate. The filtrate was concentrated, and the residue was purified by medium pressure chromatography (silica gel, 0 to 5% MeOH:DCM) to give 27.1 (2.41 g). MS ESI (pos.) m/e 241.1 (M+18). $^1$H NMR (400 MHz, DMSO-$d_6$) δ ppm 9.28 (1 H, s), 7.48 (1 H, s), 7.26 (1 H, d, J=8.6 Hz), 7.17 (1 H, t, J=7.8 Hz), 6.89 (1 H, d, J=7.4 Hz), 5.12 (1 H, t, J=5.7 Hz), 4.42 (2 H, d, J=5.5 Hz), 1.47 (9 H, s)

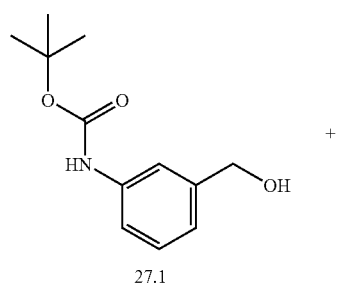

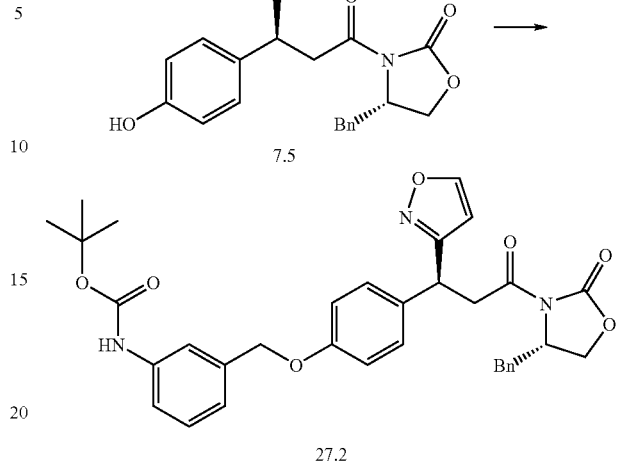

tert-Butyl 3-((4-((S)-3-((S)-4-benzyl-2-oxooxazolidin-3-yl)-1-(isoxazol-3-yl)-3-oxopropyl)phenoxy)methyl)phenylcarbamate (27.2). To a solution of alcohol 27.1 (179 mg, 0.765 mmol) in THF (7 mL), was added phenol 7.5 (300 mg, 0.765 mmol), DIAD (0.155 mL, 0.803 mmol), and triphenylphosphine (211 mg, 0.803 mmol). The solution was stirred for 16 hours and then concentrated to a reduced volume. The residue was purified by medium pressure chromatography (silica gel, 0 to 50% EtOAc:hexanes) to give 27.2 (440 mg). MS ESI (pos.) m/e 598.2 (M+H). $^1$H NMR (400 MHz, CDCl$_3$) δ ppm 8.20 (1 H, d, J=1.6 Hz), 7.38 (1 H, s), 7.08-7.29 (8 H, m), 7.00 (1 H, d), 6.82 (2 H, d, J=8.6 Hz), 6.54 (1 H, s), 6.33 (1 H, br. s.), 6.05 (1 H, d, J=1.6 Hz), 4.92 (2 H, s), 4.85-4.90 (1 H, m), 4.66 (1 H, dd, J=1.6 Hz), 4.49-4.58 (1 H, m), 4.01-4.04 (1 H, m), 3.93 (1 H, dd, J=17.6, 8.2 Hz), 3.45 (1 H, dd, J=17.6, 6.7 Hz), 3.11 (1 H, dd, J=13.5, 3.3 Hz), 2.68 (1 H, dd, J=13.3, 9.4 Hz), 1.43 (9 H, s).

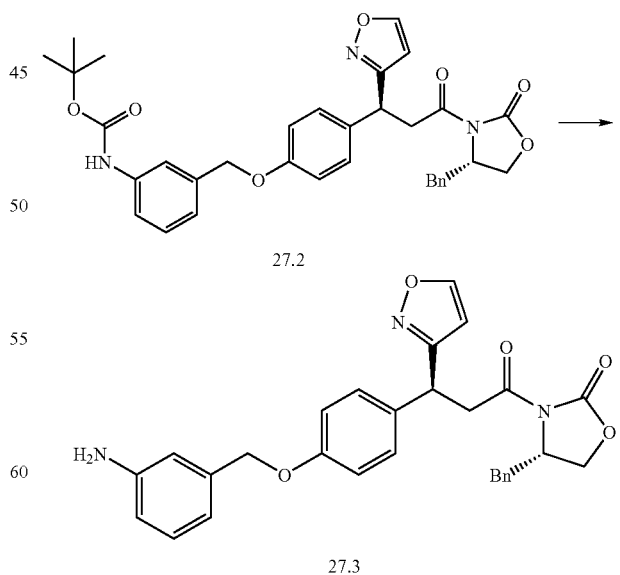

(S)-3-((S)-3-(4-(3-Aminobenzyloxy)phenyl)-3-(isoxazol-3-yl)propanoyl)-4-benzyloxazolidin-2-one (27.3). To a cooled solution (0° C.) of carbamate 27.2 (430 mg, 0.719 mmol) in DCM (4 mL), was slowly added TFA (4 mL). The reaction mixture was allowed to slowly warm to room temperature over three hours. The mixture was then concentrated to dryness under reduced pressure and dissolved in DCM (100 mL). The resulting mixture was extracted with saturated sodium bicarbonate solution (1×30 mL). The aqueous layer was then extracted with DCM (1×50 mL). The organic layers were then combined and washed with brine (1×50 mL) and dried over magnesium sulfate. The filtrate was concentrated, and the residue was purified by medium pressure chromatography (silica gel, 20 to 60% EtOAc:DCM) to give 27.3 (204 mg). MS ESI (pos.) m/e 498.1 (M+H). $^1$H NMR (400 MHz, CDCl$_3$) δ ppm 8.21 (1 H, d, J=1.6 Hz), 7.09-7.29 (8 H, m), 6.75-6.88 (4 H, m), 6.68 (1 H, dd, J=7.6, 2.2 Hz), 6.06 (1 H, d, J=1.6 Hz), 4.89 (2 H, s), 4.67 (1 H, dd, J=8.2, 6.7 Hz), 4.50-4.58 (1 H, m), 4.01-4.06 (2 H, m), 3.94 (1 H, dd, J=17.6, 8.6 Hz), 3.42-3.49 (1H, m), 3.13 (1 H, dd, J=13.5, 3.3 Hz), 2.68 (1 H, dd, J=13.5, 9.6 Hz).

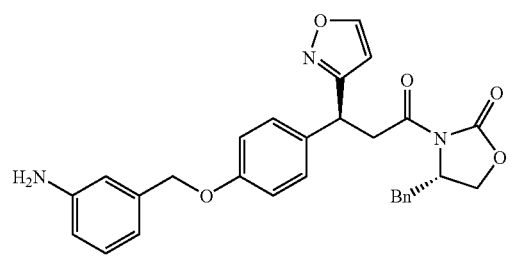

27.3

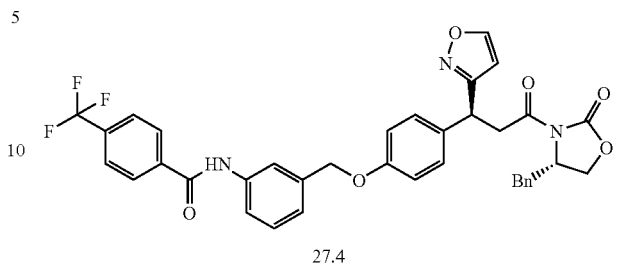

27.4

N-(3-((4-((S)-3-((S)-4-Benzyl-2-oxooxazolidin-3-yl)-1-(isoxazol-3-yl)-3-oxopropyl)phenoxy)methyl)phenyl)-4-(trifluoromethyl)benzamide (27.4). To a solution of substituted aniline 27.3 (0.050 g, 0.100 mmol) in DCM (1 mL), was added TEA (14.1 µL, 0.100 mmol) and 4-(trifluoromethyl)benzoyl chloride (15.0 µL, 0.100 mmol). The reaction mixture was stirred for 16 hours and then concentrated to dryness under reduced pressure. The residue was purified by medium pressure chromatography (silica gel, 0 to 30% EtOAc:DCM) to give 27.4 (72 mg). MS ESI (pos.) m/e 670.2 (M+H).

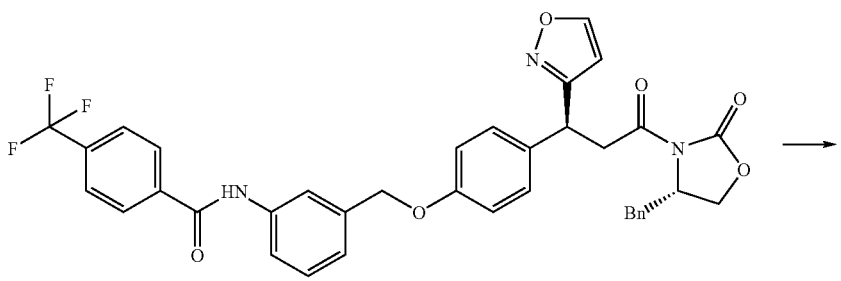

27.4

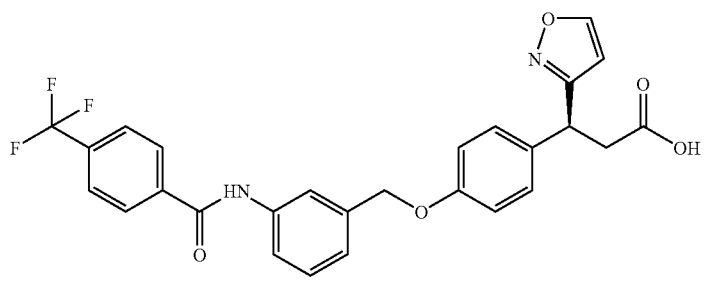

27

(S)-3-(4-(3-(4-(Trifluoromethyl)benzamido)benzyloxy)phenyl)-3-(isoxazol-3-yl)propanoic acid (27). To a solution of oxazolidinone 27.4 (71.8 mg, 0.107 mmol) dissolved in THF (10 mL), was added a 30% hydrogen peroxide solution (0.121 mL, 1.07 mmol) followed by a 2M LiOH solution (0.268 mL, 0.535 mmol). The resulting slurry was stirred for two hours. The reaction mixture was diluted with water and acidified with hydrochloric acid to a pH 3. The mixture was then extracted with EtOAc (1×50 mL), and the organic layer was washed with acidic sodium sulfite solution (2×30 mL), brine (1×30 mL), and dried over magnesium sulfate. The filtrate was concentrated under reduced pressure, and the residue was purified by reverse phase HPLC to give 27 (25.2 mg). MS ESI (pos.) m/e 511.1 (M+H). $^1$H NMR (400 MHz, DMSO-$d_6$) δ ppm 12.21 (1 H, br. s.), 10.51 (1 H, s), 8.75 (1 H, d, J=1.6 Hz), 8.15 (2 H, d, J=8.2 Hz), 7.91 (2 H, d, J=8.2 Hz), 7.87 (1 H, s), 7.74 (1 H, d, J=8.2 Hz), 7.38 (1 H, t, J=7.8 Hz), 7.23 (2 H, d, J=8.6 Hz), 7.19 (1 H, d, J=7.8 Hz), 6.96 (2 H, d, J=9.0 Hz), 6.50 (1 H, d, J=1.6 Hz), 5.08 (2 H, s), 4.48 (1 H, t, J=7.8 Hz), 3.07 (1 H, dd, J=16.4, 8.2 Hz), 2.88 (1 H, dd, J=16.2, 7.2 Hz).

6.23 Example 28

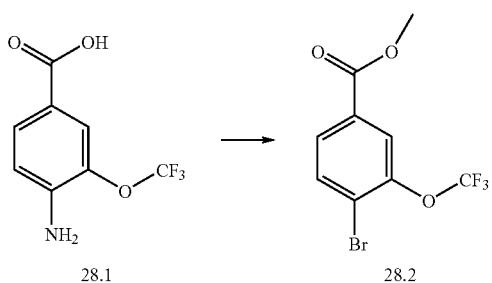

Methyl 4-bromo-3-(trifluoromethoxy)benzoate (28.2). To a solution of 4-amino-3-(trifluoromethoxy)benzoic acid (2.00 g, 9.10 mmol) in MeOH (25.0 mL), was slowly added HCl (1.0 mL, 1.0 M in ether) at room temperature. The resulting reaction mixture was stirred at room temperature overnight. Benzene (20 mL) was added, and the reaction was heated at reflux with a Dean-Stark trap to remove the half volume of the solvent. The rest of the solvent was then evaporated to give the product. MS (ESI) m/e=235.9 [M+1]$^+$, Calc'd for $C_8H_6F_3NO_3$, 235.1. The crude product was used in the next step without further purification. To an ice-cooled suspension of methyl 4-amino-3-(trifluoromethoxy)benzoate hydrogen chloride salt (8.60 g, 31.70 mmol) in 17.1 mL of water and concentrated HBr (48%, 17.1 mL), was slowly added a prepared 2.5 M solution of sodium nitrite (2.20 g in 12.7 mL) at 0° C. The reaction mixture was stirred at 0° C. for 10 minutes. Meanwhile, a solution of CuSO$_4$ (6.68 g) in 35 mL of water was heated and sodium bromide (6.52 g) was added. The solution became a green color, and a solution of Na$_2$SO$_3$ (2.80 g) in water (10 mL) was then added to it. The solution was cooled at 0° C. and washed with water (25×3 mL). The water was then decanted off. Concentrated HBr (16.7 mL) was added, and the solution became a purple color. The solution of CuBr was slowly added to the diazonium salt (prepared above) at 0° C. After addition, the ice-bath was removed, and an oil-bath was placed under the reaction vessel. The reaction mixture was then heated to 60° C. for 15 minutes, at 80° C. for 15 minutes, and then at 100° C. for 20 minutes. The reaction mixture was next cooled to room temperature and made basic with Na$_2$CO$_3$ to a pH 8. The aqueous solution was extracted with EtOAc (100×2 mL). The organic layer was washed with brine (25 mL) and dried with MgSO$_4$. The solvent was removed to give the crude product 28.2. $^1$H NMR (CDCl$_3$) δ 3.96 (s, 3H), 7.75 (d, J=8.4 Hz, 1 H), 7.86 (d, J=8.4 Hz, 1 H), 7.98 (s, 1H).

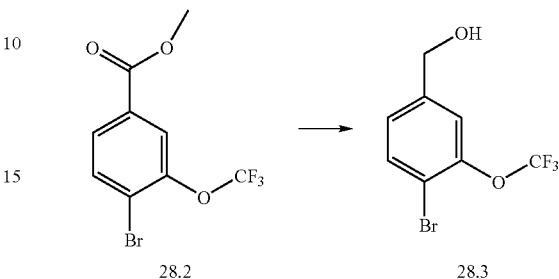

(4-Bromo-3-(trifluoromethoxy)phenyl)methanol (28.3). To a cooled and stirred solution of methyl 4-bromo-3-(trifluoromethoxy)benzoate (28.2, 2.60 g, 8.70 mmol) in THF (20 mL) under nitrogen, was added DIBAL-H (19.2 mL, 1.0 M in toluene) at −78° C. The reaction mixture was stirred at 0° C. for 10 minutes and 5.0 mL of water was added. The resulting mixture was stirred at room temperature for 2 hours. The solid was then filtered off. EtOAc (100 mL) was added, and the mixture was washed with brine (20 mL) and dried with Na$_2$SO$_4$. The solvent was removed to give 28.3. $^1$H NMR (CDCl$_3$) δ 1.91 (s, 1H), 4.71 (s, 2 H), 7.18 (d, J=6.3 Hz, 1H), 7.36 (s, 1H), 7.63 (d, J=6.3 Hz, 1 H).

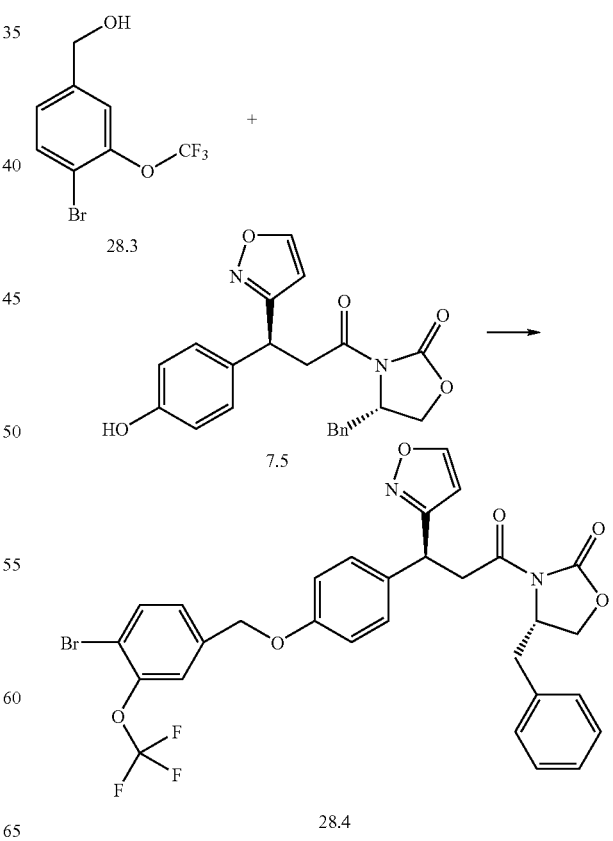

(S)-3-((S)-3-(4-(4-Bromo-3-(trifluoromethoxy)benzyloxy)-phenyl)-3-(isoxazol-3-yl)propanoyl)-4-benzyloxazolidin-2-one (28.4). A mixture of 28.3 (1.30 g, 4.80 mmol), thionyl bromide (1.01 g, 4.84 mmol), and DMF (0.1 mL) in DCM (8.0 mL) was stirred at room temperature for 50 minutes. The solvent was then removed. To the residue was added 7.5 (1.10 g, 2.80 mmol) and $Cs_2CO_3$ (1.10 g, 3.36 mmol) in DMF (8.0 mL). The mixture was stirred at room temperature for 4 hours. EtOAc (150 mL) was added, and the mixture was washed with brine (25×3 mL) and dried with $MgSO_4$. The solvent was removed, and the crude product was purified by CombiFlash, eluting with EtOAc and hexane, to give the title compound 28.4. $^1$H NMR ($CDCl_3$) δ 2.77 (dd, J=4.2, 9.5 Hz, 1 H), 3.21 (dd, J=4.2, 9.5 Hz, 1 H), 3.52 (dd, J=8.6, 17.6 Hz, 1 H), 4.04 (dd, J=8.6, 17.6 Hz, 1 H), 4.63 (m, 1 H), 4.76 (m, 1 H), 5.01 (s, 2 H), 6.14 (d, J=1.5 Hz, 1 H), 6.92 (d, J=6.9,Hz, 2 H), 7.20-7.35 (m, 9 H), 7.64 (d, J=8.3,Hz, 1H), 8.31 (d, J=1.5 Hz, 1 H). MS ESI (pos.) m/e: 647 (M+H).

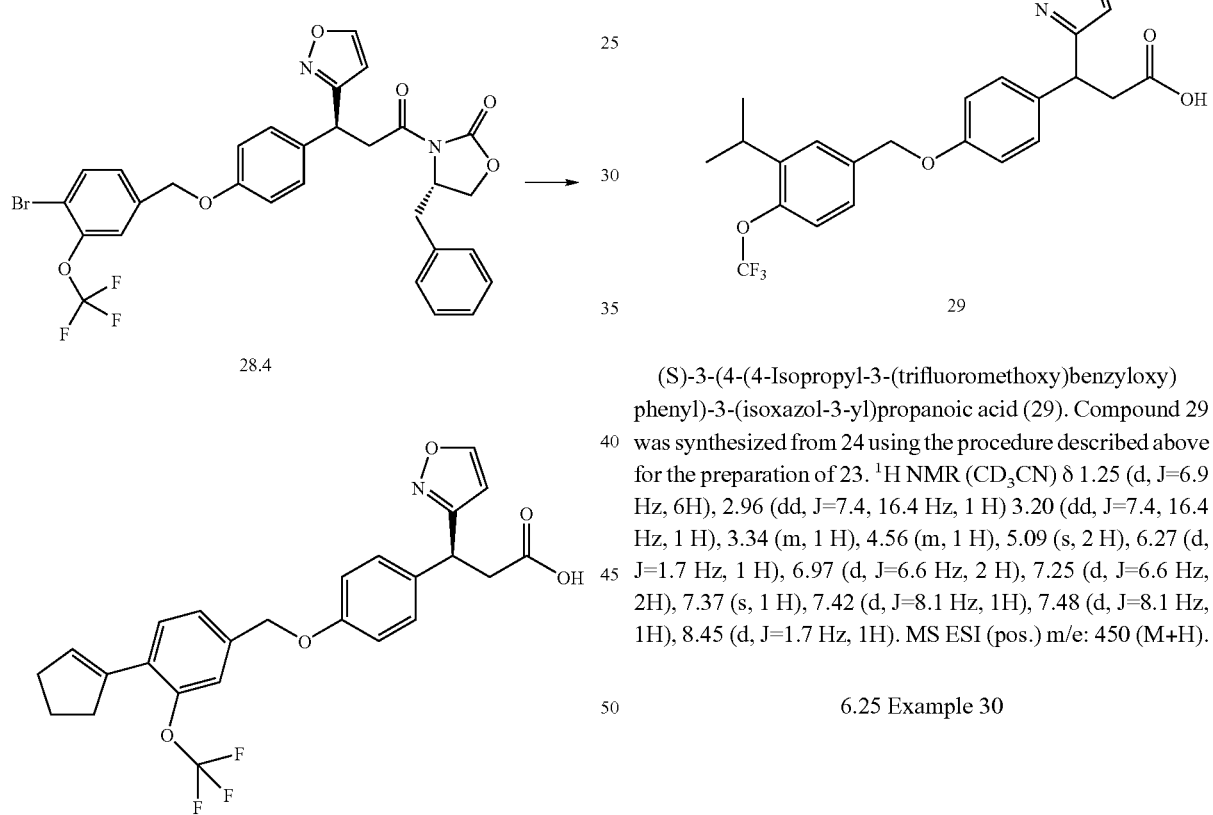

28.4

28

(S)-3-(4-(4-Cyclopentenyl-3-(trifluoromethoxy)benzyloxy)-phenyl)-3-(isoxazol-3-yl)propanoic acid (28). Compound 28 was synthesized from 28.4 using the procedure described above for the preparation of 20. $^1$H NMR ($CD_3CN$) δ 2.01 (m, 2 H), 2.55 (m 2 H), 2.96 (dd J=8.3, 16.6 Hz, 1 H), 3.30 (dd, J=8.3, 16.6 Hz, 1 H), 4.56 (m, 1 H), 5.11 (s, 2 H), 6.27 (m, 2 H), 6.97 (d, J=6.6 Hz, 2 H), 7.25 (d, J=6.6 Hz, 2H), 7.41-7.50 (m, 3 H), 8.45 (d, J=1.7 Hz, 1H). MS ESI (pos.) m/e: 474 (M+H).

6.24 Example 29

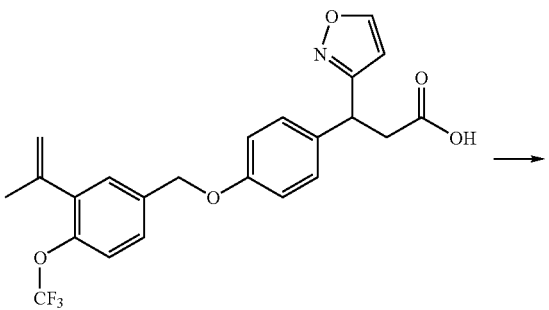

24

29

(S)-3-(4-(4-Isopropyl-3-(trifluoromethoxy)benzyloxy)phenyl)-3-(isoxazol-3-yl)propanoic acid (29). Compound 29 was synthesized from 24 using the procedure described above for the preparation of 23. $^1$H NMR ($CD_3CN$) δ 1.25 (d, J=6.9 Hz, 6H), 2.96 (dd, J=7.4, 16.4 Hz, 1 H) 3.20 (dd, J=7.4, 16.4 Hz, 1 H), 3.34 (m, 1 H), 4.56 (m, 1 H), 5.09 (s, 2 H), 6.27 (d, J=1.7 Hz, 1 H), 6.97 (d, J=6.6 Hz, 2 H), 7.25 (d, J=6.6 Hz, 2H), 7.37 (s, 1 H), 7.42 (d, J=8.1 Hz, 1H), 7.48 (d, J=8.1 Hz, 1H), 8.45 (d, J=1.7 Hz, 1H). MS ESI (pos.) m/e: 450 (M+H).

6.25 Example 30

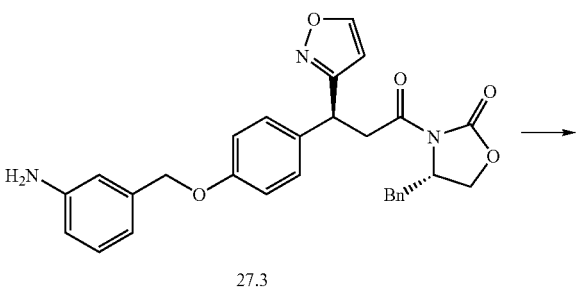

27.3

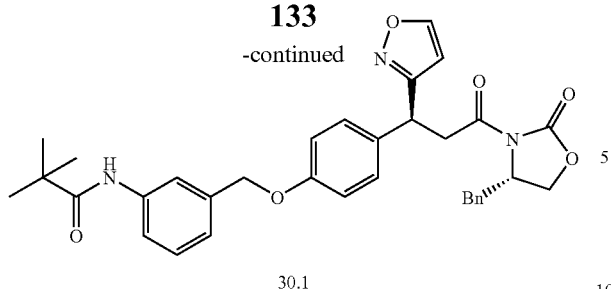

30.1

N-(3-((4-((S)-3-((S)-4-Benzyl-2-oxooxazolidin-3-yl)-1-(isoxazol-3-yl)-3-oxopropyl)phenoxy)methyl)phenyl)pivalamide (30.1). To a solution of substituted aniline 27.3 (0.050 g, 0.100 mmol) in DCM (2 mL), was added TEA (0.10 mmol) and pivaloyl chloride (0.0124 mL, 0.100 mmol). The reaction mixture was stirred for 16 hours and then concentrated to dryness under reduced pressure. The residue was purified by medium pressure chromatography (silica gel, 20 to 60% EtOAc:hexanes) to give 30.1 (62 mg). MS ESI (pos.) m/e: 582.2 (M+H).

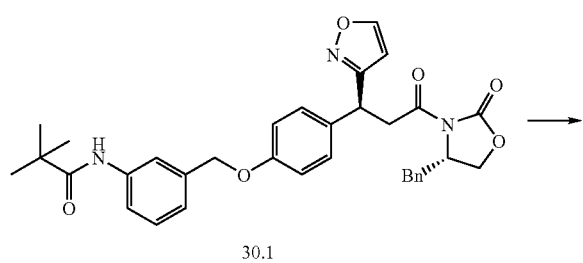

30.1

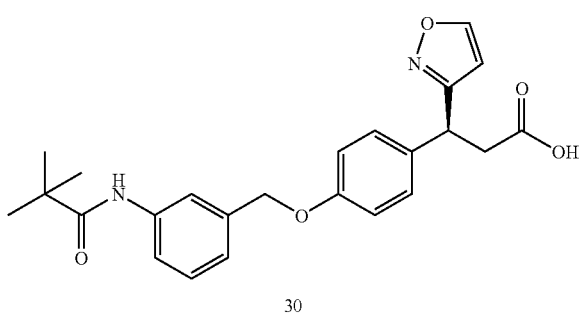

30

(S)-3-(4-(3-Pivalamidobenzyloxy)phenyl)-3-(isoxazol-3-yl)propanoic acid (30). To a solution of the oxazolidinone 30.1 (62.0 mg, 0.107 mmol) dissolved in THF (10 mL), was added a 30% hydrogen peroxide solution (0.120 mL, 1.07 mmol) followed by a 2M LiOH solution (0.266 mL, 0.533 mmol). The resulting slurry was stirred for five hours. The reaction mixture was diluted with water and acidified with hydrochloric acid to a pH 3. The mixture was then extracted with EtOAc (1×50 mL), and the organic layer was washed with acidic sodium sulfite solution (2×30 mL) and brine (1×30 mL), and dried over magnesium sulfate. The filtrate was concentrated under reduced pressure, and the residue was purified by reverse phase HPLC to give 30 (29.0 mg). MS ESI (pos.) m/e: 423.1 (M+H). $^1$H NMR (400 MHz, CD$_3$CN) δ ppm 8.32 (1 H, d, J=1.6 Hz), 7.92 (1 H, br. s.), 7.61 (1 H, s), 7.42 (1 H, d, J=7.8 Hz), 7.22 (1 H, t, J=7.8 Hz), 7.12 (2 H, d, J=9.0 Hz), 7.05 (1 H, d, J=7.4 Hz), 6.84 (2 H, d, J=9.0 Hz), 6.15 (1 H, d, J=1.6 Hz), 4.95 (2 H, s), 4.43 (1 H, t, J=7.8 Hz), 3.08 (1 H, dd, J=16.6, 8.4 Hz), 2.83 (1 H, dd, J=16.4, 7.4 Hz), 1.16 (9 H, s).

6.26 Example 31

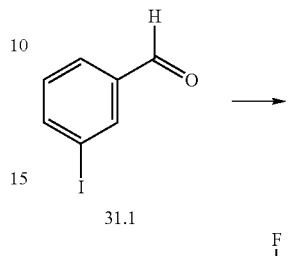

31.1

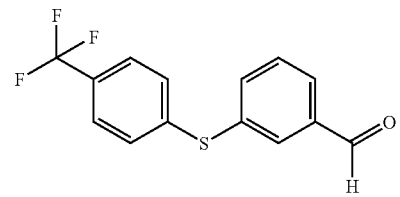

31.2

3-(4-(Trifluoromethyl)phenylthio)benzaldehyde (31.2). To a sealed tube flushed with nitrogen, was added 3-iodobenzaldehyde 31.1 (300 mg, 1.29 mmol), 4-(trifluoromethyl)benzenethiol (230 mg, 1.29 mmol), copper (I) iodide (24.6 mg, 0.129 mmol), ethylene glycol (0.144 mL, 2.59 mmol), potassium carbonate (357 mg, 2.59 mmol), and isopropanol (6.50 mL). The reaction mixture was heated at 85° C. for 48 hours. The reaction was then cooled and diluted with DCM and filtered over a pad of diatomaceous earth. The filtrate was concentrated, and the residue was purified by medium pressure chromatography (silica gel, 0 to 20% diethyl ether:hexanes) to give 31.2 (162 mg). $^1$H NMR (400 MHz, CDCl$_3$) δ ppm 9.92 (1 H, s), 7.85 (1 H, s), 7.77 (1 H, d, J=7.4 Hz), 7.59 (1 H, d, J=7.8 Hz), 7.44-7.50 (3 H, m), 7.29 (2 H, d, J=8.2 Hz).

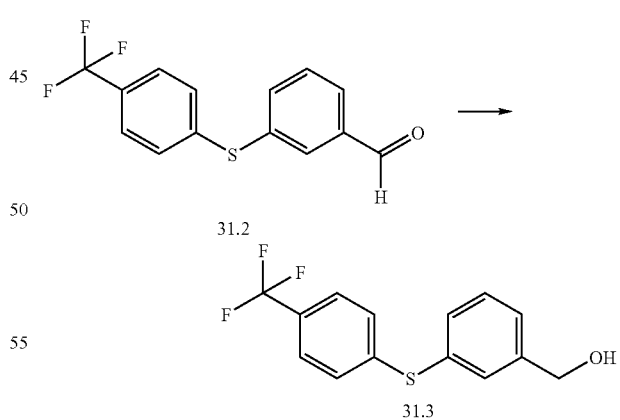

3-(4-(Trifluoromethyl)phenylthio)phenylmethanol (31.3). Aldehyde 31.2 (162 mg, 0.574 mmol) was dissolved in MeOH (6 mL) and cooled to 0° C. Sodium borohydride (22.0 mg, 0.574 mmol) was added to the reaction. The solution was allowed to slowly warm to room temperature and was stirred for 1.5 hours. The reaction was quenched with dilute hydrochloric acid and then concentrated to dryness under reduced pressure. Water (20 mL) was added to the residue, and the mixture was extracted with EtOAc (2×50 mL). The organic layers were combined, washed with brine (1×30 mL), and dried over magnesium sulfate. The filtrate was concentrated to give 31.3 (151 mg). ¹H NMR (400 MHz, CDCl₃) δ ppm 7.38-7.43 (3 H, m), 7.27-7.32 (3 H, m), 7.20 (2 H, d, J=8.2 Hz), 4.61 (2 H, s).

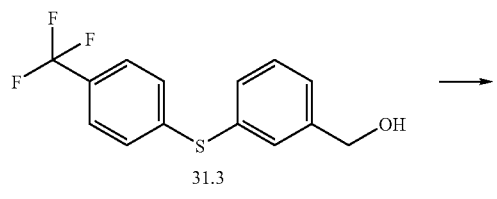

31.3

(49.1 μL, 0.633 mmol) was added followed by a catalytic amount (one drop) of DMF. The reaction was stirred for five hours. The reaction mixture was then concentrated to dryness under reduced pressure to give the corresponding crude benzyl bromide. The crude material was then dissolved in DMF (5 mL), and phenol (7.5) (198 mg, 0.504 mmol) and cesium carbonate (493 mg, 1.51 mmol) were added to the solution. The reaction mixture was stirred for 16 hours and then diluted with water and extracted with EtOAc (2×75 mL). The organic layers were combined, and washed with a 1 M lithium chloride solution (30 mL) and brine (30 mL), and dried over magnesium sulfate. The filtrate was concentrated, and the residue was purified by medium pressure chromatography (silica gel, 0 to 30% EtOAc:hexanes) to give 31.4 (224 mg). MS ESI (pos.) m/e: 659.2 (M+H).

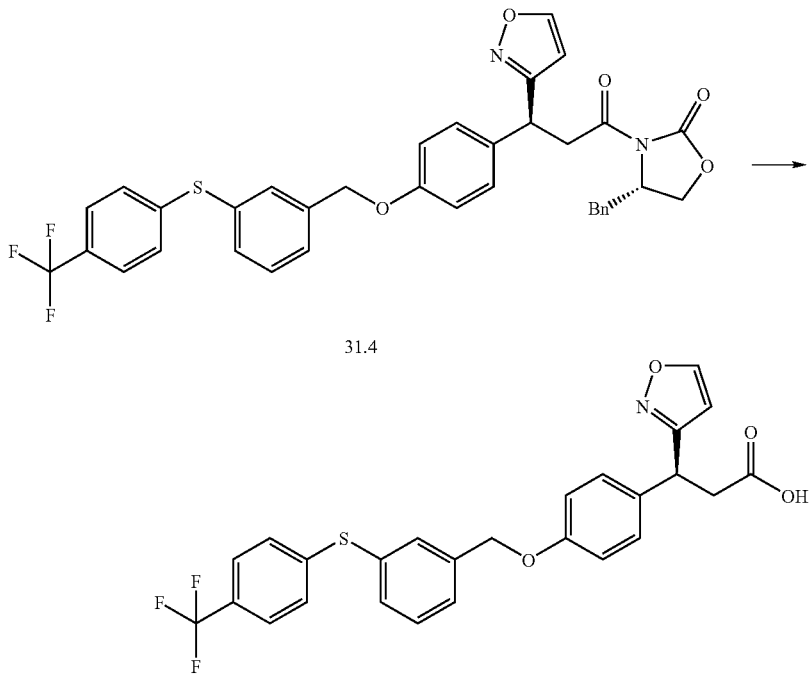

31.4

31

-continued

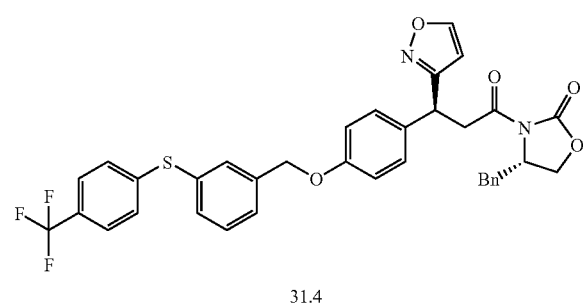

31.4

(S)-3-((S)-3-(4-(3-(4-(Trifluoromethyl)phenylthio)benzyloxy)-phenyl)-3-(isoxazol-3-yl)propanoyl)-4-benzyloxazolidin-2-one (31.4). The alcohol (31.3) (150 mg, 0.528 mmol) was dissolved in dry DCM (15 mL), and thionyl bromide (S)-3-(4-(3-(4-(Trifluoromethyl)phenylthio)benzyloxy) phenyl)-3-(isoxazol-3-yl)propanoic acid (31). To a solution of the oxazolidinone (31.4) (73.0 mg, 0.111 mmol) dissolved in THF (11 mL), was added a 30% hydrogen peroxide solution (125 μL, 1.11 mmol) followed by a 2 M LiOH solution (277 μL, 0.555 mmol). The resulting slurry was stirred for five hours. The reaction mixture was diluted with water and acidified with hydrochloric acid to a pH of 3. The mixture was then extracted with EtOAc (3×30 mL), and the organic layer was washed with an acidic sodium sulfite solution (1×30 mL) and brine (1×30 mL), and dried over magnesium sulfate. The filtrate was concentrated under reduced pressure, and the residue was purified by reverse phase HPLC to give 31 (29.0 mg). MS ESI (pos.) m/e: 500.0 (M+H). ¹H NMR (400 MHz, CD₃CN) δ 8.32 (1 H, d, J=1.6 Hz), 7.44-7.51 (3 H, m), 7.33-7.41 (3 H, m), 7.24 (2 H, d, J=8.2 Hz), 7.12 (2 H, d, J=8.6 Hz), 6.82 (2 H, d, J=9.0 Hz), 6.15 (1 H, d, J=1.6 Hz), 4.98 (2 H, s), 4.44 (1 H, t, J=7.8 Hz), 3.08 (1 H, dd, J=16.4, 8.2 Hz), 2.83 (1H, dd, J=16.4, 7.4 Hz).

6.27 Example 32

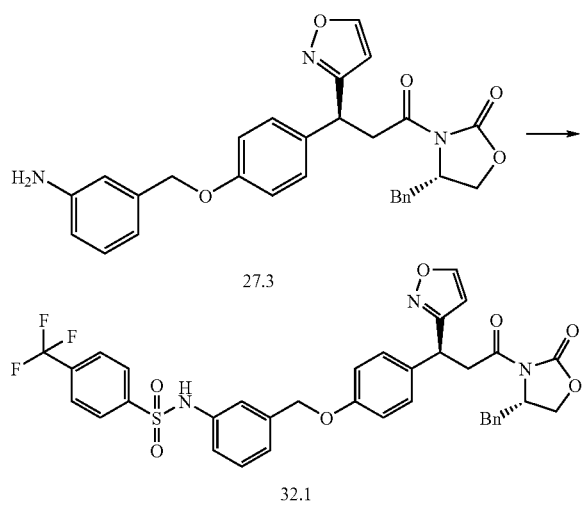

N-(3-((4-((S)-3-((S)-4-Benzyl-2-oxooxazolidin-3-yl)-1-(isoxazol-3-yl)-3-oxopropyl)phenoxy)methyl)phenyl)-4-(trifluoromethyl)-benzenesulfonamide (32.1). To a solution of the aniline (27.3) (0.050 g, 0.100 mmol) in DCM (1 mL), was added TEA (28.2 µL, 0.200 mmol) and 4-(trifluoromethyl)benzene-1-sulfonyl chloride (73.8 mg, 0.300 mmol). A catalytic amount (<5.0 mg) of DMAP was then added to drive the reaction to completion. The reaction mixture was stirred for two hours and then concentrated to dryness under reduced pressure. The residue was purified by medium pressure chromatography (silica gel, 10 to 45% EtOAc:hexanes) to give 32.1 (17.0 mg). MS ESI (pos.) m/e: 706.2 (M+H).

(S)-3-(4-(3-(4-Trifluoromethylphenylsulfonamido)benzyloxy)-phenyl)-3-(isoxazol-3-yl)propanoic acid (32). To a solution of the oxazolidinone (32.1) (17.0 mg, 0.0241 mmol) dissolved in THF (2 mL), was added a 30% hydrogen peroxide solution (27.0 µL, 0.241 mmol) followed by a 2 M LiOH solution (60.0 µL, 0.121 mmol). The resulting slurry was stirred for one hour. The reaction mixture was then diluted with water and acidified with hydrochloric acid to pH 3. The mixture was then extracted with EtOAc (1×20 mL), and the organic layer was washed with an acidic sodium sulfite solution (2×15 mL) and brine (1×15 mL), and dried over magnesium sulfate. The filtrate was concentrated under reduced pressure, and the residue was purified by reverse phase HPLC to give 32 (6.00 mg). MS ESI (pos.) m/e: 547.0 (M+H). $^1$H NMR (400 MHz, CD$_3$CN) δ ppm 8.32 (1 H, d, J=1.6 Hz), 7.81 (2 H, d, J=8.2 Hz), 7.69 (2 H, d, J=8.2 Hz), 7.04-7.23 (5 H, m), 6.95 (1 H, d, J=7.8 Hz), 6.79 (2 H, d, J=9.0 Hz), 6.15 (1 H, d, J=1.6 Hz), 4.91 (2 H, s), 4.44 (1 H, t, J=7.8 Hz), 3.08 (1H, dd, J=16.4, 8.2 Hz), 2.83 (1 H, dd, J=16.4, 7.4 Hz).

6.28 Example 33

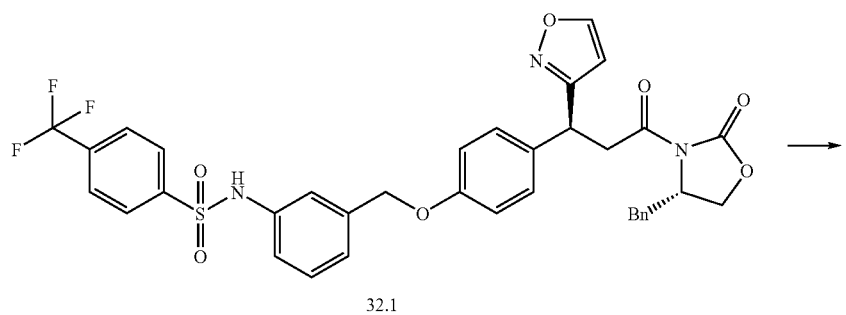

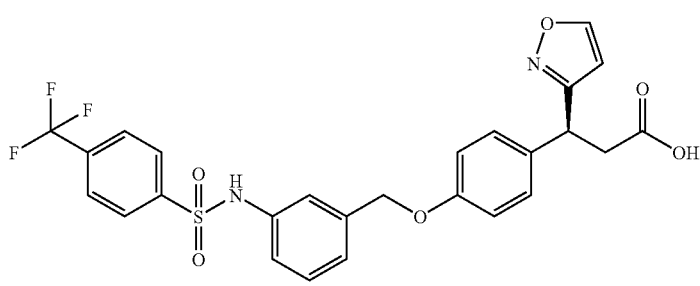

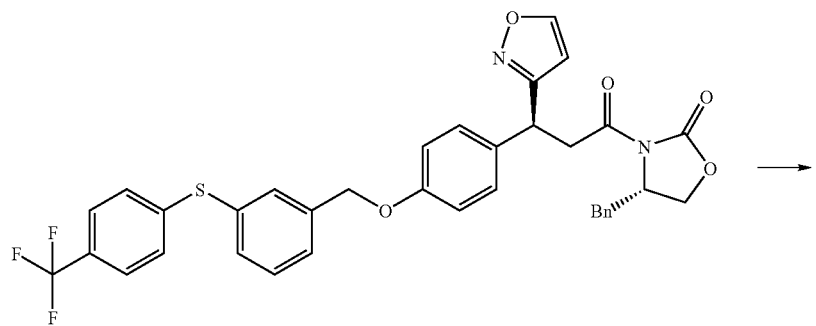

31.4

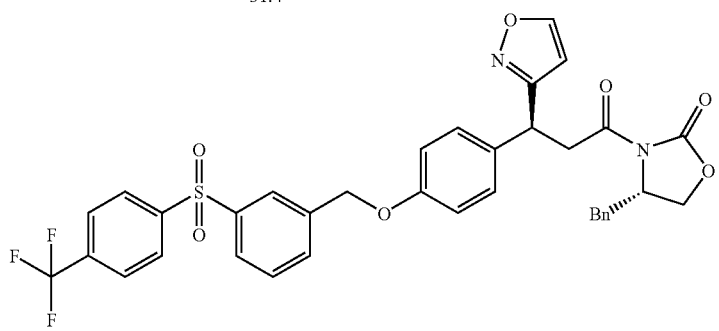

33.1

(S)-3-((S)-3-(4-(3-(4-Trifluoromethylphenylsulfonyl)benzyloxy)phenyl)-3-(isoxazol-3-yl)propanoyl)-4-benzyloxazolidin-2-one (33.1). The sulfide (31.4) (150 mg, 0.228 mmol) was dissolved in CHCl₃ (3.5 mL). To the solution was added potassium peroxymonosulfate (420 mg, 0.683 mmol) and moist alumina (228 mg). The resulting slurry was heated to reflux and stirred for 24 hours. The reaction was then allowed to cool and was filtered. The filtrate was concentrated, and the residue was purified by medium pressure chromatography (silica gel, 20 to 60% EtOAc:hexanes) to give 33.1 (106 mg). MS ESI (pos.) m/e: 691.2 (M+H).

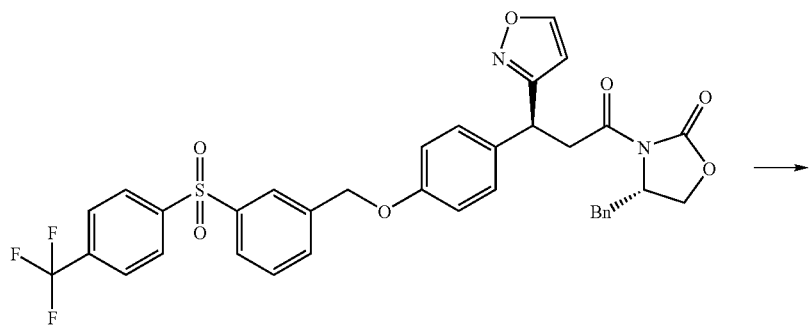

33.1

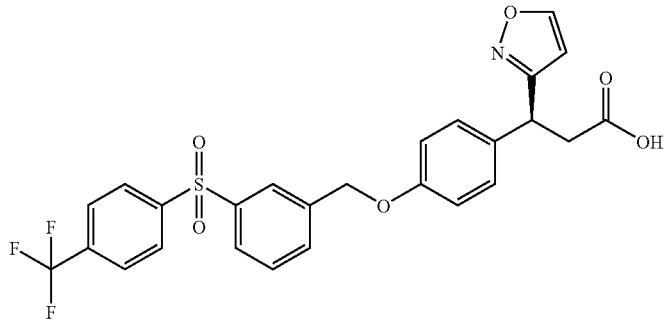

33

(S)-3-(4-(3-(4-(Trifluoromethyl)phenylsulfonyl)benzyloxy)-phenyl)-3-(isoxazol-3-yl)propanoic acid (33). To a solution of the oxazolidinone (33.1) (106 mg, 0.154 mmol) dissolved in THF (7 mL), was added a 30% hydrogen peroxide solution (175 μL, 1.54 mmol) followed by a 2 M LiOH solution (383 μL, 0.765 mmol). The resulting slurry was stirred for five hours. The reaction mixture was diluted with water and acidified with hydrochloric acid to pH ~3. The mixture was then extracted with EtOAc (3×30 mL), and the organic layer was washed with an acidic sodium sulfite solution (1×30 mL) and brine (1×30 mL), and dried over magnesium sulfate. The filtrate was concentrated under reduced pressure, and the residue was purified by reverse phase HPLC to give 33 (52.0 mg). MS ESI (pos.) m/e: 532.0 (M+H). $^1$H NMR (400 MHz, CDCl$_3$) δ 8.22 (1 H, d, J=1.6 Hz), 8.00 (2 H, d, J=8.2 Hz), 7.94 (1 H, s), 7.83 (1 H, d, J=7.8 Hz), 7.70 (2 H, d, J=8.6 Hz), 7.59 (1 H, d, J=7.8 Hz), 7.48 (1 H, t, J=7.6 Hz), 7.12 (2 H, d, J=9.0 Hz), 6.82 (2 H, d, J=8.6 Hz), 6.00 (1 H, d, J=1.6 Hz), 5.00 (2 H, s), 4.48 (1 H, t, J=7.6 Hz), 3.27 (1 H, dd, J=16.8, 7.8 Hz), 2.90 (1 H, dd, J=16.6, 7.6 Hz).

6.29 Example 34

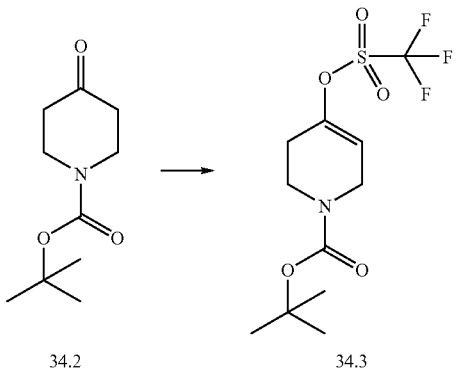

tert-Butyl 4-(trifluoromethylsulfonyloxy)-5,6-dihydropyridine-1(2H)-carboxylate (34.3). The triflate (34.3) was prepared from 34.2 using the same procedure described in Wustrow, D. J.; Wise, L. D.; Synthesis; 1991, pp. 993-995 to give 34.3 (1.27 g). $^1$H NMR (500 MHz, CDCl$_3$) δ ppm 5.77-5.86 (1 H, m), 4.04-4.10 (2 H, m), 3.66 (2 H, t, J=5.1 Hz), 2.44-2.52 (2 H, m), 1.50 (9 H, s).

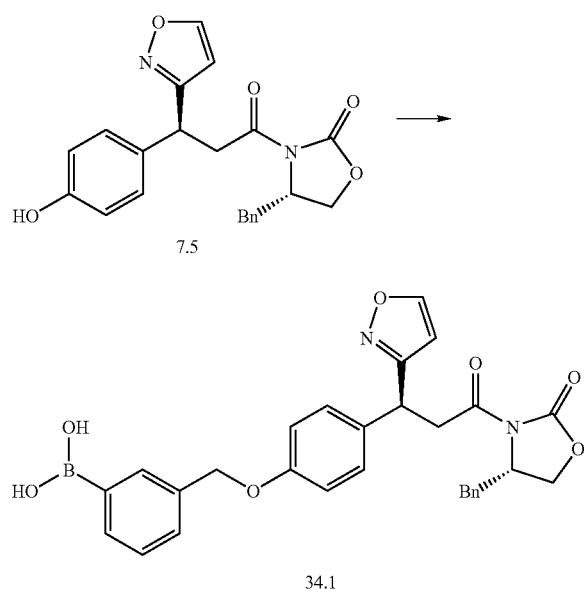

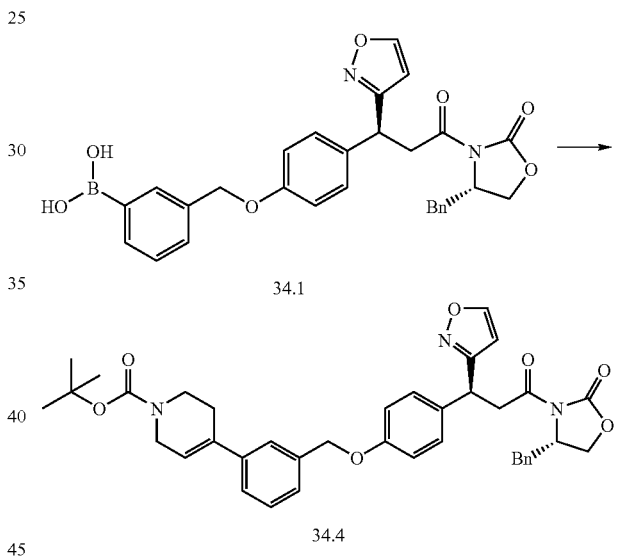

3-((4-((S)-3-((S)-4-Benzyl-2-oxooxazolidin-3-yl)-1-(isoxazol-3-yl)-3-oxopropyl)phenoxy)methyl)phenylboronic acid (34.1). The phenol (7.5) (400 mg, 1.02 mmol) and 3-(bromomethyl)phenylboronic acid (219 mg, 1.02 mmol) were dissolved in DMF (10 mL). Cesium carbonate (664 mg, 2.04 mmol) was added to the mixture, and the slurry was stirred for 48 hours. The reaction was then diluted with water and extracted with EtOAc (2×100 mL). The organic layers were combined and washed with a 1 M lithium chloride solution (1×50 mL) and brine (1×50 mL), and dried over magnesium sulfate. The filtrate was concentrated, and the residue was purified by medium pressure chromatography (silica gel, 30 to 100% EtOAc:hexanes) to give 34.1 (95.0 mg). MS ESI (pos.) m/e: 527.2 (M+H).

tert-Butyl 4-(3-((4-((S)-3-((S)-4-benzyl-2-oxooxazolidin-3-yl)-1-(isoxazol-3-yl)-3-oxopropyl)phenoxy)methyl)phenyl)-5,6-dihydropyridine-1(2H)-carboxylate (34.4). To a sealed tube flushed with nitrogen and including DMF (0.5 mL), were added boronic acid 34.1 (90.0 mg, 0.171 mmol), triflate 34.3 (56.6 mg, 0.171 mmol), a 1 M sodium carbonate solution (0.48 mL, 0.480 mmol), lithium chloride (21.7 mg, 0.513 mmol), and Pd(dppf)Cl$_2$ (13.9 mg, 0.0170 mmol). The reaction was heated and stirred at 85° C. for 1.5 hours. The reaction was then cooled and diluted with water. The mixture was extracted with EtOAc (2×50 mL). The organic layers were combined and washed with 1M lithium chloride (1×30 mL) and brine (1×30 mL), and dried over magnesium sulfate. The filtrate was concentrated, and the residue was purified by medium pressure chromatography (silica gel, 0 to 40% EtOAc:hexanes) to give 34.4 (8.90 mg). MS ESI (pos.) m/e: 664.3 (M+H). $^1$H NMR (400 MHz, CDCl$_3$) δ ppm 8.21 (1 H, d, J=1.6 Hz), 7.35 (1 H, s), 7.09-7.30 (10 H, m), 6.86 (2 H, d, J=8.6 Hz), 6.06 (1 H, d, J=1.6 Hz), 5.98 (1 H, s), 4.95 (2 H, s), 4.64-4.73 (1 H, m), 4.49-4.60 (1 H, m), 4.07 (2 H, d, J=5.1 Hz), 3.99-4.03 (2 H, m, J=2.7 Hz), 3.95 (1 H, dd, J=17.6, 8.6 Hz), 3.56 (2 H, t, J=5.7 Hz), 3.45 (1 H, dd, J=17.4, 6.5 Hz), 3.13 (1 H, dd, J=13.3, 3.1 Hz), 2.69 (1 H, dd, J=13.5, 9.6 Hz), 2.42-2.50 (2 H, m), 1.42 (9 H, s).

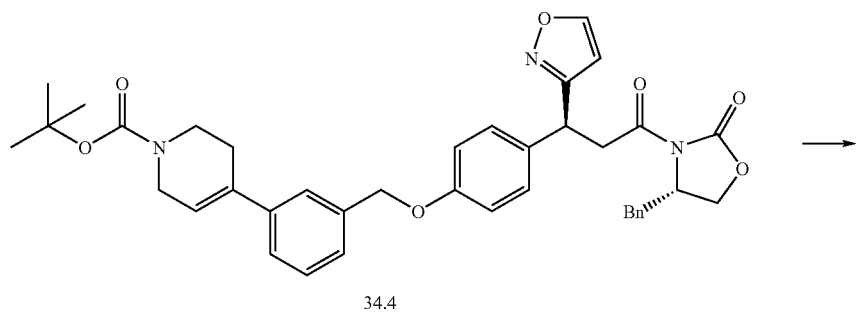

34.4

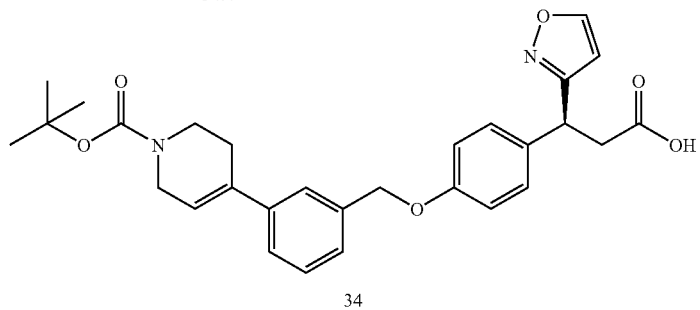

34

(S)-3-(4-(3-(1-(Tert-butoxycarbonyl)-1,2,3,6-tetrahydro-pyridin-4-yl)benzyloxy)phenyl)-3-(isoxazol-3-yl)propanoic acid (34). To a solution of the oxazolidinone (34.4) (8.9 mg, 0.013 mmol) dissolved in THF (0.5 mL), was added a 30% hydrogen peroxide solution (15.0 µL, 0.130 mmol) followed by a 2 M LiOH solution (33.0 µL, 0.065 mmol). The resulting slurry was stirred for two hours. The reaction mixture was diluted with water and acidified with hydrochloric acid to a pH 3. The mixture was then extracted with EtOAc (3×10 mL), and the organic layer was washed with an acidic sodium sulfite solution (1×5 mL) and brine (1×5 mL), and dried over magnesium sulfate. The filtrate was concentrated under reduced pressure, and the residue was purified by reverse phase HPLC to give 34 (2.60 mg). MS ESI (pos.): m/e 505.1 (M+H). $^1$H NMR (400 MHz, CD$_3$CN) δ ppm 8.33 (1 H, d, J=1.6 Hz), 7.40 (1 H, s), 7.20-7.34 (3 H, m), 7.13 (2 H, d), 6.86 (2 H, d, J=9.0 Hz), 6.16 (1 H, d, J=1.6 Hz), 6.03 (1 H, br. s.), 4.99 (2 H, s), 4.44 (1 H, t, J=7.8 Hz), 3.90-3.98 (2 H, m, J=2.7 Hz), 3.50 (2H, t, J=5.7 Hz), 3.09 (1 H, dd, J=16.4, 8.2 Hz), 2.84 (1 H, dd, J=16.4, 7.4 Hz), 2.37-2.45 (2 H, m, J=2.0 Hz), 1.37 (9 H, s).

6.30 Example 35

-continued

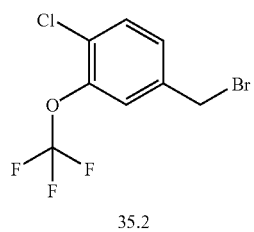

35.2

2-Chloro-5-(bromomethyl)-1-(trifluoromethoxy)benzene (35.2). Compound 35.2 was synthesized from (4-chloro-3-(trifluoromethoxy)phenyl)-methanol using the procedure described for the preparation of 19.2. $^1$H NMR (500 MHz, DMSO-d$_6$) δ 7.74 (1 H, d, J=2.0 Hz), 7.38-7.53 (2 H, m), 4.53 (2 H, d, J=5.6 Hz)

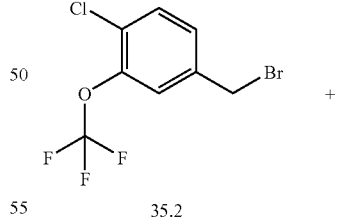

35.2

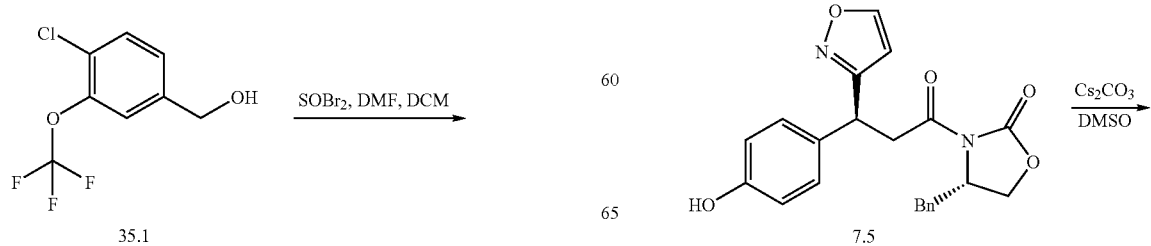

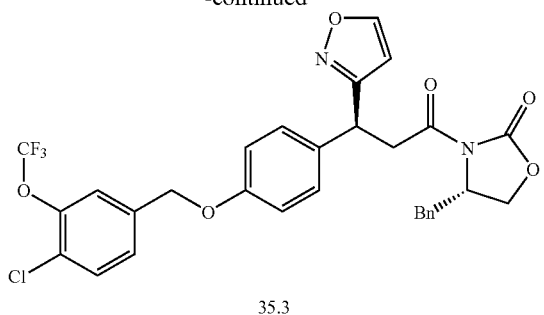

35.3

(S)-3-((S)-3-(4-(4-Chloro-3-(trifluoromethoxy)benzyloxy)-phenyl)-3-(isoxazol-3-yl)propanoyl)-4-benzyloxazolidin-2-one (35.3). The title compound 35.3 was synthesized from 35.2 and compound 7.5 using the procedure described for the preparation of 35.3. MS ESI (pos.) m/e: 601 (M+H).

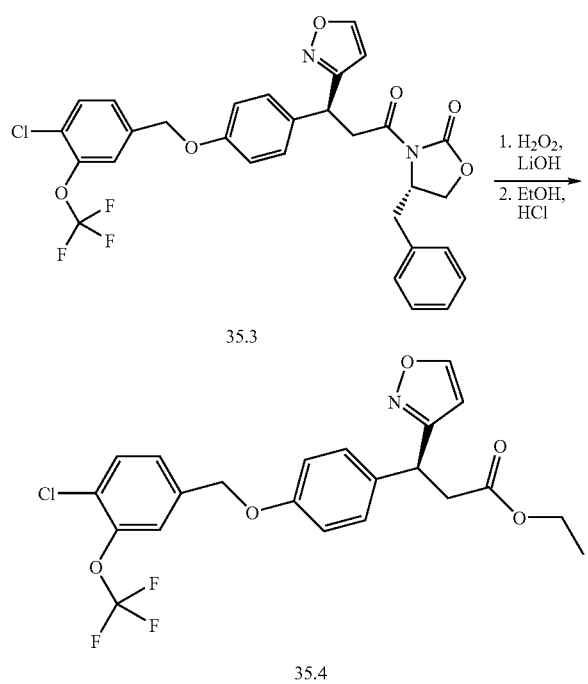

35.3

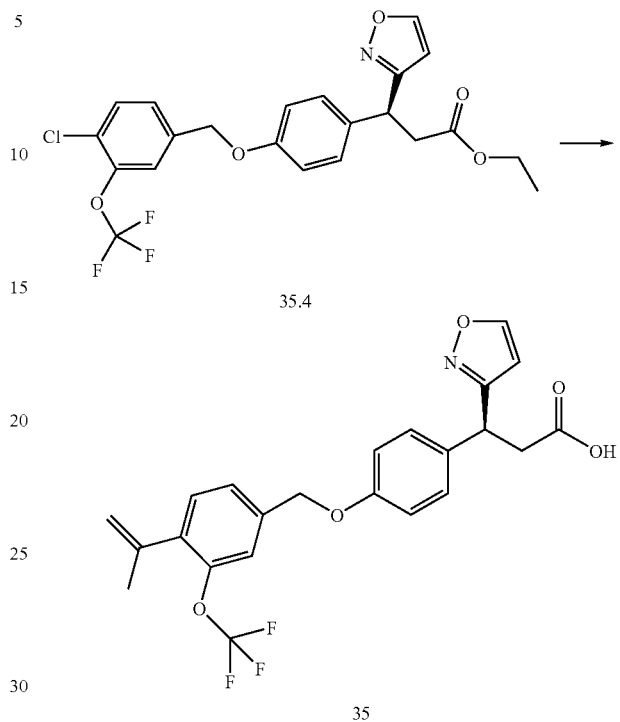

35.4

(S)-Ethyl 3-(4-(4-chloro-3-(trifluoromethoxy)benzyloxy)-phenyl)-3-(isoxazol-3-yl)propanoate (35.4). A fresh aqueous solution of LiO$_2$H, prepared from mixing a solution of LiOH (2.1 mL, 3.33 M in water) with H$_2$O$_2$ (1.54 mL, 33% in water) at 0° C., was slowly added to a cooled mixture of 35.3 (2.02 g, 3.39 mmol) in THF (20.0 mL) and water (10 mL) at 0° C. The resulting reaction mixture was stirred at 0° C. for 1.5 hours. The reaction was then quenched by adding a 1.5 N aqueous solution of Na$_2$SO$_3$ at 0° C. Water (150 mL) was added, and the aqueous solution was extracted with diethyl ether (30×3 mL) and acidified with concentrated HCl to a pH of 2. The mixture was then extracted with EtOAc (60×2 mL, 40×2 mL). The organic layer was dried with Na$_2$SO$_4$, and the solvent was removed to give the crude intermediate, (S)-3-(4-(4-chloro-3-(trifluoromethoxy)benzyloxy)phenyl)-3-(isoxazol-3-yl)propanoic acid. This intermediate was treated with EtOH (20 mL) and HCl (0.5 mL, 1.0 M in ether) at room temperature overnight. The solvent was evaporated to provide the crude product 35.4 which was used without further purification. MS ESI (pos.) m/e: 470 (M+H).

35

(S)-3-(4-(4-(Prop-1-en-2-yl)-3-(trifluoromethoxy)benzyloxy)-phenyl)-3-(isoxazol-3-yl)propanoic acid (35). The title compound (35) was synthesized from 35.4 using the procedure described for the preparation of compound 20. $^1$H NMR (CD$_3$CN) δ 2.12 (s, 3 H), 2.96 (dd, J=7.4, 16.4 Hz. 1H), 3.21 (dd, J=7.4, 16.4 Hz. 1 H), 4.56 (m, 1 H), 5.12 (m, 3 H), 5.31 (m, 1 H), 6.27 (d, J=1.7 Hz, 1H), 6.98 (d, J=6.6 Hz, 2 H), 7.25 (d, J=6.6 Hz, 2H), 7.40-7.44 (m, 3 H), 8.45 (d, J=1.7 Hz, 1H). MS ESI (pos.) m/e: 448 (M+H).

6.31 Example 36

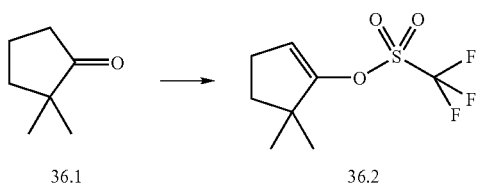

36.1         36.2

5,5-Dimethylcyclopent-1-enyl trifluoromethanesulfonate (36.2).

To a solution of 2,2-dimethylcyclopentanone 36.1 (3.00 g, 26.75 mmol) in THF (100 mL), was slowly added LDA (14.7 mL, 2.0 M, in heptane) at −78° C. The resulting mixture was stirred at −78° C. for 1 hour. A solution of N-phenyltriflimide (10.00 g, 28.00 mmol) was added to the mixture at −78° C., and stirring was continued at 0° C. for 2 hours and then at room temperature overnight. The reaction mixture was extracted with hexane (80×2 mL). The organic layer was washed with saturated Na$_2$CO$_3$ (30 mL), brine (20 mL), and dried with MgSO$_4$. The solvent was removed and the crude product was purified by CombiFlash (eluent was EtOAc and hexane) to give 36.2. ¹H NMR (CDCl₃) δ 1.16 (s, 6 H), 1.86 (t, J=7.1 Hz, 2 H), 2.36 (t, J=7.1 Hz, 2 H), 5.56 (m, 1 H).

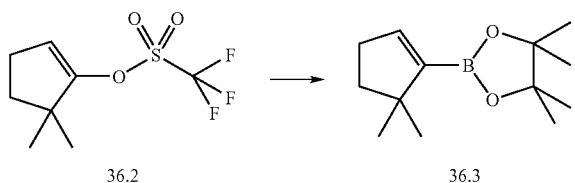

2-(5,5-Dimethylcyclopent-1-enyl)-4,4,5,5-tetramethyl-1,3,2-dioxaborolane (36.3). PdCl₂(PPh₃)₂ (0.56 g, 0.80 mmol), PPh₃ (0.63 g, 2.40 mmol), bis(pinacolato)diboron (6.80 g, 26.75 mmol) and KOPh (fine powder, 5.30 g, 40.10 mmol) were added to a flask. The flask was flushed with nitrogen and charged with toluene (100 mL) and with 36.2 (6.53 g, 26.75 mmol). The mixture was stirred at 50° C. for 2 hours. The reaction mixture was treated with water at room temperature and extracted with benzene (60×2 mL). The organic layer was dried over MgSO₄. The product was then purified by CombiFlash to give the title compound 36.3. ¹H NMR (CDCl₃) δ 1.04 (s, 6 H), 1.18 (s, 12 H), 1.57 (t, J=7.1 Hz, 2 H), 2.29 (t, J=7.1 Hz, 2 H), 6.29 (m, 1 H).

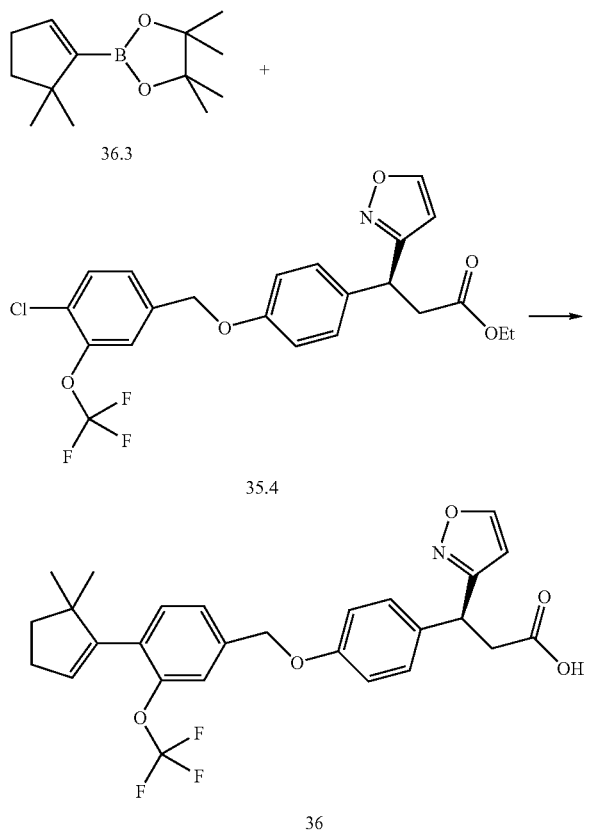

(S)-3-(4-(4-(5,5-Dimethylcyclopent-1-enyl)-3-(trifluoromethoxy)benzyloxy)phenyl)-3-(isoxazol-3-yl)propanoic acid (36). Compound 35.4 (1.60 g, 3.40 mmol), 36.3 (0.91 g, 4.10 mmol), Pd(OAc)₂ (0.11 g, 0.51 mmol), S-phos (0.42 g, 1.02 mmol) and K₃PO₄ were added to a flask. The flask was flushed with nitrogen and charged with dioxane (9.0 mL) and water (3.0 mL). The mixture was then stirred at 80° C. overnight. The solvent was removed, and the residue was purified by column chromatography to give an intermediate, (S)-ethyl 3-(4-(4-(5,5-dimethylcyclopent-1-enyl)-3-(trifluoromethoxy)benzyloxy)-phenyl)-3-(isoxazol-3-yl)propanoate (0.45 g, 0.85 mmol) that was treated with LiOH (1.0 mL, 3.33 M in water) in MeOH (6.0 mL) at room temperature overnight. The reaction mixture was purified by preparative HPLC (reverse phase) to give the title compound 36. ¹H NMR (CD₃CN) δ 1.04 (s, 6 H), 1.85 (m, 2 H), 2.41 (m, 2 H), 2.97 (dd, J=7.5, 16.4 Hz, 1 H), 3.17 (dd, J=7.5, 16.4 Hz, 1H), 4.52 (m, 1 H), 5.07 (s, 2 H), 5.26 (m, 1 H), 6.23 (d, J=1.5 Hz, 1 H), 6.94 (d, J=6.6 Hz, 2 H), 7.22 (d, J=6.6 Hz, 2 H), 7.35-7.39 (m, 3 H), 8.41, (d, J=1.5 Hz, 1 H). MS ESI (pos.) m/e: 502 (M+H).

6.32 Example 37

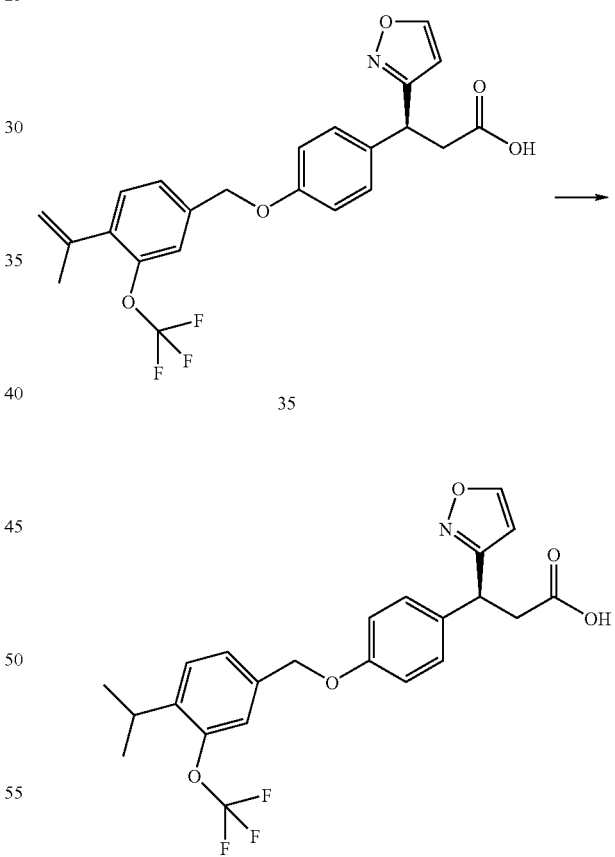

(S)-3-(4-(4-Isopropyl-3-(trifluoromethoxy)benzyloxy)phenyl)-3-(isoxazol-3-yl)propanoic acid (37). Compound 37 was synthesized from compound 35 using the procedure described above for the preparation of 23. ¹H NMR (CD₃CN) δ 1.25 (d, J=6.9 Hz, 6H), 2.96 (dd, J=7.4, 16.4 Hz, 1 H), 3.20 (dd, J=7.4, 16.4 Hz, 1 H), 3.34 (m, 1 H), 4.56 (m, 1 H), 5.09 (s, 2 H), 6.27 (d, J=1.7 Hz, 1H), 6.97 (d, J=6.6 Hz, 2 H), 7.25

(d, J=6.6 Hz, 2H), 7.37 (s, 1 H), 7.42 (d, J=8.1 Hz, 1H), 7.48 (d, J=8.1 Hz, 1 H), 8.45 (d, J=1.7 Hz, 1H). MS ESI (pos.) m/e: 450 (M+H).

6.33 Example 38

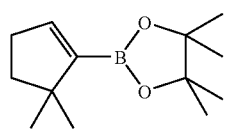

36.3

+

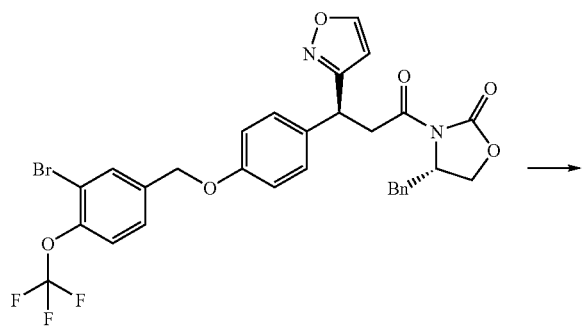

19.3

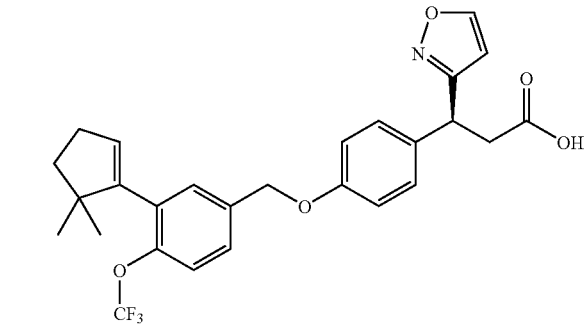

38

(S)-3-(4-(3-(5,5-Dimethylcyclopent-1-enyl)-4-(trifluoromethoxy)benzyloxy)phenyl)-3-(isoxazol-3-yl)propanoic acid (38). This title compound (38) was synthesized using the procedure described for the preparation of 20. $^1$H NMR (CD$_3$CN) δ 1.05 (s, 6 H), 1.88 (m, 2 H), 2.45 (m, 2H), 2.96 (dd, J=7.4, 16.4 Hz, 1 H), 3.20 (dd, J=7.4, 16.4 1 H), 4.56 (m, 1 H), 5.11 (s, 2 H), 5.65 (m, 1 H), 6.26 (d, J=1.7 Hz, 1 H), 6.94 (d, J=6.6 Hz, 2 H), 7.22 (d, J=6.6 Hz, 2 H), 7.32-7.46 (m, 3 H), 8.44, (d, J=1.7 Hz, 1 H). MS ESI (pos.) m/e: 502 (M+H).

6.34 Example 39

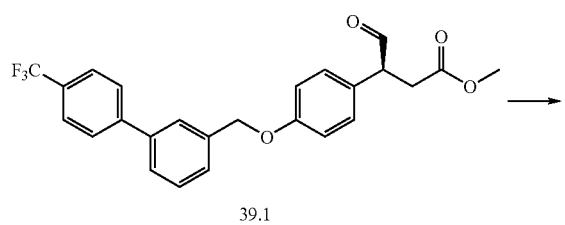

39.1

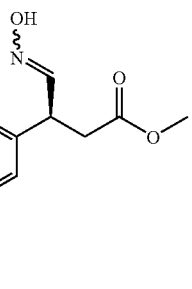

39.2

(S)-Methyl 4-(hydroxyimino)-3-(4-(3-(4-(trifluoromethyl)phenyl)benzyloxy)phenyl)butanoate (39.2). Compound 39.1 was prepared as described in US 2006/0270724, which published on Nov. 30, 2006, and is hereby incorporated by reference in its entirety and for all purposes as is specifically set forth herein. Compound 39.1 (100 mg, 0.23 mmol) was dissolved in EtOH (5 mL), and hydroxylamine HCl (25 mg, 0.36 mmol) and water (0.1 mL) were added. The resulting mixture was stirred at room temperature for 2 hours. The solvent was removed, and the residue was purified by CombiFlash to give 39.2, which was eluted with 25-40% EtOAc in hexane.

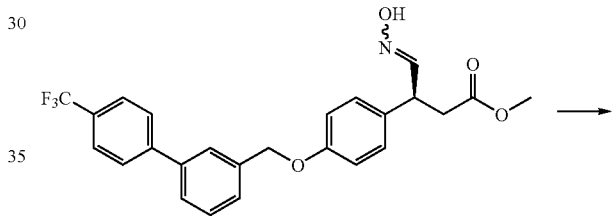

39.2

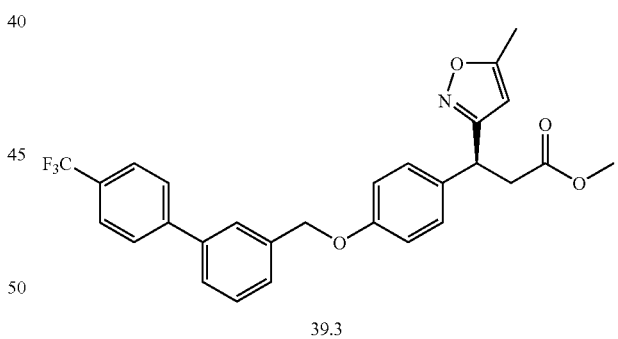

39.3

(S)-Methyl 3-(4-(3-(4-(trifluoromethyl)phenyl)benzyloxy)phenyl)-3-(5-methylisoxazol-3-yl)propanoate (39.3). Compound 39.2 (100 mg, 0.22 mmol) was dissolved in DCM, and pyridine (0.05 mL) and NCS (30 mg, 0.22 mmol) were added. The resulting mixture was stirred at room temperature for 3 hours. Additional NCS (60 mg) was added, and the mixture was left at room temperature overnight. Then TEA (0.4 mL) was added to the mixture, and a stream of methylacetylene was passed through the reaction mixture for 20 minutes. LCMS detected the desired product. The solvent was removed, and the residue was purified by CombiFlash to give 39.3.

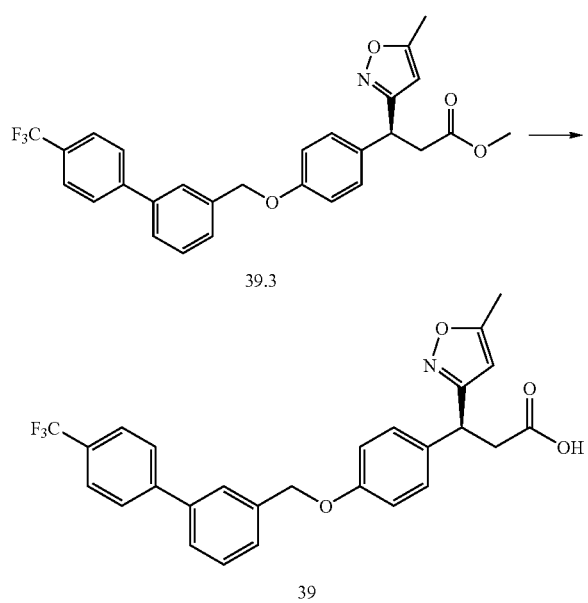

39.3

39

(S)-3-(4-(3-(4-(Trifluoromethyl)phenyl)benzyloxy)phenyl)-3-(5-methylisoxazol-3-yl)propanoic acid (39). A solution of 39.3 (25 mg) in THF/MeOH (1:1, 4 mL) was treated with 2N aqueous NaOH solution (0.2 mL) and stirred for 2 hours at room temperature. The reaction mixture was acidified with aqueous 3N HCl while cooled with ice-water, and extracted with EtOAc to obtain 39, which was chromatographed on a silica gel column, eluting with 5~10% MeOH in DCM. MS ESI (neg.) m/e: 480.1 (M−H). $^1$HNMR (CDCl$_3$) δ 7.13 (s, 1H), 7.04 (d, 2H, J=7.27Hz), 7.01-6.98 (m, 2H), 6.80 (s, 1H), 6.69 (d, 2H, J=Hz, J=8.62Hz), 6.46 (d, 2H, J=8.61Hz), 4.99 (s, 1H), 4.59 (s, 2H), 3.95 (t, 1H, J=7.60Hz), 2.80 (m, 1H), 2.46 (m, 1H), 1.82 (s, 3H).

6.35 Example 40

Synthesis of (S)-3-(Isoxazol-3-yl)-3-(4-((5,5,8,8-tetramethyl-5,6,7,8-tetrahydronaphthalen-2-yl)methoxy)phenyl)propanoic acid (40)

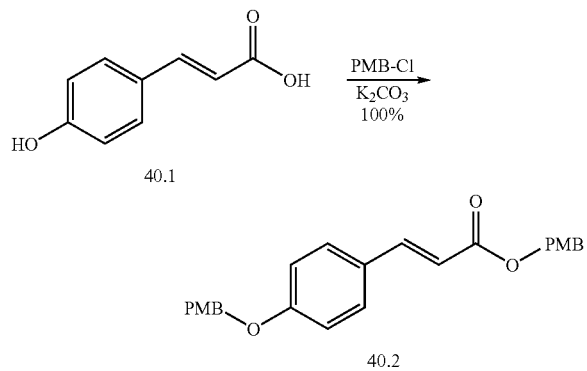

40.1

40.2

(E)-4-Methoxybenzyl 3-(4-(4-methoxybenzyloxy)phenyl)acrylate (40.2). Potassium carbonate (21 g, 152 mmol) was added to a mixture of 4-hydroxycinnamic acid 40.1 (6.25 g, 38.1 mmol) and p-methoxy benzyl chloride (10.35 mL, 76 mmol) in DMF (100 mL). The mixture was stirred at 80° C. for five hours. After cooling, the mixture was poured into water (700 mL). The solid was collected by filtration, washed with water and dried to give 40.2 (15 g). MS ESI (pos.) m/e: 405 (M+H). $^1$HNMR (CDCl$_3$) δ 7.68 (d, 1H), 7.47 (d, 2H), 7.38 (m, 4H), 6.95 (m, 6H), 6.35 (d, 1H), 5.20 (s, 2H), 5.03 (s, 2H), 3.84 (s, 3H), 3.83 (s, 3H).

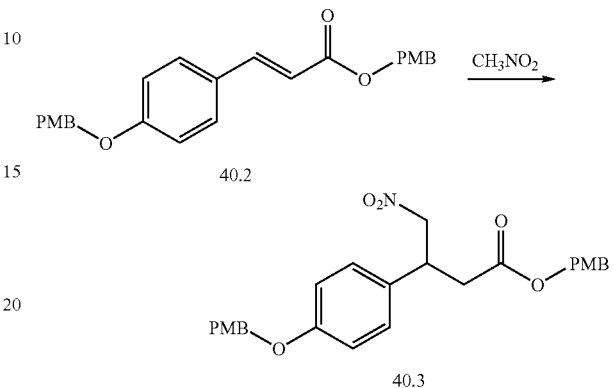

40.2

40.3

4-Methoxybenzyl 3-(4-(4-methoxybenzyloxy)phenyl)-4-nitrobutanoate (40.3). 1,1,3,3-tetramethylguanidine (0.31 mL, 2.48 mmol) was added to 40.2 (5 g, 12.4 mmol) in nitromethane (20 mL). The mixture was stirred at room temperature for 3 hours, at 50° C. for 3 hours, and at 100° C. for 8 hours. Nitromethane was removed under vacuum and the crude product was purified by flash chromatography to give 40.3 (4.5 g). MS ESI (pos.) m/e: 466 (M+H). $^1$HNMR (CDCl$_3$) δ 7.37 (d, 2H), 7.19 (d, 2H), 7.12 (d, 2H), 6.92 (m, 6H), 5.01 (s, 2H), 4.97 (s, 2H), 4.68 (m, 1H), 4.59 (m, 1H), 3.96 (m, 1H), 3.84 (s, 3H), 3.82 (s, 3H), 2.77 (m, 2H).

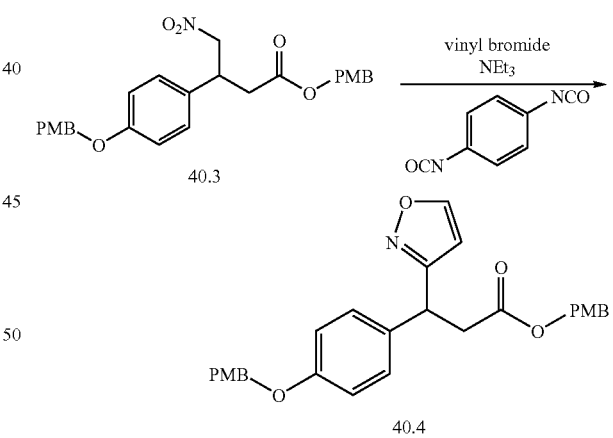

40.3

40.4

4-Methoxybenzyl 3-(4-(4-methoxybenzyloxy)phenyl)-3-(isoxazol-3-yl)propanoate (40.4). Triethylamine (1 mL) was added to a mixture of 40.3 (1.89 g, 4.1 mmol), vinyl bromide (32.5 mL, 1.0 M solution in THF) and 1,4-phenylene diisocyanate (2.3 g, 14.35 mmol). The mixture was stirred at 80° C. for 8 hours. After cooling, the solid was removed from the mixture by filtration, and the filtrate was concentrated and purified by flash chromatography to give 6.4 (3 g). MS ESI (pos.) m/e: 474 (M+H). $^1$HNMR (CDCl$_3$) δ 8.28 (d, 1H), 7.37 (d, 2H), 7.18 (m, 4H), 6.92 (m, 6H), 6.07 (d, 1H), 5.02 (s, 2H), 4.97 (s, 2H), 4.59 (t, 1H), 3.84 (s, 3H), 3.82 (s, 3H), 3.33 (dd, 1H), 3.00 (dd, 1H).

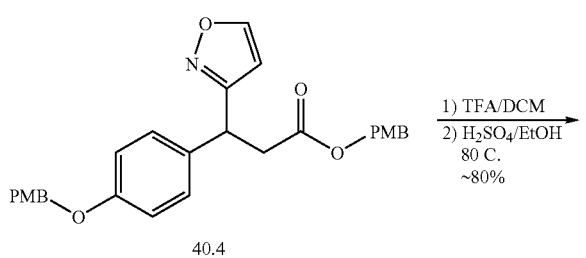

40.4

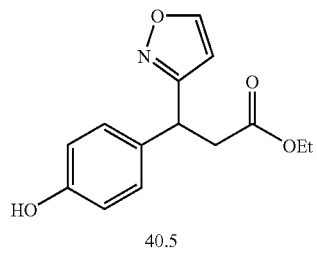

40.5

Ethyl 3-(4-hydroxyphenyl)-3-(isoxazol-3-yl)propanoate (40.5). TFA (10 mL) was added to 40.4 (940 mg) in DCM (10 mL). The mixture was stirred at room temperature for 1.5 hours. TFA and DCM were removed under vacuum, and the residue was treated with EtOH (50 mL). The insoluble solid was removed by filtration. To the filtrate was added concentrated sulfuric acid (2 drops). The mixture was stirred at 80° C. overnight. After concentration, the crude product was purified by flash chromatography to give 40.5 (410 mg). MS ESI (pos.) m/e: 262 (M+H). ¹HNMR (CDCl₃) δ 8.29 (d, 1H), 7.12 (d, 2H), 6.76 (d, 2H), 6.10 (d, 1H), 4.56 (t, 1H), 4.10 (q, 2H), 3.27 (dd, 1H), 2.97 (dd, 1H), 1.19 (t, 3H). The racemic compound 40.5 was separated into two enantiomers 40.6 and 40.7 using chiral preparative AD-H column (8% IPA/92% hexanes). The stereochemistry of 40.6 and 40.7 was assigned arbitrarily.

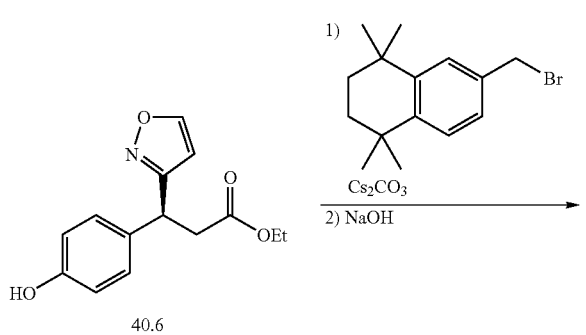

40.6

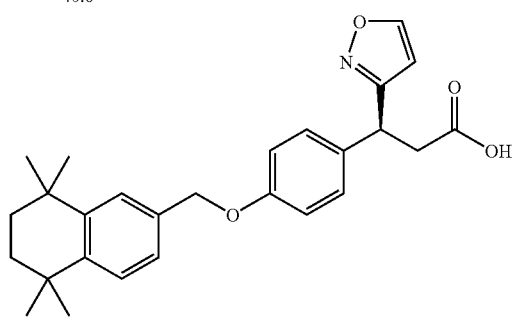

40

(S)-3-(Isoxazol-3-yl)-3-(4-((5,5,8,8-tetramethyl-5,6,7,8-tetrahydronaphthalen-2-yl)methoxy)phenyl)propanoic acid (40). Cesium carbonate (14 mg, 0.042 mmol) was added into a mixture of 40.6 (10 mg, 0.038 mmol) and 6-(bromomethyl)-1,1,4,4-tetramethyl-1,2,3,4-tetrahydronaphthalene (11 mg, 0.038 mmol) in DMSO (0.5 mL). The mixture was stirred at room temperature for 2 hours and at 35° C. for 4 hours. After cooling, the mixture was treated with EtOAc (5 mL) and brine (5 mL). The organic layer was separated, washed with brine twice, dried and concentrated. The crude product was treated with THF (1 mL), MeOH (1 mL), water (0.5 mL) and NaOH (0.05 mL, 10N). The mixture was stirred at room temperature for 4 hours. The organic solvent was blown away by nitrogen and the aqueous was acidified by HCl (0.18 mL, 3N). The aqueous was extracted with DCM. The organic layer was dried, concentrated and purified by flash chromatography to give 40 (15 mg). MS ESI (pos.) m/e: 434 (M+H). ¹HNMR (CDCl₃) δ 8.30 (d, 1H), 7.35 (m, 2H), 7.19 (m, 3H), 6.96 (d, 2H), 6.09 (d, 1H), 4.97 (s, 2H), 4.57 (t, 1H), 3.37 (dd, 1H), 2.99 (dd, 1H), 1.71 (s, 4H), 1.30 (s, 12H).

6.36 Example 41

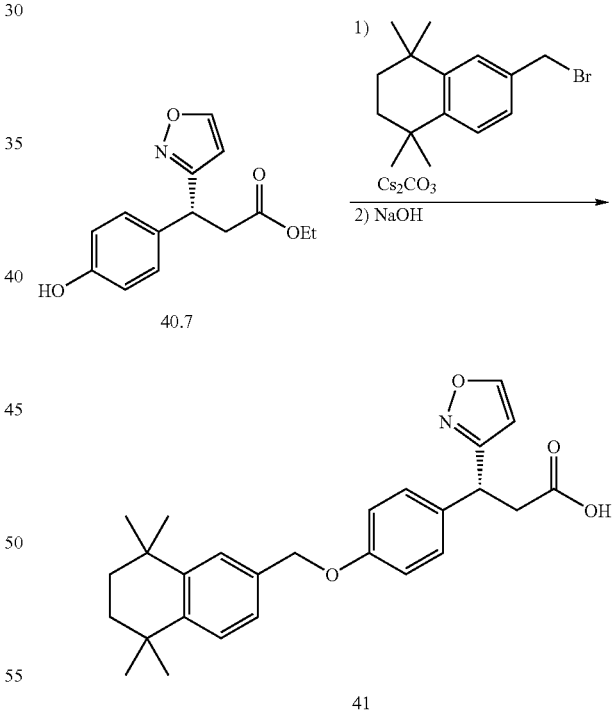

41

(R)-3-(Isoxazol-3-yl)-3-(4-((5,5,8,8-tetramethyl-5,6,7,8-tetrahydronaphthalen-2-yl)methoxy)phenyl)propanoic acid (41). Compound 7 was synthesized using the procedure above for preparing Example 40 using compound 40.7. MS ESI (pos.) m/e: 434 (M+H). ¹HNMR (CDCl₃) δ 8.30 (d, 1H), 7.35 (m, 2H), 7.19 (m, 3H), 6.96 (d, 2H), 6.09 (d, 1H), 4.97 (s, 2H), 4.57 (t, 1H), 3.37 (dd, 1H), 2.99 (dd, 1H), 1.71 (s, 4H), 1.30 (s, 12H).

6.37 Example 42

Synthesis of 3-(4,5-Dihydroisoxazol-3-yl)-3-(4-((5,5,8,8-tetramethyl-5,6,7,8-tetrahydronaphthalen-2-yl)methoxy)phenyl)propanoic acid (42)

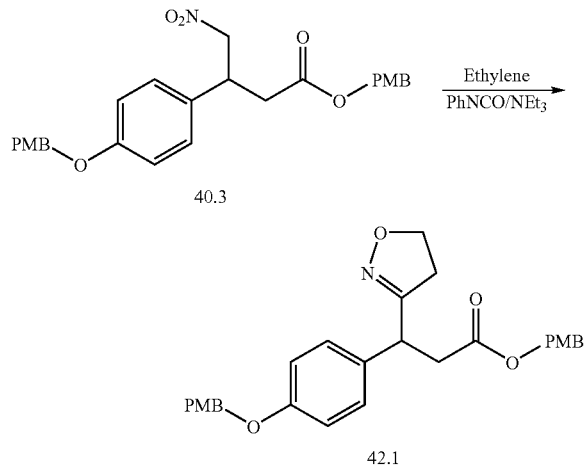

4-Methoxybenzyl 3-(4-(4-methoxybenzyloxy)phenyl)-3-(4,5-dihydroisoxazol-3-yl)propanoate (42.1). Ethylene was bubbled into a mixture of 40.3 (235 mg, 0.5 mmol, see Example 40) in benzene (2 mL) for 20 minutes. Phenyl isocyanate (0.22 mL, 2 mmol) and TEA (3 drops) were then added. The mixture was stirred at room temperature for 2 days. The solid was removed by filtration and washed by benzene. The filtrate was concentrated and purified by flash chromatography to give 42.1 (200 mg). MS ESI (pos.) m/e: 476 (M+H). $^1$HNMR (CDCl$_3$) δ 7.37 (d, 2H), 7.21 (d, 2H), 7.16 (d, 2H), 6.92 (m, 6H), 5.05 (dd, 2H), 4.98 (s, 2H), 4.25 (m, 2H), 4.10 (t, 1H), 3.84 (s, 3H), 3.82 (s, 3H), 3.24 (dd, 1H), 2.79 (m, 3H).

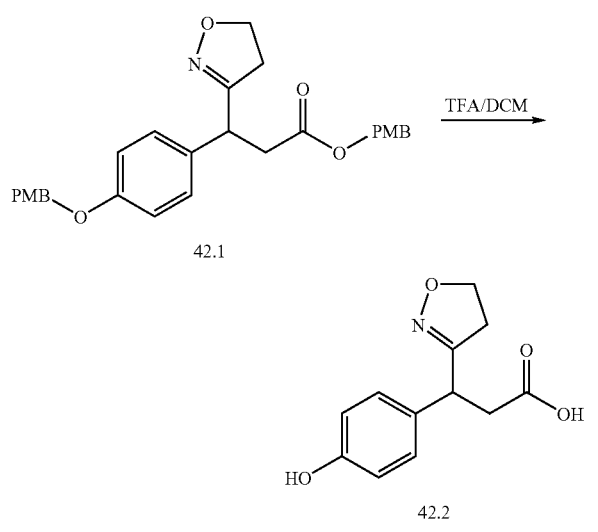

3-(4,5-Dihydroisoxazol-3-yl)-3-(4-hydroxyphenyl)propanoic acid (42.2). TFA (1 mL) was added to 42.1 (100 mg) in DCM (1 mL). The mixture was stirred at room temperature for 40 hours. TFA and DCM were removed under vacuum, and the residue was treated with EtOH (50 mL). The insoluble solid was removed by filtration. The filtrate was concentrated to give 42.2 (50 mg), which was used in the next step without further purification. MS ESI (pos.) m/e: 236 (M+H).

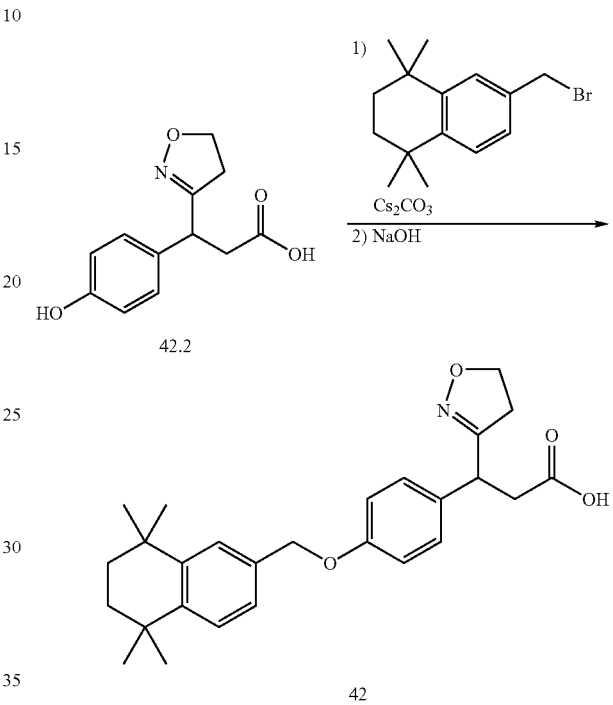

3-(4,5-Dihydroisoxazol-3-yl)-3-(4-((5,5,8,8-tetramethyl-5,6,7,8-tetrahydronaphthalen-2-yl)methoxy)phenyl)propanoic acid (42). Cesium carbonate (108 mg, 0.33 mmol) was added into a mixture of 42.2 (25 mg, 0.11 mmol) and 6-(bromomethyl)-1,1,4,4-tetramethyl-1,2,3,4-tetrahydronaphthalene (76 mg, 0.27 mmol) in DMSO (1 mL). The mixture was stirred at 45° C. for 3 hours. After cooling, the mixture was treated with EtOAc (5 mL) and brine (5 mL). The organic layer was separated, washed with brine twice, dried and concentrated. The crude product was treated with THF (1 mL), MeOH (1 mL), water (0.5 mL) and NaOH (0.05 mL, 10N). The mixture was stirred at room temperature for 4 hours. The organic solvent was blown away by nitrogen, and the aqueous layer was acidified by HCl (0.18 mL, 3N). The aqueous layer was extracted with DCM. The organic layer was dried, concentrated and purified by flash chromatography to give 42 (15 mg). MS ESI (pos.) m/e: 436 (M+H). $^1$HNMR (CDCl$_3$) δ 7.35 (m, 2H), 7.19 (m, 3H), 6.96 (d, 2H), 4.97 (s, 2H), 4.28 (m, 2H), 4.07 (t, 1H), 3.28 (dd, 1H), 2.79 (m, 3H), 1.71 (s, 4H), 1.30 (s, 12H).

6.38 Example 43

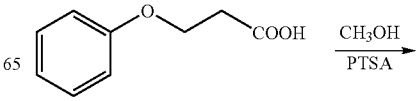

-continued

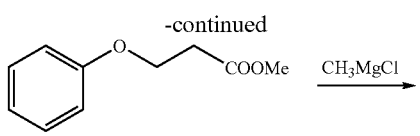

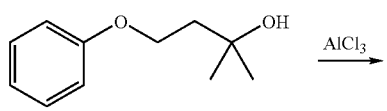

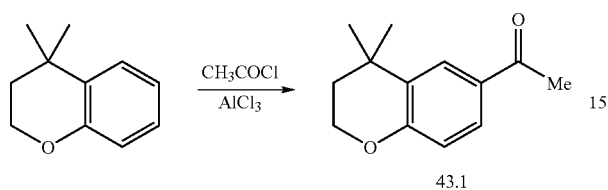

1-(4,4-Dimethylchroman-6-yl)ethanone (43.1). Compound 43.1 is synthesized using a literature procedure (*J. Med. Chem.* 1985, 28, 116-124).

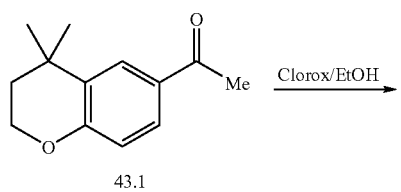

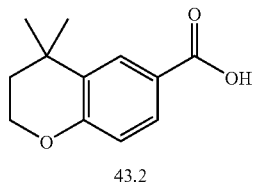

4,4-Dimethylchroman-6-carboxylic acid (43.2). Compound 43.2 is synthesized using a literature procedure (*J. Med. Chem.* 1997, 40, 3567-3583).

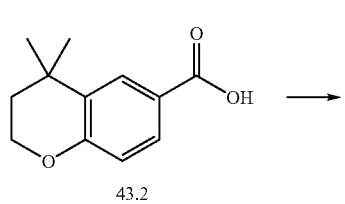

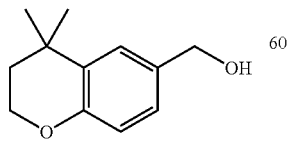

(4,4-Dimethylchroman-6-yl)methanol (43.3). Compound 43.3 is prepared using the procedure of Example 2.2 set forth in US 2006/0004012 which is hereby incorporated by reference.

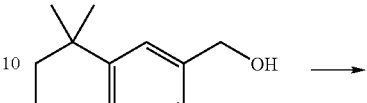

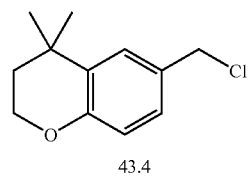

6-(Bromomethyl)-4,4-dimethylchroman (43.4). Compound 43.4 is prepared using the procedure of Example 2.3 set forth in US 2006/0004012 which is hereby incorporated by reference.

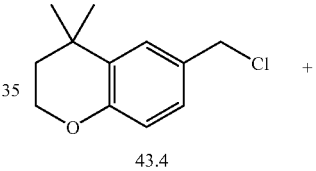

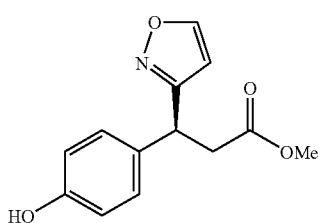

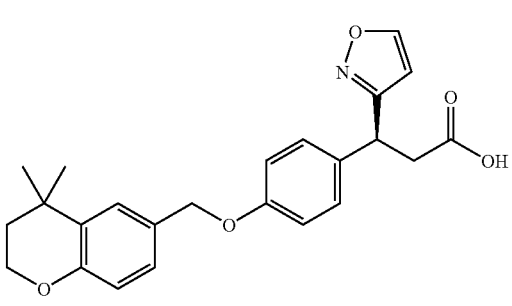

(S)-3-(4-((4,4-dimethylchroman-6-yl)methoxy)phenyl)-3-(isoxazol-3-yl)propanoic acid (43). Compound 43 is obtained from compound 43.4 and 43.5 (40.6) (see Example 40) using the procedure of Example 40.

6.39 Example 44

Synthesis of (S)-3-(4-((8,8-diethyl-5,5-dimethyl-5,6,7,8-tetrahydronaphthalen-2-yl)methoxy)phenyl)-3-(isoxazol-3-yl)propanoic acid (72)

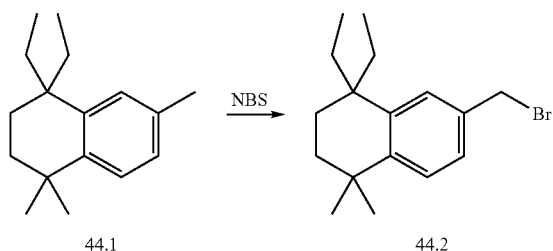

6-(Bromomethyl)-4,4-diethyl-1,1-dimethyl-1,2,3,4-tetrahydronaphthalene (44.2) Starting material 44.1 was prepared according to the published procedure of Kim, C. et al. (*Tetrahedron. Lett.* 1994, 35 (19), 3017-3020). A mixture of 44.1 (0.5 g, 2.17 mmol), NBS (0.58 g, 3.25 mmol), and dibenzoyl peroxide (53 mg) in $CCl_4$ (10 mL) was heated at reflux for 5 hours. The reaction was cooled, and the precipitate was filtered out. The solvent was removed providing crude 44.2, which was used directly in the next step.

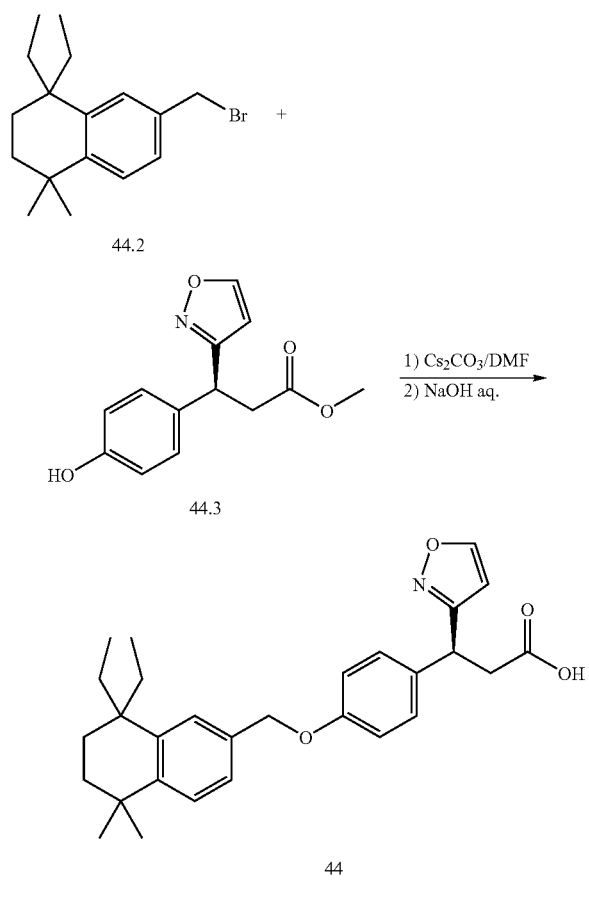

Starting from 44.2 and 44.3 (methyl ester prepared using the same procedure used to prepare ethyl ester 1.2 using methanol in place of ethanol), compound 44 was prepared using a procedure analogous to that described in Example 40. MS ESI (pos.) m/e: 462.1 (M+H). $^1$H NMR (MeOH-$d_4$) δ 8.50 (s, 1H), 7.34 (d, 1H, J=8.07Hz), 7.21-7.15 (m, 4H), 6.94 (d, 2H, J=8.80Hz), 6.28 (d, 1H, J=1.71Hz), 5.02 (s, 2H), 4.57 (t, 1H, J=7.82Hz), 3.20 (dd, 1H, J1=8.07Hz, J2=8.07Hz), 2.94 (dd, 1H, J1=7.33Hz, J2=8.80Hz), 1.73 (m, 6H), 1.55 (m, 2H), 1.27 (s, 6H), 0.72 (t, 6H, J=7.58Hz).

6.40 Example 45

Synthesis of 3-(4,5-dihydroisoxazol-3-yl)-3-(4-((5,5,8,8-tetramethyl-5,6,7,8-tetrahydronaphthalen-2-yl)methoxy)phenyl)propanoic acid

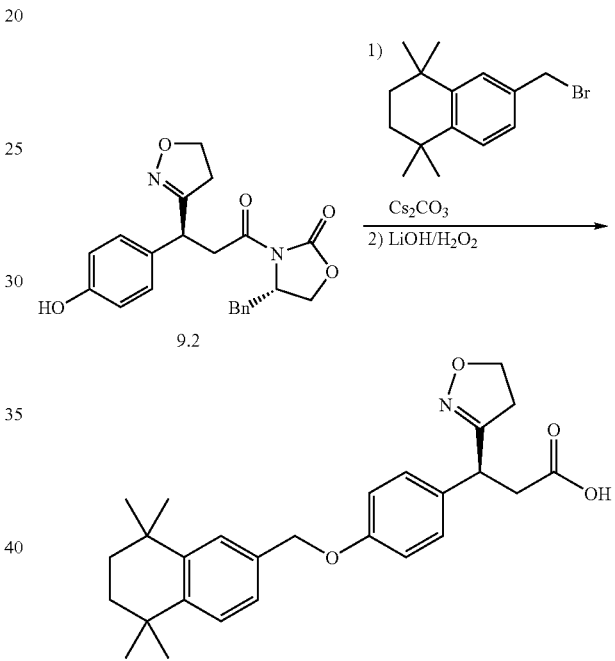

3-(4,5-Dihydroisoxazol-3-yl)-3-(4-((5,5,8,8-tetramethyl-5,6,7,8-tetrahydronaphthalen-2-yl)methoxy)phenyl)propanoic acid (45). Compound 45 was synthesized from 9.2 using the procedure above for preparing compound 7. MS ESI (pos.) m/e: 436 (M+H). $^1$HNMR (CDCl$_3$) δ 7.35 (m, 2H), 7.19 (m, 3H), 6.96 (d, 2H), 4.97 (s, 2H), 4.28 (m, 2H), 4.07 (t, 1H), 3.28 (dd, 1H), 2.79 (m, 3H), 1.71 (s, 4H), 1.30 (s, 12H).

6.41 Example 46

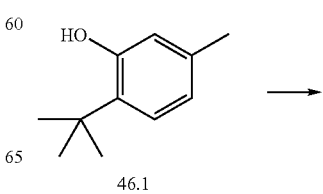

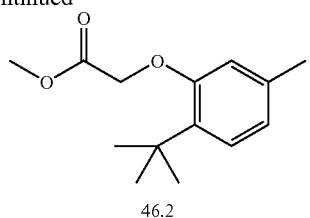

46.2

(Methyl 2-(2-tert-butyl-5-methylphenoxy)acetate (46.2). A mixture of 2-tert-butyl-5-methylphenol (10.0 g, 60.9 mmol), methyl chloroacetate (11.23 g, 103.5 mmol) and potassium carbonate (14.3 g, 103.5 mmol) in 60 mL of acetone was refluxed overnight. Upon completion, the mixture was cooled to room temperature, and the precipitate was filtered off. The filtrate was concentrated, and the residue was purified by CombiFlash to give 13.86 g (96%) of 46.2, which was eluted with 0-10% EtOAc in hexane. MS ESI (pos.) m/e: 237 (M+H). $^1$H NMR (400 MHz, CDCl$_3$) δ 7.21 (d, J=8.0Hz, 1H), 6.77 (d, J=8.0Hz, 2H), 6.56 (s, 1H), 5.67 (s, 2H), 3.84 (s, 3H), 2.32 (s, 3H), 1.43 (s, 9H).

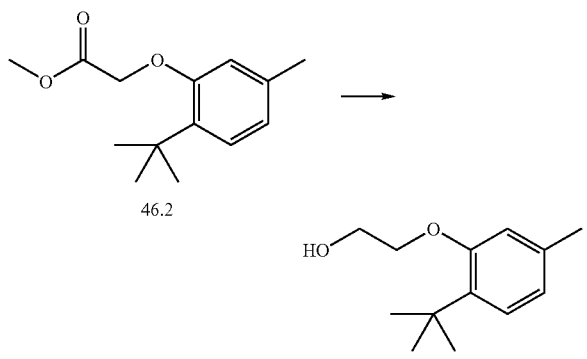

2-(2-tert-Butyl-5-methylphenoxy)ethanol (46.3). To a solution of (methyl 2-(2-tert-butyl-5-methylphenoxy)acetate (7.16 g, 30.3 mmol) was added a 2.0M solution of LAH in THF (15.2 mL, 30.3 mL) under an ice-water bath. The resulting mixture was allowed to stir at room temperature for 10 minutes before it was quenched with ice chips. The solvent was removed, and 20 mL of 2.0N aqueous HCl solution was added. The resulting mixture was extracted with DCM (30 mL×3). The extract was washed with water, saturated aqueous sodium bicarbonate solution and brine, dried over anhydrous sodium sulfate, and concentrated. The residue was purified by CombiFlash to give 6.22 g of 46.3, which was eluted with 0-40% EtOAc in hexane.). MS ESI (pos.) m/e: 209 (+H). $^1$H NMR (400 MHz, CDCl$_3$) δ 7.20 (d, J=8.0Hz, 1H), 6.76 (d, J=8.0Hz, 1H), 6.73 (s, 2H), 4.15 (dd, 2H), 4.04 (dd, 2H), 2.34 (s, 3H), 1.41 (s, 9H).

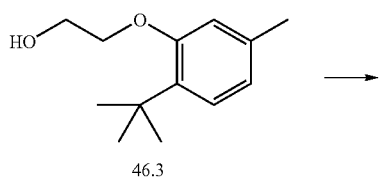

(1-tert-Butyl-2-(2-ethoxyethoxy)-4-methylbenzene (46.4). To a suspension of sodium hydride (60% dispersion in mineral oil, 371 mg, 9.28 mmol) in 20 mL of THF was dropwise added a solution of (2-(2-tert-tutyl-5-methylphenoxy)ethanol (1.29 g, 6.19 mmol) in 10 mL of THF under an ice-water bath. The resulting mixture was allowed to stir at room temperature for 30 minutes before ethyliodide was added. The mixture was allowed to stir at room temperature overnight. Upon completion, the solvent was removed, and 20 mL of 2.0N aqueous HCl solution was added. The resulting mixture was extracted with EtOAc (30 mL×3). The extract was washed with water, saturated aqueous sodium bicarbonate solution and brine, dried over anhydrous sodium sulfate, and concentrated. The residue was purified by CombiFlash to give 1.54 g of 46.4, which was eluted with 0-10% EtOAc in hexane. MS ESI (pos.) m/e: 237 (M+H). $^1$H NMR (400 MHz, CDCl$_3$) δ 7.17 (d, J=8.0Hz, 1H), 6.73 (d, J=8.0Hz, 1H), 6.70 (s, 1H), 4.14 (dd, 2H), 3.86 (dd, H), 3.63 (ddd, 2H), 2.32 (s, 3H), 1.39 (9H), 1.25 (dd, 3H).

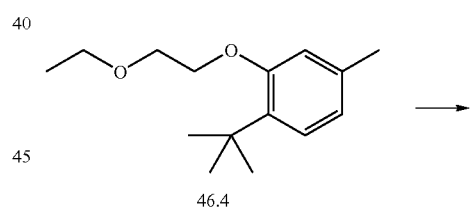

46.4

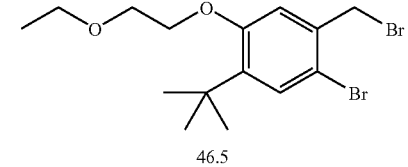

46.5

(1-Bromo-2-(bromomethyl)-5-tert-butyl-4-(2-ethoxyethoxy)benzene (46.5) Compound 46.4 (1.54 g, 6.51 mmol) was dissolved in carbon tetrachloride, and AIBN (107 mg, 0.65 mmol) and NBS (1.28 g, 7.16 mmol) were added. The resulting mixture was stirred at room temperature overnight. The mixture was filtered and the filtrate was concentrated, and the residue was purified by CombiFlash to give 2.04 g of 46.5. MS ESI (pos.) m/e: 395 (M+H).

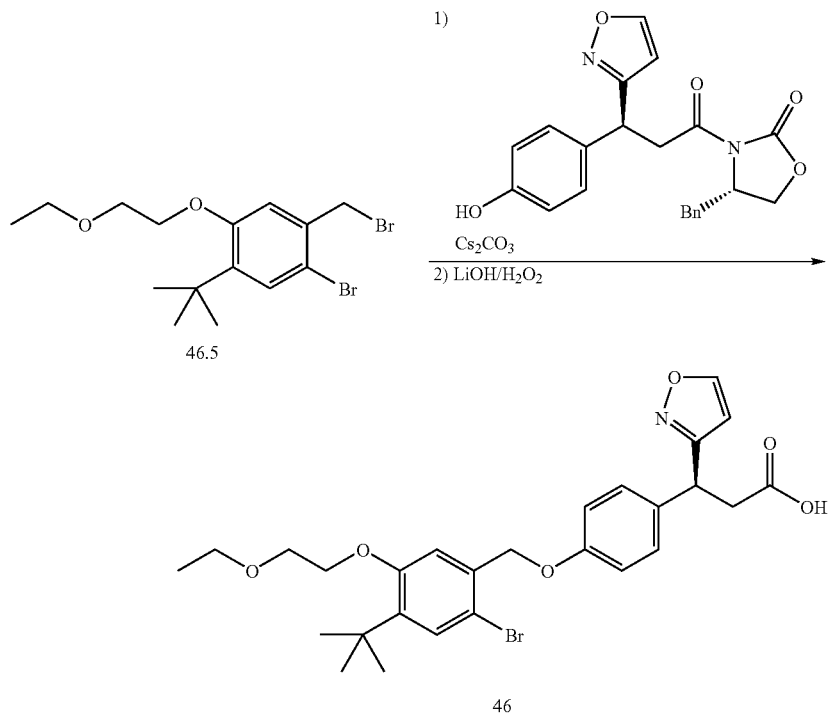

6.42 Example 47

(S)-3-(4-(2-Bromo-4-tert-butyl-5-(2-ethoxyethoxy)benzyloxy)phenyl)-3-(isoxazol-3-yl)propanoic acid (46). Compound 46 was synthesized from 46.5 and 7.5 using the procedure described above for preparing compound 7. MS ESI (pos.) m/e: 547 (M+H). $^1$H NMR (400 MHz, CDCl$_3$) δ 8.21 (s, 1H), 7.33 (s, 1H), 7.11 (d, J=8.0 Hz, 1H), 6.84 (s, 1H), 6.80 (d, 2H), 6.00 (d, J=4Hz, 1H), 5.00 (s, 1H), 4.46 (dd, J=8.0, 8.0Hz, 1H), 3.88 (m, 1H), 3.73 (dd, J=8.0, 4.0 Hz, 2H), 3.53 (ddd, J=8.0, 8.0, 8.0Hz, 2H), 3.23 (dd, J=16, 8.0Hz, 1H), 2.91 (dd, J=16, 8.0Hz, 1H), 1.28 (s, 9H), 1.14 (dd, J=8.0, 8.0Hz, 3H).

(S)-4-Benzyl-3-((S)-3-(4-(2-bromoethoxy)phenyl)-3-(isoxazol-3-yl)propanoyl)oxazolidin-2-one (47.1). A mixture of 7.5 (200 mg, 0.51 mmol), 1,2-dibromoethane (0.88 mL, 10 mmol), potassium carbonate (210 mg, 1.5 mmol) and tetrabutylammonium bromide (16 mg, 51 µmol) in water (6.0 mL) was heated to reflux and stirred for two hours. The mixture was then cooled to room temperature and extracted with EtOAc (2×50 mL). The combined organic layers were washed with brine and dried over magnesium sulfate. The filtrate was concentrated under reduced pressure and the residue was purified by medium pressure chromatography (silica gel, 20 to 100% EtOAc:hexanes) to obtain 47.1 (100 mg). MS ESI (pos.): m/e 500.0 (M+H).

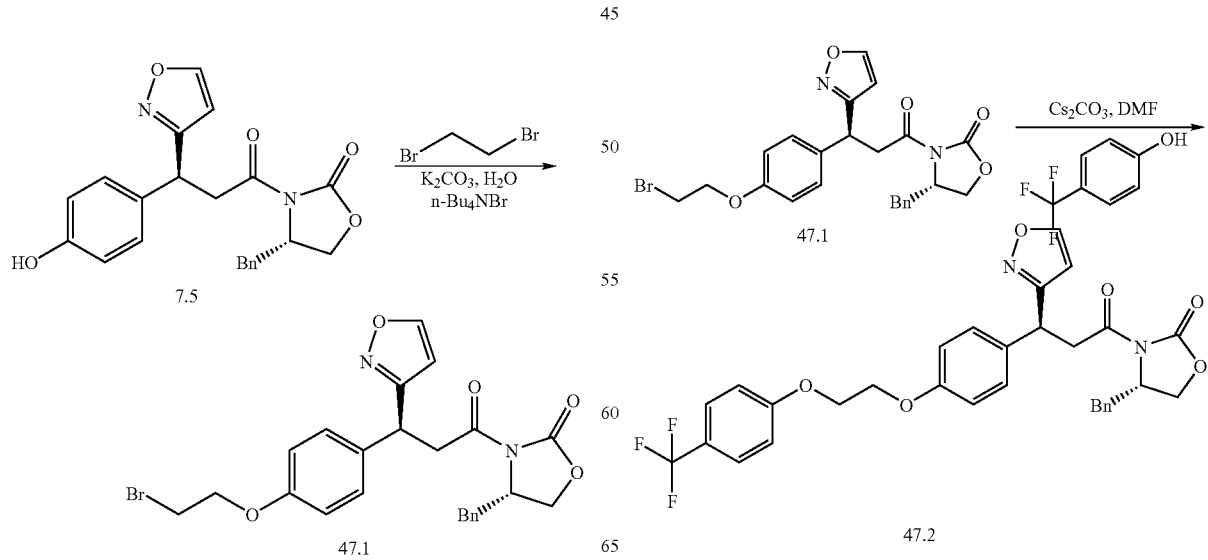

(S)-4-Benzyl-3-((S)-3-(isoxazol-3-yl)-3-(4-(2-(4-(trifluoromethyl)phenoxy)ethoxy)phenyl)propanoyl)oxazolidin-2-one (47.2). The bromide 47.1 (100 mg, 0.2 mmol) was dissolved in DMF (2.0 mL). Cesium carbonate (260 mg, 0.8 mmol) and 4-trifluoromethylphenol (130 mg, 0.8 mmol) were added to the solution and the mixture was then heated with stirring for three hours. The reaction mixture was then cooled to room temperature and diluted with water. The mixture was extracted with EtOAc (2×50 mL). The combined organic layers were washed with 1M lithium chloride solution (1×25 mL), water (1×25 mL) and brine (1×25 mL) and dried over magnesium sulfate. The filtrate was concentrated under reduced pressure and the residue purified by medium pressure chromatography (silica, 0 to 60% EtOAc: hexanes) to obtain 47.2 (58 mg). MS ESI (pos.): m/e 581.2 (M+H).

washed with an acidic sodium sulfite solution (2×15 mL) and brine (1×15 mL), and dried over magnesium sulfate. The filtrate was concentrated under reduced pressure, and the residue was purified by reverse phase HPLC to give 47 (23.6 mg). MS ESI (pos.) m/e: 422.0 (M+H). $^1$H NMR (400 MHz, CD$_3$CN) δ ppm 8.34 (1 H, s), 7.53 (2 H, d, J=8.6 Hz), 7.14 (2 H, d, J=8.6 Hz), 7.00 (2 H, d, J=8.6 Hz), 6.83 (2 H, d, J=8.6 Hz), 6.16 (1 H, d), 4.45 (1 H, t, J=7.8 Hz), 4.25-4.31 (2 H, m), 4.20-4.24 (2 H, m), 3.09 (1 H, dd, J=16.4, 8.2 Hz), 2.84 (1 H, dd, J=16.4, 7.4 Hz).

6.43 Example 48

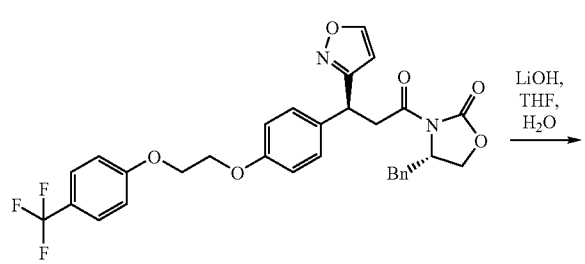

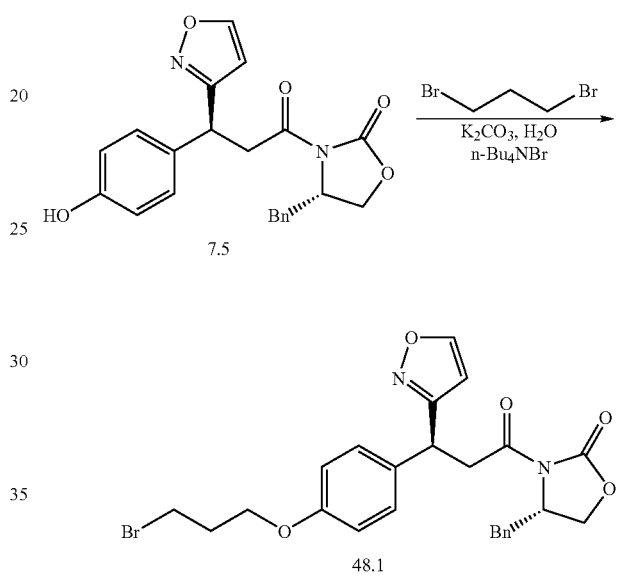

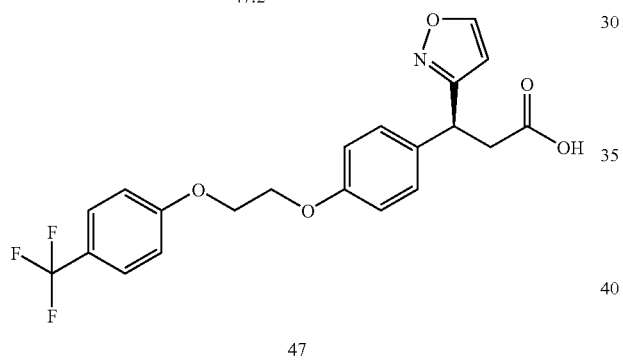

(S)-3-(Isoxazol-3-yl)-3-(4-(2-(4-(trifluoromethyl)phenoxy)ethoxy)phenyl)propanoic acid (47). To a solution of the oxazolidinone 47.2 (58.0 mg, 0.1 mmol) dissolved in THF (5 mL), was added a 30% hydrogen peroxide solution (113 μL, 1 mmol) followed by a 2 M lithium hydroxide solution (250 μL, 0.5 mmol). The resulting slurry was stirred for one hour. The reaction mixture was then diluted with water and acidified with hydrochloric acid to pH ~3. The mixture was then extracted with EtOAc (1×20 mL), and the organic layer was (S)-4-Benzyl-3-((S)-3-(4-(2-bromopropoxy)phenyl)-3-(isoxazol-3-yl)propanoyl)oxazolidin-2-one (48.1). A mixture of 7.5 (200 mg, 0.51 mmol), 1,3-dibromopropane (1.00 mL, 10 mmol), potassium carbonate (210 mg, 1.500 mmol) and tetrabutylammonium bromide (16 mg, 0.051 mmol) in water (6.0 mL) was heated to reflux and stirred for two hours. The mixture was then cooled to room temperature and extracted with EtOAc (2×50 mL). The combined organic layers were washed with brine and dried over magnesium sulfate. The filtrate was concentrated under reduced pressure and the residue was recrystallized with EtOAc and hexanes to obtain 48.1 (160 mg). MS ESI (pos.): m/e 514.0 (M+H).

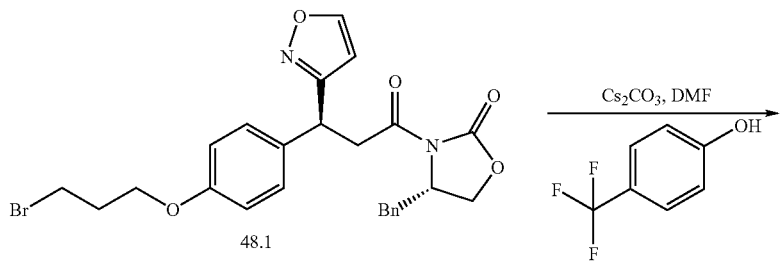

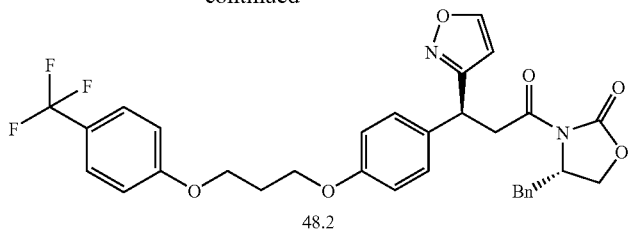

48.2

(S)-4-Benzyl-3-((S)-3-(isoxazol-3-yl)-3-(4-(2-(4-(trifluoromethyl)phenoxy)propoxy)phenyl)propanoyl)oxazolidin-2-one (48.2). The bromide 48.1 (80 mg, 0.16 mmol) was dissolved in DMF (2.0 mL). Cesium carbonate (200 mg, 0.62 mmol) and 4-trifluoromethylphenol (100 mg, 0.62 mmol) were added to the solution and the mixture was then heated with stirring for three hours. The reaction mixture was then cooled to room temperature and diluted with water. The mixture was extracted with EtOAc (2×50 mL). The combined organic layers were washed with 1M lithium chloride solution (1×25 mL), water (1×25 mL) and brine (1×25 mL) and dried over magnesium sulfate. The filtrate was concentrated under reduced pressure and the residue purified by medium pressure chromatography (silica, 0 to 60% EtOAc: hexanes) to obtain 48.2 (39 mg). MS ESI (pos.): m/e 595.2 (M+H).

Hz), 6.80 (2 H, d), 6.14 (1 H, d, J=1.6 Hz), 4.43 (1 H, t, J=7.8 Hz), 4.12 (2 H, t, J=6.3 Hz), 4.05 (2 H, t, J=6.3 Hz), 3.08 (1 H, dd, J=16.4, 8.2 Hz), 2.83 (1 H, dd, J=16.6, 7.2 Hz), 2.06-2.19 (2 H, m).

6.44 Example 49

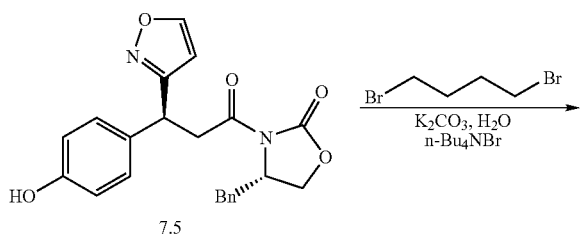

7.5

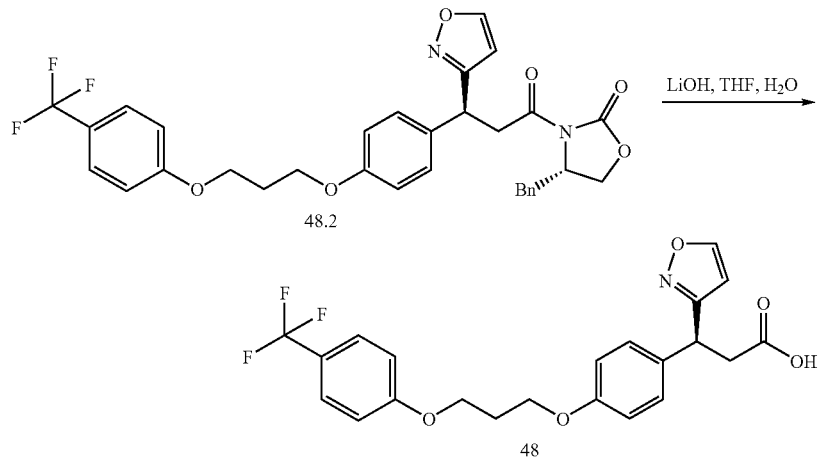

(S)-3-(Isoxazol-3-yl)-3-(4-(2-(4-(trifluoromethyl)phenoxy)propoxy)phenyl)propanoic acid (48). To a solution of the oxazolidinone (48.2) (39.0 mg, 0.066 mmol) dissolved in THF (3 mL), was added a 30% hydrogen peroxide solution (74 μL, 0.66 mmol) followed by a 2 M lithium hydroxide solution (160 μL, 0.33 mmol). The resulting slurry was stirred for one hour. The reaction mixture was then diluted with water and acidified with hydrochloric acid to pH ~3. The mixture was then extracted with EtOAc (1×20 mL), and the organic layer was washed with an acidic sodium sulfite solution (2×15 mL) and brine (1×15 mL), and dried over magnesium sulfate. The filtrate was concentrated under reduced pressure, and the residue was purified by reverse phase HPLC to give 48 (7.5 mg). MS ESI (pos.) m/e: 436.1 (M+H). $^1$H NMR (400 MHz, CD$_3$CN) δ ppm 8.33 (1 H, d, J=1.6 Hz), 7.51 (2 H, d, J=8.6 Hz), 7.12 (2 H, d, J=9.0 Hz), 6.97 (2 H, d, J=8.6

-continued

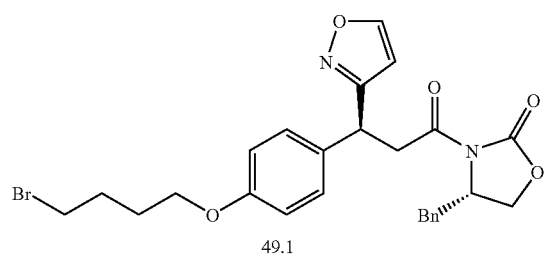

49.1

(S)-4-Benzyl-3-((S)-3-(4-(2-bromobutoxy)phenyl)-3-(isoxazol-3-yl)propanoyl)oxazolidin-2-one (49.1). A mixture of 7.5 (200 mg, 0.51 mmol), 1,4-dibromobutane (1.20 mL, 10 mmol), potassium carbonate (210 mg, 1.5 mmol) and tetrabutylammonium bromide (16 mg, 51 µmol) in water (6.0 mL) was heated to reflux and stirred for two hours. The mixture was then cooled to room temperature and extracted with EtOAc (2×50 mL). The combined organic layers were washed with brine and dried over magnesium sulfate. The filtrate was concentrated under reduced pressure and the residue was recrystallized with EtOAc and hexanes to obtain 49.1 (184 mg). MS ESI (pos.): m/e 528.1 (M+H).

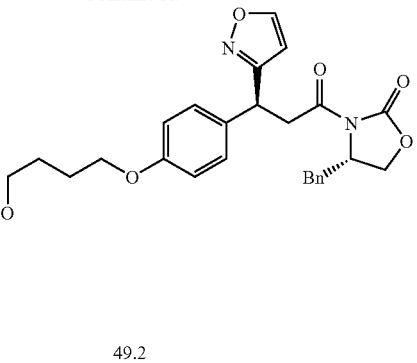

49.2

(S)-4-Benzyl-3-((S)-3-(isoxazol-3-yl)-3-(4-(2-(4-(trifluoromethyl)phenoxy)butoxy)phenyl)propanoyl)oxazolidin-2-one (49.2). The bromide 49.1 (90 mg, 0.17 mmol) was dissolved in DMF (2.0 mL). Cesium carbonate (220 mg, 0.68 mmol) and 4-trifluoromethylphenol (110 mg, 0.68 mmol) were added to the solution and the mixture was then heated with stirring for three hours. The reaction mixture was then cooled to room temperature and diluted with water. The mixture was extracted with EtOAc (2×50 mL). The combined organic layers were washed with 1M lithium chloride solution (1×25 mL), water (1×25 mL) and brine (1×25 mL), and dried over magnesium sulfate. The filtrate was concentrated under reduced pressure and the residue purified by medium pressure chromatography (silica, 0 to 60% EtOAc: hexanes) to obtain 49.2 (23 mg). MS ESI (pos.): m/e 609.1 (M+H).

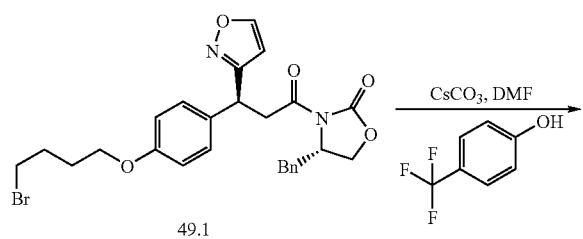

49.1

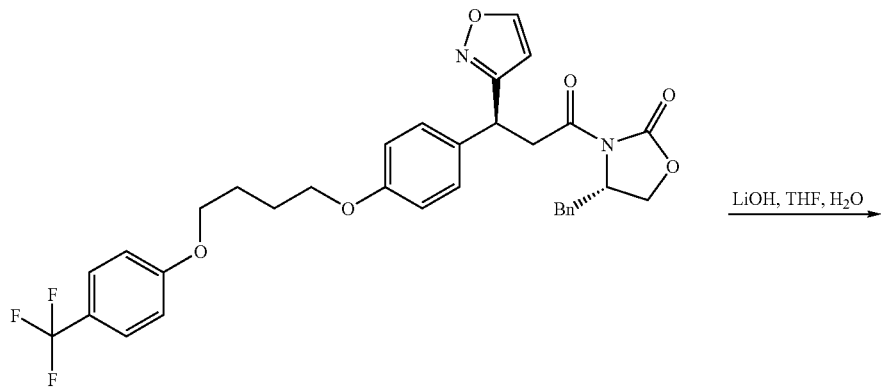

49.2

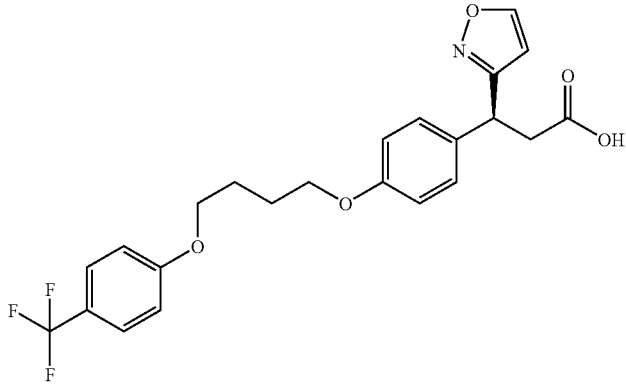

49

(S)-3-(Isoxazol-3-yl)-3-(4-(2-(4-(trifluoromethyl)phenoxy)butoxy)phenyl)propanoic acid (49). To a solution of the oxazolidinone (49.2) (23.0 mg, 0.038 mmol) dissolved in THF (2 mL), was added a 30% hydrogen peroxide solution (43 μL, 0.38 mmol) followed by a 2 M lithium hydroxide solution (94 μL, 0.19 mmol). The resulting slurry was stirred for one hour. The reaction mixture was then diluted with water and acidified with hydrochloric acid to pH ~3. The mixture was then extracted with EtOAc (1×20 mL), and the organic layer was washed with an acidic sodium sulfite solution (2×15 mL) and brine (1×15 mL), and dried over magnesium sulfate. The filtrate was concentrated under reduced pressure, and the residue was purified by reverse phase HPLC to give 49 (5.5 mg). MS ESI (pos.) m/e: 450.1 (M+H). $^1$H NMR (400 MHz, CD$_3$CN) δ ppm 8.33 (1 H, d, J=1.6 Hz), 7.51 (2 H, d, J=8.6 Hz), 7.12 (2 H, d), 6.95 (2 H, d, J=8.6 Hz), 6.78 (2 H, d, J=8.6 Hz), 6.16 (1 H, d, J=1.6 Hz), 4.44 (1 H, t, J=7.8 Hz), 4.02 (2 H, t, J=6.1 Hz), 3.94 (2 H, t, J=6.1 Hz), 3.09 (1 H, dd, J=16.6, 8.4 Hz), 2.84 (1 H, dd, J=16.4, 7.4 Hz), 1.81-1.84 (4 H, m).

6.45 Example 50

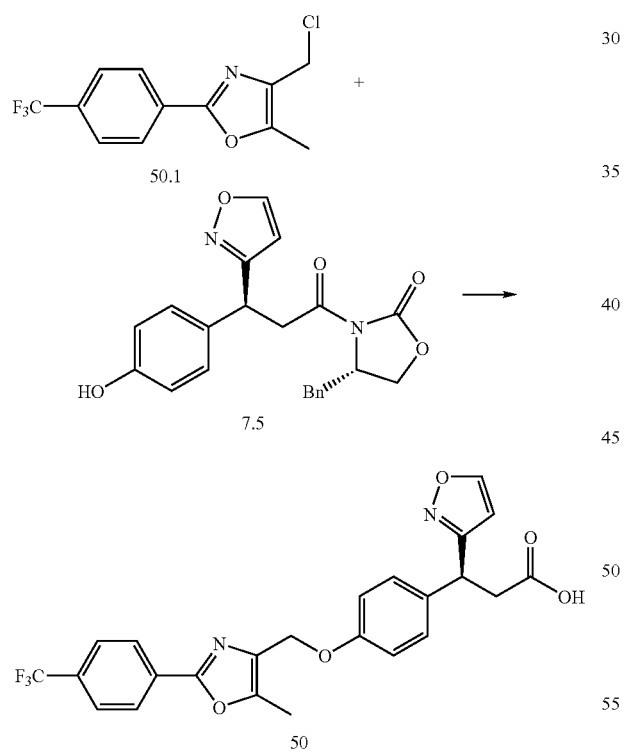

(S)-3-(Isoxazol-3-yl)-3-(4-((5-methyl-2-(4-(trifluoromethyl)phenyl)oxazol-4-yl)methoxy)phenyl)propanoic acid (50). Compound 50.1 was prepared as described in Yamane et al. *Synthesis* 2004, 2825-2832. Compound 50 was obtained from compound 50.1 by following the procedure of Example 7. MS ESI (neg.) m/e: 471 (M−H). $^1$H NMR (400 MHz, CD$_3$CN) δ ppm 8.42 (d, J=1.7 Hz, 1 H), 8.12 (d, J=8.1 Hz, 2 H), 7.79 (d, J=8.1 Hz, 2 H), 7.19-7.27 (m, 2 H), 6.91-6.99 (m, 2 H), 6.25 (d, J=1.7 Hz, 1 H), 4.97 (s, 2 H), 4.54 (t, J=7.8 Hz, 1 H), 3.14-3.20 (m, 1 H), 2.93 (dd, J=16.4, 7.3 Hz, 1H), 2.42 (s, 3 H).

6.46 Example 51

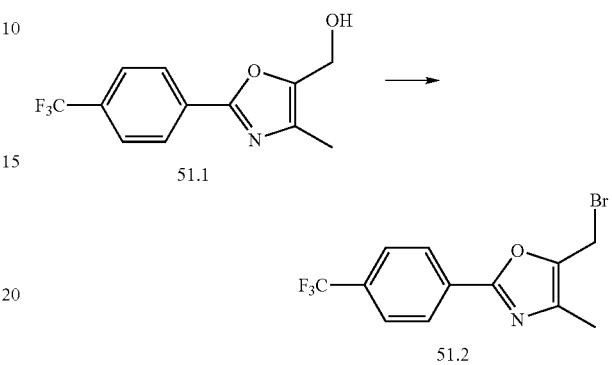

5-(Bromomethyl)-4-methyl-2-(4-(trifluoromethyl)phenyl)oxazole (51.2). Compound 51.1 was prepared as described in Sznaidman et al. *Bioorganic & Medicinal Chemistry Letters* 2003, 13, 1517-1521. Compound 51.2 was then obtained by following the procedure of Example 2.3.

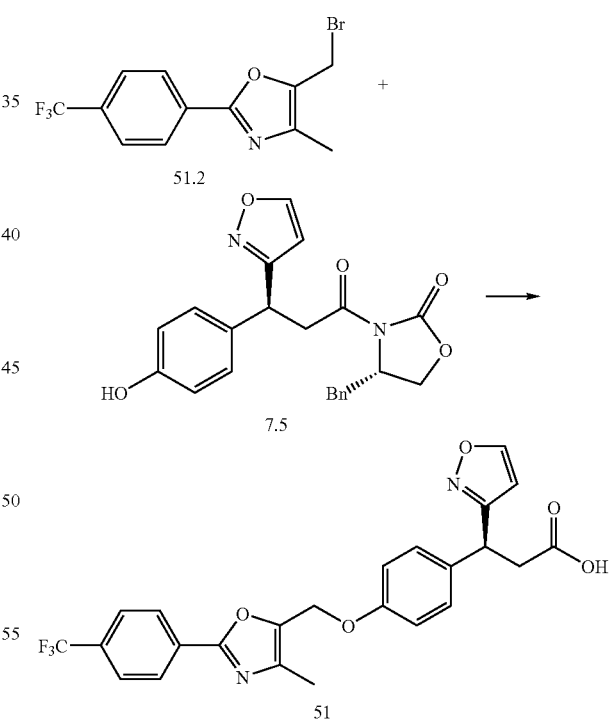

(S)-3-(Isoxazol-3-yl)-3-(4-((4-methyl-2-(4-(trifluoromethyl)phenyl)oxazol-5-yl)methoxy)phenyl)propanoic acid (51). Compound 51 was synthesized using the procedure of Example 7 using compound 51.2. MS ESI (neg.) m/e: 471 (M−H). $^1$H NMR (400 MHz, CD$_3$CN) δ ppm 8.43 (d, J=1.6 Hz, 1H), 8.14 (d, J=8.2 Hz, 2 H), 7.80 (d, J=8.2 Hz, 2 H), 7.26 (d, J=8.6 Hz, 2 H), 6.99 (d, J=9.0 Hz, 2 H), 6.26 (d, J=1.6 Hz, 1 H), 5.12 (s, 2 H), 4.55 (t, J=7.8 Hz, 1 H), 3.19 (dd, J=16.4, 8.2 Hz, 1 H), 2.95 (dd, J=16.4, 7.4 Hz, 1 H), 2.23 (s, 3 H).

6.47 Example 52

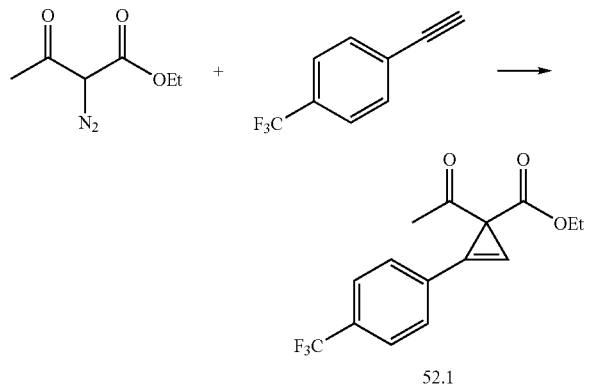

Ethyl 1-acetyl-2-(4-(trifluoromethyl)phenyl)cycloprop-2-enecarboxylate (52.1). Compound 52.1 was prepared as described in Davies et al. *Tetrahedron* 1988, 44, 3343-3348. ¹H NMR (500 MHz, CDCl₃) δ ppm 7.70-7.74 (m, 4 H), 7.07 (s, 1 H), 4.22 (q, J=7.17 Hz, 2 H), 2.32 (s, 3 H), 1.24-1.28 (m, J=7.21, 7.21, 0.98 Hz, 3 H).

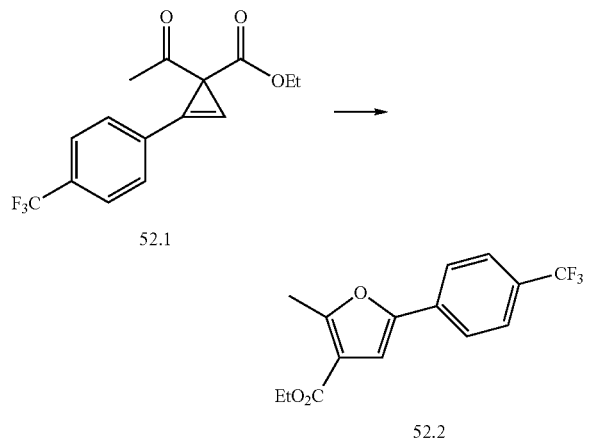

Ethyl 2-methyl-5-(4-(trifluoromethyl)phenyl)furan-3-carboxylate (52.2). Compound 52.2 was prepared as described in Ma et al. *J. Am. Chem. Soc.* 2003, 125, 12386-12387. ¹H NMR (500 MHz, CDCl₃) δ ppm 7.74 (d, J=8.31 Hz, 2 H), 7.60-7.69 (m, 2 H), 7.02 (s, 1 H), 4.34 (q, J=7.17 Hz, 2H), 2.68 (s, 3 H), 1.39 (t, J=7.21 Hz, 3 H).

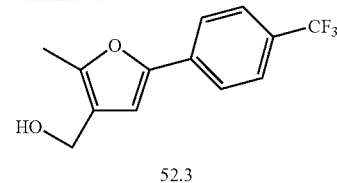

(2-Methyl-5-(4-(trifluoromethyl)phenyl)furan-3-yl) methanol (52.3). Compound 52.3 was synthesized using the procedure of Example 15.2 using compound 52.2. ¹H NMR (500 MHz, CDCl₃) δ ppm 7.71 (d, J=7.58 Hz, 2H), 7.60-7.64 (m, 2 H), 6.77 (s, 1 H), 4.52-4.57 (m, 2 H), 2.40 (s, 3 H).

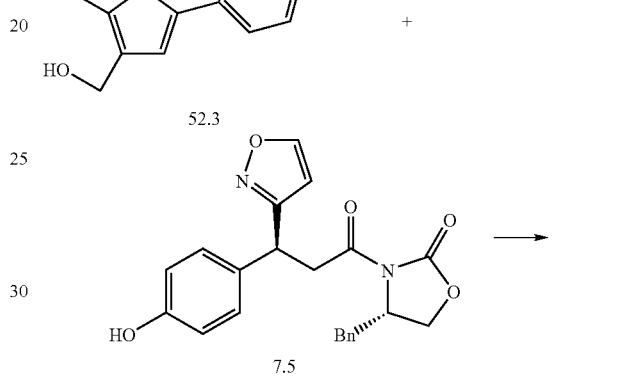

(S)-3-(Isoxazol-3-yl)-3-(4-((2-methyl-5-(4-(trifluoromethyl)phenyl)furan-3-yl)methoxy)phenyl)propanoic acid (52). Compound 52 was synthesized using the procedure of Example 15 using compound 52.3. MS ESI (neg.) m/e: 470 (M–H). ¹H NMR (400 MHz, CD₃CN) δ ppm 8.42 (d, J=2.35 Hz, 1 H), 7.80 (d, J=8.22 Hz, 2 H), 7.69 (d, J=8.22 Hz, 2 H), 7.24 (d, J=8.61 Hz, 2 H), 6.96 (s, 1 H), 6.93-6.95 (m, 2 H), 6.25 (d, J=1.56 Hz, 1H), 4.91 (s, 2 H), 4.54 (t, J=7.83 Hz, 1 H), 3.18 (dd, J=16.43, 8.22 Hz, 1 H), 2.94 (dd, J=16.43, 7.43 Hz, 1H), 2.38 (s, 3 H).

6.48 Example 53

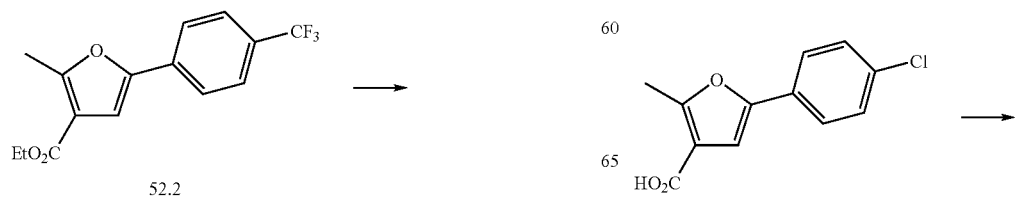

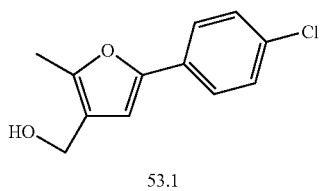

53.1

(5-(4-Chlorophenyl)-2-methylfuran-3-yl)methanol (53.1). To a solution of 5-(4-chlorophenyl)-2-methylfuran-3-carboxylic acid (0.104 g, 0.44 mmol) in THF (2 mL) and MeOH (2 mL) was added TMSCHN$_2$ (2.0 M in Et$_2$O, 0.250 mL). The reaction mixture was stirred for 18 hours at which time it was concentrated in vacuo. The residue was dissolved in 1 ml of THF at 0° C., and a solution of LAH (1.0 M in THF, 0.8 mL) was added. After addition, the reaction was stirred at room temperature for 2 hours, and then water (0.24 mL), 15% aqueous NaOH (0.24 mL), and water (0.72 mL) were added sequentially to the reaction. After 30 minutes, the reaction mixture was filtered through celite, and the filtrate was concentrated to give 53.1 (0.056 g). $^1$H NMR (400 MHz, CDCl$_3$) δ ppm 7.53-7.63 (m, 2 H), 7.31-7.40 (m, 2 H), 6.64 (s, 1 H), 4.52 (s, 2 H), 2.37 (s, 3 H).

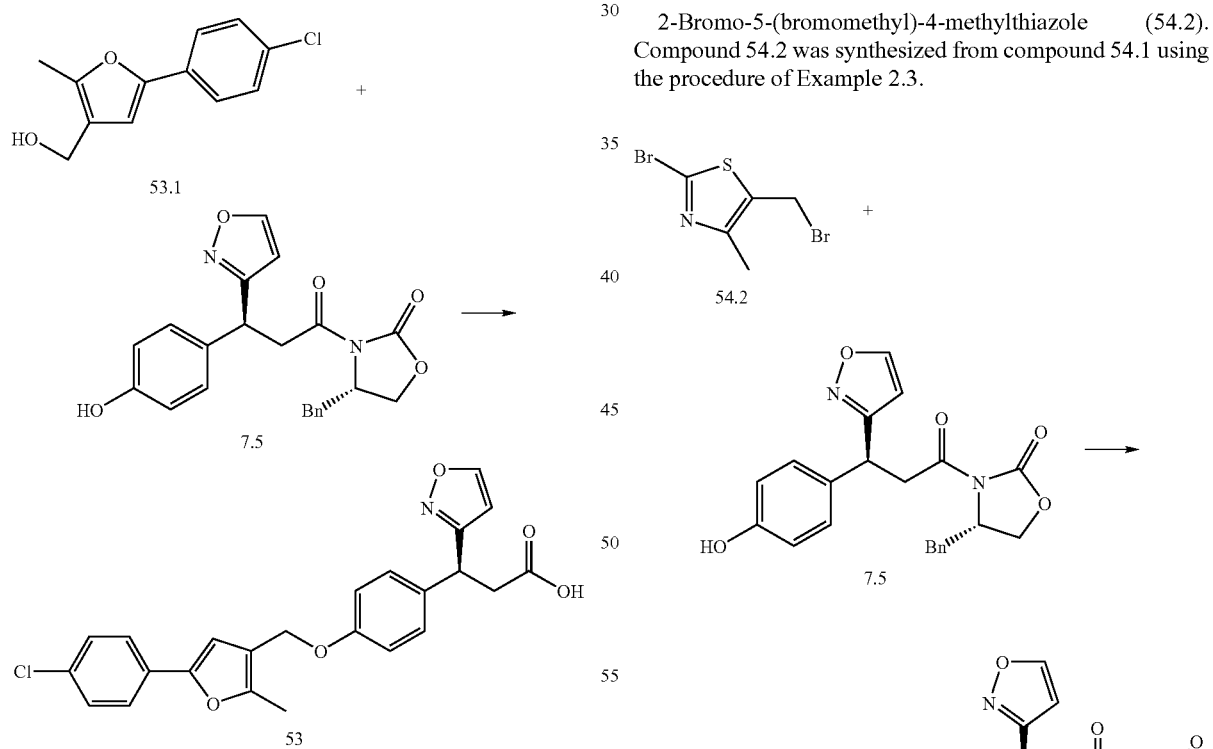

53

(S)-3-(4-((5-(4-Chlorophenyl)-2-methylfuran-3-yl)methoxy)phenyl)-3-(isoxazol-3-yl)propanoic acid (53). Compound 53 was synthesized from compound 53.1 using the procedure of Example 15. MS ESI (neg.) m/e: 436 (M–H). $^1$H NMR (400 MHz, CD$_3$CN) δ ppm 8.41 (d, J=2.3 Hz, 1H), 7.60 (d, J=9.0 Hz, 2 H), 7.39 (d, J=8.6 Hz, 2 H), 7.22 (d, J=8.6 Hz, 2 H), 6.93 (d, J=8.6 Hz, 2 H), 6.78 (s, 1 H), 6.24 (d, J=1.6 Hz, 1 H), 4.88 (s, 2 H), 4.52 (t, J=7.8 Hz, 1 H), 3.17 (dd, J=16.4, 8.2 Hz, 1 H), 2.92 (dd, J=16.4, 7.4 Hz, 1 H), 2.34 (s, 3 H).

6.49 Example 54

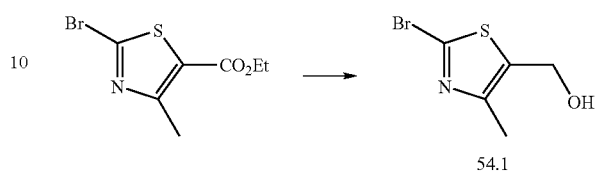

54.1

(2-Bromo-4-methylthiazol-5-yl)methanol (54.1). Compound 54.1 was synthesized using the procedure above for preparing 13.1 from commercially available ethyl 2-bromo-4-methylthiazole-5-carboxylate.

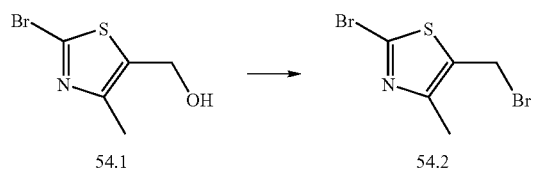

54.1           54.2

2-Bromo-5-(bromomethyl)-4-methylthiazole (54.2). Compound 54.2 was synthesized from compound 54.1 using the procedure of Example 2.3.

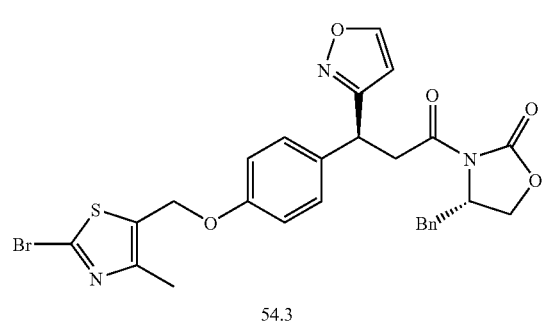

54.3

(S)-4-Benzyl-3-((S)-3-(4-((2-bromo-4-methylthiazol-5-yl)methoxy)phenyl)-3-(isoxazol-3-yl)propanoyl)oxazolidin-2-one (54.3). Compound 54.3 was synthesized from compound 54.2 using the procedure of Example 19.3.

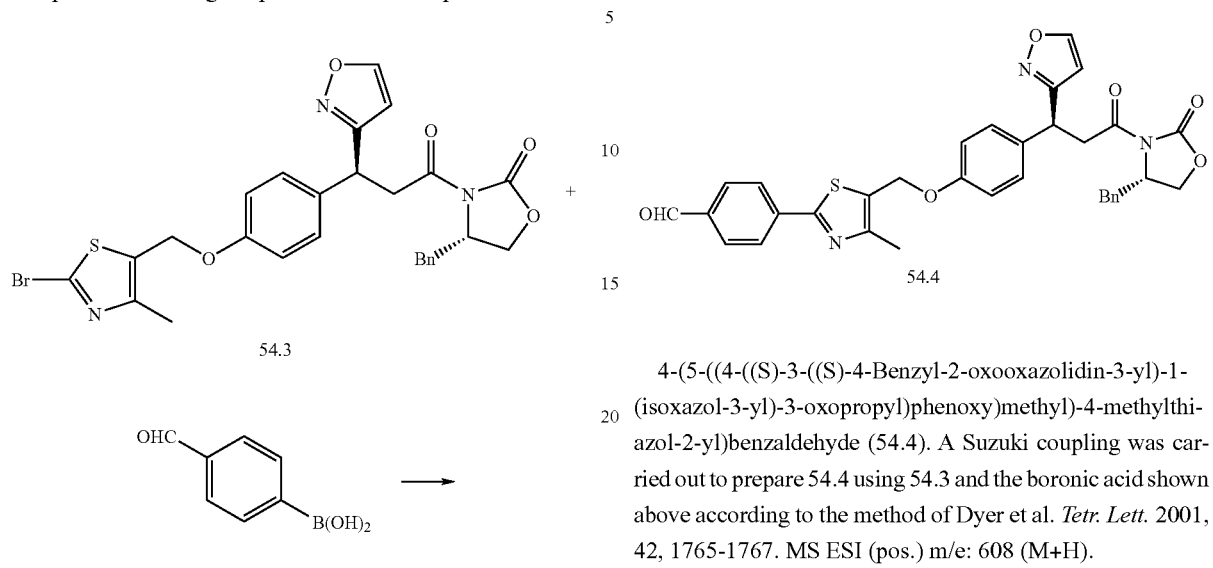

4-(5-((4-((S)-3-((S)-4-Benzyl-2-oxooxazolidin-3-yl)-1-(isoxazol-3-yl)-3-oxopropyl)phenoxy)methyl)-4-methylthiazol-2-yl)benzaldehyde (54.4). A Suzuki coupling was carried out to prepare 54.4 using 54.3 and the boronic acid shown above according to the method of Dyer et al. *Tetr. Lett.* 2001, 42, 1765-1767. MS ESI (pos.) m/e: 608 (M+H).

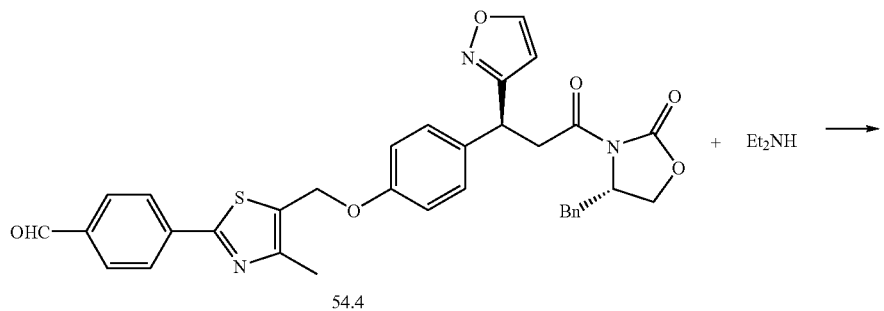

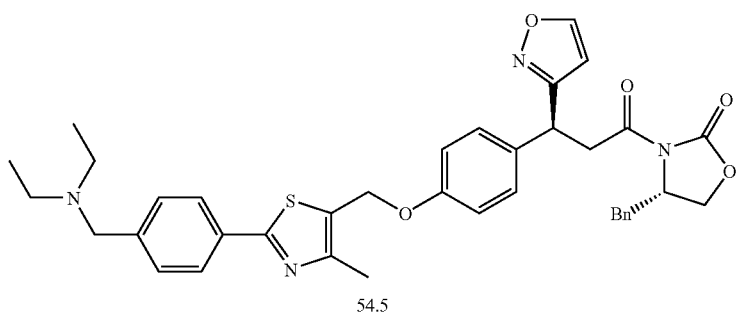

(S)-4-Benzyl-3-((S)-3-(4-((2-(4-((diethylamino)methyl)phenyl)-4-methylthiazol-5-yl)methoxy)phenyl)-3-(isoxazol-3-yl)propanoyl)oxazolidin-2-one (54.5). Diethylamine (11 μL, 0.11 mmol) and NaCNBH₃ (10 mg, 0.16 mmol) were added to a solution of compound 54.4 (54 mg, 0.089 mmol) in DCE (2 mL). The reaction mixture was stirred at 60° C. for 18 hours and then 1N HCl aqueous solution was added. The solution was stirred for 5 minutes and then partitioned between saturated aqueous NaHCO₃ solution and DCM. The organic layer was collected, dried over MgSO₄ and concentrated in vacuo. The crude product was used without further purification. MS ESI (pos.) m/e: 665 (M+H).

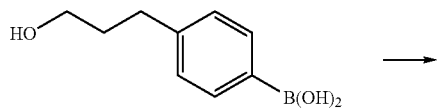

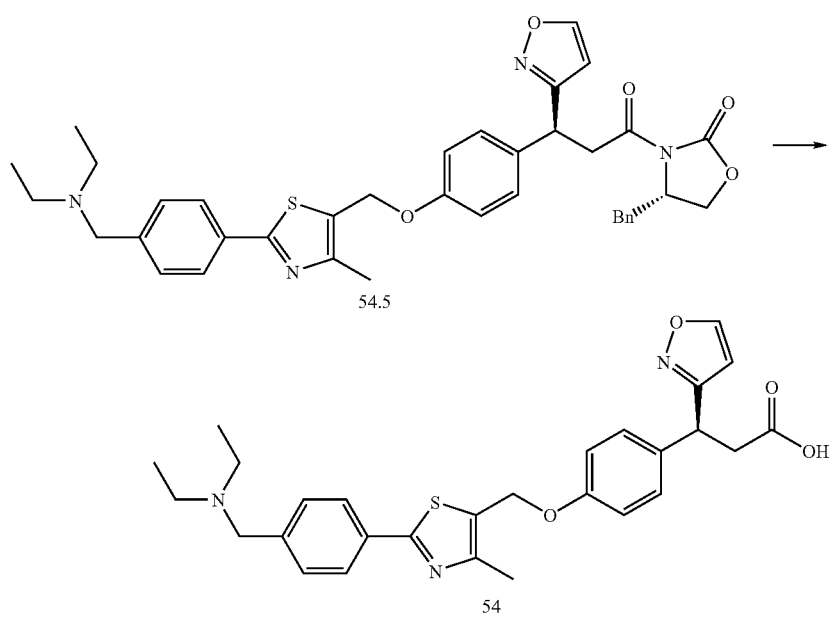

(S)-3-(4-((2-(4-((Diethylamino)methyl)phenyl)-4-methylthiazol-5-yl)methoxy)phenyl)-3-(isoxazol-3-yl)propanoic acid (54). Compound 54 was synthesized using the procedure of Example 25 from compound 54.5. MS ESI (neg.) m/e: 504 (M−H). ¹H NMR (400 MHz, CD₃CN) δ ppm 8.42 (s, 1 H), 7.96 (d, J=7.8 Hz, 2 H), 7.58-7.65 (m, 2 H), 7.20-7.29 (m, 2 H), 6.91-7.01 (m, 2 H), 6.25 (s, 1 H), 5.23 (s, 2 H), 4.54 (t, J=7.8 Hz, 1 H), 4.24 (s, 2 H), 3.49-3.63 (m, 1H), 3.03-3.25 (m, 4 H), 2.88-2.99 (m, 1 H), 2.43 (s, 3 H), 1.23-1.33 (m, 6 H).

6.50 Example 55

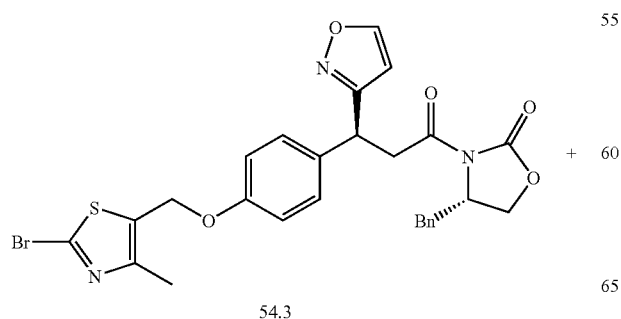

(S)-4-Benzyl-3-((S)-3-(4-((2-(4-(3-hydroxypropyl)phenyl)-4-methylthiazol-5-yl)methoxy)phenyl)-3-(isoxazol-3-yl)propanoyl)oxazolidin-2-one (55.1). The Suzuki coupling was carried out to prepare 55.1 using 54.3 and the boronic acid shown above according to the method of Dyer et al. *Tetr. Lett.* 2001, 42, 1765-1767.

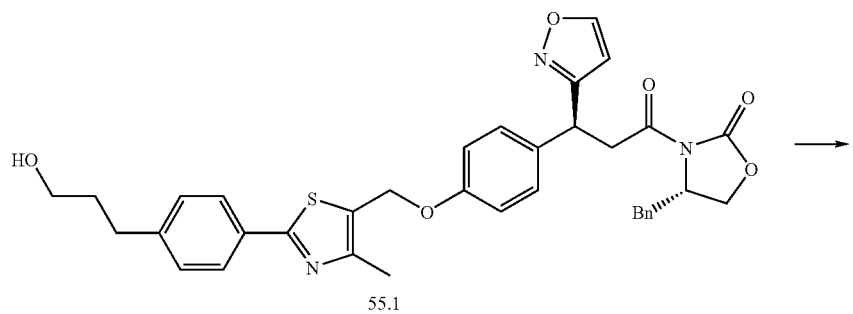

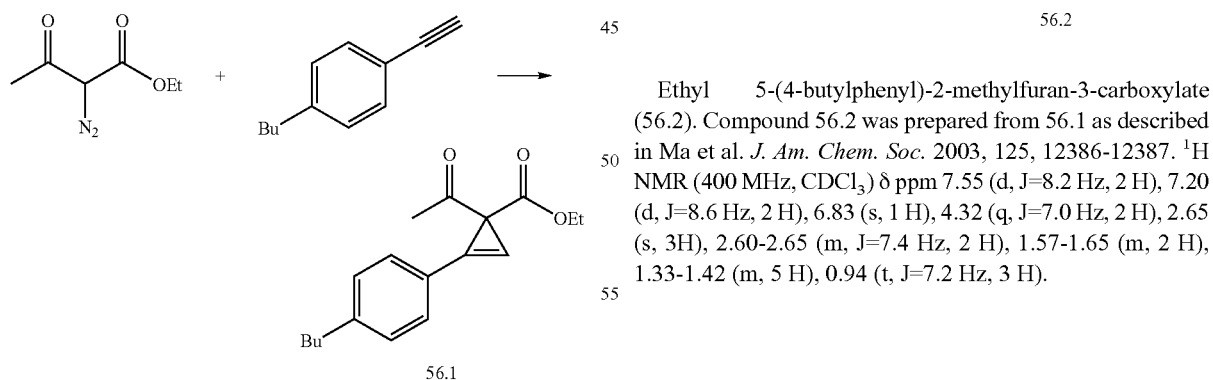

(S)-3-(4-((2-(4-(3-Hydroxypropyl)phenyl)-4-methylthiazol-5-yl)methoxy)phenyl)-3-(isoxazol-3-yl)propanoic acid (55). Compound 55 was synthesized from compound 55.1 using the procedure of Example 25. MS ESI (neg.) m/e: 477 (M−H). $^1$H NMR (400 MHz, CD$_3$CN) δ ppm 8.43 (s, 1 H), 7.82-7.87 (m, 2 H), 7.33 (dd, J=8.4, 2.2 Hz, 2 H), 7.26 (d, J=8.6 Hz, 2 H), 6.97 (d, J=9.0 Hz, 2 H), 6.26 (d, J=1.6 Hz, 1 H), 5.23 (s, 2 H), 4.55 (t, J=7.8 Hz, 1 H), 4.39 (t, J=6.5 Hz, 1 H), 3.53 (t, J=6.5 Hz, 1 H), 3.16-3.22 (m, 1 H), 2.95 (dd, J=16.4, 7.4 Hz, 1 H), 2.75 (td, J=15.7, 7.6 Hz, 2 H), 2.44 (s, 3 H), 2.05-2.13 (m, 1 H), 1.81 (dt, J=15.7, 6.3 Hz, 1 H).

6.51 Example 56

Ethyl 1-acetyl-2-(4-butylphenyl)cycloprop-2-enecarboxylate (56.1). Compound 56.1 was prepared as described in Davies et al. Tetrahedron 1988, 44, 3343-3348. $^1$H NMR (500 MHz, CDCl$_3$) δ ppm 7.51 (d, J=8.2 Hz, 2H), 7.25-7.27 (m, 2 H), 6.85 (s, 1 H), 4.20 (qd, J=7.0, 1.2 Hz, 2 H), 2.61-2.68 (m, 2 H), 2.24 (s, 3 H), 1.59-1.65 (m, 2 H), 1.38 (dt, J=15.4, 7.8 Hz, 2 H), 1.23-1.29 (m, 3 H), 0.94 (t, J=7.2 Hz, 3 H).

Ethyl 5-(4-butylphenyl)-2-methylfuran-3-carboxylate (56.2). Compound 56.2 was prepared from 56.1 as described in Ma et al. J. Am. Chem. Soc. 2003, 125, 12386-12387. $^1$H NMR (400 MHz, CDCl$_3$) δ ppm 7.55 (d, J=8.2 Hz, 2 H), 7.20 (d, J=8.6 Hz, 2 H), 6.83 (s, 1 H), 4.32 (q, J=7.0 Hz, 2 H), 2.65 (s, 3H), 2.60-2.65 (m, J=7.4 Hz, 2 H), 1.57-1.65 (m, 2 H), 1.33-1.42 (m, 5 H), 0.94 (t, J=7.2 Hz, 3 H).

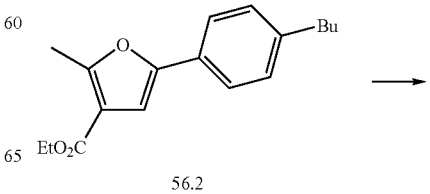

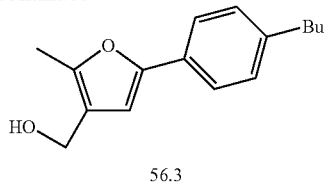

56.3

(5-(4-Butylphenyl)-2-methylfuran-3-yl)methanol (56.3). Compound 56.3 was synthesized from compound 56.2 using the procedure of Example 15.2. $^1$H NMR (400 MHz, CDCl$_3$) δ ppm 7.54 (d, J=8.2 Hz, 2 H), 7.18 (d, J=8.6 Hz, 2 H), 6.58 (s, 1 H), 4.51 (s, 2 H), 2.59-2.66 (m, 2 H), 2.36 (s, 3 H), 1.54-1.65 (m, 2 H), 1.37 (dd, J=14.9, 7.4 Hz, 2 H), 0.94 (t, J=7.2 Hz, 3 H).

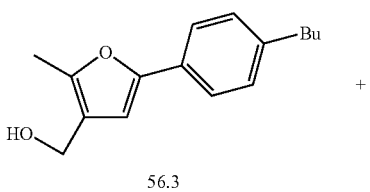

56.3

+

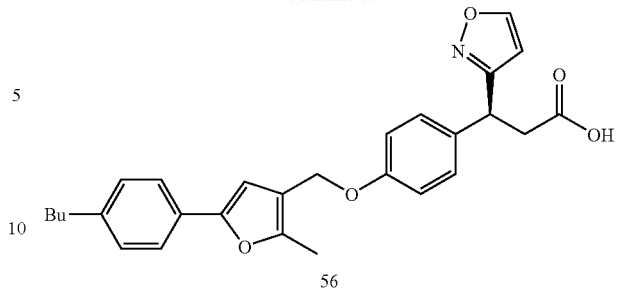

56

((S)-3-(4-((5-(4-Butylphenyl)-2-methylfuran-3-yl)methoxy)phenyl)-3-(isoxazol-3-yl)propanoic acid (56). Compound 56 was synthesized from compound 56.3 using the procedure of Example 15 using compound 56.3. MS ESI (neg.) m/e: 458 (M−H). $^1$H NMR (400 MHz, CD$_3$CN) δ ppm 8.42 (d, J=2.3 Hz, 1 H), 7.54 (d, J=8.6 Hz, 2 H), 7.19-7.27 (m, 4 H), 6.91-6.95 (m, 2 H), 6.69 (s, 1 H), 6.24 (d, J=1.6 Hz, 1 H), 4.88 (s, 2 H), 4.52 (s, 1 H), 3.12-3.21 (m, 1 H), 2.93 (dd, J=16.4, 7.4 Hz, 1 H), 2.57-2.67 (m, 2 H), 2.34 (s, 3 H), 1.59 (dt, J=15.3, 7.6 Hz, 2 H), 1.35 (dd, J=14.9, 7.4 Hz, 2 H), 0.93 (t, J=7.4 Hz, 3 H).

6.52 Example 57

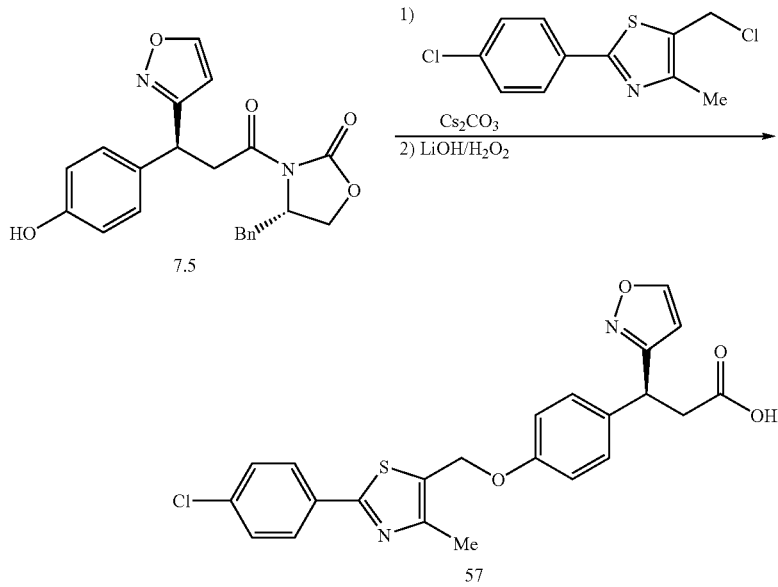

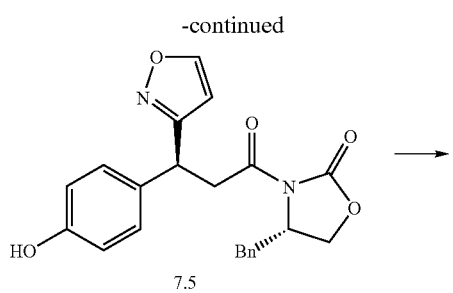

7.5

(S)-3-(Isoxazol-3-yl)-3-(4-((4-methyl-2-(4-chlorophenyl)thiazol-5-yl)methoxy)phenyl)propanoic acid (57). Cesium carbonate (170 mg, 0.52 mmol) was added to a mixture of 7.5 (140 mg, 0.36 mmol) and 5-(chloromethyl)-4-methyl-2-(4-chlorophenyl)thiazole (110 mg, 0.43 mmol, commercially available from Bionet Research Intermediates, UK) in DMSO (3 mL). The resulting mixture was stirred at room temperature for 2 hours. The mixture was treated with EtOAc (25 mL) and water (15 mL). The organic layer was separated, washed twice with brine, dried, and concentrated. The crude product (210 mg, 0.32 mmol) was treated with THF (3 mL) and hydrogen peroxide (35 wt %, 1.0 mL) and cooled to 0° C.

Aqueous LiOH (2.0 M, 1.0 mL, 2.0 mmol) was added. The resulting mixture was stirred at 0° C. for 10 minutes and then at room temperature for 2 Hours. The crude mixture LCMS analysis showed reaction to complete. The mixture was diluted with EtOAc (50 mL) and 5 mL of aqueous citric acid (0.5 M, 2.5 mmol) was added. The mixture was washed with water. The organic layer was separated, and concentrated under reduced pressure. The residue was purified by reverse phase prep HPLC (5-95% water-MeCN, gradient, with 0.1% TFA). The desired fraction was collected and treated by lyophilizing to give 57 (21 mg) as a white powder. MS API-ES m/e: 453 (M−H). $^1$H NMR (500 MHz) (CDCl$_3$) δ 8.33 (1H, s); 7.93 (2H, d, J=10Hz); 7.49 (2H, d, J=5Hz); 7.25 (2H, d, J=5 Hz); 6.95 (2H, d, J=10Hz); 6.11 (1H, s); 5.19 (2H, s); 4.60 (1H, m); 3.38 (1H, m), 3.03 (1H, m), 2.57 (3H, s).

6.53 Example 58

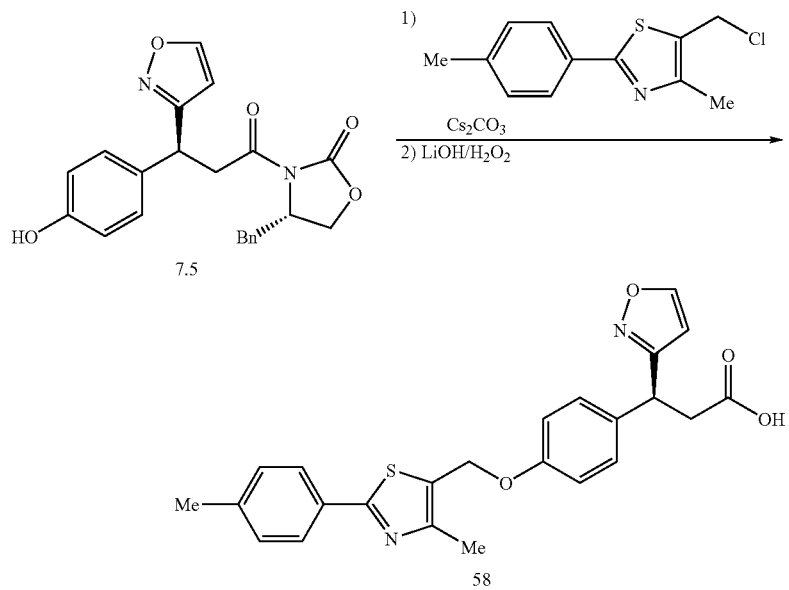

(S)-3-(Isoxazol-3-yl)-3-(4-((4-methyl-2-(4-methylphenyl)thiazol-5-yl)methoxy)phenyl)propanoic acid (58). Compound 58 was synthesized using the method of Example 57 using 5-(chloromethyl)-4-methyl-2-(4-methylphenyl)thiazole (commercially available from Bionet Research Intermediates, UK) in place of 5-(chloromethyl)-4-methyl-2-(4-chlorophenyl)thiazole. MS API-ES m/e: 433 (M−H).

6.54 Example 59

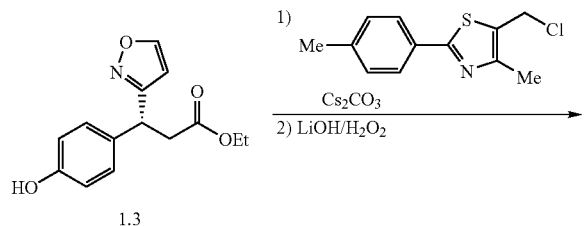

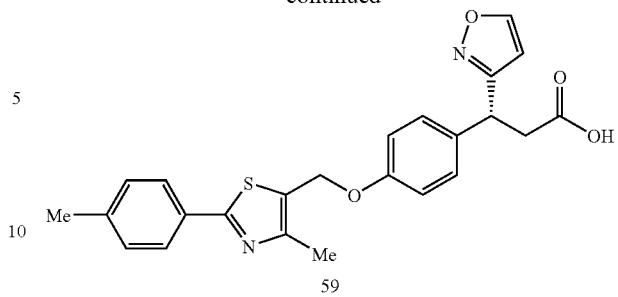

(R)-3-(Isoxazol-3-yl)-3-(4-((4-methyl-2-(4-methylphenyl)thiazol-5-yl)methoxy)phenyl)propanoic acid (59). Compound 59 was synthesized using the method of Example 6 using 1.3 and 5-(chloromethyl)-4-methyl-2-(4-methylphenyl)thiazole (commercially available from Bionet Research Intermediates, UK). MS API-ES m/e: 433 (M−H).

6.55 Example 60

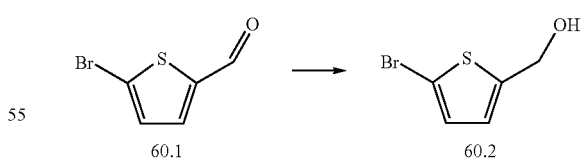

(5-Bromothiophen-2-yl)methanol (60.2). To a solution of 5-bromothiophene-2-carboxaldehyde 60.1 (2.00 g, 10.5 mmol) in MeOH (35 mL) was added NaBH$_4$ (0.40 g, 10.5 mmol) as a solid in one portion. The mixture was stirred for 15 minutes at room temperature and concentrated. The residue was suspended in 1N HCl and extracted with EtOAc. The combined organics were washed with brine, dried (Na$_2$SO$_4$), and concentrated. The crude product was chromatographed on silica gel (0-30% EtOAc/hexane) to afford 60.2 (1.56 g, 77%) as a colorless liquid. $^1$H NMR (400 MHz, CDCl$_3$) δ 6.92 (d, 1H), 6.76 (d, 1H), 4.75 (s, 2H).

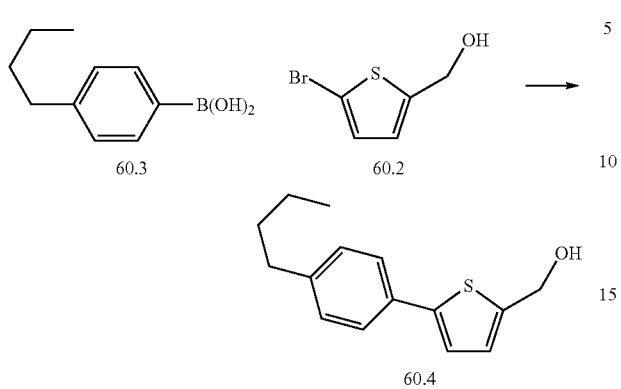

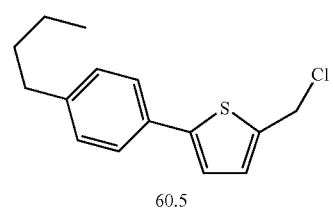

2-(Chloromethyl)-5-(4-n-butylphenyl)thiophene (60.5). To a solution of 60.4 (40 mg, 0.16 mmol) in DCM (0.8 mL) were added triethylamine (23 μL, 0.16 mmol) and thionyl chloride (18 μL, 0.24 mmol) at room temperature. The mixture was stirred overnight and concentrated to afford 60.5. The crude product was used without further purification.

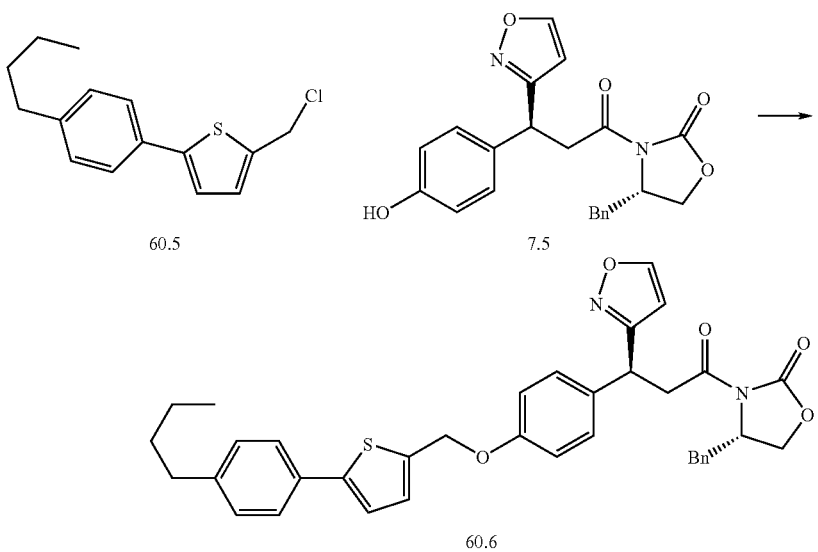

(5-(4-n-Butylphenyl)thiophen-2-yl)methanol (60.4). A mixture of 60.2 (0.300 g, 1.55 mmol), 4-n-butylbenzeneboronic acid 60.3 (0.553 g, 3.11 mmol), K$_2$CO$_3$ (0.644 g, 4.66 mmol), and Pd(PPh$_3$)$_4$ (0.180 g, 0.16 mmol) in toluene (5 mL) was stirred overnight at 95° C. The mixture was cooled to room temperature, filtered through a pad of silica gel (EtOAc), and concentrated. The crude product was chromatographed on silica gel (0-40% EtOAc/hexane) to afford 60.4 (0.072 g, 19%). $^1$H NMR (400 MHz, CDCl$_3$) δ 7.49 (d, 2H), 7.18 (d, 2H), 7.13 (d, 1H), 6.97 (d, H), 4.82 (s, 2H), 2.62 (t, 2H), 1.60 (m, 2H), 1.37 (m, 2H), 0.93 (t, 3H).

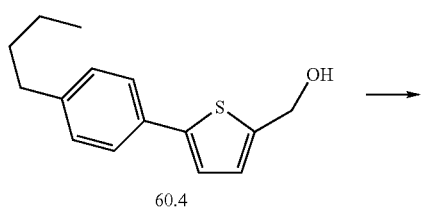

(4S)-3-((3S)-3-(4-(((5-(4-butylphenyl)-2-thienyl)methyl) oxy)phenyl)-3-(3-isoxazolyl)propanoyl)-4-(phenylmethyl)-1,3-oxazolidin-2-one (60.6). A mixture of 60.5 (0.16 mmol), 7.5 (52 mg, 0.13 mmol), and Cs$_2$CO$_3$ (135 mg, 0.41 mmol) in DMF (1.6 mL) was stirred overnight at room temperature. The mixture was diluted with EtOAc, washed with water and brine, dried (Na$_2$SO$_4$), and concentrated. The crude product was chromatographed on silica gel (0-30% EtOAc/hexane) to afford 60.6 (26 mg, 32%) as a colorless oil. $^1$H NMR (400 MHz, CDCl$_3$) δ 8.29 (d, 1H), 7.48 (d, 2H), 7.28 (m, 5H), 7.19 (m, 4H), 7.14 (d, 1H), 7.04 (d, 1H), 6.96 (d, 2H), 6.13 (d, 1H), 5.17 (s, 2H), 4.75 (t, 1H), 4.61 (m, 1H), 4.13 (m, 2H), 4.02 (dd, 1H), 3.54 (dd, 1H), 3.20 (dd, 1H), 2.76 (dd, 1H), 2.62 (t, 2H), 1.61 (m, 2H), 1.37 (m, 2H), 0.94 (t, 3H).

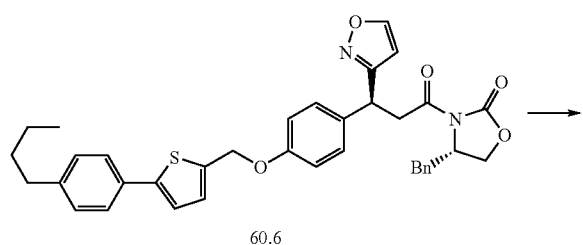

60.6

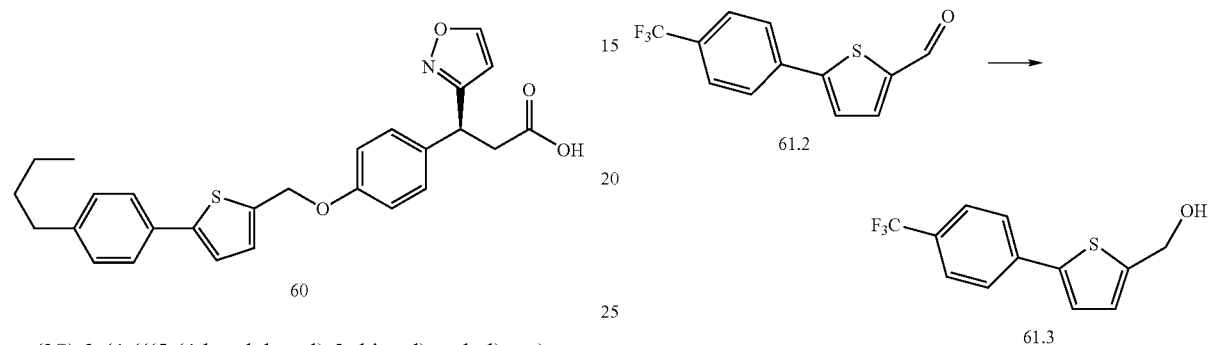

60

(3S)-3-(4-(((5-(4-butylphenyl)-2-thienyl)methyl)oxy)phenyl)-3-(3-isoxazolyl)propanoic acid (60). To a solution of 60.6 (26 mg, 0.042 mmol) in THF (0.4 mL) were added 30% H₂O₂ (47 μL, 0.42 mmol) and 1N LiOH (0.21 mL, 0.21 mmol) at 0° C. The mixture was stirred for 1 h at 0° C., adjusted to pH 3 with aqueous HCl, and extracted with EtOAc. The combined organics were washed with 1N Na₂SO₃ (pH 3) and brine, dried (Na₂SO₄), and concentrated. The crude product was chromatographed on silica gel (10-45% EtOAc/hexane) and further purified by preparative thin layer chromatography (50% EtOAc/hexane) to afford 60 (1.6 mg, 8%) as a white solid. ¹H NMR (400 MHz, CDCl₃) δ 8.28 (d, 1H), 7.48 (d, 2H), 7.18 (m, 4H), 7.14 (d, 1H), 7.04 (d, 1H), 6.94 (d, 2H), 6.07 (d, 1H), 5.17 (s, 2H), 4.55 (t, 1H), 3.35 (dd, 1H), 2.98 (dd, 1H), 2.61 (t, 2H), 1.60 (m, 2H), 1.37 (m, 2H), 0.93 (t, 2H).

6.56 Example 61

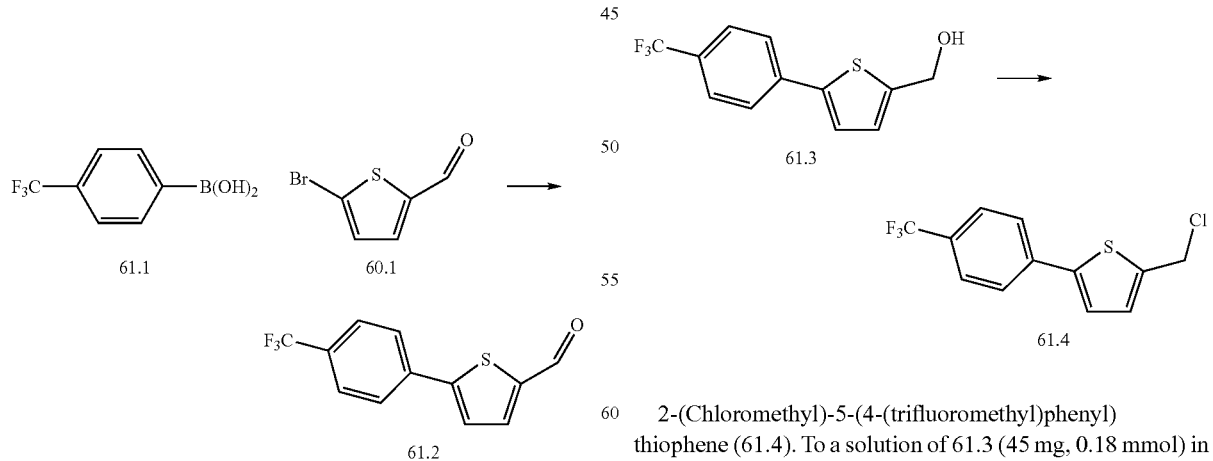

5-(4-(Trifluoromethyl)phenyl)thiophene-2-carboxaldehyde (61.2). A mixture of 5-bromothiophene-2-carboxaldehyde 60.1 (1.03 g, 5.4 mmol), 4-(trifluoromethyl)benzeneboronic acid 61.1 (2.05 g, 10.9 mmol), K₂CO₃ (2.24 g, 16.2 mmol), and Pd(PPh₃)₄ (0.60 g, 0.54 mmol) in toluene (15 mL) was stirred for 5 Hours at 95° C. The mixture was cooled to room temperature, filtered through a pad of silica gel (EtOAc), and concentrated. The crude product was chromatographed on silica gel (0-30% EtOAc/hexane) to afford 61.2 (0.87 g, 63%) as off-white crystals. ¹H NMR (400 MHz, CDCl₃) δ 9.93 (s, 1H), 7.78 (m, 3H), 7.70 (d, 2H), 7.48 (d, 1H).

(5-(4-(Trifluoromethyl)phenyl)thiophen-2-yl)methanol (61.3). To a solution of 61.2 (0.87 g, 3.40 mmol) in 3:2 MeOH/THF (25 mL) was added NaBH₄ (0.13 g, 3.40 mmol) as a solid in one portion. The mixture was stirred for 2 Hours at room temperature and concentrated. The residue was suspended in 1N HCl and extracted with EtOAc. The combined organic layers were washed with brine, dried (Na₂SO₄), and concentrated to afford 61.3 as a white powder. The crude product was used without further purification. ¹H NMR (400 MHz, CDCl₃) δ 7.68 (d, 2H), 7.62 (d, 2H), 7.26 (d, 1H), 7.01 (d, 1H), 4.86 (d, 2H), 1.84 (t, 1H).

2-(Chloromethyl)-5-(4-(trifluoromethyl)phenyl)thiophene (61.4). To a solution of 61.3 (45 mg, 0.18 mmol) in DCM (0.9 mL) were added triethylamine (24 μL, 0.18 mmol) and thionyl chloride (19 μL, 0.26 mmol) at room temperature. The mixture was stirred overnight and concentrated to afford 61.4. The crude product was used without further purification.

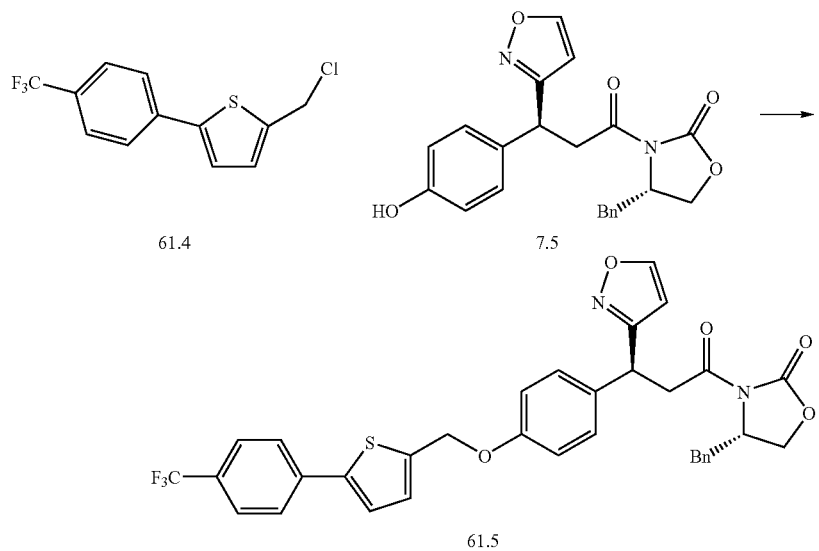

(4S)-3-((3S)-3-(3-isoxazolyl)-3-(4-(((5-(4-(trifluoromethyl)phenyl)-2-thienyl)methyl)oxy)phenyl)propanoyl)-4-(phenylmethyl)-1,3-oxazolidin-2-one (61.5). A mixture of 61.4 (0.19 mmol), 7.5 (62 mg, 0.16 mmol), and $Cs_2CO_3$ (155 mg, 0.48 mmol) in DMF (1.6 mL) was stirred overnight at room temperature. The mixture was diluted with EtOAc, washed with water and brine, dried ($Na_2SO_4$), and concentrated. The crude product was chromatographed on silica gel (25-50% EtOAc/hexane) to afford 61.5 (76 mg, 54%) as a white solid. $^1$H NMR (400 MHz, $CDCl_3$) δ 8.31 (d, 1H), 7.69 (d, 2H), 7.64 (d, 2H), 7.35 (m, 2H), 7.28 (m, 4H), 7.21 (m, 2H), 7.11 (d, 1H), 6.98 (d, 2H), 6.16 (d, 1H), 5.22 (s, 2H), 4.78 (dd, 1H), 4.64 (m, 1H), 4.16 (m, 2H), 4.05 (dd, 1H), 3.56 (dd, 1H), 3.22 (dd, 1H), 2.78 (dd, 1H).

Methyl (3S)-3-(3-isoxazolyl)-3-(4-(((5-(4-(trifluoromethyl)phenyl)-2-thienyl)methyl)oxy)phenyl)propanoate (61.6). To a solution of 61.5 (76 mg, 0.12 mmol) in THF (1 mL) were added 30% $H_2O_2$ (0.14 mL, 1.2 mmol) and 1N LiOH (0.60 mL, 0.60 mmol) at 0° C. The mixture was stirred for 1 Hour at 0° C., adjusted to pH 3 with aqueous HCl, and extracted with EtOAc. The combined organic layers were washed with 1N $Na_2SO_3$ (pH 3) and brine, dried ($Na_2SO_4$), and concentrated. The residue was dissolved in 9:1 MeCN/DMF (1 mL), and to the solution were added $K_2CO_3$ (25 mg, 0.18 mmol) and iodomethane (11 µL, 0.18 mmol). The mixture was stirred overnight at room temperature, diluted with EtOAc, washed with water and brine, dried ($Na_2SO_4$), and concentrated. The crude product was chromatographed on silica gel (0-40% EtOAc/hexane) to afford 61.6 as a white solid.

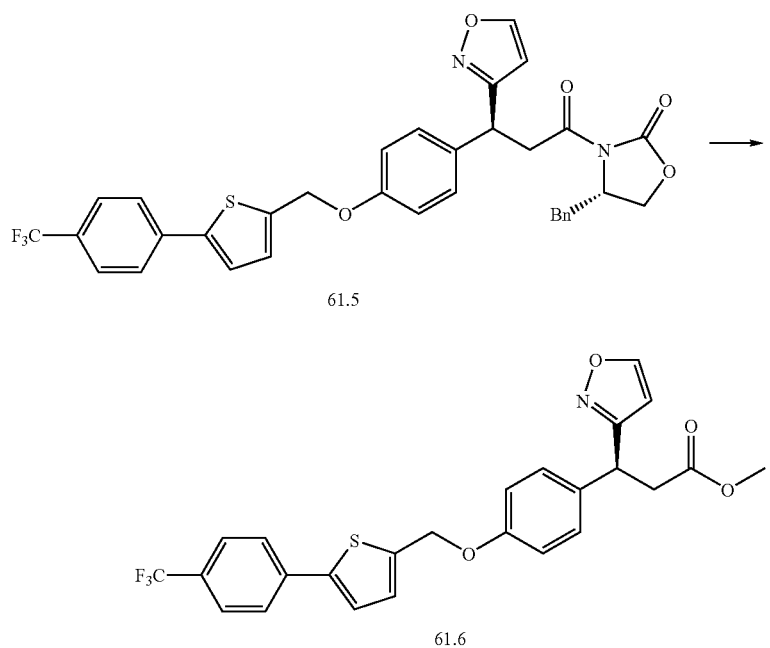

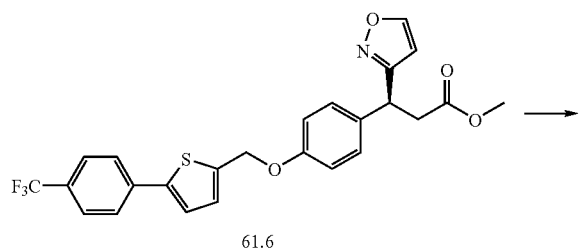

61.6

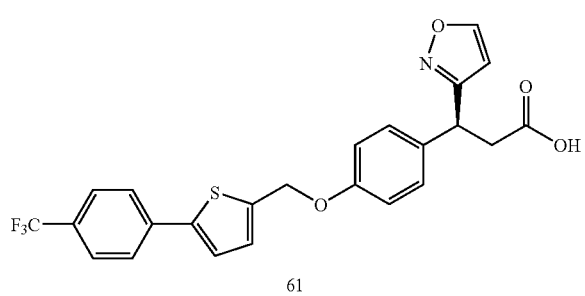

61

(3S)-3-(3-Isoxazolyl)-3-(4-(((5-(4-(trifluoromethyl)phenyl)-2-thienyl)methyl)oxy)phenyl)propanoic acid (61). To a solution of 61.6 (0.12 mmol) in 3:1 THF/MeOH (2.8 mL) was added 1N LiOH (0.7 mL). The mixture was stirred for 1 Hour at room temperature, quenched with 1N HCl (0.8 mL), and extracted with EtOAc. The combined organic layers were washed with water and brine, dried (Na$_2$SO$_4$), and concentrated to afford 61 (47 mg, 83%) as a white solid. $^1$H NMR (400 MHz, CDCl$_3$) δ 8.29 (d, 1H), 7.68 (d, 2H), 7.62 (d, 2H), 7.28 (d, 1H), 7.20 (d, 2H), 7.09 (d, 1H), 6.95 (d, 2H), 6.07 (d, 1H), 5.19 (s, 2H), 4.56 (t, 1H), 3.36 (dd, 1H), 2.99 (dd, 1H).

6.57 Example 62

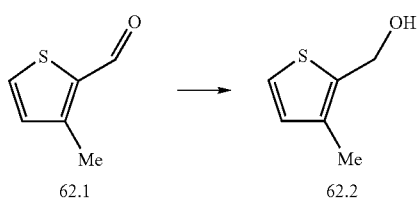

(3-Methylthiophen-2-yl)methanol (62.2). To a solution of 3-methylthiophene-2-carboxaldehyde 62.1 (3.17 g, 25.1 mmol) in MeOH (100 mL) was added NaBH$_4$ (1.05 g, 27.6 mmol) as a solid in one portion. The mixture was stirred for 15 minutes at room temperature and concentrated. The residue was suspended in 1N HCl and extracted with EtOAc. The combined organic layers were washed with brine, dried (Na$_2$SO$_4$), and concentrated. The crude product was chromatographed on silica gel (0-35% EtOAc/hexane) to afford 62.2 as a pale yellow liquid. $^1$H NMR (400 MHz, CDCl$_3$) δ 7.17 (d, 1H), 6.84 (d, 1H), 4.76 (s, 2H), 2.25 (s, 3H)

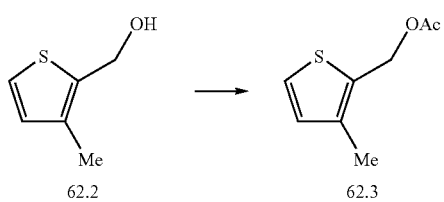

(3-Methylthiophen-2-yl)methyl acetate (62.3). To a solution of 62.2 (0.87 g, 6.79 mmol) in pyridine (20 mL) was added acetic anhydride (0.8 mL, 8.14 mmol) at room temperature. The mixture was stirred overnight at room temperature, diluted with EtOAc, washed with 1N HCl and brine, dried (Na$_2$SO$_4$), and concentrated. The crude product was chromatographed on silica gel (0-15% EtOAc/hexane) to afford 62.3. $^1$H NMR (400 MHz, CDCl$_3$) δ 7.21 (d, 1H), 6.84 (d, 1H), 5.20 (s, 2H), 2.26 (s, 3H), 2.08 (s, 3H).

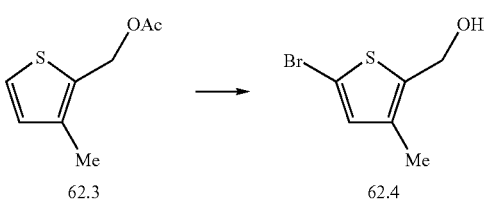

(5-Bromo-3-methylthiophen-2-yl)methyl acetate (62.4). To a solution of 62.3 (0.61 g, 3.58 mmol) and pyridine (0.29 mL, 3.58 mmol) in DCM (24 mL) was added bromine (3.58 mL, 1.0 M solution in DCM) dropwise at 0° C. The mixture was stirred for 30 minutes at 0° C. and warmed to room temperature over 1 Hour. Upon completion, the reaction was diluted with DCM, washed with saturated Na$_2$S$_2$O$_3$ and brine, dried (Na$_2$SO$_4$), and concentrated to afford 62.4. The crude product was used without further purification.

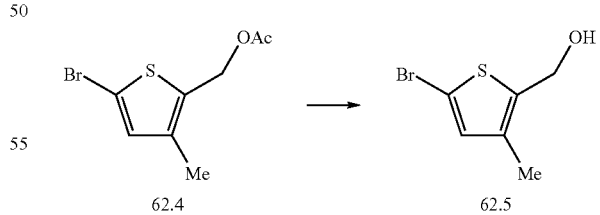

(5-Bromo-3-methylthiophen-2-yl)methanol (62.5). A mixture of 62.4 (3.58 mmol) and K$_2$CO$_3$ (0.99 g, 7.16 mmol) in MeOH (18 mL) was stirred for 5 Hours at room temperature. The mixture was filtered (DCM) and concentrated, and the crude product was chromatographed on silica gel (0-30% EtOAc/hexane) to afford 62.5 (0.61 g, 82%) as a yellow liquid. $^1$H NMR (400 MHz, CDCl$_3$) δ 6.78 (s, 1H), 4.68 (s, 2H), 2.18 (s, 3H).

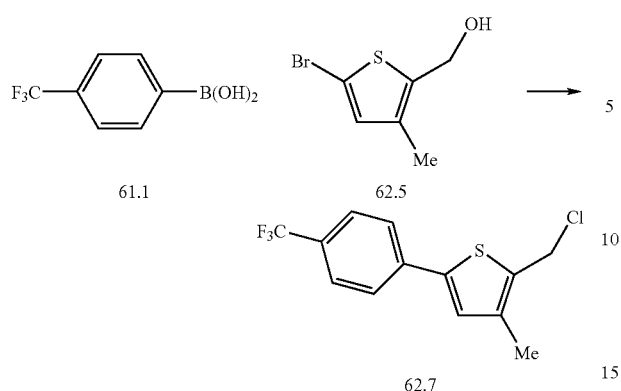

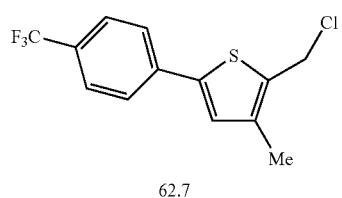

(5-(4-(Trifluoromethyl)phenyl)-3-methylthiophen-2-yl)methanol (62.6). A mixture of 62.5 (0.100 g, 0.48 mmol), 4-(trifluoromethyl)benzeneboronic acid 61.1 (0.183 g, 0.97 mmol), $K_2CO_3$ (0.200 g, 1.45 mmol), and $Pd(PPh_3)_4$ (0.056 g, 0.05 mmol) in toluene (3.2 mL) was stirred overnight at 100° C. The mixture was cooled to room temperature, filtered through a pad of silica gel (EtOAc), and concentrated. The crude product was chromatographed on silica gel (0-30% EtOAc/hexane) to afford 62.6 (0.063 g, 48%) as an oil. $^1$H NMR (400 MHz, $CDCl_3$) δ 7.66 (d, 2H), 7.61 (d, 2H), 7.14 (s, 1H), 4.79 (s, 2H), 2.27 (s, 3H).

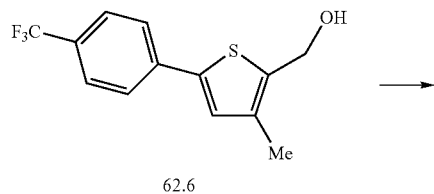

2-(Chloromethyl)-5-(4-(trifluoromethyl)phenyl)-3-methylthiophene (62.7). To a solution of 62.6 (63 mg, 0.23 mmol) in DCM (2.3 mL) were added triethylamine (32 μL, 0.23 mmol) and thionyl chloride (25 μL, 0.35 mmol) at room temperature. The mixture was stirred overnight and concentrated to afford 62.7. The crude product was used without further purification.

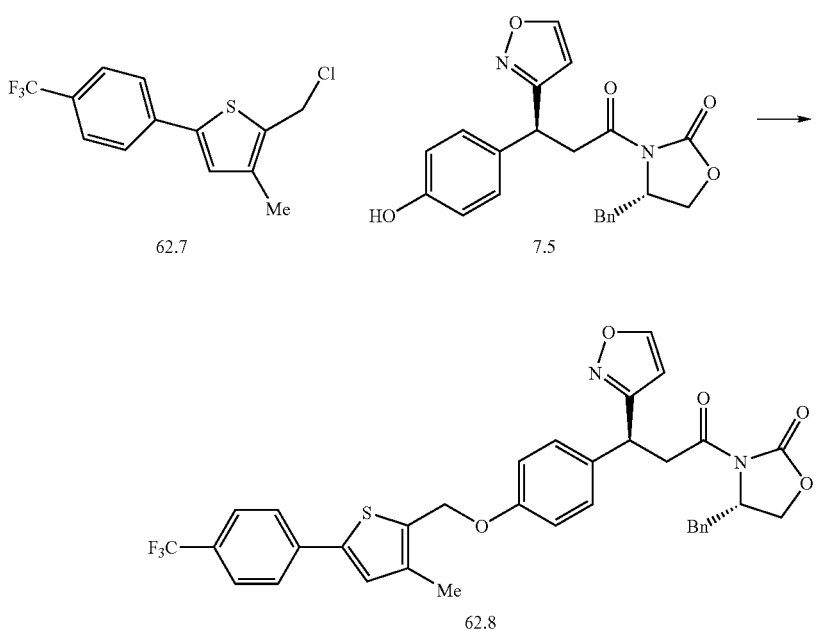

(4S)-3-((3S)-3-(3-Isoxazolyl)-3-(4-(((3-methyl-5-(4-(trifluoromethyl)phenyl)-2-thienyl)methyl)oxy)phenyl)propanoyl)-4-(phenylmethyl)-1,3-oxazolidin-2-one (62.8). A mixture of 62.7 (0.23 mmol), 7.5 (76 mg, 0.19 mmol), and $Cs_2CO_3$ (226 mg, 0.69 mmol) in DMF (2.3 mL) was stirred overnight at room temperature. The mixture was diluted with EtOAc, washed with water and brine, dried ($Na_2SO_4$), and concentrated. The crude product was chromatographed on silica gel (15-45% EtOAc/hexane) to afford 62.8 (94 mg, 75%) as a white solid.

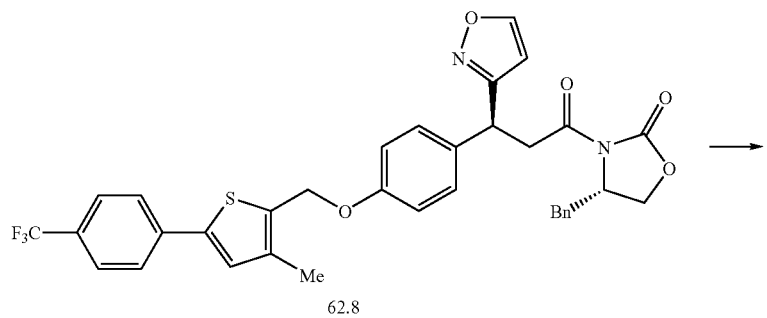

62.8

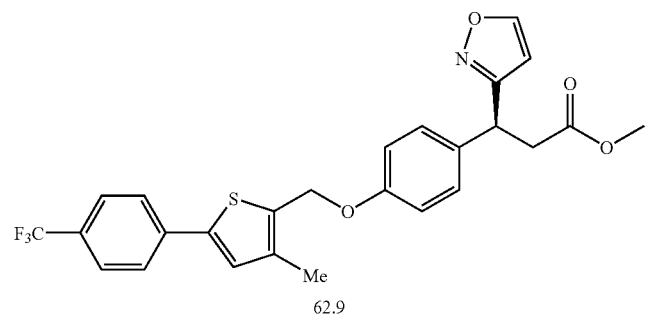

62.9

Methyl (3S)-3-(3-isoxazolyl)-3-(4-(((3-methyl-5-(4-(trifluoromethyl)phenyl)-2-thienyl)methyl)oxy)phenyl)propanoate (62.9). To a solution of 62.8 (94 mg, 0.15 mmol) in THF (1.5 mL) were added 30% $H_2O_2$ (0.17 mL, 1.50 mmol) and 1N LiOH (0.73 mL, 0.73 mmol) at 0° C. The mixture was stirred for 1 Hour at 0° C., adjusted to pH 3 with aqueous HCl, and extracted with EtOAc. The combined organics were washed with 1N $Na_2SO_3$ (pH 3) and brine, dried ($Na_2SO_4$), and concentrated. The residue was dissolved in 9:1 MeCN/DMF (1.5 mL), and to the solution were added $K_2CO_3$ (30 mg, 0.22 mmol) and iodomethane (20 μL, 0.22 mmol). The mixture was stirred overnight at room temperature, diluted with EtOAc, washed with water and brine, dried ($Na_2SO_4$), and concentrated. The crude product was chromatographed on silica gel (0-40% EtOAc/hexane) to afford 62.9 (64 mg, 88%) as a pale yellow oil. $^1$H NMR (400 MHz, CDCl$_3$) δ 8.28 (d, 1H), 7.65 (d, 2H), 7.60 (d, 2H), 7.20 (d, 2H), 7.15 (s, 1H), 6.95 (d, 2H), 6.08 (d, 1H), 5.10 (s, 2H), 4.59 (t, 1H), 3.64 (s, 3H), 3.31 (dd, 1H), 2.95 (dd, 1H), 2.28 (s, 3H).

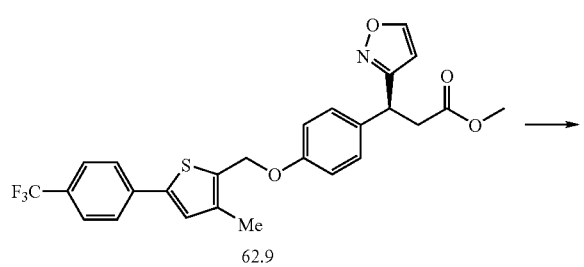

62.9

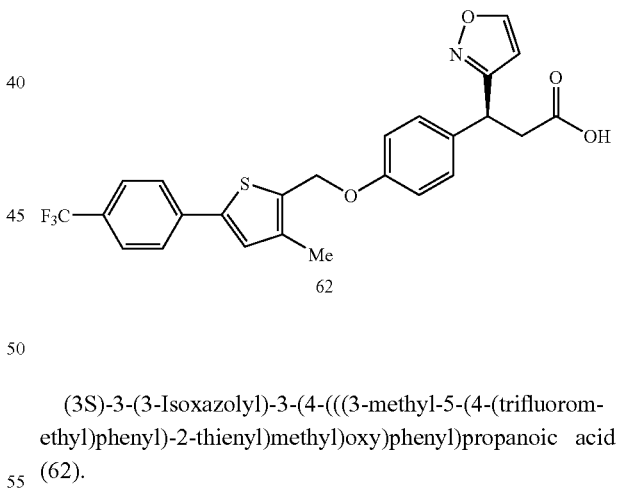

62

(3S)-3-(3-Isoxazolyl)-3-(4-(((3-methyl-5-(4-(trifluoromethyl)phenyl)-2-thienyl)methyl)oxy)phenyl)propanoic acid (62).

To a solution of 62.9 (64 mg, 0.13 mmol) in 3:1 THF/MeOH (2.8 mL) was added 1N LiOH (0.7 mL). The mixture was stirred for 1 Hour at room temperature, quenched with 1N HCl (0.8 mL), and extracted with EtOAc. The combined organics were washed with water and brine, dried ($Na_2SO_4$), and concentrated to afford 62 (45 mg, 70%) as an off-white solid. $^1$H NMR (400 MHz, CDCl$_3$) δ 8.29 (d, 1H), 7.65 (d, 2H), 7.60 (d, 2H), 7.20 (d, 2H), 7.15 (s, 1H), 6.95 (d, 2H), 6.07 (d, 1H), 5.10 (s, 2H), 4.55 (t, 1H) 3.35 (dd, 1H), 2.98 (dd, 1H), 2.28 (s, 3H).

6.58 Examples 63-71

Compounds 63-71 were synthesized in the same manner as Example 11 using the commercially available reagents described below in place of 3-(chloromethyl)-5-(4-methoxyphenyl)-1,2,4-oxadiazole.

Example 63

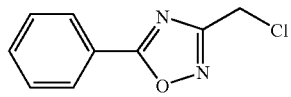

63.1

Example 63

3-(Chloromethyl)-5-phenyl-1,2,4-oxadiazole (63.1) (commercially available from Maybridge) was used in place of 3-(chloromethyl)-5-(4-methoxyphenyl)-1,2,4-oxadiazole.

Example 64

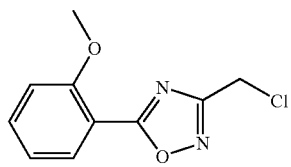

64.1

Example 64

3-(Chloromethyl)-5-(2-methoxyphenyl)-1,2,4-oxadiazole (64.1) (commercially available from Maybridge) was used in place of 3-(chloromethyl)-5-(4-methoxyphenyl)-1,2,4-oxadiazole.

Example 65

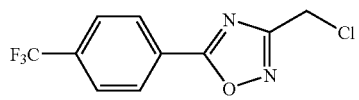

65.1

Example 65

3-(Chloromethyl)-5-(-4-trifluoromethylphenyl)-1,2,4-oxadiazole (65.1) (commercially available from Maybridge) was used in place of 3-(chloromethyl)-5-(4-methoxyphenyl)-1,2,4-oxadiazole.

Example 66

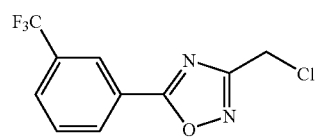

66.1

Example 66

3-(Chloromethyl)-5-(−3-trifluoromethylphenyl)-1,2,4-oxadiazole (66.1) (commercially available from Maybridge) was used in place of 3-(chloromethyl)-5-(4-methoxyphenyl)-1,2,4-oxadiazole.

Example 67

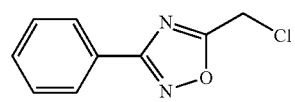

67.1

Example 67

5-(Chloromethyl)-3-phenyl-1,2,4-oxadiazole (67.1) (commercially available from Maybridge) was used in place of 3-(chloromethyl)-5-(4-methoxyphenyl)-1,2,4-oxadiazole.

Example 68

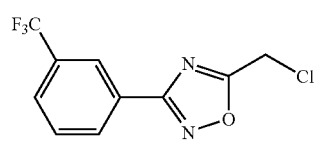

68.1

Example 68

5-(Chloromethyl)-3-(3-trifluoromethylphenyl)-1,2,4-oxadiazole (68.1) (commercially available from Bionet) was used in place of 3-(chloromethyl)-5-(4-methoxyphenyl)-1,2,4-oxadiazole.

Example 69

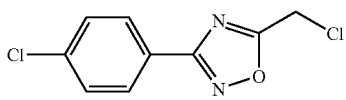

69.1

Example 69

5-(Chloromethyl)-3-(4-chlorophenyl)-1,2,4-oxadiazole (69.1) (commercially available from Maybridge) was used in place of 3-(chloromethyl)-5-(4-methoxyphenyl)-1,2,4-oxadiazole.

Example 70

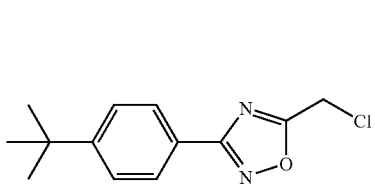

Example 70

3-(4-tert-Butylphenyl)-5-(chloromethyl)-1,2,4-oxadiazole (70.1) (commercially available from Maybridge) was used in place of 3-(chloromethyl)-5-(4-methoxyphenyl)-1,2,4-oxadiazole.

Example 71

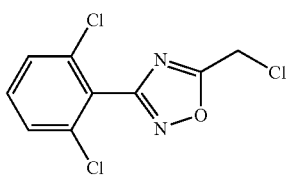

Example 71

5-(Chloromethyl)-3-(2,6-dichlorophenyl)-1,2,4-oxadiazole (71.1) (commercially available from Maybridge) was used in place of 3-(chloromethyl)-5-(4-methoxyphenyl)-1,2,4-oxadiazole.

|  | Example | | | | | | | | |
|---|---|---|---|---|---|---|---|---|---|
|  | 63 | 64 | 65 | 66 | 67 | 68 | 69 | 70 | 71 |
| MS Calculated | 392.1 | 422.1 | 460.1 | 460.1 | 392.1 | 460.1 | 426.1 | 448.2 | 460.1 |
| MS Found: m/e ESI (pos.) (M + H). | 391.9 | 422.0 | 460.0 | 460.0 | 391.9 | 460.0 | 426.0 | 448.1 | 460.0 |

6.59 Example 72

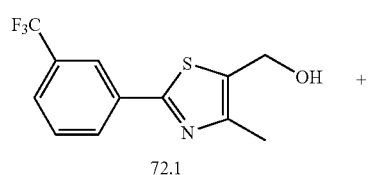

+

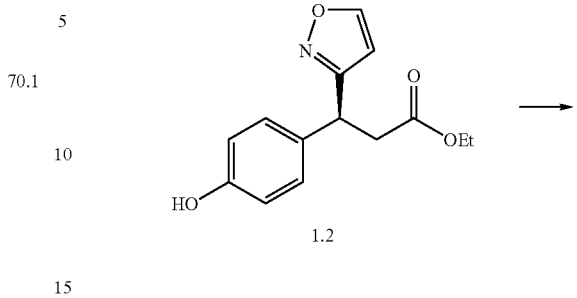

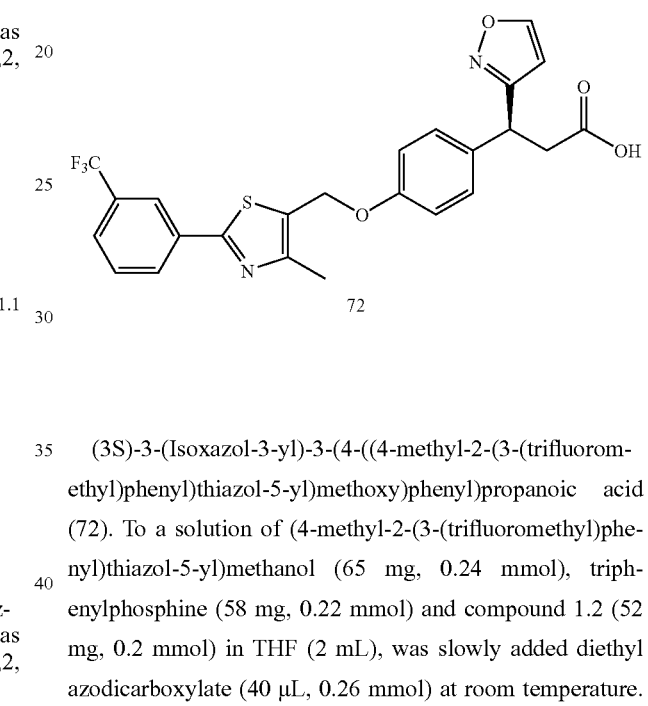

(3S)-3-(Isoxazol-3-yl)-3-(4-((4-methyl-2-(3-(trifluoromethyl)phenyl)thiazol-5-yl)methoxy)phenyl)propanoic acid (72). To a solution of (4-methyl-2-(3-(trifluoromethyl)phenyl)thiazol-5-yl)methanol (65 mg, 0.24 mmol), triphenylphosphine (58 mg, 0.22 mmol) and compound 1.2 (52 mg, 0.2 mmol) in THF (2 mL), was slowly added diethyl azodicarboxylate (40 μL, 0.26 mmol) at room temperature. The reaction mixture was stirred at room temperature for 30 minutes and then loaded on a silica gel cartridge and chromatographed (silica gel, 1:4 EtOAc/hexane) to afford the corresponding ester. The ester was dissolved in DMF (1 mL), and LiOH in water (1 mL, 1 N solution) was added. The mixture was then stirred at 50° C. for 3 Hours. The mixture was filtered and purified by reverse phase HPLC to give 72 (7.68 mg, 0.016 mmol) after lyophilization. MS ESI (pos.) m/e 489.1 (M+H).

6.60 Example 73

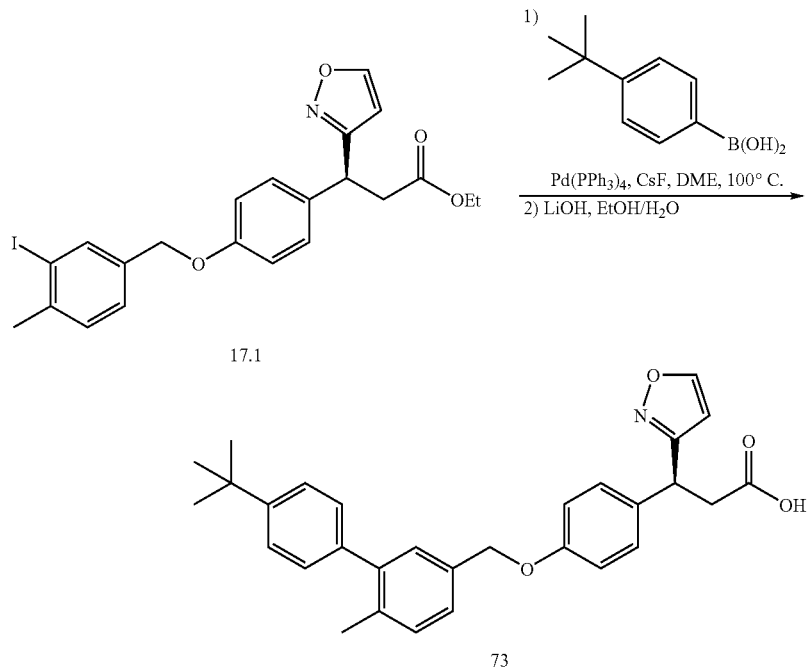

(S)-3-(4-(3-(4-tert-Butyl)-phenyl-4-methylbenzyloxy)phenyl)-3-(isoxazol-3-yl)propanoic acid (73). A solution of (S)-ethyl 3-(4-(3-iodo-4-methylbenzyloxy)phenyl)-3-(isoxazol-3-yl)propanoate 17.1 (35 mg, 0.072 mmol), tetrakis(triphenylphosphine)palladium (32 mg, 0.028 mmol), CsF (85 mg, 0.56 mmol), and 4-tert-butylphenylboronic acid (50 mg, 0.28 mmol) (commercially available from Aldrich) in DME (1 mL), was stirred at 100° C. for 5 Hours and then loaded on a silica gel cartridge and purified by flash chromatography (silica gel, 1:4 EtOAc/hexane) to afford the corresponding ester. The ester was dissolved in EtOH (1 mL), and LiOH in water (1 mL, 1 N solution) was added. The mixture was stirred at 23° C. for 2 Hours. The mixture was then filtered and purified by reverse phase HPLC to give compound 73 (0.37 mg) after lyophilization. MS ESI (pos.) m/e 470.2 (M+H).

6.61 Example 74

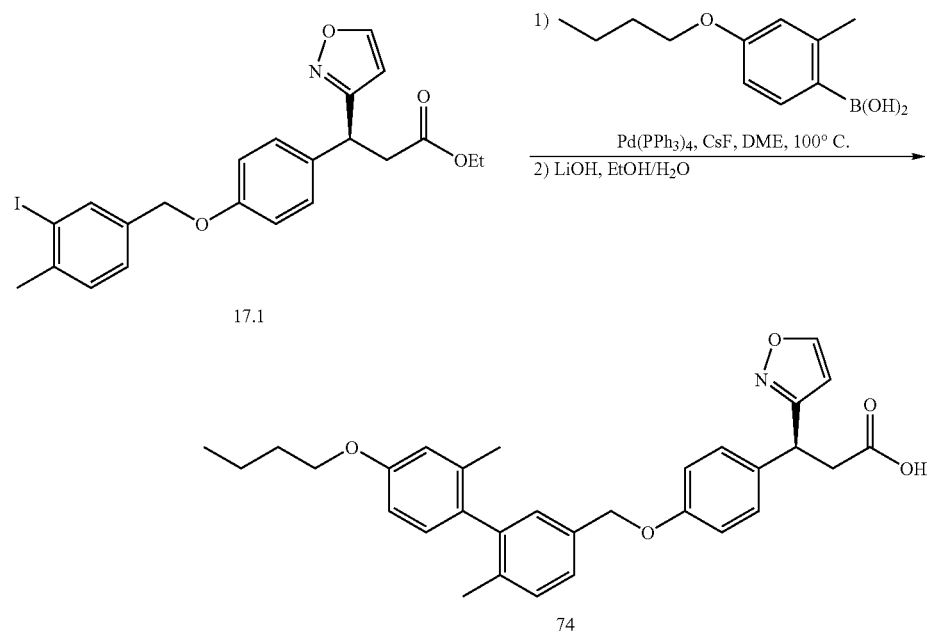

(S)-3-(4-(3-(4-Butoxy-2-methyl)-phenyl-4-methylbenzyloxy)phenyl)-3-(isoxazol-3-yl)propanoic acid (74). A solution of (S)-ethyl 3-(4-(3-iodo-4-methylbenzyloxy)phenyl)-3-(isoxazol-3-yl)propanoate 17.1 (35 mg, 0.072 mmol), tetrakis(triphenylphosphine)palladium (32 mg, 0.028 mmol), CsF (85 mg, 0.56 mmol), and 4-butoxy-2-methylphenylboronic acid (58 mg, 0.28 mmol) (commercially available from Aldrich) in DME (1 mL), was stirred at 100° C. for 5 Hours and then loaded on a silica gel cartridge and purified by flash chromatography (silica gel, 1:4 EtOAc/hexane) to afford the corresponding ester. The ester was dissolved in EtOH (1 mL) and LiOH in water (1 mL, 1 N solution) was added. The mixture was stirred at 23° C. for 2 Hours. The mixture was then filtered and purified by reverse phase HPLC to give compound 74 (0.10 mg) after lyophilization. MS ESI (pos.) m/e 500.2 (M+H).

6.62 Example 75

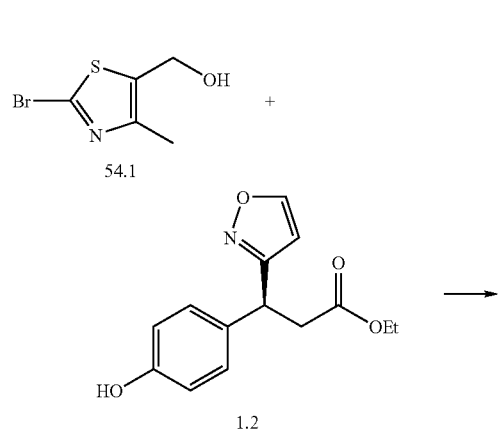

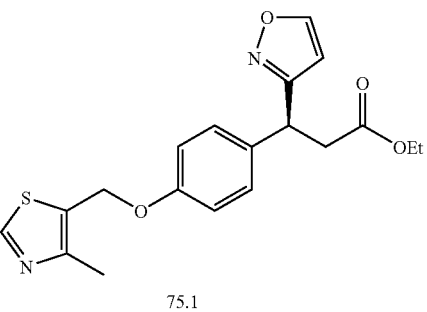

(S)-Ethyl 3-(4-((2-bromo-4-methylthiazol-5-yl)methoxy)phenyl)-3-(isoxazol-3-yl)propanoate (75.1). A solution of 54.1 (458 mg, 2.2 mmol), triphenylphosphine (576 mg, 2.2 mmol) and compound 1.2 (520 mg, 2.0 mmol) in THF (1 mL) was sonicated for 5 minutes. To this solution was slowly added diethyl azodicarboxylate (376 μL, 2.4 mmol) at room temperature. The reaction mixture was sonicated at room temperature for 5 minutes and then loaded on a silica gel cartridge and purified by flash chromatography (silica gel, 1:4 EtOAc/hexane) to afford 75.1 (635 mg, 1.4 mmol). MS ESI (pos.) m/e 451.0 (M+H).

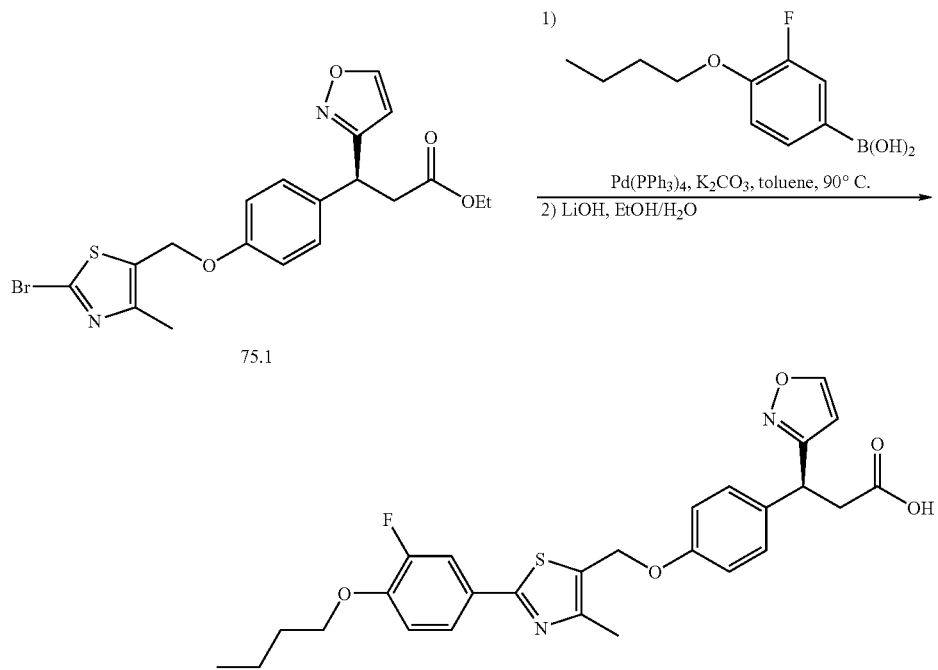

(3S)-3-(4-((2-(4-Butoxy-3-fluorophenyl)-4-methylthiazol-5-yl)methoxy)phenyl)-3-(isoxazol-3-yl)propanoic acid (75). A solution of 75.1 (45 mg, 0.1 mmol), tetrakis(triphenylphosphine)palladium (2 mg, 0.01 mmol), K₂CO₃ (42 mg, 0.3 mmol), and 4-butoxy-3-fluorophenylboronic acid (42 mg, 0.2 mmol) (commercially available from Aldrich) in toluene (1 mL), was stirred at 90° C. for 16 Hours and then loaded on a silica gel cartridge and purified by flash chromatography (silica gel, 1:4 EtOAc/hexane) to afford the corresponding ester. The ester was dissolved in EtOH (1 mL) and LiOH in water (1 mL, 1 N solution) was added. The mixture was stirred at 23° C. for 2 hours. The mixture was then filtered and purified by reverse phase HPLC to give compound 75 (20 mg) after lyophilization. MS ESI (pos.) m/e 511.0 (M+H).

6.63 Examples 76-81

Compounds 76-81 were synthesized in the same manner as Example 75 using 75.1 and the commercially available boronic acid reagents described below in place of 4-butoxy-3-fluorophenylboronic acid.

Example 76

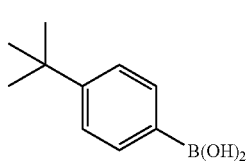

76.1

Example 76

4-tert-Butylphenylboronic acid (76.1)(commercially available from Aldrich) was used in place of 4-butoxy-3-fluorophenylboronic acid.

Example 77

77.1

Example 77

4-n-Butylphenylboronic acid (77.1) (commercially available from Aldrich) was used in place of 4-butoxy-3-fluorophenylboronic acid.

Example 78

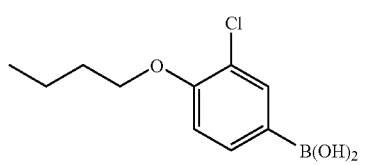

78.1

Example 78

4-iso-Butylphenylboronic acid (78.1)(commercially available from Combi-Blocks) was used in place of 4-butoxy-3-fluorophenylboronic acid.

Example 79

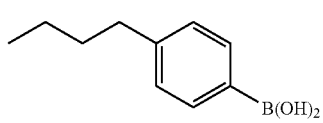

79.1

Example 79

4-Butoxy-3-chlorophenylboronic acid (79.1)(commercially available from Aldrich) was used in place of 4-butoxy-3-fluorophenylboronic acid.

Example 80

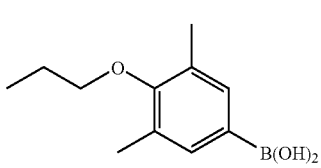

80.1

Example 80

3,5-Dimethyl-4-propoxyphenylboronic acid (80.1) (commercially available from Aldrich) was used in place of 4-butoxy-3-fluorophenylboronic acid

Example 81

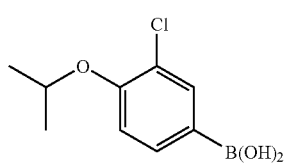

81.1

Example 81

3-Chloro-4-isopropoxyphenylboronic acid (81.1) (commercially available from Aldrich) was used in place of 4-butoxy-3-fluorophenylboronic acid.

|  | Example | | | | | |
|---|---|---|---|---|---|---|
|  | 76 | 77 | 78 | 79 | 80 | 81 |
| MS Calculated | 477.2 | 477.2 | 477.2 | 527.1 | 507.2 | 513.1 |
| MS Found: m/e ESI (pos.) (M + H). | 477.1 | 477.1 | 477.1 | 527.0 | 507.1 | 513.1 |

6.64 Examples 82 and 83

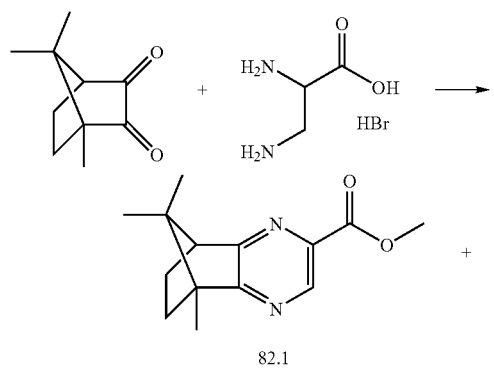

82.1

82.2

Compounds 82.1 and 82.2. To a solution of (1R)-(−)-camphorquinone (5.0 g, 30 mmol) and D,L-2,3-diaminopropionic acid (HBr salt) in methanol (200 mL) was added sodium hydroxide (4.8 g, 120 mmol) at 23° C. The resulting mixture was stirred under reflux for 70 Hours. The reaction mixture was then cooled to 0° C. and concentrated $H_2SO_4$ (24 mL) was added dropwise. The resulting mixture was refluxed for 6 Hours. Upon cooling, the mixture solidified. The mixture was broken into small pieces and was slowly added to a stirred saturated $NaHCO_3$ solution, extracted with EtOAc, washed with water, washed with brine, dried over $Na_2SO_4$, concentrated, and purified by flash chromatography to give 82.1 (619 mg) and 82.2 (1.06 g). MS ESI (pos.) m/e 247.1 (M+H).

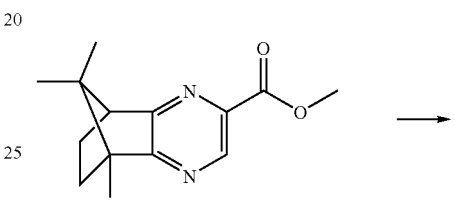

82.1

82.3

Compound 82.3. To a solution of 82.1 (600 mg, 2.44 mmol) in DCM was added dropwise a 1M solution of DIBAL-H in DCM at −78° C. The reaction was stirred at −78° C. for 3 Hours and then at 0° C. for 2 Hours. The mixture was then quenched with saturated $NH_4Cl$ solution, filtered over celite, and concentrated with silica gel. Purification by flash chromatography gave 82.3 in pure form. MS ESI (pos.) m/e 219.1 (M+H).

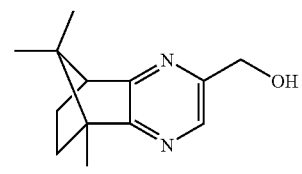

82.3

1.2

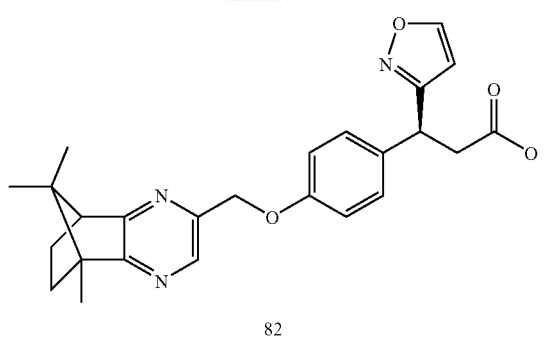

82

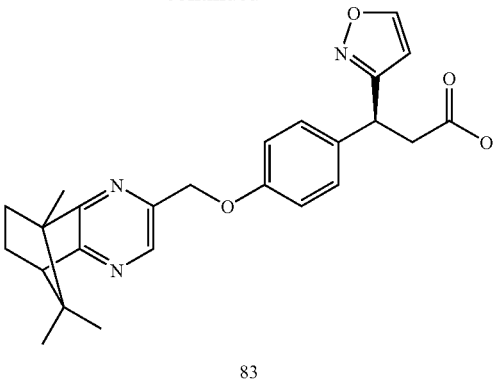

83

Compound 82. Compound 82 was synthesized from compound 82.3 and 1.2 using the procedure of Example 72. MS ESI (pos.) m/e 434.2 (M+H).

Compound 83. Compound 83 was synthesized from compound 83.1 and 1.2 using the procedure of Example 72. MS ESI (pos.) m/e 434.2 (M+H).

Cell-based Aequorin Assay

Cell-based aequorin assays were employed to characterize the modulatory activity of compounds on the GPR40 signaling pathway. In an exemplary assay, CHO cells were stably transfected with both GPR40 and Aequorin (Euroscreen). Cells were detached from the tissue culture dish with 2 mL of trypsin (0.25% (w/v)). Trypsinization was halted with 28 mL of Hanks Buffered Salt Solution containing 20 mM Hepes (H/HBSS) and 0.01% fatty acid-free human serum albumin (HSA). Coelantrazine is added to 1 ug/mL, and the cells were incubated for 2 hours at room temperature. Compounds were dissolved in DMSO for preparation of 10 mM stock solutions. Compounds were diluted in H/HBSS containing 0.01% HSA. Serial dilutions of the test compounds were prepared to determine dose response.

Aequorin luminescence measurements were made using an EG&G Berthold 96-well luminometer, and the response was measured over a 20 second interval after cells and compounds were mixed. The maximum relative light units was plotted to determine dose response. The $EC_{50}$ (effective concentration to reach 50% maximal response) was determined from the dose response plot.

Table 1 presents representative data ($EC_{50}$ values) obtained for exemplary compounds of the invention for the activation of human GPR40.

The stereoisomers in Table 1 are as specified, i.e., S-enantiomers or R-enantiomers, and if not specified, or if shown with wavy bonds, are mixtures of S-enantiomers and R-enantiomers. In addition, the present invention provides the S-enantiomers, the R-enantiomers, and mixtures of both S-enantiomers and R-enantiomers including racemates of each compound prepared according to the synthetic methods described herein or adapted with the necessary minor modifications from these methods.

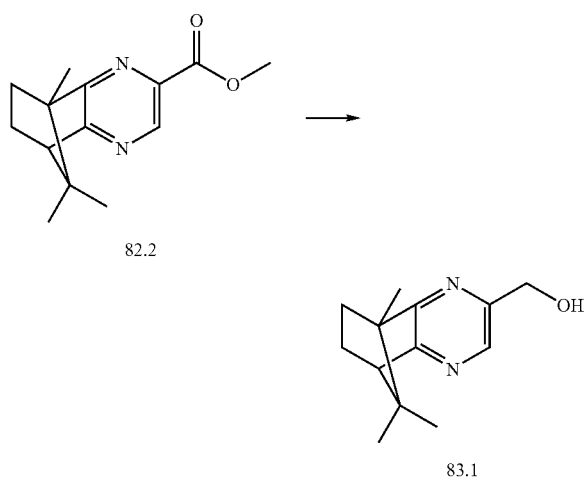

Compound 83.1. Compound 83.1 was synthesized from compound 82.2 using the procedure of Example 82.3. MS ESI (pos.) m/e 219.1 (M+H).

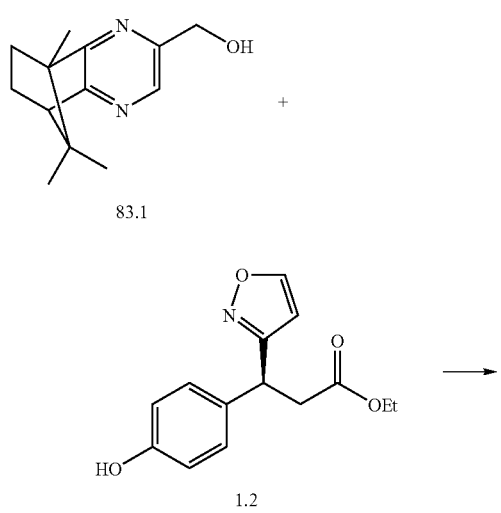

Insulin Secretion Assay

Human islets are isolated from cadaveric donors. Islets are treated with trypsin (0.25% (w/v) and cells are seeded in 96-well plates containing 3,000 cells per well. Cells are cultured in Roswell Park Memorial Institute (RMPI) media containing 10% fetal bovine serum.

For determination of insulin secretion, media is removed from islet cells and replaced with Krebs-Ringer bicarbonate buffer containing 10 mM HEPES (KRBH) and 2 mM glucose. After one hour incubation, media is replaced with KRBH containing 11.2 mM glucose and test compounds. Insulin released into the medium from the islet cells is measured using scintillation proximity assay (SPA).

For determination of insulin secretion from rodent islets, C57/B16 mice are euthanized with carbon dioxide gas. The pancreatic bile duct is clamped proximal to the duodenum and then cannulated. H/HBSS containing 0.75 mg/mL collagenase XI (Sigma) is then infused into the pancreas through the cannula. The pancreas is excised and then incubated at 37° C. for 13 minutes to complete enzymatic digestion. The collagenase digestion is quenched in H/HBSS containing 1% BSA and washed once in the same buffer. Islets can be purified using density gradient centrifugation using Histopaque (Sigma) and are hand-picked under a stereomicroscope.

Islets are cultured overnight in Roswell Park Memorial Institute (RMPI) media containing 10% fetal bovine serum and 50 uM beta-mercaptoethanol. Following overnight culture, islets are incubated in KRBH containing 2.8 mM glucose for one hour.

For determination of insulin secretion, islets are incubated in DMEM containing 12.5 mM glucose and test compounds for one hour. Insulin released into the culture medium from the islets is measured using an insulin ELISA.

TABLE 1

| | Aequorin Assay Using Human GPR40 | |
|---|---|---|
| No. | Structure[a] | EC$_{50}$[b] |
| 1 | | ++++ |
| 2 | | ++++ |
| 3 | | ++ |
| 4 | | ++++ |

TABLE 1-continued
Aequorin Assay Using Human GPR40
| No. | Structure[a] | EC$_{50}$[b] |
|---|---|---|
| 5 | 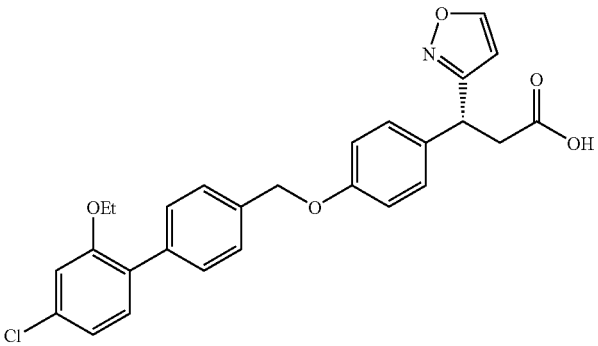 | ++ |
| 6 | 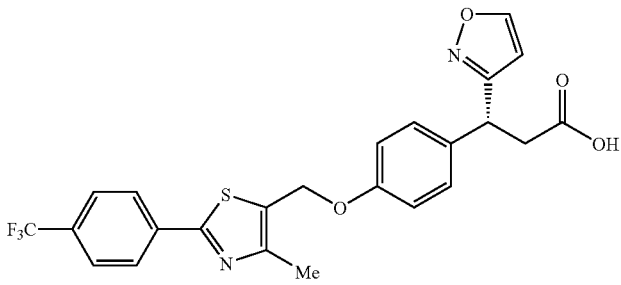 | +++ |
| 7 | 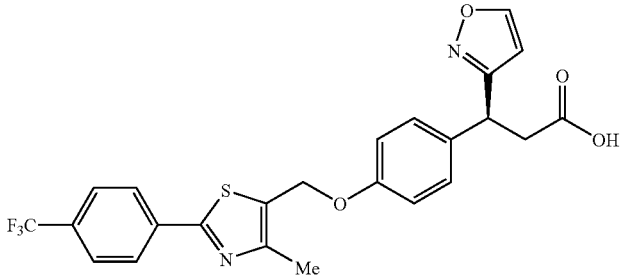 | ++++ |
| 8 | 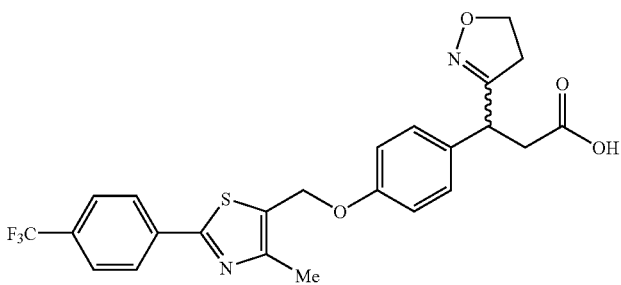 | +++ |
| 9 | 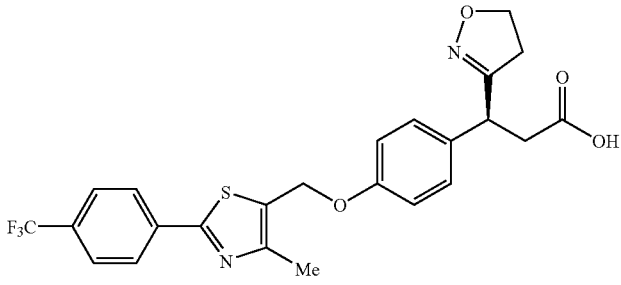 | ++++ |

TABLE 1-continued

| Aequorin Assay Using Human GPR40 | | |
|---|---|---|
| No. | Structure[a] | EC$_{50}$[b] |
| 10 | | +++ |
| 11 | | ++ |
| 12 | | +++ |
| 13 | | ++++ |
| 14 | | ++++ |

TABLE 1-continued

Aequorin Assay Using Human GPR40

| No. | Structure[a] | EC$_{50}$[b] |
|---|---|---|
| 15 | | ++++ |
| 16 | | +++ |
| 17 | | +++ |
| 18 | | +++ |
| 19 | | ++ |

TABLE 1-continued

Aequorin Assay Using Human GPR40

| No. | Structure[a] | EC$_{50}$[b] |
|---|---|---|
| 20 | | ++++ |
| 21 | | ++++ |
| 22 | | ++++ |
| 23 | | ++++ |

TABLE 1-continued

Aequorin Assay Using Human GPR40

| No. | Structure<sup>a</sup> | EC<sub>50</sub><sup>b</sup> |
|---|---|---|
| 24 | | ++++ |
| 25 | | ++++ |
| 26 | | +++ |
| 27 | | +++ |

TABLE 1-continued

Aequorin Assay Using Human GPR40

| No. | Structure[a] | EC$_{50}$[b] |
|---|---|---|
| 28 | | ++++ |
| 29 | | ++++ |
| 30 | | ++ |
| 31 | | ++++ |
| 32 | | +++ |

TABLE 1-continued

Aequorin Assay Using Human GPR40

| No. | Structure[a] | EC$_{50}$[b] |
|---|---|---|
| 33 | | +++ |
| 34 | | ++ |
| 35 | | ++++ |
| 36 | | +++ |

TABLE 1-continued

Aequorin Assay Using Human GPR40

| No. | Structure[a] | EC$_{50}$[b] |
|---|---|---|
| 37 | | ++++ |
| 38 | | ++++ |
| 39 | | ++/+++ |
| 40 | | ++++ |

TABLE 1-continued
Aequorin Assay Using Human GPR40
| No. | Structure[a] | EC$_{50}$[b] |
|---|---|---|
| 41 | 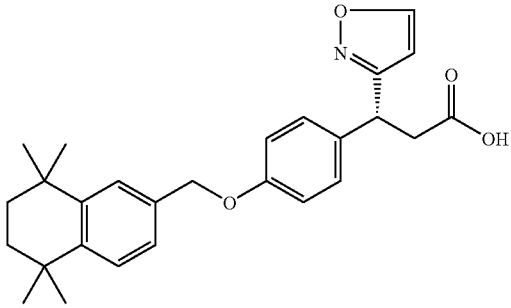 | ++ |
| 42 | 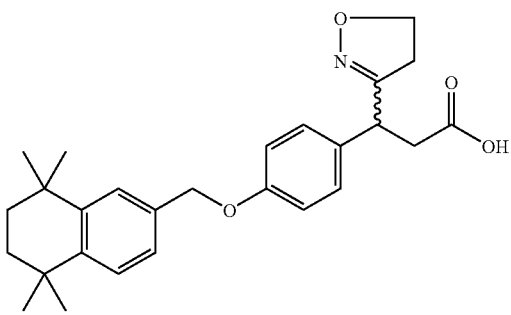 | +++ |
| 43 | 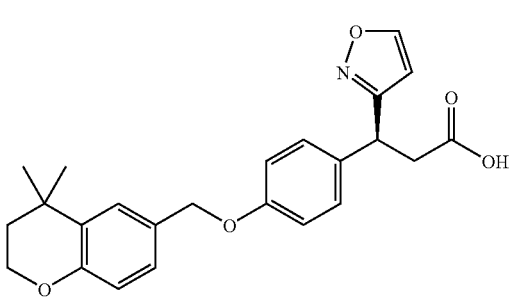 | ND[c] |
| 44 | 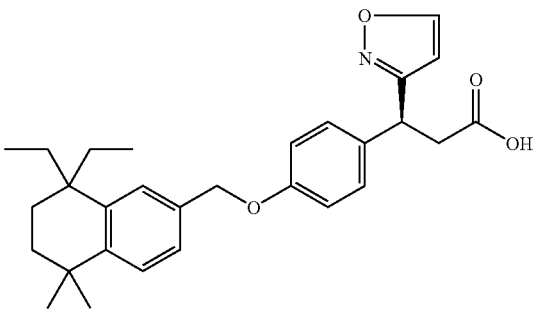 | ++++ |
| 45 | 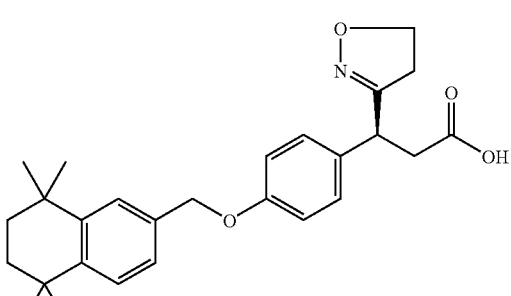 | ++++ |

TABLE 1-continued

Aequorin Assay Using Human GPR40

| No. | Structure[a] | EC$_{50}$[b] |
|---|---|---|
| 46 | | +++ |
| 47 | | +++ |
| 48 | | +++ |
| 49 | | +++ |
| 50 | | +++ |

TABLE 1-continued

Aequorin Assay Using Human GPR40

| No. | Structure[a] | EC$_{50}$[b] |
|---|---|---|
| 51 | | +++ |
| 52 | | ++++ |
| 53 | | ++++ |
| 54 | | ++ |
| 55 | | ++ |
| 56 | | +++ |

TABLE 1-continued

| | Aequorin Assay Using Human GPR40 | |
|---|---|---|
| No. | Structure | $EC_{50}$ |
| 57 | | ++++ |
| 58 | | ++++ |
| 59 | | ++ |
| 60 | | ++++ |
| 61 | | ++++ |

TABLE 1-continued

| | Aequorin Assay Using Human GPR40 | |
|---|---|---|
| No. | Structure[a] | EC$_{50}$[b] |
| 62 | | ++++ |
| 63 | | ++ |
| 64 | | ++ |
| 65 | | ++ |
| 66 | | ++ |

TABLE 1-continued

Aequorin Assay Using Human GPR40

| No. | Structure[a] | EC$_{50}$[b] |
|---|---|---|
| 67 | | ++ |
| 68 | | ++ |
| 69 | | ++ |
| 70 | | +++ |
| 71 | | ++ |

TABLE 1-continued

Aequorin Assay Using Human GPR40

| No. | Structure[a] | EC$_{50}$[b] |
|---|---|---|
| 72 | | ++++ |
| 73 | | ND[c] |
| 74 | | ND[c] |
| 75 | | ++++ |
| 76 | | ++++ |

TABLE 1-continued
Aequorin Assay Using Human GPR40
| No. | Structure[a] | EC$_{50}$[b] |
|---|---|---|
| 77 | 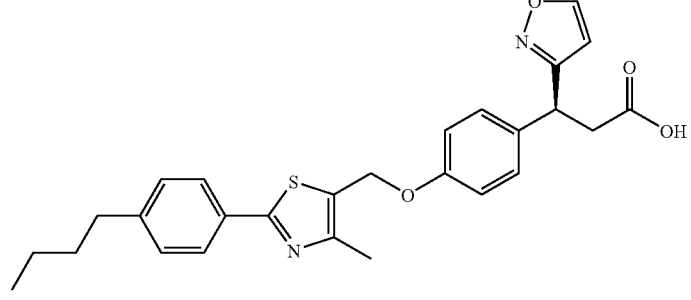 | ++++ |
| 78 | 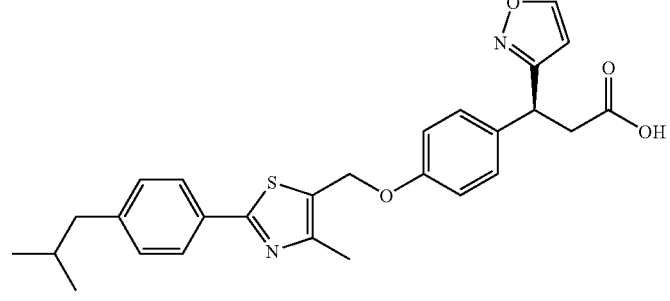 | ++++ |
| 79 | 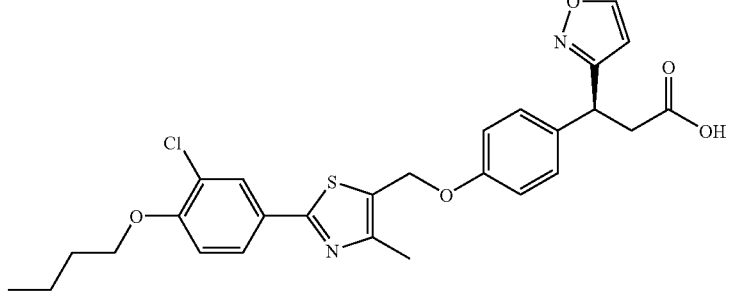 | ++++ |
| 80 | 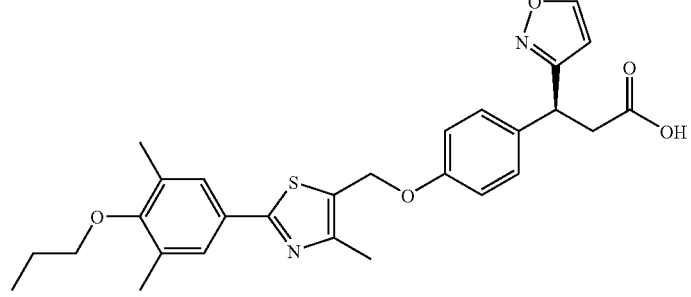 | ++++ |
| 81 | 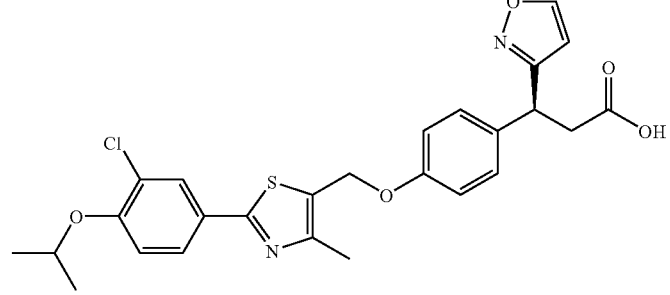 | ++++ |

TABLE 1-continued

Aequorin Assay Using Human GPR40

| No. | Structure[a] | EC$_{50}$[b] |
|---|---|---|
| 82 | 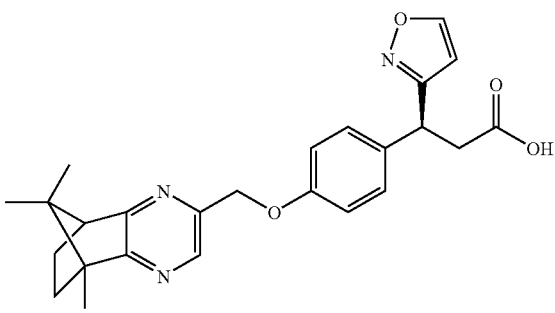 | ++ |
| 83 | 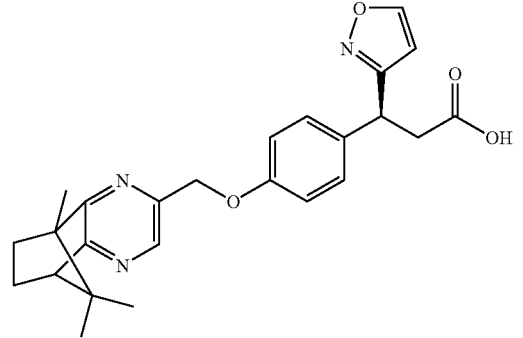 | ++ |

[a]When present, the "〰" bond indicates a mixture of stereoisomers are present in the exemplary compound.
[b]EC$_{50}$ Ranges:
+ EC$_{50}$>10 μM
++ 1 μM≦EC$_{50}$≦10 μM
+++ 0.1 μM≦EC$_{50}$<1 μM
++++ 0.01 μM≦EC$_{50}$<0.1 μM
+++++ EC$_{50}$<0.01 μM
[c]EC$_{50}$ value has not yet been determined. This compound is evaluated and found to possess an EC$_{50}$ value of less than 10 μM.

All publications and patent applications cited in this specification are hereby incorporated by reference as if each individual publication or patent application were specifically and individually indicated to be incorporated by reference. Each publication and patent application cited herein is incorporated in its entirety as if fully set forth herein. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A compound having the formula I':

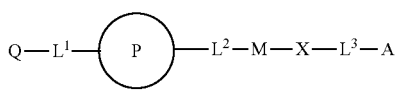

or a pharmaceutically acceptable salt, stereoisomer, or $C_1$-$C_6$ alkyl ester thereof, or a tautomer or a pharmaceutically acceptable salt, stereoisomer, or $C_1$-$C_6$ alkyl ester thereof, or a mixture thereof, wherein Q is hydrogen, aryl, heteroaryl, ($C_1$-$C_6$)alkyl, or ($C_2$-$C_6$) heteroalkyl;

$L^1$ is a bond, ($C_1$-$C_4$)alkylene, ($C_2$-$C_4$)heteroalkylene, O, S(O)$_k$, N(R$^a$), C(O)—($C_5$-$C_7$)heterocycloalkylene, ($C_1$-$C_4$)alkylene-SO$_2$N(R$^b$), ($C_1$-$C_4$)alkylene-N(R$^b$)SO$_2$, or C(O)N(R$^b$);

represents an optionally substituted benzo-fused ($C_5$-$C_8$)cycloalkane ring wherein the optionally substituted benzo-fused ($C_5$-$C_4$)alkylene-N(R$^b$)S)$_2$, or a benzene ring fused to a ($C_5$-$C_8$) cycloalkane ring, an optionally substituted heterobenzo-fused ($C_5$-$C_8$)cycloalkane ring wherein the heterobenzo-fused ($C_5$-$C_8$)cycloalkane ring has a six-membered heteroaryl ring having 1 or 2 N atoms fused to a ($C_5$-$C_8$) cycloalkane ring, or a heteroaryl-fused ($C_5$-$C_8$)cycloalkane ring wherein the heteroaryl-fused ($C_5$-$C_8$)cycloalkane ring has a five-membered heteroaryl ring having 1 or 2 heteroatoms fused to a ($C_5$-$C_8$)cycloalkane ring, wherein the benzene ring of the benzo-fused ($C_5$-$C_8$)cycloalkane ring, the heteroaryl ring of the heterobenzo-fused ($C_5$-$C_8$)cycloalkane ring, or the heteroaryl ring of the heteroaryl-fused $(C_5\text{-}C_8)$ cycloalkane ring is bonded to $L^2$ or M, if $L^2$ is a bond;

$L^2$ is a bond, $(C_1\text{-}C_6)$alkylene, $(C_2\text{-}C_6)$heteroalkylene, oxymethylene, O, $S(O)_k$, $N(R^a)$, $C(O)N(R^b)$, $SO_2N(R^b)$, $(C_1\text{-}C_4)$alkylene-$C(O)N(R^b)$, $(C_1\text{-}C_4)$alkylene-$N(R^b)C(O)$, $(C_2\text{-}C_4)$alkenylene-$C(O)N(R^b)$, $(C_2\text{-}C_4)$alkenylene-$N(R^b)C(O)$, $(C_1\text{-}C_4)$alkylene-$SO_2N(R^b)$, $(C_1\text{-}C_4)$alkylene-$N(R^b)SO_2$, $(C_2\text{-}C_4)$alkenylene-$SO_2N(R^b)$, or $(C_2\text{-}C_4)$alkenylene-$N(R^b)SO_2$;

M is an aromatic ring, a heteroaromatic ring, $(C_5\text{-}C_8)$cycloalkylene, aryl$(C_1\text{-}C_4)$alkylene, or heteroaryl$(C_1\text{-}C_4)$alkylene;

X is $CR^1R^{1'}$;

$L^3$ is a $(C_1\text{-}C_5)$alkylene or $(C_2\text{-}C_5)$heteroalkylene;

A is —$CO_2H$, tetrazol-5-yl, —$SO_3H$, —$PO_3H_2$, —$SO_2NH_2$, —$C(O)NHSO_2CH_3$, thiazolidinedionyl, hydroxyphenyl, or pyridyl;

$R^a$ is hydrogen, $(C_1\text{-}C_6)$alkyl, aryl$(C_1\text{-}C_3)$ alkyl, or $(C_2\text{-}C_6)$heteroalkyl;

$R^b$ is hydrogen, $(C_1\text{-}C_6)$alkyl, or $(C_2\text{-}C_6)$heteroalkyl;

$R^1$ is a group of formula:

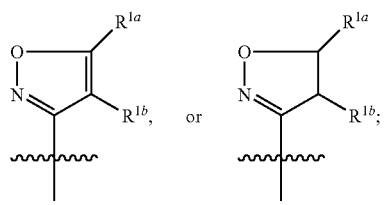

$R^{1a}$ is selected from H, or $(C_1\text{-}C_6)$alkyl;

$R^{1b}$ is selected from H, or $(C_1\text{-}C_6)$alkyl;

$R^{1'}$ is hydrogen, cyano, aryl, heteroaryl, $(C_1\text{-}C_8)$alkyl, $(C_2\text{-}C_8)$alkenyl, or $(C_2\text{-}C_8)$alkynyl; and the subscript k is, in each instance, independently selected from 0, 1, or 2.

2. The compound of claim 1, wherein

is a benzo-fused $(C_5\text{-}C_8)$cycloalkane ring.

3. The compound of claim 1, wherein

is a heterobenzo-fused $(C_5\text{-}C_8)$cycloalkane ring, wherein the heteroaryl ring of the heterobenzo-fused $(C_5\text{-}C_8)$cycloalkane ring has 1 or 2 N atoms.

4. The compound of claim 1, wherein the compound has the formula II':

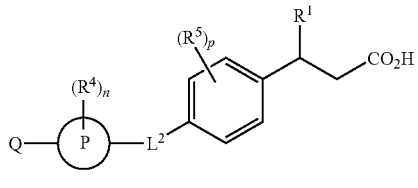

or a pharmaceutically acceptable salt, stereoisomer, or $C_1\text{-}C_6$ alkyl ester thereof, or a tautomer or a pharmaceutically acceptable salt, stereoisomer, or $C_1\text{-}C_6$ alkyl ester thereof, or a mixture thereof, wherein Q is selected from hydrogen, aryl, or heteroaryl;

$L^2$ is selected from $(C_1\text{-}C_6)$alkylene, $(C_2\text{-}C_6)$heteroalkylene, oxymethylene, O, or $S(O)_k$;

$R^4$ is independently selected from substituted $(C_1\text{-}C_6)$ alkyl, —R', —OR', =O, =NR', =N—OR', —NR'R", —SR', halogen, —OC(O)R', —C(O)R', —$CO_2R'$, —CONR'R", —OC(O)NR'R", —NR"C(O)R', —NR'—C(O)NR"R"', —NR'—$SO_2NR'R'''$, —$NR''CO_2R'$, —NH—C(NH_2)=NH, —NR'C(NH_2)=NH, —NH—C(NH_2)=NR', —SiR'R"R"', —S(O)R', —$SO_2R'$, —$SO_2NR'R''$, —$NR''SO_2R$, —CN, —$(C_2\text{-}C_5)$ alkynyl, —$(C_2\text{-}C_5)$ alkenyl, or —$NO_2$, where R', R" and R''' each independently refer to hydrogen, unsubstituted $(C_1\text{-}C_8)$ alkyl or heteroalkyl, unsubstituted aryl, aryl substituted with one to three halogens, unsubstituted alkyl, alkoxy or thioalkoxy groups, halo$(C_1\text{-}C_4)$alkyl, or aryl-$(C_1\text{-}C_4)$ alkyl groups;

$R^5$ is independently selected from $(C_1\text{-}C_6)$alkyl, halogen, $(C_1\text{-}C_6)$alkoxy, cyano, or nitro;

the subscript n is 0, 1, 2, 3, 4, 5, 6, 7, 8, 9, 10, 11, 12, 13, or 14; and the subscript p is 0, 1, 2, 3 or 4.

5. The compound of claim 4, wherein $R^4$ independently is selected from $(C_1\text{-}C_6)$alkyl, halogen, $(C_1\text{-}C_6)$alkoxy, cyano, or nitro.

6. The compound of claim 4, wherein the compound has the formula IIIA' or IIIB':

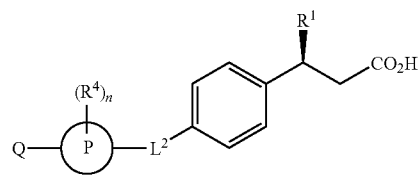

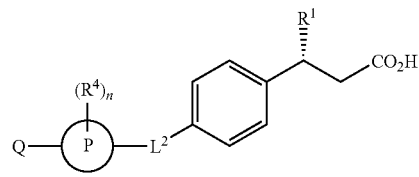

or a pharmaceutically acceptable salt, solvate, or $C_1\text{-}C_6$ alkyl ester thereof or a tautomer or a pharmaceutically acceptable salt, solvate, or $C_1\text{-}C_6$ alkyl ester thereof, or a mixture thereof.

7. The compound of claim 1, wherein the compound has the formula IV':

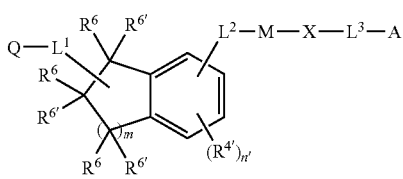

IV' or a pharmaceutically acceptable salt, stereoisomer, or $C_1$-$C_6$ alkyl ester thereof, or a tautomer or a pharmaceutically acceptable salt, stereoisomer, or $C_1$-$C_6$ alkyl ester thereof, or a mixture thereof, wherein $R^{4'}$ is independently selected from substituted ($C_1$-$C_6$) alkyl, —R', —OR', =O, =NR', =N—OR', —NR'R", —SR', halogen, —OC(O)R', —C(O)R', —CO$_2$R', —CONR'R", —OC(O)NR'R", —NR"C(O)R', —NR'—C(O)NR"R''', —NR'—SO$_2$NR"R''', —NR"CO$_2$R', —NH—C(NH$_2$)=NH, —NR'C(NH$_2$)=NH, —NH—C(NH$_2$)=NR', —SiR'R"R''', —S(O)R', —SO$_2$R', —SO$_2$NR'R", —NR"SO$_2$R, —CN, —(C$_2$-C$_5$) alkynyl, —(C$_2$-C$_5$) alkenyl, or —NO$_2$, where R', R" and R''' each independently refer to hydrogen, unsubstituted (C$_1$-C$_8$) alkyl or heteroalkyl, unsubstituted aryl, aryl substituted with one to three halogens, unsubstituted alkyl, alkoxy or thioalkoxy groups, halo(C$_1$-C$_4$)alkyl, or aryl-(C$_1$-C$_4$) alkyl groups;

one of $R^6$ and $R^{6'}$ is $L^1$ or Q, if $L^1$ is a bond, and the others of $R^6$ and $R^{6'}$ are independently selected from H, (C$_1$-C$_6$)alkyl, halogen, (C$_1$-C$_6$)alkoxy, cyano, or nitro, wherein one of $R^6$ and one of $R^{6'}$ on adjacent or non-adjacent carbon atoms, or on the same carbon atom may join together to form a C$_5$-C$_8$ cycloalkane ring, or two of $R^6$ or two of $R^{6'}$, on adjacent or non-adjacent carbon atoms, may join together to form a C$_5$-C$_8$ cycloalkane ring;

the subscript n' is 0, 1, 2, or 3; and the subscript m is 1, 2, 3, or 4.

8. The compound of claim 7, wherein the subscript m is 1 or 2.

9. The compound of claim 7, wherein $R^6$ and $R^{6'}$ are independently selected from H and methyl and at least two of $R^6$ and $R^{6'}$ are methyl groups.

10. A pharmaceutical composition, comprising the compound of claim 1 and a pharmaceutically acceptable carrier, diluent, or excipient.

* * * * *